United States Patent
Colon-Cruz et al.

(10) Patent No.: US 6,821,964 B2
(45) Date of Patent: Nov. 23, 2004

(54) MODULATORS OF CHEMOKINE RECEPTOR ACTIVITY

(75) Inventors: Roberto Colon-Cruz, Groton, CT (US); Mary T. Didiuk, Groton, CT (US); Erin M. Duffy, Deep River, CT (US); Ravi Garigipati, South Glastonbury, CT (US); Wan F. Lau, Noank, CT (US); Wayne S. McDonald, East Lyme, CT (US)

(73) Assignee: Pfizer Inc, New York, NY (US)

(*) Notice: Subject to any disclaimer, the term of this patent is extended or adjusted under 35 U.S.C. 154(b) by 0 days.

(21) Appl. No.: 10/093,273

(22) Filed: Mar. 6, 2002

(65) Prior Publication Data

US 2003/0008893 A1 Jan. 9, 2003

Related U.S. Application Data

(60) Provisional application No. 60/273,984, filed on Mar. 7, 2001.

(51) Int. Cl.$^7$ .................... A61K 31/407; C07D 401/14; C07D 403/14; C07D 413/14; C07D 487/04
(52) U.S. Cl. .................. 514/210.16; 514/412; 544/281; 546/176; 546/276.7; 548/126; 548/181; 548/248; 548/266.8; 548/453
(58) Field of Search ................................. 548/453, 126, 548/181, 248, 266.8; 544/281; 546/176, 276.7; 514/210.16, 412

(56) References Cited

U.S. PATENT DOCUMENTS

| | | | |
|---|---|---|---|
| 4,990,517 A | 2/1991 | Petersen et al. | 514/300 |
| 5,071,999 A | 12/1991 | Schenke et al. | 548/453 |
| 5,374,731 A | 12/1994 | Heitsch et al. | 546/194 |
| 5,703,091 A | * 12/1997 | Steiner et al. | 514/300 |
| 6,107,321 A | 8/2000 | Madin | 514/383 |
| 6,184,235 B1 | 2/2001 | Connor et al. | 514/322 |

FOREIGN PATENT DOCUMENTS

| | | |
|---|---|---|
| EP | 1061076 | 12/2000 |
| JP | 6025243 | 2/1994 |
| JP | 7101959 | 4/1995 |
| WO | WO 9635691 | 11/1996 |
| WO | WO 9711949 | 4/1997 |
| WO | WO 9744329 | 11/1997 |
| WO | WO 9907351 | 2/1999 |
| WO | WO 9907678 | 2/1999 |
| WO | WO 9909984 | 3/1999 |
| WO | WO 9925686 | 5/1999 |
| WO | WO 9932468 | 7/1999 |
| WO | WO 9940914 | 8/1999 |
| WO | WO 0046197 | 8/2000 |
| WO | WO 0055143 | 9/2000 |

* cited by examiner

*Primary Examiner*—Fiona T. Powers
(74) *Attorney, Agent, or Firm*—Peter C. Richardson; Gregg C. Benson; Robert T. Ronau

(57) ABSTRACT

Chemokine receptor antagonists, in particular, bicyclic diamine compounds of Formula (I) that act as antagonists of chemokine CCR2 and CCR3 receptors including pharmaceutical compositions and uses thereof to treat or prevent diseases associated with monocyte accumulation, lymphocyte accumulation or leucocyte accumulation are described herein.

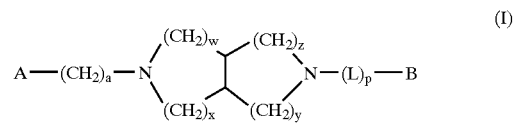

(I)

26 Claims, No Drawings

MODULATORS OF CHEMOKINE RECEPTOR ACTIVITY

This application claims the benefit of U.S. Provisional Patent Application No. 60/273,984 filed Mar. 7, 2001, which is incorporated in its entirety herein by reference.

FIELD OF THE INVENTION

The present invention relates to chemokine receptor antagonists, in particular, bicyclic diamine compounds that act as antagonists of chemokine CCR2 and CCR3 receptors including pharmaceutical compositions and uses thereof to treat or prevent diseases associated with monocyte accumulation, lymphocyte accumulation or leucocyte accumulation.

BACKGROUND

The local production and secretion of a family of 8–10 KD chemotactic cytokines (called chemokines) mediate the local accumulation of inflammatory cells in many pathological inflammatory and autoimmune disease states. Chemokines have been found to be highly expressed in a variety of pathological states, including atherosclerosis, pulmonary fibrosis, asthma, psoriasis and rheumatoid arthritis, coinciding with the chronic macrophage accumulation of inflamed tissue (see, e.g., Barker, J. N., et al., *J. Immunol.*, 146, 1192 (1991); Koch, A. E. *J. Clin. Invest*, 90, 772 (1996); Nelken, N. A., et al., *J. Clin. Invest.*, 88, 1121 (1991); Gong, J. H., *J. Exp. Med.*, 186, 131 (1997); Yla-Herttuala, S., et al., *Proc. Natl., Acad. Sci.*, 88, 5252 (1991); Rovin, B. H., et al., *Am. J. Kidney Dis.*, 31, 1065 (1998); and Gong, J. H. et al., *J. Exp. Med.*, 186, 131 (1997)). Continuous local release of chemokines at sites of inflammation mediates the excessive migration of effector cells in chronic inflammation. Thus, blocking leukocyte recruitment to target tissues by inhibiting chemokine activity in inflammatory and autoimmune disease would be an effective therapeutic intervention.

The chemoattractant chemokines belong to a super family of pro-inflammatory mediators that promote the recruitment of multiple lineages of leukocytes and lymphocytes. The human chemokine polypeptides are 70–80 residues in length that share substantial sequence homology. These polypeptides share a common structural motif: a conserved set of four cysteine residues. Based on the position of the first two or four cysteine residues and the chromosomal location of the corresponding genes, two main chemokine families, CC and CXC, have been identified. Members of the CXC subfamily attract mainly neutrophils, except for platelet factor 4 (PF4) and gamma interferon inducible protein (IP10). The CC chemokines attract mainly monocytes, eosinophils, and lymphocytes but may also attract T lymphocytes. Monocyte chemoattractant protein-1 (MCP-1) is a member of the CC chemokine family that is a potent chemotactic and activating factor for monocytes and memory T cells. The other members of the of the CC chemokine family, MCP-2, MCP-3, MCP-4, MCP-5, macrophage inflammatory protein (MIP)-1α, MIP-1β, RANTES (regulated on activation, normal T cell expressed and secreted) and eotaxin also mediate chemotaxis in distinct but overlapping leukocyte subsets.

The molecular targets for chemokines are their cell surface receptors that belong to the seven-transmembrane helix (STH), G-protein coupled receptors. This type of receptor consists of a single polypeptide chain with an extracellular amino-terminal domain and a cytoplasmic-terminal domain. The amino terminal and the third extracellular domain are important for receptor ligand interaction. The third intracellular loop (50–75 amino acids long) interacts directly with G-proteins. At least five CC chemokine receptors have been identified (CCR1–CC R5) and all five CC receptors belong to the STH G-coupled protein receptor family. Each of these receptors mediates the binding and signaling of more than one chemokine. For example, the CCR1 receptor is specific for MIP-1 α, RANTES, and MCP-3. CCR2B recognizes both MCP-1 and MCP-3; CCR3 is expressed on eosinophils and recognizes eotaxin; and CCR4 is found on basophils and responds to MIP1-α, RANTES and MCP-1. The MCP-1 receptor CCR2b signals through multiple G-proteins including Gαl, Gαq, and Gα16. See, e.g., Monteclaro, F. S., *J. Biol. Chem.*, 37, 23186 (1997). Thus, in addition to promoting the transmigration and emigration of circulating monocytes into tissues, MCP-1 interaction with the CCR2 receptor increases histamine release, calcium influx, cAMP activation, increases integrin expression and acts as a chemotactic factor for monocytes/macrophages. For further discussions, see Rollins, B. J., *Blood*, 78, 112 (1991); Neote, K., et al., *Cell*, 72, 415 (1993); Charo, I. F., et al., *Proc Natl., Acad. Sci. USA*, 91, 2752 (1994).

Various cell types including endothelial cells, smooth muscle cells, macrophages and fibroblasts produce MCP-1 and its murine homolog JE that was identified initially as a platelet-derived growth factor inducible gene. Although MCP-1 expression has been documented in a variety of human diseases that have inflammatory components, including atherosclerosis, multiple sclerosis, asthma and rheumatoid arthritis among many others, a direct cause and effect relationship has been difficult to prove. MCP-1 along with many other chemokines is expressed in many inflammatory lesions. Direct injection of MCP-1 into rodent's skin provides only a mild infiltrate or no infiltrate at all. See, Zachariae, C. O., *J. Exp. Med.*, 171, 2177 (1990). However, MCP-1 has been demonstrated to play a role in atherosclerosis. Overexpression of MCP-1 by macrophages in apolipoprotein E deficient mice increases monocytic infiltration and atherosclerosis. See, Aiello, R. J., et al., *Arteriosclero Thromb Vasc Biol.*, 19, 1518 (1999). Several studies using MCP-1 transgenic mice have suggested that the ability of MCP-1 to elicit monocyte infiltration depends on MCP-1 being expressed at specific sites. See, Fuentes, M. E., *J. Immunology*, 155, 5769 (1995). Recently MCP-1 deficient mice and MCP-1 receptor (CCR2) deficient mice were shown to have decreased atherosclerotic lesion formation. See, Boring, L. *Nature*, 394, 894 (1998).

Leukocyte entry into tissue involves a cascade of molecular events including chemotactic signaling to circulating cells, interaction with endothelial cells and transmigration through tissues. Significant advances have been made in the identification of leukocyte adhesion molecules and their cellular and extracellular matrix legends. Leukocyte-endothelial interactions occur in several phases which include rolling, firm adhesion and transmigration. See, Traffic Signals for Lymphocyte Recirculation and Leukocyte Emigration: The Multistep Paradigm; Springer, *Cell*, 76,301 (1994). Primarily a specific class of adhesion molecules mediates each of the phases of adhesion. Integrins are one of the specific classes and exist as heteromeric-cell surface proteins. Recent cell culture studies have shown that the expression of monocyte chemokines MCP-1, MIP-1 α, and RANTES increases the expression of the α chain of 2 members of the β2 family of integrins, CD11a and CD11b. CD11b (one of two subunits of the CD11b/CD18 (Mac-1, CR3 receptor) β2 integrin) is highly regulated and is expressed maximally in terminally differentiated myeloid cells. See, Corbi, A. J., *Biol. Chem*, 263, 12403 (1988). Additionally MCP-1 has been reported to selectively activate the β1 integrin family of leukocyte molecules, suggesting a role in leukocyte adhesion. See, Woldemar, et al., *Immunity*, 4, 179 (1996). Thus, in addition to acting as a chemoattractant, MCP-1 may further potentiate the inflammatory response by promoting integrin expression and cellular adhesion.

Chemoattractants appear to be required for the transendothelial migration both in vivo and in vitro and can induce many of the steps required for transmigration in vivo. MCP-1 is also abundantly expressed at the sites of inflammation, antigen challenge and autoimmune diseases and is an excellent candidate to inhibit tissue trafficking of monocytes during inflammation and autoimmune diseases. Therefore, compounds which inhibit the binding of MCP-1 to the chemokine CCR2 receptor (MCP-1 receptor antagonists) provide useful leads for drugs that will inhibit the action of MCP-1 on target cells.

PCT publications WO 97/44329; WO 99/25686; WO 00/07678; WO 99/07351; WO 99/09984; WO 00/31032; WO 00/35452; WO 99/32468; WO 00/69820; WO 00/69815; and WO 00/69848; WO 00/46195; WO 00/46196; WO 00/46197; WO 00/46198 and WO 00/46199 describe classes of cyclic amines and cyclic diamines which reportedly modulate chemokine receptor activity.

Homing and activation of eosinophils, basophils, and memory CD4+ Th2+ lymphocytes in lung tissues are considered important to the etiology of chronic airway inflammatory diseases. These cells most likely orchestrate asthmatic and allergic responses by secreting leukotrienes, histamine, and pro-inflammatory Th2 cytokines such as GM-CSF, IL-3, IL-4, IL-5 and IL-13. Further evidence for the role of Th2 cytokines comes from studies with atopic asthmatics where bronchial cytokine expression correlates with the patient's baseline FEV1, histamine $PC_{20}$, serum IgE levels, and disease severity. Studies in animal asthma models also support a causative role of eosinophils, basophils and Th2 cells in disease induction (see, Rothenberg, M. E., *Am. J. Respir. Cell Mol. Biol.*, 21, 291 (1999)).

Many chemokines have been shown to mediate the recruitment and activation of eosinophils, basophils and Th2+ cells, which express several chemokine receptors during different stages of cell differentiation and/or activation. For example, eotaxin, eotaxin 2, MCP-3, MCP-4, and RANTES, which are produced from human lung mast cells, epithelial cells and to macrophages as well as circulating leukocytes, activate eosinophils, basophils and Th-2 cells through binding to the cell surface receptor CCR3. See, Kitaura, M., et al., *J. Biol. Chem.*, 271, 7725 (1996) and Corrigan, C., *Current Opinion Invest. Drugs*, 1, 321 (2000). Although they differ in potency, they have a very similar range of biological actions. See, Griffiths, J. D. et al., *Biochem. Biophys. Res. Commun.*, 197, 1167 (1993); Jose, P. J. et al., *J. Exp. Med.*, 179, 881 (1994); and Rothenberg, M. E., *New England J. Med.*, 338. 1592 (1998). Eotaxin levels are elevated in induced sputum of atopic asthmatics compared with normal controls. See, Yamada, H. et al., *Allergy*, 54, 730 (1999). Nasal challenge of eotaxin causes airway eosinophil infiltration and activation, and produces clinically symptomatic inflammatory responses in humans. See, Hanazawa, T. et al., *J. Allergy Clin. Immunol.*, 105, 58 (1999). Animal model studies also demonstrate that the biological activity of eotaxin is involved in selective infiltration of eosinophils into lungs. In addition, the antibody against eotaxin and CCR3 partially reduces antigen-induced pulmonary eosinophilia in a guinea pig model of allergic asthma. See, Sabroe, I., et al., *J. Immunol.*, 161, 6139 (1998). Similar to the anti-eotaxin treatment, knockout of CCR3 shows reduced pulmonary infiltration of eosinophils in allergic mice. Hence, antagonists of CCR3 provide useful compound leads for the treatment of chronic inflammatory diseases such as allergy and asthma.

SUMMARY

The present invention provides a novel class of bicyclic amine compounds that act as antagonists of chemokine receptors, in particular CCR2 and CCR3 receptors. The bicyclic amine compounds of the present invention include the following compounds of Formula (I):

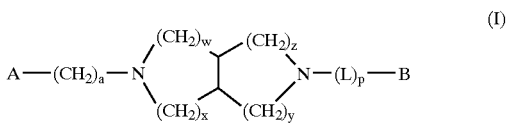

wherein

A is a substituted or unsubstituted ($C_1$–$C_6$)alkyl, substituted or unsubstituted ($C_2$–$C_6$)alkenyl, substituted or unsubstituted partially saturated or fully saturated ($C_3$–$C_6$) cycloalkyl, substituted or unsubstituted partially saturated or fully saturated 5 to 6 membered heterocyclic ring, substituted or unsubstituted aryl, or substituted or unsubstituted heteroaryl group;

a is 0, 1, 2 or 3;

w, x, y and z are each independently 0, 1, 2, 3 or 4, with the proviso that (i) x is not 0 when w is 0; (ii) y is not 0 when z is 0; (iii) x is not 0 when w is 1, y is 0 and z is 1; (iv) x is not 0 when w is 1, z is 0 and y is 1; (v) x is not 0 when y is 0; (vi) w is not 0 when z is 0; (vii) w+x is less than 8; and (viii) y+z is less than 8;

p is 0 or 1;

L is a linking group selected from the group consisting of —$(CH_2)_q$—X—, where X is NH, O, or oxo (i.e., keto) and q is an integer from 1 to 4,—$S(O)_r$—$(CH_2)_t$—NH—, where r is 0, 1 or 2 and t is an integer from 1 to 4, -(aryl)-NH— (i.e., The aryl group is attached to the nitrogen of the bicyclic diamine and the —NH— group is attached to B. The aryl group may also contain additional substituents on the aromatic ring.), -(heteroaryl)-NH— (i.e., The heteroaryl group is attached to the nitrogen of the bicyclic diamine and the —NH— group is attached to B. The heteroaryl group may also contain additional substituents on the heteroaromatic ring), and an amino acid residue where the amino nitrogen of the amino acid residue is attached to B and the carbonyl of said amino acid residue is attached to the ring nitrogen; and B is a substituted or unsubstituted ($C_1$–$C_6$)alkylcarbonyl, substituted or unsubstituted arylcarbonyl, substituted or unsubstituted ($C_1$–$C_6$)alkoxy-carbonyl, substituted or unsubstituted aryloxycarbonyl, substituted or unsubstituted ($C_1$–$C_6$)alkylsulfonyl, substituted or unsubstituted arylsulfonyl, substituted or unsubstituted ($C_1$–$C_6$) alkylthiocarbonyl, substituted or unsubstituted arylthiocarbonyl, substituted or unsubstituted ($C_1$–$C_6$)alkylcarbamoyl, substituted or unsubstituted arylcarbamoyl, substituted or unsubstituted ($C_1$–$C_6$)alkyl-C(=NH)—, substituted or unsubstituted aryl-C(=NH)—, or a protecting group (Pg);

a prodrug thereof, or a pharmaceutically acceptable salt, hydrate, or solvate of the compound or the prodrug.

An example of an amino acid residue is a unit having the following formula

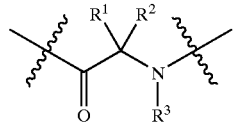

where the α-amino nitrogen of said amino acid residue is attached to B;

$R^1$ and $R^2$ are each independently hydrogen, substituted or unsubstituted ($C_1$–$C_6$)alkyl, substituted or unsubstituted ($C_2$–$C_6$)alkenyl, substituted or unsubstituted partially saturated or fully saturated ($C_3$–$C_6$)cycloalkyl, substituted or unsubstituted partially saturated or fully saturated 5 to 6 membered heterocyclic ring, substituted or unsubstituted aryl, or substituted or unsubstituted heteroaryl group; or $R^1$ or $R^2$ is taken together with $R^3$ to form a 5 to 6 membered ring; or $R^1$ and $R^2$ is taken together to form a 3 to 6 membered ring; and $R^3$ is hydrogen, taken together with a substituent of B forms a substituted or unsubstituted five or six membered partially saturated or fully saturated heterocyclic ring (e.g., pyrrolidine, pyrazole, imidazole, imidazoline, imidazolidine, morpholine, butyrolactam, valerolactam, piperidine, piperazine, imidazolidinone, phthalimide, and hydantoin), or taken together with $R^1$ or $R^2$ forms a 5 to 6 membered ring.

Preferred compounds of formula (I) are those where A is selected from ($C_1$–$C_6$)alkyl, ($C_2$–$C_6$)alkenyl, partially saturated or fully saturated ($C_3$–$C_6$)cycloalkyl, partially saturated or fully saturated 5 to 6 membered heterocyclic ring, aryl, or heteroaryl group, wherein each of these groups are unsubstituted or substituted with one or more groups (preferably 1, 2 or 3 groups) each independently selected from ($C_1$–$C_6$)alkyl, ($C_2$–$C_6$)alkenyl, aryl, heteroaryl, halo (e.g., chloro, bromo, iodo and fluoro), cyano, hydroxy, ($C_1$–$C_6$)alkoxy, aryloxy, sulfhydryl (mercapto), ($C_1$–$C_6$)alkylthio, arylthio, mono- and di-($C_1$–$C_6$)alkyl amino, quaternary ammonium salts, amino($C_1$–$C_6$)alkoxy, hydroxy($C_1$–$C_6$)alkylamino, amino($C_1$–$C_6$)alkylthio, cyanoamino, nitro, carbamyl, keto (oxy), carbonyl, carboxy, glycolyl, glycyl, hydrazino, guanyl, sulfamyl, sulfonyl, sulfinyl, thiocarbonyl, thiocarboxy, and combinations thereof; a is 1; w and x are 0, 1 or 2; z and y are 0 or 1; p is 1; and L is

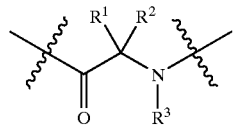

where $R^3$ is hydrogen and $R^1$ and $R^2$ are each indepedently selected from hydrogen and $C_1$–$C_6$ alkyl; and B is selected from ($C_1$–$C_6$)-alkylcarbonyl, arylcarbonyl, ($C_1$–$C_6$)alkoxycarbonyl, aryloxycarbonyl, ($C_1$–$C_6$)alkylsulfonyl, arylsulfonyl, ($C_1$–$C_6$) alkylthiocarbonyl, arylthiocarbonyl, ($C_1$–$C_6$)alkyl-carbamoyl, arylcarbamoyl, ($C_1$–$C_6$)alkyl-C(=NH)—, and aryl-C(=NH)—, wherein each of these groups are unsubstituted or substituted with one or more groups (preferably 1, 2, or 3 groups) each independently selected from ($C_1$–$C_6$)alkyl, ($C_2$–$C_6$)alkenyl, aryl, heteroaryl, halo (e.g., chloro, bromo, iodo and fluoro), cyano, hydroxy, ($C_1$–$C_6$)alkoxy, aryloxy, sulfhydryl (mercapto), ($C_1$–$C_6$)alkylthio, arylthio, mono- and di-($C_1$–$C_6$)alkyl amino, quaternary ammonium salts, amino ($C_1$–$C_6$)alkoxy, hydroxy($C_1$–$C_6$)alkylamino, amino($C_1$–$C_6$)alkylthio, cyanoamino, nitro, carbamyl, keto (oxy), carbonyl, carboxy, glycolyl, glycyl, hydrazino, guanyl, sulfamyl, sulfonyl, sulfinyl, thiocarbonyl, thiocarboxy, and combinations thereof.

More preferred compounds of formula (I) are those where A is selected from ($C_1$–$C_6$)alkyl, ($C_2$–$C_6$)alkenyl, partially saturated or fully saturated ($C_3$–$C_6$)cycloalkyl, partially saturated or fully saturated 5 to 6 membered heterocyclic ring, aryl, or heteroaryl group, wherein each of these groups are unsubstituted or substituted with one or more $R^{1a}$ groups (preferably 1, 2, or 3 $R^{1a}$ groups) each independently selected from hydrogen, halo, $C_1$–$C_6$ alkyl, $C_1$–$C_6$ alkoxy and aryl($C_1$–$C_6$)alkoxy (e.g., benzyloxy); a is 1; (i) w, x, z and y are 1,(ii) w is 2, x is 0, and z and y are 1, (iii) w is 0, x is 2, and z and y are 1, (iv) w, x and y are 1, and z is 0; or (v) w, x, and z are 1, and y is 0; p is 1; L is —(CH$_2$)$_q$—C(=O)—, where q is an integer from 1 to 4; and B is selected from ($C_1$–$C_6$) alkylcarbonyl, arylcarbonyl, ($C_1$–$C_6$) alkoxy-carbonyl, aryloxycarbonyl, ($C_1$–$C_6$)alkylsulfonyl, arylsulfonyl, ($C_1$–$C_6$) alkylthiocarbonyl, arylthiocarbonyl, ($C_1$–$C_6$)alkyl-carbamoyl, arylcarbamoyl, ($C_1$–$C_6$)alkyl-C(=NH)— and aryl-C(=NH)—, wherein each of these groups are unsubstituted or substituted with one or more $R^{1b}$ groups (preferably 1, 2, or 3 $R^{1b}$ groups) each independently selected from halo, $C_1$–$C_6$ alkyl, halo($C_1$–$C_6$)alkyl (e.g., trifluoromethyl), $C_1$–$C_6$ alkoxy, halo($C_1$–$C_6$)alkoxy (e.g., trifluoromethoxy, difluoromethoxy and the like), amino, amido (e.g., acetamido), nitro, aryloxy (e.g., phenoxy) and $C_1$–$C_6$ alkylthio (e.g., methylthio, ethylthio and the like).

Even more preferred are those compounds of formula (I) where A is aryl or heteroaryl, unsubstituted or substituted with one or more $R^{1a}$ groups (preferably, 1, 2, or 3 $R^{1a}$ groups) each independently selected from hydrogen, halo, $C_1$–$C_6$ alkyl, $C_1$–$C_6$ alkoxy and aryl($C_1$–$C_6$)alkoxy (e.g., benzyloxy); and B is selected from ($C_1$–$C_6$)alkylcarbonyl and arylcarbonyl, wherein each of these groups are unsubstituted or substituted with 1, 2, or 3 $R^{1b}$ groups each independently selected from halo, $C_1$–$C_6$ alkyl, halo($C_1$–$C_6$) alkyl (e.g., trifluoromethyl), $C_1$–$C_6$ alkoxy, halo($C_1$–$C_6$) alkoxy (e.g., trifluoromethoxy, difluoromethoxy and the like), amino, amido (e.g., acetamido), nitro, aryloxy (e.g., phenoxy) and $C_1$–$C_6$ alkylthio (e.g., methylthio, ethylthio, and the like).

Most preferred compounds of formula (I) are those compounds where A is phenyl, unsubstituted or substituted with 1, 2, or 3 $R^{1a}$ groups each independently selected from hydrogen, halo, $C_1$–$C_6$ alkyl, and $C_1$–$C_6$ alkoxy.

In a preferred embodiment of the present invention, compounds of Formula (IA) below are provided:

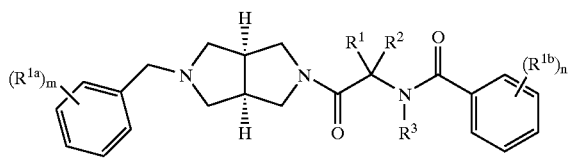

(IA)

wherein $R^{1a}$ for each occurance is independently hydrogen, halo, $C_1$–$C_6$ alkyl, $C_1$–$C_6$ alkoxy, aryl($C_1$–$C_6$)alkoxy (e.g., benzyloxy), or two adjacent $R^{1a}$ groups taken together form a substituted or unsubstitued carbocyclic, heterocyclic, aromatic or heteroaromatic 5 to 6 membered fused ring;

m is 0, 1, 2, 3, 4, or 5 (preferably 3 or less);

$R^1$ and $R^2$ are each independently hydrogen, $C_1$–$C_6$ alkyl, aryl($C_1$–$C_6$)-alkyl (e.g., benzyl), or $R^1$ and $R^2$ is taken together to form a 3 to 6 membered ring, or R¹ or R² is taken together with R³ to form a five- or six-membered ring;

R³ is hydrogen, taken together with R¹ᵇ forms a substituted or unsubstituted five or six membered partially saturated or fully saturated heterocyclic ring, or taken together with R¹ or R² form a five- or six-membered ring;

R¹ᵇ for each occurance is independently hydrogen, halo, $C_1$–$C_6$ alkyl, halo($C_1$–$C_6$)alkyl (e.g., trifluoromethyl), $C_1$–$C_6$ alkoxy, halo($C_1$–$C_6$)alkoxy (e.g., trifluoromethoxy, difluoromethoxy and the like), amino, amido (e.g., acetamido), nitro, aryloxy (e.g., phenoxy), $C_1$–$C_6$ alkylthio (e.g., methylthio, ethylthio and the like), taken together with R³ forms a substituted or unsubstituted five or six membered partially saturated or fully saturated heterocyclic ring, or two adjacent R¹ᵇ substituents taken together form a substituted or unsubstitued carbocyclic, heterocyclic, aromatic or heteroaromatic 5 to 6 membered fused ring; and n is 0, 1, 2, 3, 4 or 5 (preferably 3 or less);

a prodrug thereof, or a pharmaceutically acceptable salt, hydrate, or solvate of the compound or the prodrug.

Preferred compounds are those where R¹ᵃ is methyl or chloro; m is 2; R¹ is hydrogen; R² is hydrogen; R³ is hydrogen, R¹ᵇ is methyl, trifluoromethyl, amino, iodo, bromo, chloro or nitro; and n is 1 or 2; a prodrug thereof, or a pharmaceutically acceptable salt, hydrate, or solvate of the compound or the prodrug.

Also preferred are the following compounds:
N-{2-[5-(2,4-dimethyl-benzyl)-hexahydro-pyrrolo[3,4-c]pyrrol-2-yl]-2-oxo-ethyl}-3-trifluoromethyl-benzamide;
2-amino-N-{2-[5-(2,4-dimethyl-benzyl)-hexahydro-pyrrolo[3,4-c]pyrrol-2-yl]-2-oxo-ethyl}-5-nitro-benzamide;
2-amino-N-{2-[5-(2,4-dimethyl-benzyl)-hexahydro-pyrrolo[3,4-c]pyrrol-2-yl]-2-oxo-ethyl}-5-iodo-benzamide;
2-amino-5-bromo-N-{2-[5-(2,4-dimethyl-benzyl)-hexahydro-pyrrolo[3,4-c]pyrrol-2-yl]-2-oxo-ethyl}-benzamide;
3-bromo-4-chloro-N-{2-[5-(2,4-dimethyl-benzyl)-hexahydro-pyrrolo[3,4-c]pyrrol-2-yl]-2-oxo-ethyl}-benzamide;
3,4-dichloro-N-{2-[5-(2,4-dimethyl-benzyl)-hexahydro-pyrrolo[3,4-c]pyrrol-2-yl]-2-oxo-ethyl}-benzamide;
3-chloro-N-{2-[5-(2,4-dichloro-benzyl)-hexahydro-pyrrolo[3,4-c]pyrrol-2-yl]-2-oxo-ethyl}-4-fluoro-benzamide;
3,4-dichloro-N-{2-[5-(2,4-dichloro-benzyl)-hexahydro-pyrrolo[3,4-c]pyrrol-2-yl]-2-oxo-ethyl}-benzamide;
3-bromo-4-chloro-N-{2-[5-(2,4-dichloro-benzyl)-hexahydro-pyrrolo[3,4-c]pyrrol-2-yl]-2-oxo-ethyl}-benzamide;
3-bromo-N-{2-[5-(2,4-dichloro-benzyl)-hexahydro-pyrrolo[3,4-c]pyrrol-2-yl]-2-oxo-ethyl}-benzamide; and
3-chloro-N-{2-[5-(2,4-dichloro-benzyl)-hexahydro-pyrrolo[3,4-c]pyrrol-2-yl]-2-oxo-ethyl}-benzamide;
a prodrug thereof, or a pharmaceutically acceptable salt, hydrate or solvate of the compound or the prodrug.

Each of the compounds described herein contain at least one chiral center; consequently, those skilled in the art will appreciate that all enantiomers and/or diasteroisomers of the compounds disclosed and discussed herein are within the scope of the present invention. However, when the bicyclic rings are 4- or 5-membered rings, then the fused rings are preferably in the cis configuration.

Compounds of Formula I above are useful chemokine receptor antagonists; therefore, another embodiment of the present invention is a pharmaceutical composition containing a therapeutically effective amount of a compound of Formula I (including prodrugs thereof, and pharmaceutically acceptable salts, hydrates, and/or solvates of the compounds or the prodrugs) and a pharmaceutically acceptable excipient, diluent or carrier.

In yet another embodiment of the present invention, a method for treating or preventing diseases associated with monocyte and/or lymphocyte accumulation is provided which comprises administering a therapeutically effective amount of a compound of the present invention (or a pharmaceutical composition containing a therapeutically effective amount of a compound of the present invention) to an animal in need thereof. The method is useful for treating or preventing diseases such as atherosclerosis, restenosis, gingivitis, psoriasis, rheumatoid arthritis, glomerulonephritis, wound healing, Crohn's disease, encephalomyelitis and transplant rejection in animals, in particular mammals including humans. Accordingly, the compounds of the present invention may be used in the manufacture of a medicament for the treatment or prevention of diseases associated with monocyte and/or lymphocyte accumulation.

In a preferred embodiment, a compound of Formula (1B)

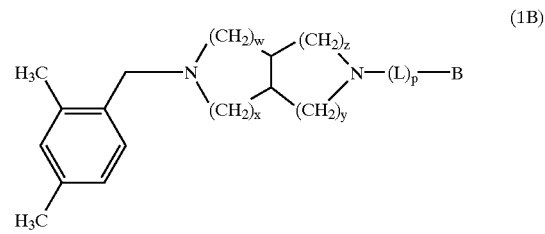

(1B)

where x, y, z, w, L, p and B have the same meaning as described above for compounds of Formula (I) (including prodrugs thereof and pharmaceutically acceptable salts, hydrates and solvates of the compounds and the prodrugs) is administered to an animal in need of treatment.

Preferred compounds for inhibition of binding to CCR2 receptors include the following:
N-{2-[5-(2,4-dimethyl-benzyl)-hexahydro-pyrrolo[3,4-c]pyrrol-2-yl]-2-oxo-ethyl}-3-trifluoromethyl-benzamide;
2-amino-N-{2-[5-(2,4-dimethyl-benzyl)-hexahydro-pyrrolo[3,4-c]pyrrol-2-yl]-2-oxo-ethyl}-5-nitro-benzamide
2-amino-N-{2-[5-(2,4-dimethyl-benzyl)-hexahydro-pyrrolo[3,4-c]pyrrol-2-yl]-2-oxo-ethyl}-5-iodo-benzamide;
2-amino-5-bromo-N-{2-[5-(2,4-dimethyl-benzyl)-hexahydro-pyrrolo[3,4-c]pyrrol-2-yl]-2-oxo-ethyl}-benzamide;
3,4-dichloro-N-{2-[5-(2,4-dimethyl-benzyl)-hexahydro-pyrrolo[3,4-c]pyrrol-2-yl]-2-oxo-ethyl}-benzamide; and
3-bromo-4-chloro-N-{2-[5-(2,4-dimethyl-benzyl)-hexahydro-pyrrolo[3,4-c]pyrrol-2-yl]-2-oxo-ethyl}-benzamide;
a prodrug thereof, or a pharmaceutically acceptable salt, hydrate or solvate of the compound or the prodrug.

In yet another aspect of the present invention, a pharmaceutical kit for use by a consumer having or at risk of having a disease or condition such as atherosclerosis, restenosis, gingivitis, psoriasis, rheumatoid arthritis, glomerulonephritis, wound healing, Crohn's disease, encephalomyelitis and transplant rejection in animals, is provided. The kit comprises a) a suitable dosage form comprising a compound of Formula I, a prodrug thereof, or a pharmaceutically acceptable salt, hydrate or solvate of the compound or the prodrug; and b) instructions describing a method of using the dosage form to treat or prevent diseases associated with monocyte and/or lymphocyte accumulation.

Compounds of the present invention are also useful as antagonists of eotaxin 2, MCP-3, MCP-4, and RANTES binding to the CCR3 receptor; therefore, another embodiment of the present invention is a method for treating or preventing diseases associated with leucocyte accumulation is provided which entails administering a therapeutically effective amount of a compound of the present invention (or a pharmaceutical composition described above) to an animal in need thereof. The method is useful for treating or preventing chronic inflammatory diseases such as allergy and asthma, including but not limited to allergic rhinitis, eczema and atopic dermatitis in animals (preferably humans). Accordingly, the compounds of the present invention may be used in the manufacture of a medicament for the treatment or prevention of diseases associated with leucocyte accumulation.

In a preferred embodiment, a compound of Formula (1C)

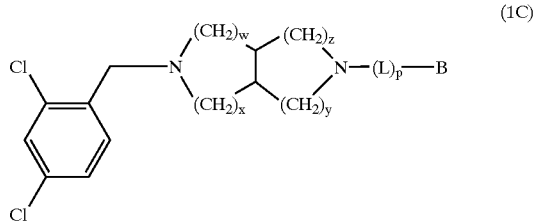

(1C)

where x, y, z, w, L, p and B have the same meaning as described above for compounds of Formula (I) (including prodrugs thereof and pharmaceutically acceptable salts, hydrates and solvates of the compounds and the prodrugs) is administered to an animal in need of such treatment.

Preferred compounds for inhibition of binding to CCR3 receptors include the following:

3,4-dichloro-N-{2-[5-(2,4-dichloro-benzyl)-hexahydro-pyrrolo[3,4-c]pyrrol-2-yl]-2-oxo-ethyl}-benzamide;

3-bromo-4-chloro-N-{2-[5-(2,4-dichloro-benzyl)-hexahydro-pyrrolo[3,4-c]pyrrol-2-yl]-2-oxo-ethyl)-benzamide;

3-bromo-N-{2-[5-(2,4-dichloro-benzyl)-hexahydro-pyrrolo[3,4-c]pyrrol-2-yl]-2-oxo-ethyl}-benzamide;

3-chloro-N-(2-[5-(2,4-dichloro-benzyl)-hexahydro-pyrrolo[3,4-c]pyrrol-2-yl]-2-oxo-ethyl)-benzamide; and 3-chloro-N-{2-[5-(2,4-dichloro-benzyl)-hexahydro-pyrrolo[3,4-c]pyrrol-2-yl]-2-oxo-ethyl}-4-fluoro-benzamide; a prodrug thereof, or a pharmaceutically acceptable salt, hydrate or solvate of the compound or prodrug.

In yet another aspect of the present invention, a pharmaceutical kit for use by a consumer having or at risk of having a disease or condition resulting from a chronic inflammatory diseases such as allergy and asthma is provided. The kit comprises a) a suitable dosage form comprising a compound of Formula I, a prodrug thereof, or a pharmaceutically acceptable salt, hydrate or solvate of the compound or the prodrug; and b) instructions describing a method of using the dosage form to treat or prevent diseases associated with leucocyte accumulation.

The compounds of the present invention may also be used in conjunction with at least one other pharmaceutical agent for the treatment or prevention of diseases/conditions described herein. Suitable pharmaceutical agents that may be used in combination with the compounds of the present invention include nutraceuticals, cholesterol absorption inhibitors, HMG-CoA reductase inhibitors, MTP/Apo B secretion inhibitors, HMG-CoA synthase inhibitors, HMG-CoA reductase transcription inhibitors, HMG-CoA reductase translation inhibitors, CETP inhibitors, squalene synthetase inhibitors, squalene epoxidase inhibitors, squalene cyclase inhibitors, combined squalene epoxidase/squalene cyclase inhibitors, ACAT inhibitors, lipase inhibitors (including pancreatic lipase inhibitors and gastric lipase inhibitors), peroxisome proliferator-activated receptor (PPAR) agonists, nonsteroidal anti-inflammatory drugs (NSAIDS) and cyclooxygenase enzyme inhibitors (COX-2 inhibitors). Therefore, a method is provided for treating or preventing a disease associated with monocyte accumulation, lymphocyte accumulation or leucocyte accumulation which comprising administering to a mammal in need of such treatment a compound of the present invention and at least one of the pharmaceutical agents described above.

The combination therapy may be administered as (a) a single pharmaceutical composition which comprises a compound of the present invention, at least one of the pharmaceutical agents described above and a pharmaceutically acceptable excipient, diluent, carrier or mixtures thereof; or (b) two separate pharmaceutical compositions comprising (i) a first composition comprising a compound of the present invention and a pharmaceutically acceptable excipient, diluent, carrier or mixtures thereof, and (ii) a second composition comprising at least one of the pharmaceutical agents described above and a pharmaceutically acceptable excipient, diluent, carrier or mixtures thereof. The pharmaceutical compositions may be administered simultaneously or sequentially and in any order.

In yet another embodiment of the present invention is a pharmaceutical kit comprising: a) a compound of the present invention, and a pharmaceutically acceptable carrier, excipient or diluent in a first unit dosage form; b) a pharmaceutical agent selected from the group consisting of a nutraceutical, a cholesterol absorption inhibitor, a HMG-CoA reductase inhibitor, a MTP/Apo B secretion inhibitor, a HMG-CoA synthase inhibitor, a HMG-CoA reductase transcription inhibitor, a HMG-CoA reductase translation inhibitor, a CETP inhibitor, a squalene synthetase inhibitor, a squalene epoxidase inhibitor, a squalene cyclase inhibitor, an ACAT inhibitor, a lipase inhibitor. a peroxisome proliferator-activated receptor agonist, a nonsteroidal anti-inflammatory drug and a COX-2 inhibitor, and a pharmaceutically acceptable carrier, excipient or diluent in a second unit dosage form; and c) a container.

Definitions

As used herein, the term "alkyl" refers to a hydrocarbon radical of the general formula $C_nH_{2n+1}$. The alkane radical may be straight or branched. For example, the term "$(C_1-C_6)$alkyl" refers to a monovalent, straight, branched, or cyclic aliphatic group containing 1 to 6 carbon atoms (e.g., methyl, ethyl, n-propyl, i-propyl, n-butyl, i-butyl, s-butyl, t-butyl, n-pentyl, 1-methylbutyl, 2-methylbutyl, 3-methylbutyl, neopentyl, 3,3-dimethylpropyl, hexyl, 2-methylpentyl, and the like). The alkane radical may be unsubstituted or substituted with one or more substituents defined below. For example, a "haloalkyl" refers to an alkyl group substituted with one or more halogen atoms (e.g., fluoromethyl, difluoromethyl, trifluoromethyl, perfluoroethyl, and the like). Similarly, the alkyl portion of an alkoxy, alkylamino, dialkylamino, or alkylthio group have the same definition as above.

The term "partially saturated or fully saturated cycloalkyl" or "partially saturated or fully saturated heterocyclic ring" refers to nonaromatic rings that are either partially or fully hydrogenated. For example, partially or fully saturated cycloalkyl includes groups such as cyclopropyl, cyclopropenyl, cyclobutyl, cyclobutenyl, cyclopentyl, cyclpentenyl, cyclopentadienyl, cyclohexyl, cyclohexenyl, cyclohexadienyl, and the like. Partially saturated or fully saturated heterocyclic rings include groups such as dihydropyridinyl, pyrrolidinyl, (2-, 3- or 4)-N-methylpyrrolidinyl, piperidinyl, piperazinyl, pyrazolidyl, imidazolyl, imidazolidyl, 2H-pyranyl, 4H-pyranyl, 2H-chromenyl, morpholino, thiomorpholino, tetrahydrothienyl, and the like.

The term "alkenyl" refers to a hydrocarbon containing at least one carbon-carbon double bond. As described above for alkyl, the alkene radical may be straight or branched and the alkene radical may be unsubstituted or substituted with one or more substituents defined below.

The term "aryl" refers to aromatic moieties having single (e.g., phenyl) or fused ring system containing 6 to 14 carbon atoms (e.g., naphthalene, anthracene, phenanthrene, etc.). The aryl groups may be unsubstituted or substituted with one or more substituents (preferably no more than three substituents) defined below. Substituted aryl groups include a chain of aromatic moieties (e.g., biphenyl, terphenyl, phenylnaphthalyl, etc.) The term "heteroaryl" refers to aromatic moieties containing at least one heteroatom (preferably, 1, 2, 3 or 4 heteratoms, more preferably 1 or 2 heteroatoms) within the aromatic ring system which may be the same or different (e.g., pyrrole, pyridine, indole, thiophene, furan, benzofuran, imidazole, pyrimidine, purine, benzimidazole, quinoline, etc.). The heteroatoms in the ring system are generally selected from oxygen, sulfur, nitrogen or combinations thereof. The aromatic moiety may consist of a single or fused ring system containing 5 to 14 members. The heteroaryl groups may be unsubstituted or substituted with one or more substituents (preferably no more than three substituents) defined below.

The term "amino acid residue" refers to a structural unit of a natural, modified or unusual amino acid (as defined herein) remaining after the loss of a hydroxy group from the carboxylic acid group and the loss of a hydrogen from the amino group. For example, a residue of valine would have the following structure;

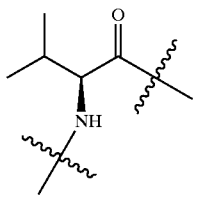

The term "substituted" specifically envisions and allows for substitutions which are common in the art. However, it is generally understood by those skilled in the art that the substituents should be selected so as to not adversely affect the pharmacological characteristics of the compound or adversely interfere with the use of the medicament. Suitable substituents for any of the groups defined above include alkyl, alkenyl, aryl, heteroaryl, halo (e.g., chloro, bromo, iodo and fluoro), cyano, hydroxy, alkoxy, aryloxy, sulfhydryl (mercapto), alkylthio, arylthio, mono- and di-alkyl amino, quaternary ammonium salts, aminoalkoxy, hydroxyalkylamino, aminoalkylthio, cyanoamino, nitro, carbamyl, keto (oxy), carbonyl, carboxy, glycolyl, glycyl, hydrazino, guanyl, sulfamyl, sulfonyl, sulfinyl, thiocarbonyl, thiocarboxy, and combinations thereof.

The term "protecting group" or "Pg" refers to a substitutent that is commonly employed to block or protect a particular functionality while reacting other functional groups on the compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBz) and 9-fluorenylmethylenoxycarbonyl (Fmoc). Similarly, a "hydroxy-protecting group" refers to a substituent of a hydroxy group that blocks or protects the hydroxy functionality. Suitable hydroxy-protecting groups include acetyl and silyl. A "carboxy-protecting group" refers to a substituent of the carboxy group that blocks or protects the carboxy functionality. Common carboxy-protecting groups include —CH$_2$CH$_2$SO$_2$Ph, cyanoethyl, 2-(trimethylsilyl) ethyl, 2-(trimethylsilyl)ethoxymethyl, 2-(p-toluenesulfonyl) ethyl, 2-(p-nitrophenylsulfenyl)ethyl, 2-(diphenylphosphino)ethyl, nitroethyl and the like. For a general description of protecting groups and their use, see T. W. Greene, *Protective Groups in Organic Synthesis*, John Wiley & Sons, New York, 1991.

The term "solvate" refers to a molecular complex of a compound represented by Formula I (including prodrugs and pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The phrase "therapeutically effective amount" means an amount of a compound of the present invention that attenuates, ameliorates, or eliminates one or more symptoms of a particular disease, condition, or disorder, or prevents or delays the onset of one or more symptoms of a particular disease, condition, or disorder.

The phrase "pharmaceutically acceptable" indicates that the substance or composition must be compatible chemically and/or toxicologically, with the other ingredients comprising a formulation, and/or the animal being treated therewith.

The term "animal" refers to humans, companion animals (e.g., dogs, cats and horses), food-source animals (e.g., cows, pigs, sheep and poultry), zoo animals, marine animals, birds and other similar animal species.

The term "compounds of the present invention" refers to compounds of Formula (I), prodrugs thereof, and pharmaceutically acceptable salts, hydrates and/or solvates of the compounds and/or prodrugs, as well as, all stereoisomers (including diastereomers (except trans configurations of four and five members fused rings that are unstable) and enantiomers), tautomers and isotopically labelled compounds.

DETAILED DESCRIPTION

In general, the compounds of the present invention can be made by synthetic routes that include processes analogous to those known in the chemical arts, particularly in light of the description contained herein.

For illustrative purposes, the reaction schemes depicted below provide potential routes for synthesizing the inventive compounds. Although Scheme I illustrates attaching the "A" group first and then the "B" group, those skilled in the art will appreciate that "A" and "B" can be attached in reverse order using the same general chemical procedures described herein. For a more detailed description of the individual reaction steps, see the Examples section. Those skilled in the art will appreciate that other synthetic routes may be used to synthesize the inventive compounds. Although specific starting materials are depicted in the schemes below, other starting materials can be easily substituted. For example, bicyclic diamine compounds having different ring sizes, configurations, and combination of ring sizes may be used instead of the mono amino-protected hexahydropyrrolo[3,4-c]pyrrole I(a) shown in Schemes I and II. Preparations of bicyclic diamines having different ring configurations is illustrated in the Examples.

Scheme I illustrates the preparation of compounds of Formula I where "A" is attached to the bicyclic diamine by means of a reductive alkylation process and "B" is attached directly to the bicyclic diamine system (i.e., p=0) by means of an amine coupling reaction.

2-aminobenzaldehyde, 3-aminobenzaldehyde, 4-aminobenzaldehyde), 2-naphthalenecarboxyaldehyde, and 6-methoxy-2-naphthalene-carboxyaldehyde), unsubstituted or substituted alkyl-aldehydes (e.g., (e.g., α-phenyl-acetaldehyde, 2-phenylpropionaldehyde, and 3-phenylbutyraldehyde,), unsubstituted or substituted alkenyl-aldehydes (e.g., cinnamaldehyde, α-methyl-trans-cinnamaldehyde, and 2,2-dimethyl-4-pentenal), substituted or unsubstituted partially saturated or fully saturated cycloalkyl-aldehydes (e.g., cyclopropane-carboxaldehyde, cyclobutane-carboxaldehyde, cyclopentane-carboxaldehyde, and cyclohexane-carboxaldehyde), substituted or unsubstituted partially saturated or fully saturated 5 to 6 membered heterocyclic aldehydes, and substituted or

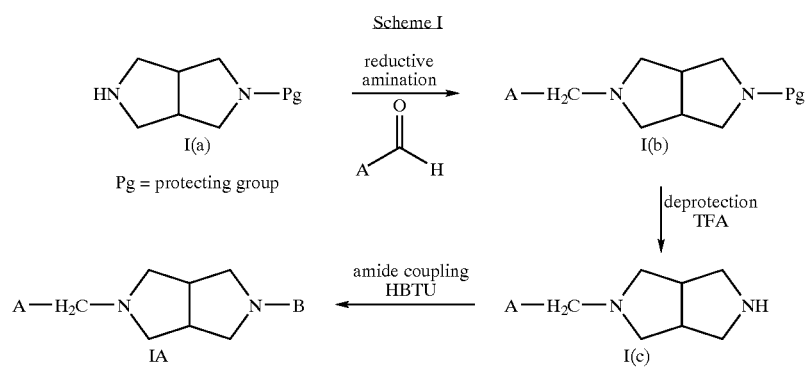

Scheme I

Pg = protecting group

In the preparation of compounds of Formula I, protection of remote functionality (e.g., primary amine, secondary amine) of intermediates may be necessary. The need for such protection will vary depending on the nature of the remote functionality and the conditions of the preparation methods.

Suitable amino-protecting groups include acetyl, trifluoroacetyl, t-butoxycarbonyl (BOC), benzyloxycarbonyl (CBz) and 9-fluorenylmethylenoxycarbonyl (Fmoc). The need for such protection is readily determined by one skilled in the art. For a general description of protecting groups and their use, see T. W. Greene, *Protective Groups in Organic Synthesis*, John Wiley & Sons, New York, 1991.

Intermediate I(b) is prepared by reacting the mono amino-protected hexahydropyrrolo[3,4-c]pyrrole I(a) with the desired aldehyde or ketone containing the functional group "A." For example, when "A" is a 2,4-dimethyl phenyl group, then one would react I(a) with 2,4-dimethyl benzaldehdye. Suitable aldehydes that may be used include unsubstituted or substituted aryl-aldehydes (e.g., benzaldehyde, 2-methylbenzaldehyde, 3-methylbenzaldehyde, 4-methylbenzaldehyde, 2,4-difluorobenzaldehyde, 2,3-difluorobenzaldehyde, 3,5-difluorobenzaldehyde, 2,5-difluorobenzaldehyde, 2-chloro-benzaldehdye, 3-chloro-benzaldehyde, 4-chloro-benzaldehyde, 2-chloro-6-fluorobenzaldehyde, 3,4-dichlorobenzaldehyde, 2,4-dichlorobenzaldehyde 2-chloro-6-fluorobenzaldehyde, 2,3-dimethoxybenzaldehyde, 2,4-dimethoxybenzaldehyde, 2,3-dimethylbenzaldehyde, 2,6-dimethoxybenzaldehyde, 2,4-dimethylbenzaldehyde, 2,5-dimethyl-4-methoxybenzaldehyde, 2-chloro-3,4-dimethoxybenzaldehyde, 2-benzyloxybenzaldehyde, 2-trifluoromethylbenzaldehyde, 4-trifluoromethylbenzaldehyde, 2-hydroxybenzaldehyde, 3-hydroxybenzaldehyde, 4-hydroxybenzaldehyde, unsubstituted heteroaryl-aldehydes (e.g., indole-5-carboxaldehyde, pyrrole-2-carbox-aldehyde, 2-pyridinecarbox-aldehyde, 3-pyridinecarbox-aldehyde, 4-pyridinecarbox-aldehyde, 2-furaldehyde, 3-furaldehyde, 2-thiophenecarbox-aldehyde, 3-thiophenecarbox-aldehyde, 2-quinolinecarbox-aldehyde, 3-quinolinecarbox-aldehyde, and 4-quinolinecarbox-aldehyde). Generally, reductive amination reactions convert an aldehyde or ketone into a Schiff base by reaction with amine intermediate I(a) in a polar solvent at a temperature from about 10° C. to about 40° C. for about 2 to about 24 hours. Typically, an equivalent or a slight excess (i.e., 1.1 equivalents) amount of the aldehyde or ketone is added to the amine. Suitable polar solvents include methylene chloride, 1,2-dichloroethane, dimethylsulfoxide, dimethylformamide, alcohols (e.g., methanol or ethanol), or mixtures thereof. A preferred solvent is methanol. In the same reaction vessel, the imine is then reduced to the tertiary amine in the presence of a reducing agent at a temperature from about 0° C. to about 10° C. and then warmed to a temperature from about 20° C. to about 40° C. for about 30 minutes to about 2 hours. Suitable reducing agents include pyridine.borane complex and metal borohydrides, such as sodium borohydride, sodium triacetoxy borohydride and sodium cyanoborohydride.

In general, intermediate I(b) is deprotected by treating with an anhydrous acid (e.g., trifluoroactetic acid) in an aprotic solvent (e.g., methylene chloride) at a temperature from about 10° C. to about 40° C. for about So 20 minutes to about 12 hours. Compound IA is then produced by combining the appropriate coupling agent (e.g., carboxylic acid, acid chloride, acid anhydride, sulfonyl chloride, isocyanates, etc.) containing "B" with the deprotected amine I(c). When a carboxylic acid is used as the coupler, the reaction is generally accomplished in the presence of o-benzotriazol-1-yl-N,N,N',N'-tetramethyl-uronium-hexafluorophosphate (HBTU) at a temperature of about 60° C. For a more detailed description of the reaction conditions see Example 1 in the Examples section. Suitable carboxylic acids include unsubstituted and substituted aromatic or alkanoic acids, such as benzoic acid, 2-fluorobenzoic acid, 3-fluorobenzoic acid, 4-fluorobenzoic acid, 2-trifluoromethylbenzoic acid, 3-trifluoromethylbenzoic acid, 4-trifluoromethylbenzoic acid, 2-fluoro-3-trifluoromethylbenzoic acid, 2-fluoro-4-trifluoromethylbenzoic acid, 2-fluoro-5-trifluoromethylbenoic acid, 2-fluoro-6-trifluoromethylbenzoic acid, 3-fluoro-4-trifluoromethylbenzoic acid, 3-fluoro-5-trifluoromethylbenzoic acid, 4-fluoro-2-trifluoromethylbenzoic acid, 5-fluoro-2-methylbenzoic acid, 2,4-bis-trifluoromethylbenzoic acid, 2,5-bis-trifluoromethylbenzoic acid, 3,5-bis-trifluoromethylbenzoic acid, 2,3-difluorobenzoic acid, 2,4-difluorobenzoic acid, 2,5-difluorobenzoic acid, 2,6-difluorobenzoic acid, 3,4-difluorobenzoic acid, 3,5-difluorobenzoic acid, 2,3,4-trifluorobenzoic acid, 2,3,6-trifluorobenzoic acid, 2,4,5-trifluorobenzoic acid, 2,4,6-trifluorobenzoic acid, 3,4,5-trifluorobenzoic acid, 2-difluoromethoxybenzoic acid, 2-trifluoromethyoxybenzoic acid, 4-trifluoromethoxybenzoic acid, 3-fluoro-4-methylbenzoic acid, 2-chloro-4-fluorobenzoic acid, 2-chloro-6-fluorobenzoic acid, 3-chloro-2-fluorobenzoic acid, 3-chloro-4-fluorobenzoic acid, 4-chloro-2-fluorobenzoic acid, 2-chloro-4,5-difluorobenzoic acid, 2-chloro-3-trifluoromethylbenzoic acid, 3-chloro-2,6-dimethoxybenzoic acid, 2-chlorobenzoic acid, 3-chlorobenzoic acid, 4-chlorobenzoic acid, 2,3-dichlorobenzoic acid, 2,4-dichlorobenzoic acid, 2,5-dichlorobenzoic acid, 2,6-dichlorobenzoic acid, 3,4-dichlorobenzoic acid, 3-chloro-2,6-dimethoxybenzoic acid, 2-chloro-3,4-dimethoxybenzoic acid, 5-chloro-2-methylbenzoic acid, 2-bromobenzoic acid, 3-bromobenzoic acid, 4-bromobenzoic acid, 2-bromo-4-chlorobenzoic acid, 2-bromo-5-chlorobenzoic acid, 3-bromo-4-chlorobenzoic acid, 3-bromo-2-fluorobenzoic acid, 4-bromo-2-chlorobenzoic acid, 5-bromo-2-chlorobenzoic acid, 3-bromo-4-methylbenzoic acid, 2-bromo-5-methoxybenzoic acid, 2-bromo-3-methylbenzoic acid, 2-bromo-5-methylbenzoic acid, 3-bromo-2-methylbenzoic acid, 3-bromo-4-methylbenzoic acid, 4-bromo-2-methylbenzoic acid, 4-bromo-3-methylbenzoic acid, 2-methylbenzoic acid, 3-methylbenzoic acid, 4-methylbenzoic acid, 4-isopropylbenzoic acid, 4-n-butylbenzoic acid, 4-tert-butylbenzoic acid, 2,5-dimethylbenzoic acid, 2,6-dimethylbenzoic acid, 3,4-dimethylbenzoic acid, 2-methoxybenzoic acid, 2-ethoxybenzoic acid, 4-propoxybenzoic acid, 2,4-dimethoxybenzoic acid, 2,6-dimethoxybenzoic acid, 2,3,6-trimethoxybenzoic acid, 2-amino-5-iodobenzoic acid, 2-amino-5-bromobenzoic acid, 2-amino-5-chlorobenzoic acid, 2-amino-5-fluorobenzoic acid, 2-amino-5-nitrobenzoic acid, 2-amino-3-trifluoromethylbenzoic acid, 2-amino-3,5-dibromobenzoic acid, 2-acetoamino-5-bromobenzoic acid, 2-methyl-5-nitrobenzoic acid, 2-nitrobenzoic acid, 3-nitrobenzoic acid, 5-chloro-2-nitrobenzoic acid, 3-nitro-5-trifluoromethylbenzoic acid, 2-phenoxybenzoic acid, naphthalene-2-carboxylic acid, 3-methylsulfanylbenzoic acid, 4-ethylsulfanylbenzoic acid, 1H-pyrrole-2-carboxylic acid, 1H-3-pyrrole-carboxylic acid, furan-2-carboxylic acid, furan-3-carboxylic acid, thiophene-2-carboxylic acid, thiophene 3-carboxylic acid, pyridine-2-carboxylic acid, pyridine-3-carboxylic acid, pyridine-4-carboxylic acid, acetic acid, propionic acid, butanoic acid, isobutyric acid, 3-methyl-butyric acid, pentanoic, hexanoic acid, and phenyl acetic acid. Suitable acid anhydrides include phthalic anhydride.

Alternatively, the intermediate compound (Ic) may be acylated with the appropriate acyl chloride or the appropriate sulfonyl chloride in a reaction-inert solvent such as methylene chloride in the presence of an amine base such as triethylamine at a temperature of about 10° C. to about 50° C., typically ambient for about 6 to about 18 hours. Another alternative method for attaching B is by reacting intermediate (Ic) with the appropriate isocyanate in a reaction-inert solvent such as toluene in the presence of a tertiary amine base such as Hunig's base at a temperature of about 10° C. to about 150° C., typically ambient for about 6 to about 18 hours; or with the appropriate carboxylic acid in a reaction-inert solvent such as methylene chloride in the presence of a carbodiimide (e.g., 1-(3-dimethylaminopropyl)-3-ethylcarbodiimide hydrochloride) at a temperature of about 10° C. to about 50° C., typically ambient for about 6 to about 24 hours. Suitable sulfonyl chlorides include benzenesulfonyl chloride, 4-methyl-benzenesulfonyl chloride, methanesulfonyl chloride, ethanesulfonyl chloride, and propanesulfonyl chloride. Suitable acid chlorides include the acid chloride derivatives of the carboxylic acids listed earlier. Conversion of a carboxylic acid to its corresponding acid chloride is well know to those skilled in the art. Generally, the carboxylic acid may be converted by reacting with a suitable chlorinating agent such as thionyl chloride or oxalyl chloride. Suitable isocyanates include phenyl isocyanate, 2-naphthyl isocyanate, o-tolyl isocyanate, 2-ethoxyphenyl isocyanate, m-tolyl isocyanate, p-tolyl isocyanate, 4-biphenyl isocyanate, o-nitrophenyl isocyanate, 4-nitrophenyl isocyanate, m-chlorophenyl isocyanate, m-nitrophenyl isocyanate, p-bromophenyl isocyanate, 3,4-dichlorophenyl isocyanate, 3-bromophenylisocyanate, 2,5-dichlorophenyl isocyanate, p-ethoxyphenyl isocyanate, 1-naphthyl isocyanate, p-chlorophenyl isocyanate, o-chlorophenyl isocyanate, o-methoxyphenyl isocyanate, 4-methoxyphenyl isocyanate, 2,4-dimethoxyphenyl isocyanate, 5-chloro-2,4-dimethoxyphenyl isocyanate, o-fluorophenyl isocyanate, p-fluorophenyl isocyanate, 3-(trifluoromethyl)phenyl isocyanate, 4-iodophenyl isocyanate, 4-n-butylphenyl isocyanate, 4-chloro-2-methoxyphenyl isocyanate, 2-isopropylphenyl isocyanate, 2-methoxycarbonylphenyl isocyanate, 4-phenoxyphenyl isocyanate, 2-ethyl-6-methylphenyl isocyanate, 2,6-diethylphenyl isocyanate, 3,5-dimethoxyphenyl isocyanate, 3,4,5-trimethoxyphenyl isocyanate, 2,4-dichlorophenyl isocyanate, 2,4-difluorophenyl isocynanate, 4-butoxyphenyl isocyanate, 3-fluorophenyl isocyanate, 4-ethylphenyl isocyanate, 3,4-dimethylphenyl isocyanate, 2,4dimethylphenyl isocyanate, 2,3 dichlorophenyl isocyanate, 2,4,5-trimethylphenyl isocyanate, 2,6-difluoro-2-nitrophenyl isocyanate, 2,5-difluorophenyl isocyanate, alpha, alpha, alpha-trifluoro-otolyl-isocyanate, and 3,5-bis(trifluoromethyl)phenyl isocyanate.

Group B may also be attached by means of a linking group (L). Scheme II illustrates the preparation of compounds of Formula I where B is attached to the bicyclic diamine by means of an amino acid linking group (L).

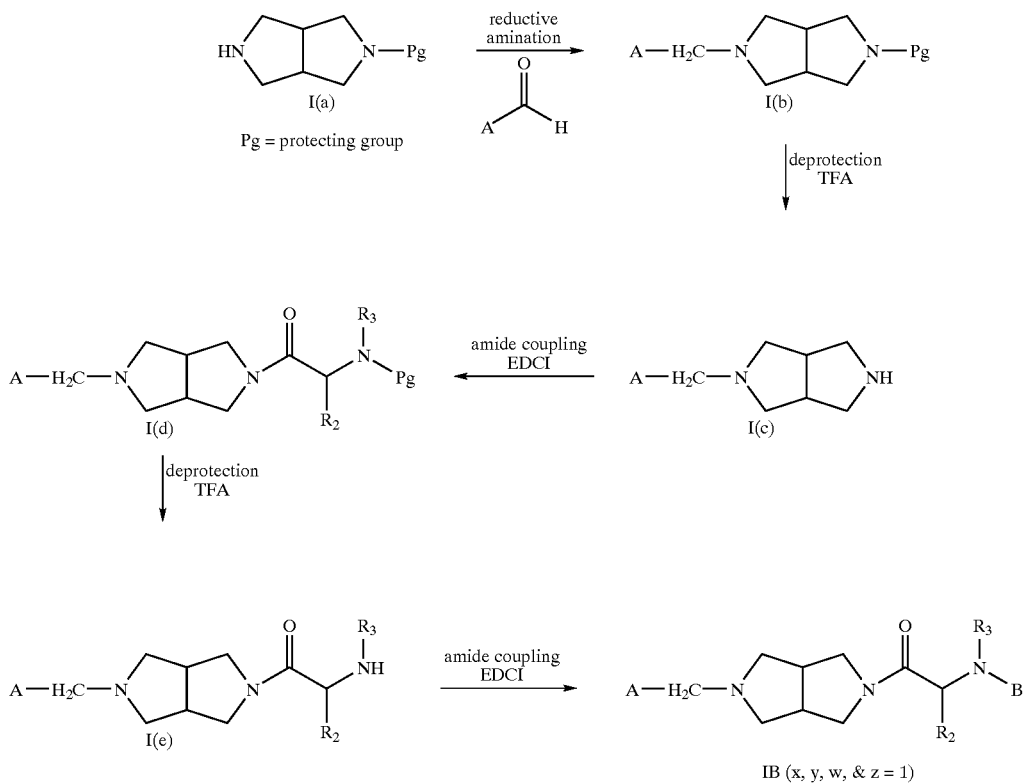

Scheme II

The same procedures as described above in Scheme I may be used to produce intermediate I(c). The deprotected amine I(c) is then coupled with the desired amino-protected amino acid linking group to obtain intermediate I(d). The coupling reaction is generally accomplished by reacting the deprotected amine with the amino acid in the presence of a carbodiimide (e.g., 1-(3-dimethylaminopropyl)-3-ethylcarbodiimide hydrochloride) in an inert solvent (e.g., methylene chloride) at a temperature from about 10° C. to about 40° C. for about 2 to about 24 hours. Any natural, modified or unusual amino acid may be used as the linking group (L). Suitable natural amino acids include L-amino acids commonly found in naturally occurring proteins and are listed in WIPO Standard ST.25 (1998), Appendix 2, Table 3 (alanine, cysteine, aspartic acid, glutamic acid, phenylalanine, glycine, histidine, isoleucine, lysine, leucine, methionine, asparagine, proline, glutamine, arginine, serine, threonine, valine, tryptophan and tyrosine). Suitable modified or unusual amino acids include those listed in WIPO Standard ST.25 (1998), Appendix 2, Table 4 (2-aminoadipic acid, 3-aminoadipic acid, beta-alanine (beta-aminopropionic acid), 2-aminobutyric acid, 4-aminobutyric acid, piperidinic acid, 6-aminocaproic acid, 2-aminoheptanoic acid, 2-aminoisobutyric acid, 3-aminoisobutyric acid, 2-aminopimelic acid, 2,4-diaminobutyric acid, desmosine, 2,2'-diaminopimelic acid, 2,3-diaminopropionic acid, N-ethylglycine, N-ethylasparagine, hydroxylysine, allo-hydroxylysine, 3-hydroxyproline, 4-hydroxyproline, isodesmosine, allo-isoleucine, N-methylglycine (sarcosine), N-methylisoleucine, 6-N-methyllysine, N-methylvaline, norvaline, norleucine, and ornithine). The amino acids listed above may be modified to provide additional amino acids for coupling by chemical means well known to those skilled in the art (e.g., esterfication, alkylation, amidation, etc.).

The intermediate I(d) is then deprotected to produce the free amino compound I(e) using the same general procedures used to deprotect I(b). Compound IB is then produced by combining the appropriate coupling agent (e.g., carboxylic acid, acyl chloride, sulfonyl chloride, isocyanate, etc.) containing "B" with the deprotected amine I(e) in the presence of a carbodiimide (e.g., 1-(3-dimethylaminopropyl)-3-ethylcarbodiimide hydrochloride) in a reaction inert solvent (e.g., methylene chloride) at a temperature from about 10° C. to about 40° C. for about 2 to about 24 hours. Suitable coupling agents containing B include those described above.

Although Scheme II illustrates the use of an amino acid as a linking group, other linking groups may be used as a means for attaching group B to the bicyclic diamine (e.g., intermediate I(c) in Scheme II, intermediate 3(a) in Scheme III or intermediate 4(a) in Scheme IV). For example, Scheme III below illustrates the use of a sulfonylalkylamino linking group.

Scheme III

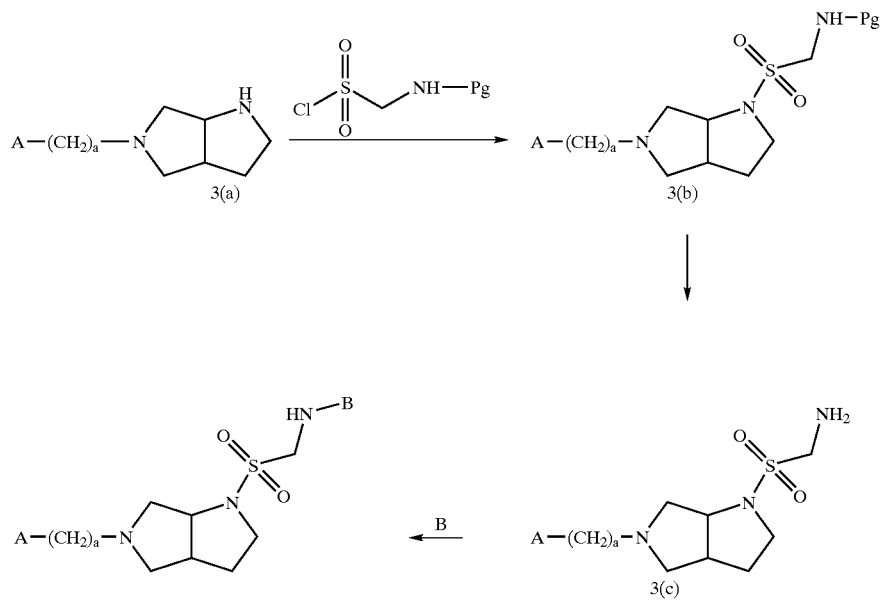

Compounds of the present invention where L is a sulfonamide linker with a nitrogen functional group can be prepared by reacting the bicyclic amine (3(a)) with the desired amino-protected amino methyl sulfonyl chloride in an inert solvent such as methylene chloride or chloroform containing a suitable base such as triethylamine or diisopropylethylamine at a temperature between about 0° C. and about 50° C. for about 10 minutes to about 3 hours. The reaction mixture can be quenched with water and organic layers collected to provide the desired material (3(b)). No further purification is necessary. The amino-protecting group can be removed using conventional chemistry described earlier to provide 3(c). Group B may be attached to the deprotected amino group using any of the procedures described herein.

Scheme IV below illustrates the use of an alkylamino linker (L) to attach B to the bicyclic diamine.

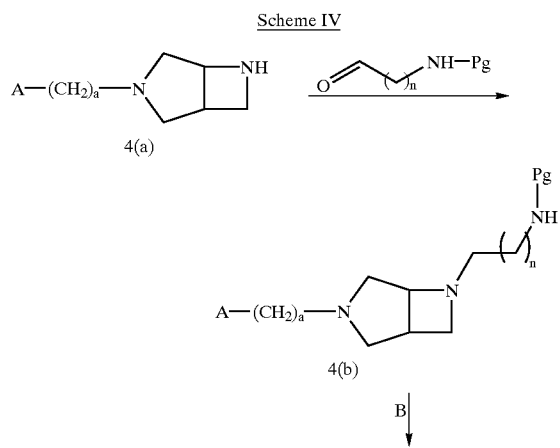

-continued

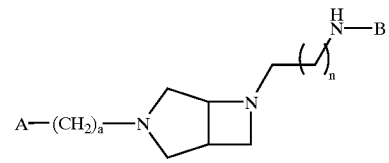

Compounds of the present invention where L is a ($C_1$–$C_3$) alkylamino linker can be prepared by reacting the bicyclic amine 4(a) with a commercially available aldehyde (or ketone), or aldehyde (or ketone) prepared from the literature by one skilled in the art in a solvent (e.g., methanol or ethanol) at room temperature for about 3 hours to about 24 hours. A reducing agent (e.g., sodium borohydride or sodium cyanoborohydride) is then added to the mixture at about 0° C. The reaction temperature is allowed to warm to room temperature and allowed to stir for another 1 to about 10 hours. The solvent is removed under vacuum and the material washed with 1 M NaOH and extracted with a polar solvent such as ethyl acetate or methylene chloride. The organic layer is collected and concentrated to provide the desired product (4(b)). The protecting group is then removed and the free amine can be coupled to B using any of the procedures described earlier (e.g., reaction with an acid chloride, sulfonyl chloride, etc.).

Compounds of the present invention where L is an aryl or heteroaryl amino linker can be prepared by the palladium-catalyzed amination of an aryl or a heterocycle to the bicyclic diamine as illustrated in Scheme V.

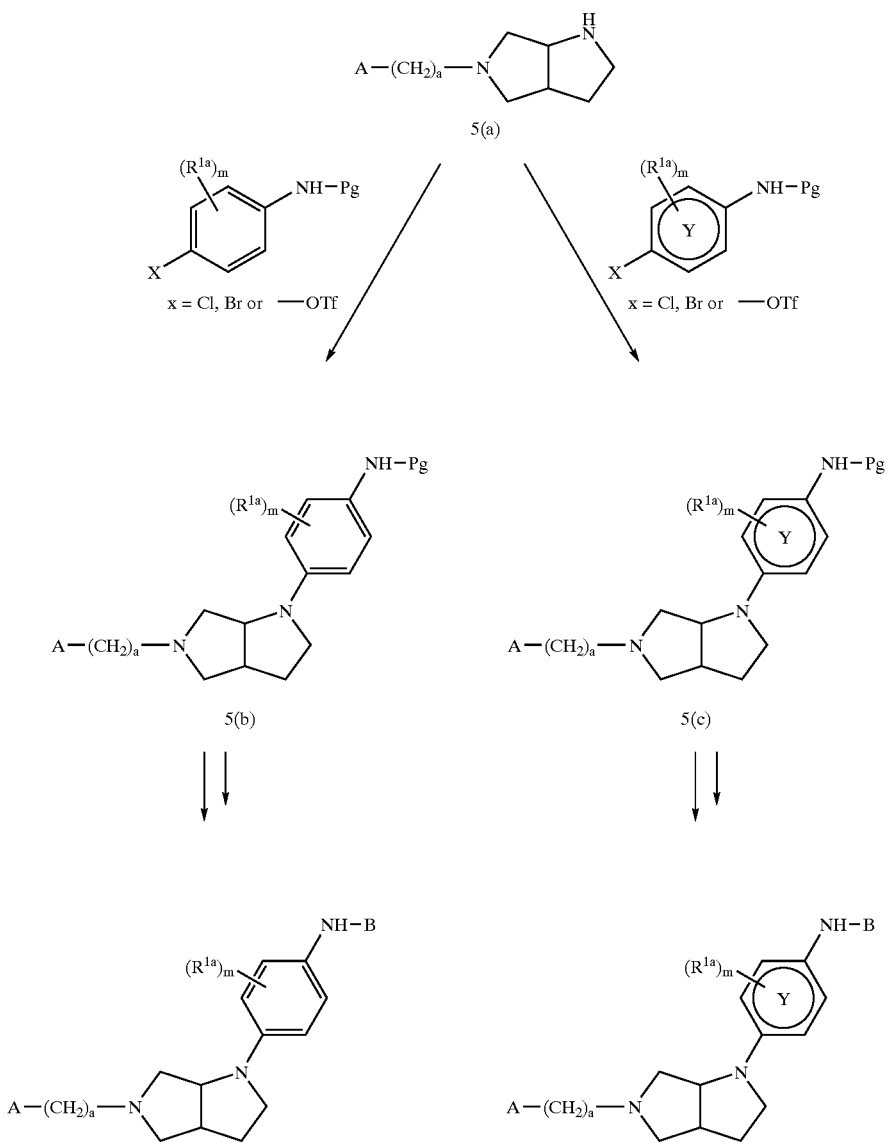

Scheme V

Intermediates 5(b) and 5(c) can be prepared by the palladium-catalyzed amination of an amino-protected aryl or heterocycle (heteroatom such as N, representated by Y) substituted with a halide or a triflate (—OTf) as depicted in the Scheme V above. Pd(dibenzylideneacetone)$_2$ or PdC$_{12}$ may be used. Ligands such as triphenyl phosphine and 1,1-bis(diphenyphosphino)ferrocene (available from Strem Chemicals Inc., Newburyport, Mass.) maybe also be used. A variety of amines and amino-substituted aryl or heteroaryl halides or triflates (e.g., p-aminophenylchloride, p-aminophenylbromide, or p-aminophenyltriflate) having no additional substituents or substituted with one or more $R^{1a}$ groups may be used. The reaction conditions also tolerate the presence of functional groups. In general, the bicyclic amine (1.2 equiv) is mixed with the aryl halide or triflate (1.0 equiv) followed by the addition of sodium t-butoxide (1.4 equiv) and Pd (0.5 mol %) and ligand (1.5 mol %) in an inert solvent such as toluene or ethylene glycol dimethyl ether and heated to about 80° C. to about 100° C. for about 1 to about 27 hours. The reaction mixture is then cooled to room temperature, diluted with ether, filtered through a filter aid (e.g., Celite™ diatomaceous earth filter aid available from World Minerals Corporation, Santa Barbara, Calif.) and concentrated in vacuo to obtain the desired material. For more detailed information, see Guram, A. S., Buchwald, S. L. *J. Am. Chem. Soc.*, 116, 7901 (1994); Boger, D. L, et al., *J Org Chem,* 50, 5790 (1965); and Kosugi, M, et al., *Chem. Lett,* 927 (1983). The protecting group is then removed using conventional chemistry described earlier and the deprotected amino group coupled to B using any of the procedures described earlier.

Scheme VI below illustrates the use of a hydroxy- or carboxy-alkyl linker (L) for attaching B to the bicyclic diamine.

Scheme VI

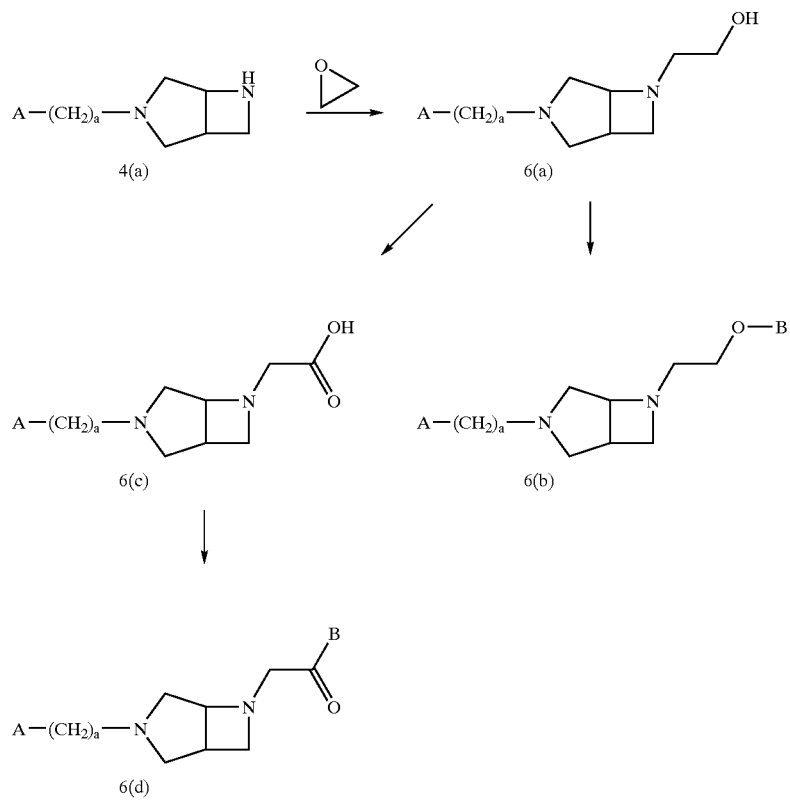

Compounds of the present invention where L is a hydroxyalkyl or a carboxyalkyl can be prepared by reacting the secondary amine with sodium hydride or alkyl lithium (e.g., butyl lithium) and adding it to a commercially available ethylene oxide in a solvent such tetrahydrofuran or diethyl ether at about −78° C. to about 0° C. for about 1 hour to about 24 hours. Group B may be attached directly to the intermediate 6(a) containing the free alcohol to produce compound 6(b). Group B may be attached using conventional chemistry well known to those skilled in the art for the formation of ethers (e.g., formation of the oxygen anion followed by alkylation with the desired alkylating agent such as an alkyl halide). Alternatively, the hydroxy group can be oxidized to the carboxylic acid 6(c) using oxidizing agents such as NaOCl or $CrO_3$-pyr-HCl (PCC). The acid 6(c) can then be coupled to B to provide compound 6(d).

Compounds of the present invention where "a" is zero may be prepared using the general synthetic route depicted in Scheme VII.

Scheme VII

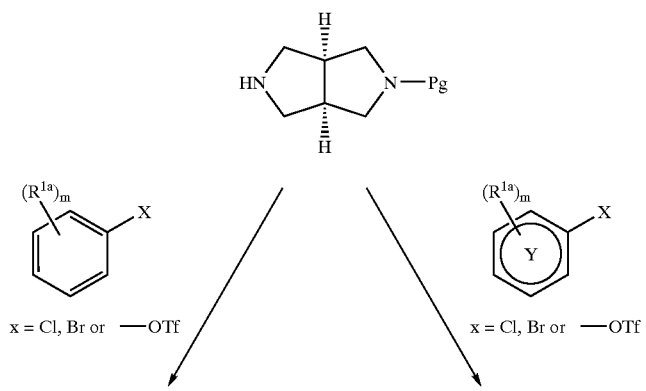

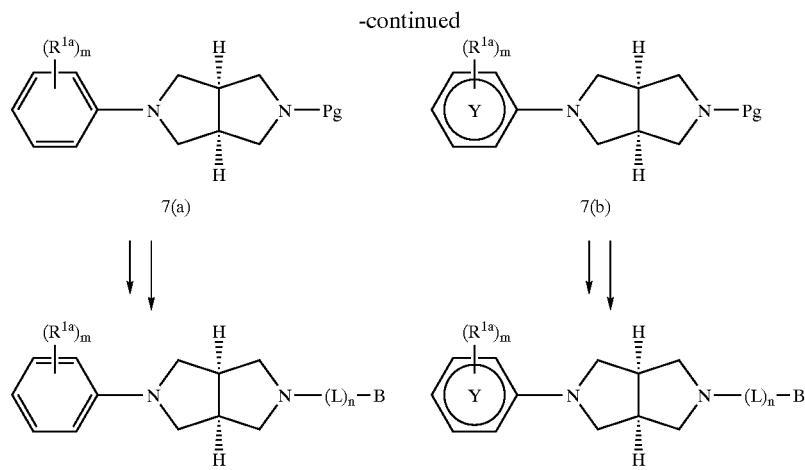

Intermediates 7(a) and 7(b) can be prepared by the palladium-catalyzed amination of aryl or heterocyclic (heteroatom such as N, represented by Y) halides or triflates as described in the Scheme V above. Group B is then attached using any of the general procedures described above with or without a linking group (L).

Conventional methods and/or techniques of separation and purification known to one of ordinary skill in the art can be used to isolate the compounds of Formula (I), as well as the various intermediates related thereto. Such techniques will be well-known to one of ordinary skill in the art and may include, for example, all types of chromatography (high pressure liquid chromatography (HPLC), column chromatography using common adsorbents such as silica gel (SPE column) or SCX Column, and thin-layer chromatography), recrystallization, and differential (i.e., liquid-liquid) extraction techniques.

The Formula I compounds may be isolated and used per se or in the form of a pharmaceutically acceptable salt, solvate and/or hydrate. The term "pharmaceutically acceptable salt" refers to non-toxic acid addition salts derived from inorganic and organic acids. Suitable salt derivatives include halides, thiocyanates, sulfates, bisulfates, sulfites, bisulfites, arylsulfonates, alkylsulfates, phosphonates, monohydrogenphosphates, dihydrogenphosphates, metaphosphates, pyrophosphonates, alkanoates, cycloalkylalkanoates, arylalkonates, adipates, alginates, aspartates, benzoates, fumarates, glucoheptanoates, glycerophosphates, lactates, maleates, nicotinates, oxalates, palmitates, pectinates, picrates, pivalates, succinates, tartarates, citrates, camphorates, camphorsulfonates, digluconates, trifluoroacetates, and the like. The salts also include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, for example, Berge, et al., *J. Pharm. Sci.*, 66, 1–19 (1977).

The term "prodrug" means a compound that is transformed in vivo to yield a compound of Formula (I) or a pharmaceutically acceptable salt, hydrate or solvate of the compound. The transformation may occur by various mechanisms, such as through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-$(C_1-C_2)$alkylamino$(C_2-C_3)$alkyl (such as β-dimethylaminoethyl), carbamoyl-$(C_1-C_2)$alkyl, N,N-di $(C_1-C_2)$alkylcarbamoyl-$(C_1-C_2)$alkyl and piperidino-, pyrrolidino- or morpholino$(C_2-C_3)$alkyl.

Similarly, if a compound of Formula (I) contains an alcohol functional group, a prodrug can be formed by the replacement of the hydrogen atom of the alcohol group with a group such as $(C_1-C_6)$alkanoyloxymethyl, 1-(($C_1-C_6$) alkanoyloxy)ethyl, 1-methyl-1-(($C_1-C_6$)alkanoyloxy)ethyl, $(C_1-C_6)$alkoxycarbonyloxymethyl, N-$(C_1-C_6)$ alkoxycarbonylaminomethyl, succinoyl, $(C_1-C_6)$alkanoyl, α-amino$(C_1-C_4)$alkanoyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)$alkyl$)_2$ or glycosyl (the radical resulting from the removal of a hydroxyl group of the hemiacetal form of a carbohydrate).

If a compound of Formula (I) incorporates an amine functional group, a prodrug can be formed by the replacement of a hydrogen atom in the amine group with a group such as R-carbonyl, RO-carbonyl, NRR'-carbonyl where R and R' are each independently $(C_1-C_{10})$alkyl, $(C_3-C_7)$ cycloalkyl, benzyl, or R-carbonyl is a natural α-aminoacyl or natural α-aminoacyl-natural α-aminoacyl, —C(OH)C(O) $OY^1$ wherein $Y^1$ is H, $(C_1-C_6)$alkyl or benzyl, —C(O$Y^2$)$Y^3$ wherein $Y^2$ is $(C_1-C_4)$ alkyl and $Y^3$ is $(C_1-C_6)$alkyl, carboxy $(C_1-C_6)$alkyl, amino$(C_1-C_4)$alkyl or mono-N— or di-N,N-$(C_1-C_6)$alkylaminoalkyl, —C($Y^4$)$Y^5$ wherein $Y^4$ is H or methyl and $Y^5$ is mono-N— or di-N,N-$(C_1-C_6)$alkylamino, morpholino, piperidin-1-yl or pyrrolidin-1-yl.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Diasteromeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diasteromeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of a chiral HPLC column.

The compounds of Formula (I) may exist in unsolvated as well as solvated forms with pharmaceutically acceptable solvents such as water, ethanol, and the like, and it is intended that the invention embrace both solvated and unsolvated forms.

It is also possible that the compounds of Formula (I) may exist in different tautomeric forms, and all such forms are embraced within the scope of the invention. For example, all of the tautomeric forms of the imidazole moiety are included in the invention. Also, for example, all keto-enol and imine-enamine forms of the compounds are included in the invention.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of Formula (I) (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically labelled compounds of Formula (I) can generally be prepared by following procedures analogous to those disclosed in the Schemes and/or in the Examples hereinbelow, by substituting an isotopically labelled reagent for a non-isotopically labelled reagent.

Compounds of the present invention are useful MCP-1 antagonists; therefore, another embodiment of the present invention is pharmaceutical compositions comprising a compound of the present invention and a pharmaceutically acceptable excipient, diluent or carrier.

A typical pharmaceutical composition is prepared by mixing a compound of the present invention with a carrier, diluent, excipient or mixtures thereof. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the active ingredient is being applied. Solvents are generally selected based on solvents recognized by persons skilled in the art as safe (GRAS) to be administered to a mammal. In general, safe solvents are non-toxic aqueous solvents such as, water and other non-toxic solvents that are soluble or miscible in water. Suitable solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug or aid in the manufacturing of the pharmaceutical product (i.e., medicament).

The pharmaceutical compositions may be prepared using conventional dissolution and mixing procedures. For example, the bulk drug substance (e.g., a compound of the present invention in bulk form) is dissolved in a suitable solvent in the presence of one or more of the excipients described above. The compound is typically formulated into pharmaceutical dosage forms to provide an easily controllable dosage of the drug and to give the patient an elegant and easily handleable product.

Another aspect of the present invention is methods for treating or preventing diseases associated with monocyte and/or lymphocyte accumulation which comprises administering a therapeutically effective amount of a compound of the present invention to an animal in need thereof. CCR2 receptor antagonists have been shown to inhibit the binding of MCP-1 to its receptor. The compounds of the present invention block the migration of monocytes in vitro and inhibit integrin expression induced by MCP-1 and are therefore useful as agents for the treatment of inflammatory diseases, especially those associated with monocyte accumulation, including but not limited to, atherosclerosis, restenosis, gingivitis, glomerulonephritis, psoriasis, colitis, multiple sclerosis, pulmonary fibrosis, Crohn's disease, encephalomyelitis, sepsis, nephritis, asthma, rheumatoid arthritis, wound healing and tissue transplant rejection in animals (preferably humans). Accordingly, the compounds of the present invention (including the pharmaceutical compositions and processes used therein) may be used in the manufacture of a medicament for the therapeutic applications described herein (e.g., treatment or prevention of diseases/conditions associated with monocyte and/or lymphocyte accumulation).

The compounds of the present invention can be administered to a patient at dosage levels in the range of from about 0.01 to about 100 mg per day. As used herein, the term "unit dose" or "unit dosage" refers to physically discrete units that contain a predetermined quantity of a compound of the present invention calculated to produce a desired therapeutic effect. The dosage to be administered may vary depending upon the physical characteristics of the patient, the severity of the patient's symptoms, and the means used to administer the drug. The specific dose for a given patient is usually set by the judgment of the attending physician. It is also noted that the compounds of the present invention can be used in sustained release, controlled release, and delayed release formulations, which forms are also well known to one of ordinary skill in the art.

The pharmaceutical composition for application may be packaged in a variety of ways depending upon the method used for administering the drug. Generally, an article for distribution includes a container which contains the pharmaceutical composition in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon (or made a part of the container) a label which describes the contents of the container. The label may also include appropriate warnings.

The compounds of this invention may also be used in conjunction with other pharmaceutical agents for the treatment of the diseases/conditions described herein. Suitable pharmaceutical agents that may be used in combination with the compounds of the present invention include nutraceuticals, cholesterol absorption inhibitors, HMG-CoA reductase inhibitors, MTP/Apo B secretion inhibitors, HMG-CoA synthase inhibitors, HMG-CoA reductase transcription inhibitors, HMG-COA reductase translation inhibitors, CETP inhibitors, squalene synthetase inhibitors, squalene epoxidase inhibitors, squalene cyclase inhibitors, combined squalene epoxidase/squalene cyclase inhibitors, ACAT inhibitors, lipase inhibitors (including pancreatic lipase inhibitors and gastric lipase inhibitors) and peroxisome proliferator-activated receptor (PPAR) agonists (preferably PPARα agonists).

Any naturally occurring compound that acts to lower plasma cholesterol levels may be administered in combination with the compounds of the present invention. These naturally occurring compounds are referred to herein as "nutraceuticals" and include, for example, garlic extract and niacin.

Any cholesterol absorption inhibitor may be used as the second compound in the combination aspect of this invention. The term "cholesterol absorption inhibition" refers to the ability of a compound to prevent cholesterol contained within the lumen of the intestine from entering into the intestinal cells and/or passing from within the intestinal cells into the blood stream. Such cholesterol absorption inhibition activity is readily determined by those skilled in the art according to standard assays (e.g., J. Lipid Res. 34, 377–395 (1993)). Suitable cholesterol absorption inhibitors are well known to those skilled in the art and include compounds such as steroidal glycosides which are described in WO 94/00480.

Any HMG-CoA reductase inhibitor may be used as the second compound in the combination aspect of this invention. The term "HMG-COA reductase inhibitor" refers to compounds which inhibit the bioconversion of hydroxymethylglutaryl-coenzyme A to mevalonic acid catalyzed by the enzyme HMG-COA reductase. Such inhibition is readily determined by those skilled in the art according to standard assays (e.g., Meth. Enzymol., 71,455–509 (1981) and references cited therein). A variety of these compounds are described and referenced below however other HMG-COA reductase inhibitors will be known to those skilled in the art. For example, U.S. Pat. No. 4,231,938 discloses certain compounds isolated after cultivation of a microorganism belonging to the genus Aspergillus, such as lovastatin. U.S. Pat. No. 4,444,784 discloses synthetic derivatives of the aforementioned compounds, such as simvastatin. U.S. Pat. No. 4,739,073 discloses certain substituted indoles, such as fluvastatin. U.S. Pat. No. 4,346,227 discloses ML-236B derivatives, such as pravastatin. EP-491226A discloses certain pyridyldihydroxyheptenoic acids, such as rivastatin. U.S. Pat. Nos. 4,681,893 and 5,273,995 disclose certain 6-[2-(substituted-pyrrol-1-yl)alkyl]pyran-2-ones such as atorvastatin and the hemicalcium salt thereof (Lipitor®). Additional HMG-CoA reductase inhibitors include itavostatin (aka nisvastatin, pitavastatin, NK-104) and rosuvastatin (ZD-4522).

Any MTP/Apo B secretion (microsomal triglyceride transfer protein and/or apolipoprotein B secretion) inhibitor may be used as the second compound in the combination aspect of this invention. The term "MTP/Apo B secretion inhibitor" refers to compounds which inhibit the secretion of triglycerides, cholesteryl ester, and phospholipids. Such inhibition is readily determined by those skilled in the art according to standard assays (e.g., Wetterau, J. R., Science, 258, 999 (1992)). A variety of these compounds are known to those skilled in the art. Suitable MTP/Apo B secretion inhibitors include biphenyl-2-carboxylic acid-tetrahydroisoquinolin-6-yl amide derivatives as described in U.S. Pat. Nos. 5,919,795 and 6,121,283.

Any HMG-COA synthase inhibitor may be used as the second compound in the combination aspect of this invention. The term "HMG-CoA synthase inhibitor" refers to compounds which inhibit the biosynthesis of hydroxymethylglutaryl-coenzyme A from acetyl-coenzyme A and acetoacetyl-coenzyme A, catalyzed by the enzyme HMG-CoA synthase. Such inhibition is readily determined by those skilled in the art according to standard assays (e.g., Meth Enzymol., 35,155–160 (1975): Meth. Enzymol. 110, 19–26 (1985) and references cited therein). A variety of these compounds are described and referenced below, however other HMG-COA synthase inhibitors will be known to those skilled in the art. U.S. Pat. No. 5,120,729 discloses certain beta-lactam derivatives. U.S. Pat. No. 5,064,856 discloses certain spiro-lactone derivatives prepared by culturing a microorganism (MF5253). U.S. Pat. No. 4,847,271 discloses certain oxetane compounds such as 11-(3-hydroxymethyl-4-oxo-2-oxetayl)-3,5,7-trimethyl-2,4-undeca-dienoic acid derivatives.

Any compound that decreases HMG-CoA reductase gene expression may be used as the second compound in the combination aspect of this invention. These agents may be HMG-CoA reductase transcription inhibitors that block or decrease the transcription of DNA or translation inhibitors that prevent or decrease translation of mRNA coding for HMG-CoA reductase into protein. Such compounds may either affect transcription or translation directly, or may be biotransformed to compounds that have the aforementioned activities by one or more enzymes in the cholesterol biosynthetic cascade or may lead to the accumulation of an isoprene metabolite that has the aforementioned activities. Such regulation is readily determined by those skilled in the art according to standard assays (e.g., Meth. Enzymol., 110, 9–19 (1985)). Inhibitors of HMG-CoA reductase gene expression are well known to those skilled in the art. For example, U.S. Pat. No. 5,041,432 discloses certain 15-substituted lanosterol derivatives. Other oxygenated sterols that suppress synthesis of HMG-CoA reductase are discussed by E. I. Mercer (Prog.Lip. Res., 32, 357–416 (1993)).

Any compound having activity as a CETP inhibitor can serve as the second compound in the combination therapy aspect of the instant invention. The term "CETP inhibitor" refers to compounds that inhibit the cholesteryl ester transfer protein (CETP) mediated transport of various cholesteryl esters and triglycerides from HDL to LDL and VLDL. Such CETP inhibition activity is readily determined by those skilled in the art according to standard assays (e.g., U.S. Pat. No. 6,140,343). A variety of CETP inhibitors will be known to those skilled in the art. For example, 4-amino substituted-2-substituted-1,2,3,4-tetrahydroquinolines disclosed in U.S. Pat. No. 6,140,343. U.S. Pat. No. 5,512,548 discloses certain polypeptide derivatives having activity as CETP inhibitors, while certain CETP-inhibitory rosenonolactone derivatives and phosphate-containing analogs of cholesteryl ester are disclosed in *J. Antibiot.*, 49(8), 815–816 (1996), and *Bioorg. Med. Chem. Lett.*, 6, 1951–1954 (1996), respectively.

Any squalene synthetase inhibitor may be used as the second compound of this invention. The term "squalene synthetase inhibitor" refers to compounds which inhibit the condensation of 2 molecules of farnesylpyrophosphate to form squalene, catalyzed by the enzyme squalene synthetase. Such inhibition is readily determined by those skilled in the art according to standard assays (e.g., *Meth. Enzymol,* 15, 393–454 (1969) and *Meth. Enzymol,* 110, 359–373 (1985) and references contained therein). A variety of these compounds are known to those skilled in the art. For example, U.S. Pat. No. 5,026,554 discloses fermentation products of the microorganism MF5465 (ATCC 74011) including zaragozic acid. A summary of other squalene synthetase inhibitors has been compiled (*Curr.Op.Ther. Patents*, 3, 861–4 (1993)).

Any squalene epoxidase inhibitor may be used as the second compound in the combination aspect of this invention. The term "squalene epoxidase inhibitor" refers to compounds which inhibit the bioconversion of squalene and molecular oxygen into squalene-2,3-epoxide, catalyzed by the enzyme squalene epoxidase. Such inhibition is readily determined by those skilled in the art according to standard assays (e.g., *Biochim Biophys Acta*, 794, 466–471 (1984)). A variety of these compounds are well known to those skilled in the art. For example, U.S. Pat. Nos. 5,011,859 and 5,064,864 disclose certain fluoro analogs of squalene; EP publication 395,768 A discloses certain substituted allylamine derivatives; PCT publication WO 9312069 discloses certain amino alcohol derivatives; and U.S. Pat. No. 5,051,534 discloses certain cyclopropyloxy-squalene derivatives.

Any squalene cyclase inhibitor may be used as the second component in the combination aspect of this invention. The term "squalene cyclase inhibitor" refers to compounds which inhibit the bioconversion of squalene-2,3-epoxide to lanosterol, catalyzed by the enzyme squalene cyclase. Such inhibition is readily determined by those skilled in the art according to standard assays (e.g., *FEBS Lett.*, 244, 347–350 (1989)). Squalene cyclase inhibitors are well known to those skilled in the art. For example, U.S. Pat. No. 5,580,881 discloses the use of 1,2,3,5,6,7,8,8a-octahydro-5,5,8a-trimethyl-(8aβ)-6-isoquinolineamine derivatives as squalene cyclase inhibitors.

Any combined squalene epoxidase/squalene cyclase inhibitor may be used as the second component in the combination aspect of this invention. The term "combined squalene epoxidase/squalene cyclase inhibitor" refers to compounds that inhibit the bioconversion of squalene to lanosterol via a squalene-2,3-epoxide intermediate. In some assays it is not possible to distinguish between squalene epoxidase inhibitors and squalene cyclase inhibitors. However, these assays are recognized by those skilled in the art. Thus, inhibition by combined squalene epoxidase/squalene cyclase inhibitors is readily determined by those skilled in art according to the aforementioned standard assays for squalene cyclase or squalene epoxidase inhibitors. A variety of squalene epoxidase/squalene cyclase inhibitors are well known to those skilled in the art. For example, U.S. Pat. Nos. 5,084,461 and 5,278,171 disclose certain azadecalin derivatives; EP publication 468,434 discloses certain piperidyl ether and thio-ether derivatives such as 2-(1-piperidyl)pentyl isopentyl sulfoxide and 2-(1-piperidyl) ethyl ethyl sulfide; PCT publication WO 94/01404 discloses certain acyl-piperidines such as 1-(1-oxopentyl-5-phenylthio)-4-(2-hydroxy-1-methyl)-ethyl)piperidine; and U.S. Pat. No. 5,102,915 discloses certain cyclopropyloxy-squalene derivatives.

Any ACAT inhibitor can serve as the second compound in the combination therapy aspect of this invention. The term "ACAT inhibitor" refers to compounds that inhibit the intracellular esterification of dietary cholesterol by the enzyme acyl CoA: cholesterol acyltransferase. Such inhibition may be determined readily by one of skill in the art according to standard assays, such as the method described in Heider et al., *Journal of Lipid Research.*, 24,1127 (1983). A variety of these compounds are well known to those skilled in the art. For example, U.S. Pat. No. 5,510,379 discloses certain carboxysulfonates, while WO 96/26948 and WO 96/10559 both disclose urea derivatives having ACAT inhibitory activity.

Examples of ACAT inhibitors include DL-melinamide disclosed in British Patent No. 1,123,004 and *Japan. J. Pharmacol.*, 42, 517–523 (1986); 2,2-dimethyl-N-(2,4,6-trimethoxyphenyl)dodecanamide disclosed in U.S. Pat. No. 4,716,175; N-[2,6-bis(1-methylethyl)phenyl]-N'-[[1-(4-dimethylaminophenyl)cyclopentyl]-methyl]urea disclosed in U.S. Pat. No. 5,015,644; 2,6-bis(1-methylethyl)-phenyl [[2,4,6-tris(1-methylethyl)phenyl]-acetyl]sulfamate disclosed in copending U.S. patent application Ser. No. 08/233,932 filed Apr. 13, 1994; and the like.

Any lipase inhibitor may be used in combination with the compounds of the present invention. The term "lipase inhibitor" refers to a compound that inhibits the metabolic cleavage of dietary triglycerides into free fatty acids and monoglycerides. Under normal physiological conditions, lipolysis occurs via a two-step process that involves acylation of an activated serine moiety of the lipase enzyme. This leads to the production of a fatty acid-lipase hemiacetal intermediate, which is then cleaved to release a diglyceride. Following further deacylation, the lipase-fatty acid intermediate is cleaved, resulting in free lipase, a monoglyceride and a fatty acid. The resultant free fatty acids and monoglycerides are incorporated into bile acid-phospholipid micelles, which are subsequently absorbed at the level of the brush border of the small intestine. The micelles eventually enter the peripheral circulation as chylomicrons. Such lipase inhibition activity is readily determined by those skilled in the art according to standard assays (e.g., *Methods Enzymol,* 286, 190–231 (1997)).

Pancreatic lipase mediates the metabolic cleavage of fatty acids from triglycerides at the 1- and 3-carbon positions. The primary site of the metabolism of ingested fats is in the duodenum and proximal jejunum by pancreatic lipase, which is usually secreted in vast excess of the amounts necessary for the breakdown of fats in the upper small intestine. Because pancreatic lipase is the primary enzyme required for the absorption of dietary triglycerides, inhibitors have utility in the treatment of obesity and the other related conditions. Such pancreatic lipase inhibition activity is readily determined by those skilled in the art according to standard assays (e.g., *Methods Enzymol,* 286, 190–231 (1997)).

Gastric lipase is an immunologically distinct lipase that is responsible for approximately 10 to 40% of the digestion of dietary fats. Gastric lipase is secreted in response to mechanical stimulation, ingestion of food, the presence of a fatty meal or by sympathetic agents. Gastric lipolysis of ingested fats is of physiological importance in the provision of fatty acids needed to trigger pancreatic lipase activity in the intestine and is also of importance for fat absorption in a variety of physiological and pathological conditions associated with pancreatic insufficiency. See, for example, C. K. Abrams, et al., *Gastroenterology,* 92, 125 (1987). Such gastric lipase inhibition activity is readily determined by those skilled in the art according to standard assays (e.g., *Methods Enzymol,* 286, 190–231 (1997)).

A variety of gastric and/or pancreatic lipase inhibitors are well known to one of ordinary skill in the art. Preferred lipase inhibitors are those inhibitors selected from the group consisting of lipstatin, tetrahydrolipstatin (orlistat), valilactone, esterastin, ebelactone A, and ebelactone B. The compound tetrahydrolipstatin is especially preferred. The lipase inhibitor, N-3-trifluoromethylphenyl-N'-3-chloro-4'-trifluoromethylphenylurea, and the various urea derivatives related thereto, are disclosed in U.S. Pat. No. 4,405,644. The lipase inhibitor, esteracin, is disclosed in U.S. Pat. Nos. 4,189,438 and 4,242,453. The lipase inhibitor, cyclo-O,O'-[(1,6-hexanediyl)-bis-(iminocarbonyl)]dioxime, and the various bis(iminocarbonyl)dioximes related thereto may be prepared as described in Petersen et al., *Liebig's Annalen,* 562, 205–229 (1949).

A variety of pancreatic lipase inhibitors are well known to those skilled in the art. For example, the pancreatic lipase inhibitors lipstatin, (2S, 3S, 5S, 7Z, 10Z)-5-[(S)-2-formamido-4-methyl-valeryloxy]-2-hexyl-3-hydroxy-7,10-hexadecanoic acid lactone, and tetrahydrolipstatin (orlistat), (2S, 3S, 5S)-5-[(S)-2-formamido-4-methyl-valeryloxy]-2-hexyl-3-hydroxy-hexadecanoic 1,3 acid lactone, and the variously substituted N-formylleucine derivatives and stereoisomers thereof, are disclosed in U.S. Pat. No. 4,598,089. Tetrahydrolipstatin is prepared as described in, e.g., U.S. Pat. Nos. 5,274,143; 5,420,305; 5,540,917; and 5,643,874. The pancreatic lipase inhibitor, FL-386, 1-[4-(2-methylpropyl)cyclohexyl]-2-[(phenylsulfonyl)oxy]-ethanone, and the variously substituted sulfonate derivatives related thereto, are disclosed in U.S. Pat. No. 4,452,813. The pancreatic lipase inhibitor, WAY-121898, 4-phenoxyphenyl-4-methylpiperidin-1-yl-carboxylate, and the various carbamate esters and pharmaceutically acceptable salts related thereto, are disclosed in U.S. Pat. Nos. 5,512,565; 5,391,571 and 5,602,151. The pancreatic lipase inhibitor, valilactone, and a process for the preparation thereof by the microbial cultivation of Actinomycetes strain MG147—CF2, are disclosed in Kitahara, et al., *J. Antibiotics,* 40 (11), 1647–1650 (1987). The pancreatic lipase inhibitors, ebelactone A and ebelactone B, and a process for the preparation thereof by the microbial cultivation of Actinomycetes strain MG7-G1, are disclosed in Umezawa, et al., *J. Antibiotics,* 33, 1594–1596 (1980). The use of ebelactones A and B in the suppression of monoglyceride formation is disclosed in Japanese Kokai 08-143457, published Jun. 4, 1996.

Other compounds that are marketed for hyperlipidemia may also be used in combination with compounds of the present invention, including those compounds marketed for hypercholesterolemia which are intended to help prevent or treat atherosclerosis, for example, bile acid sequestrants, such as Welchol®, Colestid®, LoCholest® and Questran®; and fibric acid derivatives, such as Atromid®, Lopid® and Tricor®. Examples of bile acid sequestrants are also discussed in U.S. Pat. Nos. 3,692,895 and 3,803,237 (colestipol); U.S. Pat. No. 3,383,281 (cholestyramine) and Casdorph R. in Lipid Pharmacology, 1976;2:222–256, Paoletti C., Glueck J., eds. Academic Press, N.Y.

Any peroxisome proliferator-activated receptor (PPAR) agonists (preferably PPARα agonists) can be used in combination with compounds of the present invention. Suitable PPAR agonists include fibrates (e.g., bezafibrate, ciprofibrate, clofibrate, fenofibrate, and gemfibrozil, which are all commercially available) and glitazones (e.g., pioglitazone, and rosiglitazone, which are both commercially available). Gemfibrozil is described in U.S. Pat. No. 3,674,836; bezafibrate is described in U.S. Pat. No. 3,781,328; clofibrate is described in U.S. Pat. No. 3,262,850; and fenofibrate is described in U.S. Pat. No. 4,058,552.

Other compounds that may be used in combination with the compounds of the present invention include NSAIDs, COX-2 inhibitors, and antiallergics. Suitable nonsteroidal anti-Inflammatory drugs (NSAIDS) include compounds such as ibuprofen (Motrin™, Advil™), naproxen (Naprosyn™), sulindac (Clinori™), diclofenac (Voltare™), piroxicam (Feldene™), ketoprofen (Orudis™), diflunisal (Dolobid™), nabumetone (Relafen™), etodolac (Lodine™), oxaprozin (Daypr™), and indomethacin (Indocin™). Suitable COX-2 inhibitors (cyclooxygenase enzyme inhibitors) include compounds such as celecoxib (Celebrex™) and rofecoxib (Vioxx™).

All of the references cited above relating to pharmaceutical agents that may be used in combination with the compounds of the present invention are incorporated herein by reference.

According to the methods of the invention, a compound of the present invention or a combination therapy is administered to a subject in need of such treatment, preferably in the form of a pharmaceutical composition. In the combination aspect of the invention, the compound of the present invention and the second pharmaceutical agent may be administered either separately or in a pharmaceutical composition comprising both. It is generally preferred that such administration be oral. However, if the subject being treated is unable to swallow, or oral administration is otherwise impaired or undesirable, parenteral or transdermal administration may be appropriate. In combination therapy treatment, both the compounds of this invention and the other drug therapies are administered to mammals (e.g., humans) by conventional methods well known to those skilled in the art.

According to the methods of the invention, when a combination of a compound of the present invention and a second pharmaceutical agent are administered together, such administration can be sequential in time or simultaneous with the simultaneous method being generally preferred. For sequential administration, a compound of the present invention and the second pharmaceutical agent can be administered in any order. It is generally preferred that such administration be oral. It is especially preferred that such administration be oral and simultaneous. When a compound of the present invention and the second pharmaceutical agent are administered sequentially, the administration of each can be by the same or by different methods.

According to the methods of the invention, a compound of the present invention or a combination of drugs is preferably administered in the form of a pharmaceutical composition comprising a pharmaceutically acceptable carrier, excipient, diluent or mixture thereof. Accordingly, a compound of the present invention or a combination of a compound of the present invention with a second pharmaceutical agent can be administered to a patient separately or together in any conventional oral, rectal, transdermal, parenteral, (for example, intravenous, intramuscular, or subcutaneous) intracisternal, intravaginal, intraperitoneal, intravesical, local (for example, powder, ointment or drop), buccal, or nasal dosage form.

Compositions suitable for parenteral injection may comprise pharmaceutically acceptable sterile aqueous or non-aqueous solutions, dispersions, suspensions, or emulsions, and sterile powders for reconstitution into sterile injectable solutions or dispersions. Examples of suitable aqueous and nonaqueous carriers, diluents, solvents, or excipients include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Prevention of microorganism contamination of the compositions can be accomplished with various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, for example, aluminum monostearate and gelatin.

Solid dosage forms for oral administration include capsules, tablets, powders, and granules. In such solid dosage forms, the drug (e.g., active compound or prodrug thereof) is admixed with at least one inert customary pharmaceutical excipient (or carrier) such as sodium citrate or dicalcium phosphate or (a) fillers or extenders (e.g., starches, lactose, sucrose, mannitol, silicic acid, and the like); (b) binders (e.g., carboxymethylcellulose, alginates, gelatin, polyvinylpyrrolidone, sucrose, acacia and the like); (c) humectants (e.g., glycerol); (d) disintegrating agents (e.g., agar-agar, calcium carbonate, potato or tapioca starch, alginic acid, certain complex silicates, sodium carbonate and the like); (e) solution retarders (e.g., paraffin); (f) absorption accelerators (e.g., quaternary ammonium compounds); (g) wetting agents (e.g., cetyl alcohol and glycerol monostearate); (h) adsorbents (e.g., kaolin and bentonite); and/or (i) lubricants (e.g., talc, calcium stearate, magnesium stearate, solid polyethylene glycols, sodium lauryl sulfate, or mixtures thereof). In the case of capsules and tablets, the dosage forms may also comprise buffering agents.

Solid compositions of a similar type may also be used as fillers in soft or hard filled gelatin capsules using such excipients as lactose or milk sugar, as well as high molecular weight polyethylene glycols, and the like.

Solid dosage forms such as tablets, dragees, capsules, and granules can be prepared with coatings and shells, such as enteric coatings and others well known in the art. They may also contain opacifying agents, and can also be of such composition that they release the drug or compounds in a delayed manner. Examples of embedding compositions that can be used are polymeric substances and waxes. The drug can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the drug(s), the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents.

Suspensions, in addition to the drug, may further comprise suspending agents, e.g., ethoxylated isostearyl alcohols, polyoxyethylene sorbitol or sorbitan esters, microcrystalline cellulose, aluminum metahydroxide, bentonite, agar-agar, tragacanth, or mixtures of these substances, and the like.

Compositions for rectal or vaginal administration preferably comprise suppositories, which can be prepared by mixing a compound of the present invention or combination of drugs with suitable non-irritating excipients or carriers such as cocoa butter, polyethylene glycol or a suppository wax, which are solid at ordinary room temperature, but liquid at body temperature, and therefore, melt in the rectum or vaginal cavity thereby releasing the active component.

Dosage forms for topical administration of the compounds of the present invention and combination therapies may comprise ointments, powders, sprays and inhalants. The drugs are admixed under sterile condition with a pharmaceutically acceptable carrier, and any preservatives, buffers, or propellants that may be required. Opthalmic formulations, eye ointments, powders, and solutions are also intended to be included within the scope of the present invention.

Advantageously, the present invention also provides kits for use by a consumer having, or at risk of having, a disease or condition associated with monocyte, lymphocyte or leucocyte accumulation, which can be ameliorated by a CCR2 or CCR3 antagonist. Such kits include a suitable dosage form such as those described above and instructions describing the method of using such dosage form to mediate, reduce or prevent inflammation. The instructions would direct the consumer or medical personnel to administer the dosage form according to administration modes known to those skilled in the art. Such kits could advantageously be packaged and sold in single or multiple kit units.

Since the present invention has an aspect that relates to the treatment of the disease/conditions described herein with a combination of active ingredients which may be administered separately, the invention also relates to combining separate pharmaceutical compositions in kit form. The kit comprises two separate pharmaceutical compositions: a compound of the present invention and a second pharmaceutical agent as described above. The kit comprises a container (e.g., a divided bottle or a divided foil packet). Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . . Second Week, Monday, Tuesday, . . . " etc. Other variations of memory aids will be readily apparent. A "daily dose" can be a single tablet or capsule or several pills or capsules to be taken on a given day. Also, a daily dose of a first compound can consist of one tablet or capsule while a daily dose of the second compound can consist of several tablets or capsules and vice versa. The memory aid should reflect this.

The following Examples illustrate the preparation of compounds represented by Formula 1. The examples are not intended to be limiting to the scope of the invention in any respect, and should not be so construed.

EXAMPLES

Unless specified otherwise, starting materials are generally available from commerical sources such as Aldrich Chemicals Co. (Milwaukee, Wis.), Lancaster Synthesis, Inc. (Windham, N.H.), Acros Organics (Fairlawn, N.J.), Maybridge Chemical Company, Ltd. (Cornwall, England), Tyger Scientific (Princeton, N.J.), and AstraZeneca Pharmaceuticals (London, England).

General Experimental Procedures

NMR spectra were recorded on a Varian Unity™ 400 (available from Varian Inc., Palo Alto, Calif.) at room temperature at 400 MHz for proton. Chemical shifts are expressed in parts per million (δ) relative to residual solvent as an internal reference. The peak shapes are denoted as follows: s, singlet; d, doublet; t, triplet; q, quartet; m, multiplet; br s, broad singlet; 2s, two singlets. Atmospheric pressure chemical ionization mass spectra (APCl) were obtained on a Fisons™ Platform II Spectrometer (carrier gas: acetonitrile, available from Micromass Ltd, Manchester, UK). Chemical ionization mass spectra (CI) were obtained on a Hewlett-Packard™ 5989 instrument (ammonia ionization, PBMS: available from Hewlett-Packard Company, Palo Alto, Calif.). Where the intensity of chlorine or bromine-containing ions are described, the expected intensity ratio was observed (approximately 3:1 for $^{35}Cl/^{37}Cl$-containing ions and 1:1 for $^{79}Br/^{81}Br$-containing ions) and the intensity of only the lower mass ion is given.

In some cases only representative $^1H$ NMR peaks are given. MS peaks are reported for all examples. Optical rotations were determined on a PerkinElmer™ 241 polarimeter (available from PerkinElmer Inc., Wellesley, Mass.) using the sodium D line (λ=589 nm) at the indicated temperature and are reported as follows $[\alpha]_D^{temp}$, concentration (c=g/100 mL), and solvent.

Column chromatography was performed with either Baker™ silica gel (40 μm; J. T. Baker, Phillipsburg, N.J.) or Silica Gel 50 (EM Sciences™, Gibbstown, N.J.) in glass columns or in Flash 40 Biotage™ columns (ISC, Inc., Shelton, Conn.) under low nitrogen pressure.

Example 1 illustrates the preparation of bicyclic diamine compounds having formula I where w, x, y and z are all equal to 1 and no linking group (L).

Example 1

Preparation of 1,4-dibenzyl-diazabicyclo[3.3.0]octane-2,6-dione (I-1a):

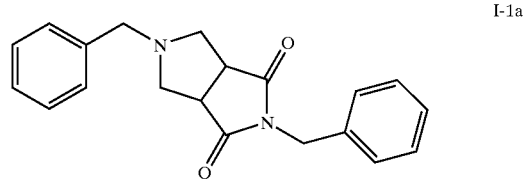

I-1a

Paraformaldehyde (13.5 g) was added to a solution of N-benzylmaleimide (10.8 g; 60 mmol) and N-benzylglycine (9.9 g; 60 mmol) in toluene (400 mL) and the resulting mixture was refluxed with azeotropic removal of water, for 10 hours. The mixture was cooled to room temperature and was concentrated in vacuo. The mixture was purified by flash chromatography (30% EtOAc in hexane) to afford 15 g (78%) of the title product (I-1 a), as an amorphous solid.

Preparation of 1-benzyl-diazabicyclo[3.3.0]octane-2,6-dione (I-1b):

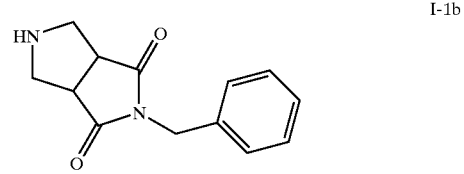

I-1b

A solution of the dibenzyl compound I-1a (8.6 g; 27 mmol.) in dichloromethane (100 mL) was cooled to 0° C. and α-chloroethylchloroformate (7.7 g; 54 mmol) was added dropwise over 30 min. The solution was then stirred for an additional 30 minutes. The resulting solution was refluxed for 4 hours. The solution was cooled to room temperature and was concentrated in vacuo and methanol was added to the residue. This mixture was stirred at 50° C. for 1 hour. The mixture was concentrated in vacuo and ether was added to afford the product (I-1 b) as white crystals (5.8 g, 94%).

Preparation of 1-benzyl-diazabicyclo[3.3.0]octane (I-1c):

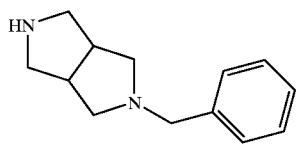

I-1c

To a solution of the imide I-1 b (0.48 g, 1.8 mmol.) in anhydrous THF (65 mL) was added a solution of borane-dimethylsulfide complex in THF (2M, 4.5 mL, 0.9 mmol) dropwise. The mixture was stirred overnight at room temperature and 2N HCl solution (45 mL) was added dropwise over 4 hours. The resulting mixture was refluxed for 30 min. The solution was cooled and concentrated in vacuo. The pH of the resulting suspension was adjusted to 10 (aq. NaOH) and the mixture was extracted with $CH_2Cl_2$. The organic extract was dried ($MgSO_4$) and concentrated in vacuo to afford a colorless oil (335 mg; 91%).

Preparation of 1-benzyl-4-boc-diazabicyclo[3.3.0]octane (I-1d):

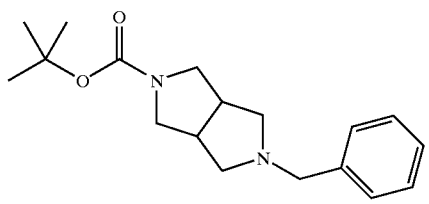

I-1d

To a solution of the diamine I-1c (0.283 g, 1.4 mmol.) in dry $CH_2Cl_2$ (2 mL) was added boc-anhydride in $CH_2Cl_2$ (1 mL) over 5 minutes and the resulting mixture was stirred overnight at room temperature. The solution was concentrated in vacuo and the crude product was purified by preparative chromatography to afford the carbamate I-1d (275 mg, 65%).

Preparation of Hexahydro-pyrrolo[3,4-c]pyrrole-2-carboxylic acid tert-butyl ester (I-1e):

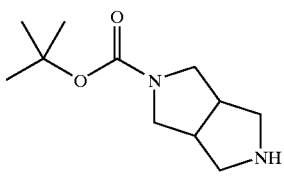

I-1e

To a solution of the N-benzyl compound I-1d (0.325 g, 0.1 mmol) in EtOH (5 mL) was added 10% palladium on carbon (0.3 g) and ammonium formate (0.34 g, 0.5 mmol). The resulting mixture was refluxed for 2 hours and cooled. The solids were filtered off with the aid of a Florisil™ pad (available from US Silica Company, Berkeley Springs, W. Va.). The crude product was purified using preparative chromatography to afford 0.185 g (82%) of the title compound I-1e as a low melting solid. $^1$H NMR ($CDCl_3$) δ 3.5 (m, 2H), 3.32 (m, 1H), 3.15 (m, 1H), 3.00 (M, 2H), 2.75 (br, 1H), 2.72 (br, 1H), 2.45 (m, 1H), 1.4 (s, 9H).

Preparation of [5-(2,4-difluoro-benzyl)-hexahydro-pyrrolo[3,4-c]pyrrole-2-carboxylic acid tert-butyl ester (I-1f):

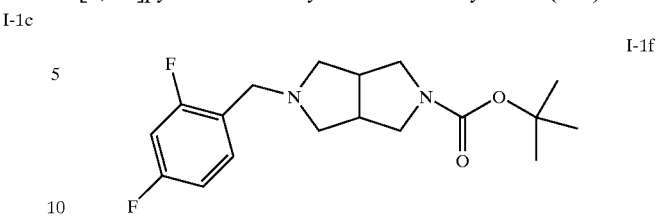

I-1f 6.0 mmols of 2,4-difluorobenzaldehyde was added to a 1.0 M tetrahydrofuran solution containing 3.0 mmols of hexahydro-pyrrolo[3,4-c]pyrrole-2-carboxylic acid tert-butyl ester (I-1e). To this solution was added 24 mL of anhydrous methanol containing 1% glacial acetic acid. This mixture was allowed to proceed at room temperature under gentle agitation on a shaker plate for 1 hour. Then, 9.0 mmols of sodium tri-acetoxy-borohydride was added in one batch at room temperature. The reaction mixture was allowed to stir overnight at room temperature. The solvent was then removed in vacuo and 25 mL of 1.0 M sodium hydroxide was added. The crude product was extracted into ethyl acetate, dried over sodium sulfate and the solvent removed in vacuo. The material was purified by liquid chromatography to afford intermediate I-1f in 75% yield (2.27 mmol).

Preparation of 1-(2,4-difluoro-benzyl)-octahydro-pyrrolo[3,4]-pyrrol (I-1g):

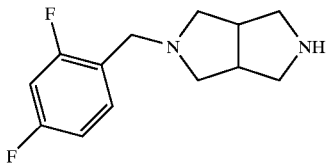

I-1g 2.27 mmols of I-1f was dissolved in 50 mL of methylene chloride and 50 mL of trifluoroacetic acid. The reaction was stirred for 45 minutes at room temperature. Then, the solvent was removed in vacuo and the material was dissolved in 25 mL of ethyl acetate. The reaction was cooled to 0° C. and basified with 6.0 M sodium hydroxide. The organic layer was collected dried over sodium sulfate and concentrated in vacuo to dryness. 542 mg (99% yield) of I-1g was obtained as a yellow oil.

Preparation of [5-(2,4-difluoro-benzyl)-hexahydro-pyrrolo[3,4-c]pyrrol-2-yl]-(2-ethoxy-phenyl)-methanone (1):

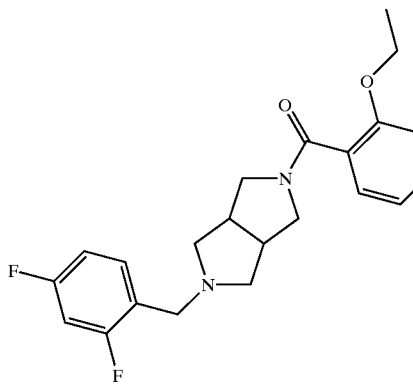

1

150 μL of 2-ethoxy benzoic acid (0.2M in N,N-dimethylacetamide (DMA) and 3.75% TEA) was added to 100 μL of 2-amino-1-[5-(2,4-difluoro-benzyl)-hexahydro-pyrrolo[3,4-c]pyrrol-2-yl]-ethanone (I-1g)(0.2M in 1:1 toluene/DMA) and 3.75% n-methyl morpholine (NMM) followed by the addition of 150 μL (30 μmol) of O-benzotriazol-1-yl-N,N,N',N'-tetramethyl-uronium-hexafluoro-phosphate (HBTU) solution (0.2M in DMA). The reaction was heated to 60° C. for six hours and then allowed to stir overnight at room temperature. Then, the reaction was quenched with 450 μL 10% NaOH, followed by the addition of 900 μL of ethyl acetate. The reaction was vigorously shaken for 15 minutes, and then allowed to stand at room temperature for 30 minutes.

The reaction mixture was purified by liquid chromatography on a 1 g SCX SPE cartridge conditioned with MeOH. The cartridge was eluted with 1M $NH_3$/MeOH to afford 5.0 mg of the desired product [5-(2,4-difluoro-benzyl)-hexahydro-pyrrolo[3,4-c]pyrrol-2-yl]-(2-ethoxy-phenyl)-methanone (1) as a yellow oil.

MS (CI) m/z=386.18 (M+1). $^1$H NMR ($CDCl_3$) was consistent with compound (1).

The following compounds were prepared using the same general procedures described above with the appropriate starting materials. Table 1 below lists the compounds made and their corresponding retention times (in minutes) using HPLC and their molecular weight (ms (CI) m/z (M+1)) as determined by chemical ionization mass spectroscopy.

TABLE 1

| Compound Name | Time (mins) | MW (found) |
|---|---|---|
| 2-Biphenyl-4-yl-1-[5-(2,3-dimethoxy-benzyl)-hexahydro-pyrrolo[3,4-c]pyrrol-2-yl]-ethanone | 1.78 | 456.24 |
| 2-Biphenyl-4-yl-1-[5-(2,4-dimethyl-benzyl)-hexahydro-pyrrolo[3,4-c]pyrrol-2-yl]-ethanone | 1.89 | 424.25 |
| 2-Biphenyl-4-yl-1-[5-(2-chloro-3,4-dimethoxy-benzyl)-hexahydro-pyrrolo[3,4-c]pyrrol-2-yl]-ethanone | 1.82 | 490.2 |
| 1-[5-(2,4-Dimethoxy-benzyl)-hexahydro-pyrrolo[3,4-c]pyrrol-2-yl]-2-(4-isopropyl-phenyl)-ethanone | 1.77 | 422.26 |
| 1-[5-(2,3-Dimethoxy-benzyl)-hexahydro-pyrrolo[3,4-c]pyrrol-2-yl]-2-(4-isopropyl-phenyl)-ethanone | 1.74 | 422.26 |
| 1-[5-(2,4-Dimethyl-benzyl)-hexahydro-pyrrolo[3,4-c]pyrrol-2-yl]-2-(4-isopropyl-phenyl)-ethanone | 1.86 | 390.27 |
| 1-[5-(2-Chloro-3,4-dimethoxy-benzyl)-hexahydro-pyrrolo[3,4-c]pyrrol-2-yl]-2-(4-isopropyl-phenyl)-ethanone | 1.78 | 456.22 |
| 1-[5-(2,4-Dimethoxy-benzyl)-hexahydro-pyrrolo[3,4-c]pyrrol-2-yl]-2-m-tolyl-ethanone | 1.52 | 394.23 |
| 1-[5-(2,3-Dimethoxy-benzyl)-hexahydro-pyrrolo[3,4-c]pyrrol-2-yl]-2-m-tolyl-ethanone | 1.49 | 394.23 |
| 1-[5-(2,4-Dimethyl-benzyl)-hexahydro-pyrrolo[3,4-c]pyrrol-2-yl]-2-m-tolyl-ethanone | 1.62 | 362.24 |
| 1-[5-(2-Chloro-3,4-dimethoxy-benzyl)-hexahydro-pyrrolo[3,4-c]pyrrol-2-yl]-2-m-tolyl-ethanone | 1.53 | 428.19 |
| 1-[5-(2,4-Dimethoxy-benzyl)-hexahydro-pyrrolo[3,4-c]pyrrol-2-yl]-2-p-tolyl-ethanone | 1.53 | 394.23 |
| 1-[5-(2,3-Dimethoxy-benzyl)-hexahydro-pyrrolo[3,4-c]pyrrol-2-yl]-2-p-tolyl-ethanone | 1.49 | 394.23 |
| 1-[5-(2,4-Dimethyl-benzyl)-hexahydro-pyrrolo[3,4-c]pyrrol-2-yl]-2-p-tolyl-ethanone | 1.62 | 362.24 |
| 1-[5-(2-Chloro-3,4-dimethoxy-benzyl)-hexahydro-pyrrolo[3,4-c]pyrrol-2-yl]-2-p-tolyl-ethanone | 1.54 | 428.19 |
| 1-[5-(2,4-Dimethoxy-benzyl)-hexahydro-pyrrolo[3,4-c]pyrrol-2-yl]-2-(2,5-dimethyl-phenyl)-ethanone | 1.62 | 408.24 |
| 1-[5-(2,3-Dimethoxy-benzyl)-hexahydro-pyrrolo[3,4-c]pyrrol-2-yl]-2-(2,5-dimethyl-phenyl)-ethanone | 1.59 | 408.24 |
| 1-[5-(2,4-Dimethyl-benzyl)-hexahydro-pyrrolo[3,4-c]pyrrol-2-yl]-2-(2,5-dimethyl-phenyl)-ethanone | 1.7 | 376.25 |
| 1-[5-(2-Chloro-3,4-dimethoxy-benzyl)-hexahydro-pyrrolo[3,4-c]pyrrol-2-yl]-2-(2,5-dimethyl-phenyl)-ethanone | 1.63 | 442.2 |
| 1-[5-(2,4-Dimethoxy-benzyl)-hexahydro-pyrrolo[3,4-c]pyrrol-2-yl]-2-naphthalen-1-yl-ethanone | 1.65 | 430.23 |
| 1-[5-(2,3-Dimethoxy-benzyl)-hexahydro-pyrrolo[3,4-c]pyrrol-2-yl]-2-naphthalen-1-yl-ethanone | 1.63 | 430.23 |
| 1-[5-(2,4-Dimethyl-benzyl)-hexahydro-pyrrolo[3,4-c]pyrrol-2-yl]-2-naphthalen-1-yl-ethanone | 1.73 | 398.24 |
| 1-[5-(2-Chloro-3,4-dimethoxy-benzyl)-hexahydro-pyrrolo[3,4-c]pyrrol-2-yl]-2-naphthalen-1-yl-ethanone | 1.66 | 464.19 |
| 1-[5-(2,4-Dimethoxy-benzyl)-hexahydro-pyrrolo[3,4-c]pyrrol-2-yl]-2-(2,3,6-trifluoro-phenyl)-ethanone | 1.51 | 434.18 |
| 1-[5-(2,3-Dimethoxy-benzyl)-hexahydro-pyrrolo[3,4-c]pyrrol-2-yl]-2-(2,3,6-trifluoro-phenyl)-ethanone | 1.48 | 434.18 |
| 1-[5-(2,4-Dimethyl-benzyl)-hexahydro-pyrrolo[3,4-c]pyrrol-2-yl]-2-(2,3,6-trifluoro-phenyl)-ethanone | 1.6 | 402.19 |
| 1-[5-(2-Chloro-3,4-dimethoxy-benzyl)-hexahydro-pyrrolo[3,4-c]pyrrol-2-yl]-2-(2,3,6-trifluoro-phenyl)-ethanone | 1.52 | 468.14 |
| 1-[5-(2,4-Dimethoxy-benzyl)-hexahydro-pyrrolo-[3,4-c]pyrrol-2-yl]-2-phenyl-ethanone | 1.4 | 380.21 |
| 1-[5-(2,3-Dimethoxy-benzyl)-hexahydro-pyrrolo-[3,4-c]pyrrol-2-yl]-2-phenyl-ethanone | 1.36 | 380.21 |
| 1-[5-(2,4-Dimethyl-benzyl)-hexahydro-pyrrolo-[3,4-c]pyrrol-2-yl]-2-phenyl-ethanone | 1.5 | 348.22 |
| 1-[5-(2-Chloro-3,4-dimethoxy-benzyl)-hexahydro-pyrrolo[3,4-c]pyrrol-2-yl]-2-phenyl-ethanone | 1.42 | 414.17 |
| 1-[5-(2,4-Dimethoxy-benzyl)-hexahydro-pyrrolo[3,4-c]pyrrol-2-yl]-2-(3,5-dimethyl-phenyl)-ethanone | 1.65 | 408.24 |
| 1-[5-(2,3-Dimethoxy-benzyl)-hexahydro-pyrrolo[3,4-c]pyrrol-2-yl]-2-(3,5-dimethyl-phenyl)-ethanone | 1.61 | 408.24 |
| 1-[5-(2,4-Dimethyl-benzyl)-hexahydro-pyrrolo[3,4-c]pyrrol-2-yl]-2-(3,5-dimethyl-phenyl)-ethanone | 1.68 | 376.25 |
| 1-[5-(2-Chloro-3,4-dimethoxy-benzyl)-hexahydro-pyrrolo[3,4-c]pyrrol-2-yl]-2-(3,5-dimethyl-phenyl)-ethanone | 1.65 | 442.2 |
| 1-[5-(2,4-Dimethoxy-benzyl)-hexahydro-pyrrolo[3,4-c]pyrrol-2-yl]-2-(2,4-dimethyl-phenyl)-ethanone | 1.63 | 408.24 |
| 1-[5-(2,3-Dimethoxy-benzyl)-hexahydro-pyrrolo[3,4-c]pyrrol-2-yl]-2-(2,4-dimethyl-phenyl)-ethanone | 1.59 | 408.24 |
| 1-[5-(2,4-Dimethyl-benzyl)-hexahydro-pyrrolo[3,4-c]pyrrol-2-yl]-2-(2,4-dimethyl-phenyl)-ethanone | 1.7 | 376.25 |
| 1-[5-(2-Chloro-3,4-dimethoxy-benzyl)-hexahydro-pyrrolo[3,4-c]pyrrol-2-yl]-2-(2,4-dimethyl-phenyl)-ethanone | 1.63 | 442.2 |
| 5-[5-(2,4-Difluoro-benzyl)-hexahydro-pyrrolo[3,4-c]pyrrole-2-carbonyl]-pyrrolidin-2-one | 0.79 | 349.16 |
| 5-[5-(2,3-Difluoro-benzyl)-hexahydro-pyrrolo[3,4-c]pyrrole-2-carbonyl]-pyrrolidin-2-one | 0.8 | 349.16 |
| 5-[5-(2,5-Difluoro-benzyl)-hexahydro-pyrrolo[3,4-c]pyrrole-2-carbonyl]-pyrrolidin-2-one | 0.75 | 349.16 |

TABLE 1-continued

| Compound Name | Time (mins) | MW (found) |
|---|---|---|
| 5-[5-(3,5-Difluoro-benzyl)-hexahydro-pyrrolo[3,4-c]pyrrole-2-carbonyl]-pyrrolidin-2-one | 0.86 | 349.16 |
| N-{2-[5-(2,4-Difluoro-benzyl)-hexahydro-pyrrolo[3,4-c]pyrrole-2-carbonyl]-cyclohexyl}-benzamide | 1.55 | 467.24 |
| N-{2-[5-(2,3-Difluoro-benzyl)-hexahydro-pyrrolo[3,4-c]pyrrole-2-carbonyl]-cyclohexyl}-benzamide | 1.56 | 467.24 |
| N-{2-[5-(2,5-Difluoro-benzyl)-hexahydro-pyrrolo[3,4-c]pyrrole-2-carbonyl]-cyclohexyl}-benzamide | 1.53 | 467.24 |
| N-{2-[5-(3,5-Difluoro-benzyl)-hexahydro-pyrrolo[3,4-c]pyrrole-2-carbonyl]-cyclohexyl}-benzamide | 1.62 | 467.24 |
| [1-(3,5-Bis-trifluoromethyl-phenyl)-5-methyl-1H-pyrazol-4-yl]-[5-(2-methyl-benzoyl)-hexahydro-pyrrolo-[3,4-c]pyrrol-2-yl]-methanone | 2.6 | 551.2 |
| {5-[1-(3,5-Bis-trifluoromethyl-phenyl)-5-methyl-1H-pyrazole-4-carbonyl]-hexahydro-pyrrolo[3,4-c]pyrrol-2-yl}-(2,6-dichloro-phenyl)-methanone | 2.7 | 604.9 |
| [1-(3,5-Bis-trifluoromethyl-phenyl)-5-methyl-1H-pyrazol-4-yl]-[5-(3-trifluoromethyl-benzoyl)-hexahydro-pyrrolo[3,4-c]pyrrol-2-yl]-methanone | 2.8 | 605.2 |
| [1-(3,5-Bis-trifluoromethyl-phenyl)-5-methyl-1H-pyrazol-4-yl]-[5-(2-chloro-benzyl)-hexahydro-pyrrolo-[3,4-c]pyrrol-2-yl]-methanone | 2.3 | 557.2 |
| [1-(3,5-Bis-trifluoromethyl-phenyl)-5-methyl-1H-pyrazol-4-yl]-[5-(3,4-dichloro-benzyl)-hexahydro-pyrrolo-[3,4-c]pyrrol-2-yl]-methanone | 2.5 | 591.1 |
| [1-(3,5-Bis-trifluoromethyl-phenyl)-5-methyl-1H-pyrazol-4-yl]-[5-(2-chloro-6-fluoro-benzyl)-hexahydro-pyrrolo[3,4-c]pyrrol-2-yl]-methanone | 2.3 | 575.2 |
| [1-(3,5-Bis-trifluoromethyl-phenyl)-5-methyl-1H-pyrazol-4-yl]-[5-(2,4-difluoro-benzyl)-hexahydro-pyrrolo[3,4-c]pyrrol-2-yl]-methanone | 2.3 | 559.2 |
| [1-(3,5-Bis-trifluoromethyl-phenyl)-5-methyl-1H-pyrazol-4-yl]-[5-(2,6-difluoro-benzyl)-hexahydro-pyrrolo[3,4-c]pyrrol-2-yl]-methanone | 2.3 | 559.2 |
| [1-(3,5-Bis-trifluoromethyl-phenyl)-5-methyl-1H-pyrazol-4-yl]-[5-(3-chloro-benzyl)-hexahydro-pyrrolo-[3,4-c]pyrrol-2-yl]-methanone | 2.4 | 557.2 |
| [1-(3,5-Bis-trifluoromethyl-phenyl)-5-methyl-1H-pyrazol-4-yl]-[5-(3-fluoro-benzyl)-hexahydro-pyrrolo-[3,4-c]pyrrol-2-yl]-methanone | 2.3 | 541.2 |
| [1-(3,5-Bis-trifluoromethyl-phenyl)-5-methyl-1H-pyrazol-4-yl]-[5-(2,3,4-trifluoro-benzyl)-hexahydro-pyrrolo[3,4-c]pyrrol-2-yl]-methanone | 2.4 | 577.2 |
| [1-(3,5-Bis-trifluoromethyl-phenyl)-5-methyl-1H-pyrazol-4-yl]-[5-(3-chloro-4-fluoro-benzyl)-hexahydro-pyrrolo[3,4-c]pyrrol-2-yl]-methanone | 2.5 | 575.1 |
| [1-(3,5-Bis-trifluoromethyl-phenyl)-5-methyl-1H-pyrazol-4-yl]-[5-(2-chloro-4-fluoro-benzyl)-hexahydro-pyrrolo[3,4-c]pyrrol-2-yl]-methanone | 2.4 | 575.1 |
| [1-(3,5-Bis-trifluoromethyl-phenyl)-5-methyl-1H-pyrazol-4-yl]-[5-(2-fluoro-benzyl)-hexahydro-pyrrolo-[3,4-c]pyrrol-2-yl]-methanone | 2.3 | 541.2 |
| [1-(3,5-Bis-trifluoromethyl-phenyl)-5-methyl-1H-pyrazol-4-yl]-[5-(4-chloro-benzyl)-hexahydro-pyrrolo-[3,4-c]pyrrol-2-yl]-methanone | 2.4 | 557.1 |
| [1-(3,5-Bis-trifluoromethyl-phenyl)-5-methyl-1H-pyrazol-4-yl]-[5-(2,4-dichloro-benzyl)-hexahydro-pyrrolo[3,4-c]pyrrol-2-yl]-methanone | 2.5 | 591.1 |
| [1-(3,5-Bis-trifluoromethyl-phenyl)-5-methyl-1H-pyrazol-4-yl]-[5-(2,3,6-trichloro-benzyl)-hexahydro-pyrrolo[3,4-c]pyrrol-2-yl]-methanone | 2.6 | 625.1 |
| [1-(3,5-Bis-trifluoromethyl-phenyl)-5-methyl-1H-pyrazol-4-yl]-[5-(2,3,5-trichloro-benzyl)-hexahydro-pyrrolo[3,4-c]pyrrol-2-yl]-methanone | 2.9 | 627.1 |
| [1(3,5-Bis-trifluoromethyl-phenyl)-5-methyl-1H-pyrazol-4-yl]-[5-(2,6-dichloro-benzyl)-hexahydro-pyrrolo[3,4-c]pyrrol-2-yl]-methanone | 2.4 | 591.1 |
| [1(3,5-Bis-trifluoromethyl-phenyl)-5-methyl-1H-pyrazol-4-yl]-[5-(2,5-difluoro-benzyl)-hexahydro-pyrrolo[3,4-c]pyrrol-2-yl]-methanone | 2.4 | 559.2 |
| [1-(3,5-Bis-trifluoromethyl-phenyl)-5-methyl-1H-pyrazol-4-yl]-[5-(2,3,6-trifluoro-benzyl)-hexahydro-pyrrolo[3,4-c]pyrrol-2-yl]-methanone | 2.3 | 577.1 |
| (1-(3,5-Bis-trifluoromethyl-phenyl)-5-methyl-1H-pyrazol-4-yl]-[5-(2,4,5-trifluoro-benzyl)-hexahydro-pyrrolo[3,4-c]pyrrol-2-yl]-methanone | 2.4 | 577.2 |
| [1-(3,5-Bis-trifluoromethyl-phenyl)-5-methyl-1H-pyrazol-4-yl]-[5-(4-fluoro-benzyl)-hexahydro-pyrrolo-[3,4-c]pyrrol-2-yl]-methanone | 2.3 | 541.2 |
| [1-(3,5-Bis-trifluoromethyl-phenyl)-5-methyl-1H-pyrazol-4-yl]-[5-(3,5-dichloro-benzyl)-hexahydro-pyrrolo-[3,4-c]pyrrol-2-yl]-methanone | 2.5 | 591.1 |
| [1-(3,5-Bis-trifluoromethyl-phenyl)-5-methyl-1H-pyrazol-4-yl]-[5-(3,4-difluoro-benzyl)-hexahydro-pyrrolo-[3,4-c]pyrrol-2-yl]-methanone | 2.4 | 559.2 |
| [1-(3,5-Bis-trifluoromethyl-phenyl)-5-methyl-1H-pyrazol-4-yl]-[5-(2,3-dichloro-benzyl)-hexahydro-pyrrolo-[3,4-c]pyrrol-2-yl]-methanone | 2.5 | 591.1 |
| [1-(3,5-Bis-trifluoromethyl-phenyl)-5-methyl-1H-pyrazol-4-yl]-[5-(2,3-difluoro-benzyl)-hexahydro-pyrrolo-[3,4-c]pyrrol-2-yl]-methanone | 2.3 | 559.2 |
| [5-(2-Chloro-benzyl)-hexahydro-pyrrolo-[3,4-c]pyrrol-2-yl]-[1-(3,4-dichloro-phenyl)-5-methyl-1H-pyrazol-4-yl]-methanone | 2.2 | 491.1 |
| [5-(3,4-Dichloro-benzyl)-hexahydro-pyrrolo-[3,4-c]pyrrol-2-yl]-[1-(3,4-dichloro-phenyl)-5-methyl-1H-pyrazol-4-yl]-methanone | 2.4 | 525 |
| [5-(2-Chloro-6-fluoro-benzyl)-hexahydro-pyrrolo[3,4-c]pyrrol-2-yl]-[1-(3,4-dichloro-phenyl)-5-methyl-1H-pyrazol-4-yl]-methanone | 2.1 | 509 |

TABLE 1-continued

| Compound Name | Time (mins) | MW (found) |
|---|---|---|
| [1-(3,4-Dichloro-phenyl)-5-methyl-1H-pyrazol-4-yl]-[5-(2,4-difluoro-benzyl)-hexahydro-pyrrolo[3,4-c]-pyrrol-2-yl]-methanone | 2.1 | 491.1 |
| [1-(3,4-Dichloro-phenyl)-5-methyl-1H-pyrazol-4-yl]-[5-(2,6-difluoro-benzyl)-hexahydro-pyrrolo[3,4-c]-pyrrol-2-yl]-methanone | 2.1 | 491.1 |
| [5-(3-Chloro-benzyl)-hexahydro-pyrrolo-[3,4-c]pyrrol-2-yl]-[1-(3,4-dichloro-phenyl)-5-methyl-1H-pyrazol-4-yl]-methanone | 2.3 | 491.1 |
| [1-(3,4-Dichloro-phenyl)-5-methyl-1H-pyrazol-4-yl]-[5-(3-fluoro-benzyl)-hexahydro-pyrrolo[3,4-c]-pyrrol-2-yl]-methanone | 2.1 | 473.1 |
| [1-(3,4-Dichloro-phenyl)-5-methyl-1H-pyrazol-4-yl]-[5-(2,3,4-trifluoro-benzyl)-hexahydro-pyrrolo-[3,4-c]pyrrol-2-yl]-methanone | 2.2 | 509.1 |
| [5-(3-Chloro-4-fluoro-benzyl)-hexahydro-pyrrolo[3,4-c]pyrrol-2-yl]-[1-(3,4-dichloro-phenyl)-5-methyl-1H-pyrazol-4-yl]-methanone | 2.3 | 507.1 |
| [5-(2-Chloro-4-fluoro-benzyl)-hexahydro-pyrrolo[3,4-c]pyrrol-2-yl]-[1-(3,4-dichloro-phenyl)-5-methyl-1H-pyrazol-4-yl]-methanone | 2.2 | 507.1 |
| [1-(3,4-Dichloro-phenyl)-5-methyl-1H-pyrazol-4-yl]-[5-(2-fluoro-benzyl)-hexahydro-pyrrolo[3,4-c]-pyrrol-2-yl]-methanone | 2.1 | 473.1 |
| [5-(4-Chloro-benzyl)-hexahydro-pyrrolo[3,4-c]pyrrol-2-yl]-[1-(3,4-dichloro-phenyl)-5-methyl-1H-pyrazol-4-yl]-methanone | 2.3 | 491.1 |
| [5-(2,4-Dichloro-benzyl)-hexahydro-pyrrolo[3,4-c]pyrrol-2-yl]-[1-(3,4-dichloro-phenyl)-5-methyl-1H-pyrazol-4-yl]-methanone | 2.3 | 525.1 |
| [1-(3,4-Dichloro-phenyl)-5-methyl-1H-pyrazol-4-yl]-[5-(2,3,6-trichloro-benzyl)-hexahydro-pyrrolo-[3,4-c]pyrrol-2-yl]-methanone | 2.4 | 559 |
| [1-(3,4-Dichloro-phenyl)-5-methyl-1H-pyrazol-4-yl]-[5-(2,3,5-trichloro-benzyl)-hexahydro-pyrrolo-[3,4-c]pyrrol-2-yl]-methanone | 2.5 | 559 |
| [5-(2,6-Dichloro-benzyl)-hexahydro-pyrrolo[3,4-c]pyrrol-2-yl]-[1-(3,4-dichloro-phenyl)-5-methyl-1H-pyrazol-4-yl]-methanone | 2.2 | 525.1 |
| [1-(3,4-Dichloro-phenyl)-5-methyl-1H-pyrazol-4-yl]-[5-(2,5-difluoro-benzyl)-hexahydro-pyrrolo[3,4-c]-pyrrol-2-yl]-methanone | 2.1 | 491.1 |
| [1-(3,4-Dichloro-phenyl)-5-methyl-1H-pyrazol-4-yl]-[5-(2,3,6-trifluoro-benzyl)-hexahydro-pyrrolo-[3,4-c]pyrrol-2-yl]-methanone | 2.1 | 509.1 |
| [1-(3,4-Dichloro-phenyl)-5-methyl-1H-pyrazol-4-yl]-[5-(2,4,5-trifluoro-benzyl)-hexahydro-pyrrolo-[3,4-c]pyrrol-2-yl]-methanone | 2.2 | 509.1 |
| [1-(3,4-Dichloro-phenyl)-5-methyl-1H-pyrazol-4-yl]-[5-(4-fluoro-benzyl)-hexahydro-pyrrolo[3,4-c]-pyrrol-2-yl]-methanone | 2.1 | 473.1 |
| [5-(3,5-Dichloro-benzyl)-hexahydro-pyrrolo[3,4-c]pyrrol-2-yl]-[1-(3,4-dichloro-phenyl)-5-methyl-1H-pyrazol-4-yl]-methanone | 2.4 | 525.1 |
| [1-(3,4-Dichloro-phenyl)-5-methyl-1H-pyrazol-4-yl]-[5-(3,4-difluoro-benzyl)-hexahydro-pyrrolo[3,4-c]-pyrrol-2-yl]-methanone | 2.2 | 491.1 |
| [5-(2,3-Dichloro-benzyl)-hexahydro-pyrrolo[3,4-c]pyrrol-2-yl]-[1-(3,4-dichloro-phenyl)-5-methyl-1H-pyrazol-4-yl]-methanone | 2.3 | 525.1 |
| [1-(3,4-Dichloro-phenyl)-5-methyl-1H-pyrazol-4-yl]-[5-(2,3-difluoro-benzyl)-hexahydro-pyrrolo[3,4-c]pyrrol-2-yl]-methanone | 2.1 | 491.1 |
| [1-(3,4-Dichloro-phenyl)-5-methyl-1H-pyrazol-4-yl]-[5-(2,4-dimethyl-benzyl)-hexahydro-pyrrolo[3,4-c]pyrrol-2-yl]-methanone | 2.1 | 483.3 |
| [1-(3,5-Bis-trifluoromethyl-phenyl)-5-methyl-1H-pyrazol-4-yl]-[5-(2,4-dimethyl-benzyl)-hexahydro-pyrrolo-[3,4-c]pyrrol-2-yl]-methanone | 2.3 | 551.3 |
| 1-{5-[1-(3,5-Bis-trifluoromethyl-phenyl)-5-methyl-1H-pyrazole-4-carbonyl]-hexahydro-pyrrolo-[3,4-c]pyrrol-2-yl}-2-o-tolyl-ethanone | 2.7 | 565 |
| [1-(3,5-Bis-trifluoromethyl-phenyl)-5-methyl-1H-pyrazol-4-yl]-(5-cyclohexanecarbonyl-hexahydro-pyrrolo-[3,4-c]pyrrol-2-yl)-methanone | 2.6 | 543.2 |
| 1-{5-[1-(3,5-Bis-trifluoromethyl-phenyl)-5-methyl-1H-pyrazole-4-carbonyl]-hexahydro-pyrrolo-[3,4-c]pyrrol-2-yl}-butan-1-one | 2.4 | 503.2 |
| [5-(2,4-Difluoro-benzyl)-hexahydro-pyrrolo[3,4-c]pyrrol-2-yl]-(2-ethoxy-phenyl)-methanone | 1.35 | 386.18 |
| [5-(2,3-Difluoro-benzyl)-hexahydro-pyrrolo[3,4-c]pyrrol-2-yl]-(2-ethoxy-phenyl)-methanone | 1.37 | 386.18 |
| [5-(3,5-Difluoro-benzyl)-hexahydro-pyrrolo[3,4-c]pyrrol-2-yl]-(2-ethoxy-phenyl)-methanone | 1.4 | 386.18 |
| [5-(2,4-Difluoro-benzyl)-hexahydro-pyrrolo[3,4-c]pyrrol-2-yl]-(2-trifluoromethyl-phenyl)-methanone | 1.41 | 410.14 |
| [5-(2,3-Difluoro-benzyl)-hexahydro-pyrrolo[3,4-c]pyrrol-2-yl]-(2-trifluoromethyl-phenyl)-methanone | 1.43 | 410.14 |
| [5-(2,5-Difluoro-benzyl)-hexahydro-pyrrolo[3,4-c]pyrrol-2-yl]-(2-trifluoromethyl-phenyl)-methanone | 1.4 | 410.14 |
| [5-(3,5-Difluoro-benzyl)-hexahydro-pyrrolo[3,4-c]pyrrol-2-yl]-(2-trifluoromethyl-phenyl)-methanone | 1.47 | 410.14 |
| [5-(2,4-Difluoro-benzyl)-hexahydro-pyrrolo[3,4-c]pyrrol-2-yl]-(fluoro-4-trifluoromethyl-phenyl)-methanone | 1.6 | 428.13 |
| [5-(2,3-Difluoro-benzyl)-hexahydro-pyrrolo[3,4-c]pyrrol-2-yl]-(2-fluoro-4-trifluoromethyl-phenyl)-methanone | 1.63 | 428.13 |
| [5-(3,5-Difluoro-benzyl)-hexahydro-pyrrolo[3,4-c]pyrrol-2-yl]-(2-fluoro-4-trifluoromethyl-phenyl)-methanone | 1.67 | 428.13 |
| (2,5-Bis-trifluoromethyl-phenyl)-[5-(2,4-difluoro-benzyl)-hexahydro-pyrrolo[3,4-c]-pyrrol-2-yl]-methanone | 1.68 | 478.13 |
| (2,5-Bis-trifluoromethyl-phenyl)-[5-(2,3-difluoro-benzyl)-hexahydro-pyrrolo[3,4-c]-pyrrol-2-yl]-methanone | 1.72 | 478.13 |
| 2,5-Bis-trifluoromethyl-phenyl)-[5-(2,5-difluoro-benzyl)-hexahydro-pyrrolo[3,4-c]pyrrol-2-yl]-methanone | 1.7 | 478.13 |
| (2,5-Bis-trifluoromethyl-phenyl)-[5-(3,5-difluoro-benzyl)-hexahydro-pyrrolo[3,4-c]-pyrrol-2-yl]-methanone | 1.76 | 478.13 |

TABLE 1-continued

| Compound Name | Time (mins) | MW (found) |
|---|---|---|
| [5-(2,4-Difluoro-benzyl)-hexahydro-pyrrolo[3,4-c]pyrrol-2-yl]-(2,3,4-trifluoro-phenyl)-methanone | 1.42 | 396.13 |
| [5-(2,3-Difluoro-benzyl)-hexahydro-pyrrolo[3,4-c]pyrrol-2-yl]-(2,3,4-trifluoro-phenyl)-methanone | 1.45 | 396.13 |
| [5-(3,5-Difluoro-benzyl)-hexahydro-pyrrolo[3,4-c]pyrrol-2-yl]-(2,3,4-trifluoro-phenyl)-methanone | 1.48 | 396.13 |
| [5-(2,4-Difluoro-benzyl)-hexahydro-pyrrolo[3,4-c]pyrrol-2-yl]-(2-fluoro-3-trifluoromethyl-phenyl)-methanone | 1.58 | 428.13 |
| [5-(2,3-Difluoro-benzyl)-hexahydro-pyrrolo[3,4-c]pyrrol-2-yl]-(2-fluoro-3-trifluoromethyl-phenyl)-methanone | 1.6 | 428.13 |
| [5-(3,5-Difluoro-benzyl)-hexahydro-pyrrolo[3,4-c]pyrrol-2-yl]-(2-fluoro-3-trifluoromethyl-phenyl)-methanone | 1.65 | 428.13 |
| (2,4-Bis-trifluoromethyl-phenyl)-[5-(2,4-difluoro-benzyl)-hexahydro-pyrrolo[3,4-c]pyrrol-2-yl]-methanone | 1.75 | 478.13 |
| (2,4-Bis-trifluoromethyl-phenyl)-[5-(2,3-difluoro-benzyl)-hexahydro-pyrrolo[3,4-c]pyrrol-2-yl]-methanone | 1.79 | 478.13 |
| (2,4-Bis-trifluoromethyl-phenyl)-[5-(2,5-difluoro-benzyl)-hexahydro-pyrrolo[3,4-c]pyrrol-2-yl]-methanone | 1.78 | 478.13 |
| (2,4-Bis-trifluoromethyl-phenyl)-[5-(3,5-difluoro-benzyl)-hexahydro-pyrrolo[3,4-c]pyrrol-2-yl]-methanone | 1.83 | 478.13 |
| [5-(2,4-Difluoro-benzyl)-hexahydro-pyrrolo[3,4-c]pyrrol-2-yl]-(4-fluoro-2-trifluoromethyl-phenyl)-methanone | 1.49 | 428.13 |
| [5-(2,3-Difluoro-benzyl)-hexahydro-pyrrolo[3,4-c]pyrrol-2-yl]-(4-fluoro-2-trifluoromethyl-phenyl)-methanone | 1.51 | 428.13 |
| [5-(2,5-Difluoro-benzyl)-hexahydro-pyrrolo[3,4-c]pyrrol-2-yl]-(4-fluoro-2-trifluoromethyl-phenyl)-methanone | 1.48 | 428.13 |
| [5-(3,5-Difluoro-benzyl)-hexahydro-pyrrolo[3,4-c]pyrrol-2-yl]-(4-fluoro-2-trifluoromethyl-phenyl)-methanone | 1.55 | 428.13 |
| [5-(2,4-Difluoro-benzyl)-hexahydro-pyrrolo[3,4-c]pyrrol-2-yl]-(2-trifluoromethoxy-phenyl)-methanone | 1.48 | 426.14 |
| [5-(2,3-Difluoro-benzyl)-hexahydro-pyrrolo[3,4-c]pyrrol-2-yl]-(2-trifluoromethoxy-phenyl)-methanone | 1.51 | 426.14 |
| [5-(3,5-Difluoro-benzyl)-hexahydro-pyrrolo[3,4-c]pyrrol-2-yl]-(2-trifluoromethoxy-phenyl)-methanone | 1.55 | 426.14 |
| (2-Chloro-3-trifluoromethyl-phenyl)-[5-(2,4-difluoro-benzyl)-hexahydro-pyrrolo[3,4-c]pyrrol-2-yl]-methanone | 1.62 | 444.1 |
| (2-Chloro-3-trifluoromethyl-phenyl)-[5-(2,3-difluoro-benzyl)-hexahydro-pyrrolo[3,4-c]pyrrol-2-yl]-methanone | 1.65 | 444.1 |
| (2-Chloro-3-trifluoromethyl-phenyl)-[5-(3,5-difluoro-benzyl)-hexahydro-pyrrolo[3,4-c]pyrrol-2-yl]-methanone | 1.68 | 444.1 |
| [5-(2,4-Difluoro-benzyl)-hexahydro-pyrrolo[3,4-c]pyrrol-2-yl]-(2-difluoromethoxy-phenyl)-methanone | 1.37 | 408.15 |
| [5-(2,3-Difluoro-benzyl)-hexahydro-pyrrolo[3,4-c]pyrrol-2-yl]-(2-difluoromethoxy-phenyl)-methanone | 1.38 | 408.15 |
| [5-(3,5-Difluoro-benzyl)-hexahydro-pyrrolo[3,4-c]pyrrol-2-yl]-(2-difluoromethoxy-phenyl)-methanone | 1.42 | 408.15 |
| [5-(2,3-Dimethoxy-benzyl)-hexahydro-pyrrolo[3,4-c]pyrrol-2-yl]-(2-ethoxy-phenyl)-methanone | 1.4 | 410.22 |
| [5-(2,4-Dimethyl-benzyl)-hexahydro-pyrrolo[3,4-c]pyrrol-2-yl]-(2-ethoxy-phenyl)-methanone | 1.52 | 378.23 |
| [5-(2-Chloro-3,4-dimethoxy-benzyl)-hexahydro-pyrrolo[3,4-c]pyrrol-2-yl]-(2-ethoxy-phenyl)-methanone | 1.45 | 444.18 |
| [5-(2,3-Dimethoxy-benzyl)-hexahydro-pyrrolo[3,4-c]pyrrol-2-yl]-(2-trifluoromethyl-phenyl)-methanone | 1.45 | 434.18 |
| [5-(2,4-Dimethyl-benzyl)-hexahydro-pyrrolo[3,4-c]pyrrol-2-yl]-(2-trifluoromethyl-phenyl)-methanone | 1.55 | 402.19 |
| [5-(2-Chloro-3,4-dimethoxy-benzyl)-hexahydro-pyrrolo[3,4-c]pyrrol-2-yl]-(2-trifluoromethyl-phenyl)-methanone | 1.5 | 468.14 |
| [5-(2,4-Dimethoxy-benzyl)-hexahydro-pyrrolo[3,4-c]pyrrol-2-yl]-(2-fluoro-4-trifluoromethyl-phenyl)-methanone | 1.65 | 452.17 |
| [5-(2,3-Dimethoxy-benzyl)-hexahydro-pyrrolo[3,4-c]pyrrol-2-yl]-(2-fluoro-4-trifluoromethyl-phenyl)-methanone | 1.62 | 452.17 |
| [5-(2,4-Dimethyl-benzyl)-hexahydro-pyrrolo[3,4-c]pyrrol-2-yl]-(2-fluoro-4-trifluoromethyl-phenyl)-methanone | 1.74 | 420.18 |
| [5-(2-Chloro-3,4-dimethoxy-benzyl)-hexahydro-pyrrolo[3,4-c]pyrrol-2-yl]-(2-fluoro-4-trifluoromethyl-phenyl)-methanone | 1.68 | 486.13 |
| (2,5-Bis-trifluoromethyl-phenyl)-[5-(2,4-dimethoxy-benzyl)-hexahydro-pyrrolo[3,4-c]pyrrol-2-yl]-methanone | 1.73 | 502.17 |
| (2,5-Bis-trifluoromethyl-phenyl)-[5-(2,3-dimethoxy-benzyl)-hexahydro-pyrrolo[3,4-c]pyrrol-2-yl]-methanone | 1.7 | 502.17 |
| (2,5-Bis-trifluoromethyl-phenyl)-[5-(2,4-dimethyl-benzyl)-hexahydro-pyrrolo[3,4-c]pyrrol-2-yl]-methanone | 1.82 | 470.18 |
| (2,5-Bis-trifluoromethyl-phenyl)-[5-(2-chloro-3,4-dimethoxy-benzyl)-hexahydro-pyrrolo[3,4-c]pyrrol-2-yl]-methanone | 1.74 | 536.13 |
| [5-(2,4-Dimethoxy-benzyl)-hexahydro-pyrrolo[3,4-c]pyrrol-2-yl]-(2,3,4-trifluoro-phenyl)-methanone | 1.5 | 420.17 |
| [5-(2,3-Dimethoxy-benzyl)-hexahydro-pyrrolo[3,4-c]pyrrol-2-yl]-(2,3,4-trifluoro-phenyl)-methanone | 1.46 | 420.17 |
| [5-(2,4-Dimethyl-benzyl)-hexahydro-pyrrolo[3,4-c]pyrrol-2-yl]-(2,3,4-trifluoro-phenyl)-methanone | 1.59 | 388.18 |
| [5-(2-Chloro-3,4-dimethoxy-benzyl)-hexahydro-pyrrolo[3,4-c]pyrrol-2-yl]-(2,3,4-trifluoro-phenyl)-methanone | 1.51 | 454.13 |
| [5-(2,4-Dimethoxy-benzyl)-hexahydro-pyrrolo[3,4-c]pyrrol-2-yl]-(2-fluoro-3-trifluoromethyl-phenyl)-methanone | 1.63 | 452.17 |
| [5-(2,3-Dimethoxy-benzyl)-hexahydro-pyrrolo[3,4-c]pyrrol-2-yl]-(2-fluoro-3-trifluoromethyl-phenyl)-methanone | 1.61 | 452.17 |
| [5-(2,4-Dimethyl-benzyl)-hexahydro-pyrrolo[3,4-c]pyrrol-2-yl]-(2-fluoro-3-trifluoromethyl-phenyl)-methanone | 1.73 | 420.18 |
| [5-(2-Chloro-3,4-dimethoxy-benzyl)-hexahydro-pyrrolo[3,4-c]pyrrol-2-yl]-(2-fluoro-3-trifluoromethyl-phenyl)-methanone | 1.65 | 486.13 |

TABLE 1-continued

| Compound Name | Time (mins) | MW (found) |
|---|---|---|
| (2,4-Bis-trifluoromethyl-phenyl)-[5-(2,4-dimethoxy-benzyl)-hexahydro-pyrrolo[3,4-c]-pyrrol-2-yl]-methanone | 1.79 | 502.17 |
| (2,4-Bis-trifluoromethyl-phenyl)-[5-(2,3-dimethoxy-benzyl)-hexahydro-pyrrolo[3,4-c]-pyrrol-2-yl]-methanone | 1.77 | 502.17 |
| (2,4-Bis-trifluoromethyl-phenyl)-[5-(2,4-dimethyl-benzyl)-hexahydro-pyrrolo[3,4-c]-pyrrol-2-yl]-methanone | 1.87 | 470.18 |
| (2,4-Bis-trifluoromethyl-phenyl)-[5-(2-chloro-3,4-dimethoxy-benzyl)-hexahydro-pyrrolo[3,4-c]-pyrrol-2-yl]-methanone | 1.8 | 536.13 |
| [5-(2,4-Dimethoxy-benzyl)-hexahydro-pyrrolo[3,4-c]pyrrol-2-yl]-(4-fluoro-2-trifluoromethyl-phenyl)-methanone | 1.54 | 452.17 |
| [5-(2,3-Dimethoxy-benzyl)-hexahydro-pyrrolo[3,4-c]pyrrol-2-yl]-(4-fluoro-2-trifluoromethyl-phenyl)-methanone | 1.52 | 452.17 |
| 5-(2,4-Dimethyl-benzyl)-hexahydro-pyrrolo-[3,4-c]pyrrol-2-yl]-(4-fluoro-2-trifluoromethyl-phenyl)-methanone | 1.65 | 420.18 |
| [5-(2-Chloro-3,4-dimethoxy-benzyl)-hexahydro-pyrrolo[3,4-c]pyrrol-2-yl]-(4-fluoro-2-trifluoromethyl-phenyl)-methanone | 1.57 | 486.13 |
| [5-(2,4-Dimethoxy-benzyl)-hexahydro-pyrrolo[3,4-c]pyrrol-2-yl]-(2-trifluoromethoxy-phenyl)-methanone | 1.55 | 450.18 |
| [5-(2,3-Dimethoxy-benzyl)-hexahydro-pyrrolo[3,4-c]pyrrol-2-yl]-(2-trifluoromethoxy-phenyl)-methanone | 1.51 | 450.18 |
| [5-(2,4-Dimethyl-benzyl)-hexahydro-pyrrolo[3,4-c]pyrrol-2-yl]-(2-trifluoromethoxy-phenyl)-methanone | 1.64 | 418.19 |
| [5-(2-Chloro-3,4-dimethoxy-benzyl)-hexahydro-pyrrolo[3,4-c]pyrrol-2-yl]-(2-trifluoromethoxy-phenyl)-methanone | 1.56 | 484.14 |
| (2-Chloro-3-trifluoromethyl-phenyl)-[5-(2,4-dimethoxy-benzyl)-hexahydro-pyrrolo[3,4-c]pyrrol-2-yl]-methanone | 1.66 | 468.14 |
| (2-Chloro-3-trifluoromethyl-phenyl)-[5-(2,3-dimethoxy-benzyl-hexahydro-pyrrolo[3,4-c]pyrrol-2-yl]-methanone | 1.64 | 468.14 |
| (2-Chloro-3-trifluoromethyl-phenyl)-[5-(2,4-dimethyl-benzyl)-hexahydro-pyrrolo[3,4-c]-pyrrol-2-yl]-methanone | 1.76 | 436.15 |
| [5-(2-Chloro-3,4-dimethoxy-benzyl)-hexahydro-pyrrolo[3,4-c]-pyrrol-2-yl]-(2-chloro-3-trifluoromethyl-phenyl)-methanone | 1.67 | 502.1 |
| (2-Difluoromethoxy-phenyl)-[5-(2,4-dimethoxy-benzyl)-hexahydro-pyrrolo[3,4-c]pyrrol-2-yl]-methanone | 1.44 | 432.19 |
| (2-Difluoromethoxy-phenyl)-[5-(2,3-dimethoxy-benzyl)-hexahydro-pyrrolo[3,4-c]pyrrol-2-yl]-methanone | 1.42 | 432.19 |
| (2-Difluoromethoxy-phenyl)-[5-(2,4-dimethyl-benzyl)-hexahydro-pyrrolo[3,4-c]pyrrol-2-yl]-methanone | 1.54 | 400.2 |
| [5-(2-Chloro-3,4-dimethoxy-benzyl)-hexahydro-pyrrolo[3,4-c]pyrrol-2-yl]-(2-difluoromethoxy-phenyl)-methanone | 1.46 | 466.15 |
| (2,6-Dichloro-phenyl)-[5-(2,4-difluoro-benzyl)-hexahydro-pyrrolo[3,4-c]pyrrol-2-yl]-methanone | 1.36 | 410.08 |
| (2,6-Dichloro-phenyl)-[5-(2,3-difluoro-benzyl)-hexahydro-pyrrolo[3,4-c]pyrrol-2-yl]-methanone | 1.39 | 410.08 |
| [5-(2,4-Difluoro-benzyl)-hexahydro-pyrrolo[3,4-c]pyrrol-2-yl]-(2,6-dimethyl-phenyl)-methanone | 1.38 | 370.19 |
| [5-(2,3-Difluoro-benzyl)-hexahydro-pyrrolo[3,4-c]pyrrol-2-yl]-(2,6-dimethyl-phenyl)-methanone | 1.4 | 370.19 |
| [5-(2,5-Difluoro-benzyl)-hexahydro-pyrrolo[3,4-c]pyrrol-2-yl]-(2,6-dimethyl-phenyl)-methanone | 1.37 | 370.19 |
| [5-(3,5-Difluoro-benzyl)-hexahydro-pyrrolo[3,4-c]pyrrol-2-yl]-(2,6-dimethyl-phenyl)-methanone | 1.44 | 370.19 |
| (2-Chloro-6-fluoro-phenyl)-[5-(2,4-difluoro-benzyl)-hexahydro-pyrrolo[3,4-c]pyrrol-2-yl]-methanone | 1.3 | 394.11 |
| (2-Chloro-6-fluoro-phenyl)-[5-(2,3-difluoro-benzyl)-hexahydro-pyrrolo[3,4-c]pyrrol-2-yl]-methanone | 1.34 | 394.11 |
| (2-Chloro-6-fluoro-phenyl)-[5-(3,5-difluoro-benzyl)-hexahydro-pyrrolo[3,4-c]pyrrol-2-yl]-methanone | 1.38 | 394.11 |
| [5-(2,4-Difluoro-benzyl)-hexahydro-pyrrolo[3,4-c]pyrrol-2-yl]-(2,6-difluoro-phenyl)-methanone | 1.24 | 378.14 |
| [5-(2,3-Difluoro-benzyl)-hexahydro-pyrrolo[3,4-c]pyrrol-2-yl]-(2,6-difluoro-phenyl)-methanone | 1.26 | 378.14 |
| [5-(3,5-Difluoro-benzyl)-hexahydro-pyrrolo[3,4-c]pyrrol-2-yl]-(2,6-difluoro-phenyl)-methanone | 1.3 | 378.14 |
| [5-(2,4-Difluoro-benzyl)-hexahydro-pyrrolo[3,4-c]pyrrol-2-yl]-(2,3,6-trifluoro-phenyl)-methanone | 1.33 | 396.13 |
| [5-(2,3-Difluoro-benzyl)-hexahydro-pyrrolo[3,4-c]pyrrol-2-yl]-(2,3,6-trifluoro-phenyl)-methanone | 1.35 | 396.13 |
| [5-(3,5-Difluoro-benzyl)-hexahydro-pyrrolo[3,4-c]pyrrol-2-yl]-(2,3,6-trifluoro-phenyl)-methanone | 1.4 | 396.13 |
| [5-(2,4-Difluoro-benzyl)-hexahydro-pyrrolo[3,4-c]pyrrol-2-yl]-(2-fluoro-6-trifluoromethyl-phenyl)-methanone | 1.42 | 428.13 |
| [5-(2,3-Difluoro-benzyl)-hexahydro-pyrrolo[3,4-c]pyrrol-2-yl]-(2-fluoro-6-trifluoromethyl-phenyl)-methanone | 1.45 | 428.13 |
| [5-(2,5-Difluoro-benzyl)-hexahydro-pyrrolo[3,4-c]pyrrol-2-yl]-(2-fluoro-6-trifluoromethyl-phenyl)-methanone | 1.42 | 428.13 |
| [5-(3,5-Difluoro-benzyl)-hexahydro-pyrrolo[3,4-c]pyrrol-2-yl]-(2-fluoro-6-trifluoromethyl-phenyl)-methanone | 1.49 | 428.13 |
| [5-(2,4-Difluoro-benzyl)-hexahydro-pyrrolo[3,4-c]pyrrol-2-yl]-(2,4,6-trifluoro-phenyl)-methanone | 1.31 | 396.13 |
| [5-(2,3-Difluoro-benzyl)-hexahydro-pyrrolo[3,4-c]pyrrol-2-yl]-(2,4,6-trifluoro-phenyl)-methanone | 1.34 | 396.13 |
| [5-(2,5-Difluoro-benzyl)-hexahydro-pyrrolo[3,4-c]pyrrol-2-yl]-(2,4,6-trifluoro-phenyl)-methanone | 1.28 | 396.13 |
| [5-(3,5-Difluoro-benzyl)-hexahydro-pyrrolo[3,4-c]pyrrol-2-yl]-(2,4,6-trifluoro-phenyl)-methanone | 1.38 | 396.13 |
| [5-(2,4-Difluoro-benzyl)-hexahydro-pyrrolo[3,4-c]pyrrol-2-yl]-(2,6-dimethoxy-phenyl)-methanone | 1.26 | 402.18 |
| [5-(2,3-Difluoro-benzyl)-hexahydro-pyrrolo[3,4-c]pyrrol-2-yl]-(2,6-dimethoxy-phenyl)-methanone | 1.28 | 402.18 |
| [5-(2,5-Difluoro-benzyl)-hexahydro-pyrrolo[3,4-c]pyrrol-2-yl]-(2,6-dimethoxy-phenyl)-methanone | 1.24 | 402.18 |
| [5-(3,5-Difluoro-benzyl)-hexahydro-pyrrolo[3,4-c]pyrrol-2-yl]-(2,6-dimethoxy-phenyl)-methanone | 1.31 | 402.18 |

TABLE 1-continued

| Compound Name | Time (mins) | MW (found) |
|---|---|---|
| [5-(2,4-Difluoro-benzyl)-hexahydro-pyrrolo[3,4-c]pyrrol-2-yl]-(2,3,6-trimethoxy-phenyl)-methanone | 1.31 | 432.19 |
| [5-(2,3-Difluoro-benzyl)-hexahydro-pyrrolo[3,4-c]pyrrol-2-yl]-(2,3,6-trimethoxy-phenyl)-methanone | 1.32 | 432.19 |
| [5-(2,5-Difluoro-benzyl)-hexahydro-pyrrolo[3,4-c]pyrrol-2-yl]-(2,3,6-trimethoxy-phenyl)-methanone | 1.28 | 432.19 |
| [5-(3,5-Difluoro-benzyl)-hexahydro-pyrrolo[3,4-c]pyrrol-2-yl]-(2,3,6-trimethoxy-phenyl)-methanone | 1.36 | 432.19 |
| (3-Chloro-2,6-dimethoxy-phenyl)-[5-(2,4-difluoro-benzyl)-hexahydro-pyrrolo[3,4-c]-pyrrol-2-yl]-methanone | 1.49 | 436.14 |
| (3-Chloro-2,6-dimethoxy-phenyl)-[5-(2,3-difluoro-benzyl)-hexahydro-pyrrolo[3,4-c]-pyrrol-2-yl]-methanone | 1.48 | 436.14 |
| (3-Chloro-2,6-dimethoxy-phenyl)-[5-(2,5-difluoro-benzyl)-hexahydro-pyrrolo[3,4-c]-pyrrol-2-yl]-methanone | 1.45 | 436.14 |
| (3-Chloro-2,6-dimethoxy-phenyl)-[5-(3,5-difluoro-benzyl)-hexahydro-pyrrolo[3,4-c]-pyrrol-2-yl]-methanone | 1.54 | 436.14 |
| (2,6-Dichloro-phenyl)-[5-(2,4-dimethoxy-benzyl)-hexahydro-pyrrolo[3,4-c]pyrrol-2-yl]-methanone | 1.44 | 434.12 |
| (2,6-Dichloro-phenyl)-[5-(2,3-dimethoxy-benzyl)-hexahydro-pyrrolo[3,4-c]pyrrol-2-yl]-methanone | 1.4 | 434.12 |
| [5-(2-Chloro-3,4-dimethoxy-benzyl)-hexahydro-pyrrolo[3,4-c]pyrrol-2-yl]-(2,6-dichloro-phenyl)-methanone | 1.45 | 468.08 |
| [5-(2,4-Dimethoxy-benzyl)-hexahydro-pyrrolo[3,4-c]pyrrol-2-yl]-(2,6-dimethyl-phenyl)-methanone | 1.44 | 394.23 |
| [5-(2,3-Dimethoxy-benzyl)-hexahydro-pyrrolo[3,4-c]pyrrol-2-yl]-(2,6-dimethyl-phenyl)-methanone | 1.41 | 394.23 |
| [5-(2,4-Dimethyl-benzyl)-hexahydro-pyrrolo[3,4-c]pyrrol-2-yl]-(2,6-dimethyl-phenyl)-methanone | 1.55 | 362.24 |
| [5-(2-Chloro-3,4-dimethoxy-benzyl)-hexahydro-pyrrolo[3,4-c]pyrrol-2-yl]-(2,6-dimethyl-phenyl)-methanone | 1.47 | 428.19 |
| (2-Chloro-6-fluoro-phenyl)-[5-(2,4-dimethoxy-benzyl)-hexahydro-pyrrolo[3,4-c]pyrrol-2-yl]-methanone | 1.38 | 418.15 |
| (2-Chloro-6-fluoro-phenyl)-[5-(2,3-dimethoxy-benzyl)-hexahydro-pyrrolo[3,4-c]pyrrol-2-yl]-methanone | 1.35 | 418.15 |
| (2-Chloro-6-fluoro-phenyl)-[5-(2,4-dimethyl-benzyl)-hexahydro-pyrrolo[3,4-c]pyrrol-2-yl]-methanone | 1.5 | 386.16 |
| [5-(2-Chloro-3,4-dimethoxy-benzyl)-hexahydro-pyrrolo[3,4-c]pyrrol-2-yl]-(2-chloro-6-fluoro-phenyl)-methanone | 1.41 | 452.11 |
| (2,6-Difluoro-phenyl)-[5-(2,4-dimethoxy-benzyl)-hexahydro-pyrrolo[3,4-c]pyrrol-2-yl]-methanone | 1.34 | 402.18 |
| (2,6-Difluoro-phenyl)-[5-(2,3-dimethoxy-benzyl)-hexahydro-pyrrolo[3,4-c]pyrrol-2-yl]-methanone | 1.3 | 402.18 |
| (2,6-Difluoro-phenyl)-[5-(2,4-dimethyl-benzyl)-hexahydro-pyrrolo[3,4-c]pyrrol-2-yl]-methanone | 1.45 | 370.19 |
| [5-(2-Chloro-3,4-dimethoxy-benzyl)-hexahydro-pyrrolo[3,4-c]pyrrol-2-yl]-(2,6-difluoro-phenyl)-methanone | 1.35 | 436.14 |
| [5-(2,4-Dimethoxy-benzyl)-hexahydro-pyrrolo[3,4-c]pyrrol-2-yl]-(2,3,6-trifluoro-phenyl)-methanone | 1.42 | 420.17 |
| [5-(2,3-Dimethoxy-benzyl)-hexahydro-pyrrolo[3,4-c]pyrrol-2-yl]-(2,3,6-trifluoro-phenyl)-methanone | 1.38 | 420.17 |
| [5-(2,4-Dimethoxy-benzyl)-hexahydro-pyrrolo[3,4-c]pyrrol-2-yl]-(2-fluoro-6-trifluoromethyl-phenyl)-methanone | 1.48 | 452.17 |
| [5-(2,3-Dimethoxy-benzyl)-hexahydro-pyrrolo[3,4-c]pyrrol-2-yl]-(2-fluoro-6-trifluoromethyl-phenyl)-methanone | 1.45 | 452.17 |
| [5-(2,4-Dimethyl-benzyl)-hexahydro-pyrrolo[3,4-c]pyrrol-2-yl]-(2-fluoro-6-trifluoromethyl-phenyl)-methanone | 1.61 | 420.18 |
| [5-(2-Chloro-3,4-dimethoxy-benzyl)-hexahydro-pyrrolo[3,4-c]pyrrol-2-yl]-(2-fluoro-6-trifluoromethyl-phenyl)-methanone | 1.5 | 486.13 |
| [5-(2,4-Dimethoxy-benzyl)-hexahydro-pyrrolo[3,4-c]pyrrol-2-yl]-(2,4,6-trifluoro-phenyl)-methanone | 1.4 | 420.17 |
| [5-(2,3-Dimethoxy-benzyl)-hexahydro-pyrrolo[3,4-c]pyrrol-2-yl]-(2,4,6-trifluoro-phenyl)-methanone | 1.36 | 420.17 |
| [5-(2,4-Dimethyl-benzyl)-hexahydro-pyrrolo[3,4-c]pyrrol-2-yl]-(2,4,6-trifluoro-phenyl)-methanone | 1.51 | 388.18 |
| [5-(2-Chloro-3,4-dimethoxy-benzyl)-hexahydro-pyrrolo[3,4-c]pyrrol-2-yl]-(2,4,6-trifluoro-phenyl)-methanone | 1.43 | 454.13 |
| [5-(2,4-Dimethoxy-benzyl)-hexahydro-pyrrolo[3,4-c]pyrrol-2-yl]-(2,6-dimethoxy-phenyl)-methanone | 1.34 | 426.22 |
| [5-(2,3-Dimethoxy-benzyl)-hexahydro-pyrrolo[3,4-c]pyrrol-2-yl]-(2,6-dimethoxy-phenyl)methanone | 1.31 | 426.22 |
| (2,6-Dimethoxy-phenyl)-[5-(2,4-dimethyl-benzyl)-hexahydro-pyrrolo[3,4-c]pyrrol-2-yl]-methanone | 1.44 | 394.23 |
| [5-(2-Chloro-3,4-dimethoxy-benzyl)-hexahydro-pyrrolo[3,4-c]pyrrol-2-yl]-(2,6-dimethoxy-phenyl)-methanone | 1.36 | 460.18 |
| [5-(2,4-Dimethoxy-benzyl)-hexahydro-pyrrolo[3,4-c]pyrrol-2-yl]-(2,3,6-trimethoxy-phenyl)-methanone | 1.39 | 456.23 |
| [5-(2,3-Dimethoxy-benzyl)-hexahydro-pyrrolo[3,4-c]pyrrol-2-yl]-(2,3,6-trimethoxy-phenyl)-methanone | 1.35 | 456.23 |
| [5-(2,4-Dimethyl-benzyl)-hexahydro-pyrrolo[3,4-c]pyrrol-2-yl]-(2,3,6-trimethoxy-phenyl)-methanone | 1.46 | 424.24 |
| [5-(2-Chloro-3,4-dimethoxy-benzyl)-hexahydro-pyrrolo[3,4-c]pyrrol-2-yl]-(2,3,6-trimethoxy-phenyl)-methanone | 1.4 | 490.19 |
| (3-Chloro-2,6-dimethoxy-phenyl)-[5-(2,4-dimethoxy-benzyl)-hexahydro-pyrrolo[3,4-c]-pyrrol-2-yl]-methanone | 1.56 | 460.18 |

TABLE 1-continued

| Compound Name | Time (mins) | MW (found) |
|---|---|---|
| (3-Chloro-2,6-dimethoxy-phenyl)-[5-(2,3-dimethoxy-benzyl)-hexahydro-pyrrolo[3,4-c]-pyrrol-2-yl]-methanone | 1.5 | 460.18 |
| (3-Chloro-2,6-dimethoxy-phenyl)-[5-(2,4-dimethyl-benzyl)-hexahydro-pyrrolo[3,4-c]-pyrrol-2-yl]-methanone | 1.66 | 428.19 |
| [5-(2-Chloro-3,4-dimethoxy-benzyl)-hexahydro-pyrrolo[3,4-c]pyrrol-2-yl]-(3-chloro-2,6-dimethoxy-phenyl)-methanone | 1.56 | 494.14 |
| 5-[5-(2,4-Dimethoxy-benzyl)-hexahydro-pyrrolo[3,4-c]pyrrole-2-carbonyl]-pyrrolidin-2-one | 0.92 | 373.2 |
| 5-[5-(2,3-Dimethoxy-benzyl)-hexahydro-pyrrolo[3,4-c]pyrrole-2-carbonyl]-pyrrolidin-2-one | 0.86 | 373.2 |
| 5-[5-(2,4-Dimethyl-benzyl)-hexahydro-pyrrolo[3,4-c]pyrrole-2-carbonyl]-pyrrolidin-2-one | 1.01 | 341.21 |
| 5-[5-(2-Chloro-3,4-dimethoxy-benzyl)-hexahydro-pyrrolo[3,4-c]pyrrole-2-carbonyl]-pyrrolidin-2-one | 0.93 | 407.16 |
| N-{2-[5-(2,4-Dimethoxy-benzyl)-hexahydro-pyrrolo[3,4-c]pyrrole-2-carbonyl]-cyclohexyl}-benzamide | 1.59 | 491.28 |
| N-{2-[5-(2,3-Dimethoxy-benzyl)-hexahydro-pyrrolo[3,4-c]pyrrole-2-carbonyl]-cyclohexyl}-benzamide | 1.56 | 491.28 |
| N-{2-[5-(2,4-Dimethyl-benzyl)-hexahydro-pyrrolo[3,4-c]pyrrole-2-carbonyl]-cyclohexyl}-benzamide | 1.7 | 459.29 |
| N-{2-[5-(2-Chloro-3,4-dimethoxy-benzyl)-hexahydro-pyrrolo[3,4-c]pyrrole-2-carbonyl]-cyclohexyl}-benzamide | 1.61 | 525.24 |
| 1-[5-(2,4-Difluoro-benzyl)-hexahydro-pyrrolo[3,4-c]pyrrol-2-yl]-2-o-tolyl-ethanone | 1.43 | 370.19 |
| 1-[5-(2,3-Difluoro-benzyl)-hexahydro-pyrrolo[3,4-c]pyrrol-2-yl]-2-o-tolyl-ethanone | 1.44 | 370.19 |
| 1-[5-(2,5-Difluoro-benzyl)-hexahydro-pyrrolo[3,4-c]pyrrol-2-yl]-2-o-tolyl-ethanone | 1.4 | 370.19 |
| 1-[5-(3,5-Difluoro-benzyl)-hexahydro-pyrrolo[3,4-c]pyrrol-2-yl]-2-o-tolyl-ethanone | 1.47 | 370.19 |
| 2-Biphenyl-4-yl-1-[5-(2,4-difluoro-benzyl)-hexahydro-pyrrolo[3,4-c]pyrrol-2-yl]-ethanone | 1.77 | 432.2 |
| 2-Biphenyl-4-yl-1-[5-(2,3-difluoro-benzyl)-hexahydro-pyrrolo[3,4-c]pyrrol-2-yl]-ethanone | 1.78 | 432.2 |
| 2-Biphenyl-4-yl-1-[5-(2,5-difluoro-benzyl)-hexahydro-pyrrolo[3,4-c]pyrrol-2-yl]-ethanone | 1.77 | 432.2 |
| 1-[5-(2,4-Difluoro-benzyl)-hexahydro-pyrrolo[3,4-c]pyrrol-2-yl]-2-(4-isopropyl-phenyl)-ethanone | 1.72 | 398.22 |
| 1-[5-(2,3-Difluoro-benzyl)-hexahydro-pyrrolo[3,4-c]pyrrol-2-yl]-2-(4-isopropyl-phenyl)-ethanone | 1.74 | 398.22 |
| 1-[5-(2,5-Difluoro-benzyl)-hexahydro-pyrrolo[3,4-c]pyrrol-2-yl]-2-(4-isopropyl-phenyl)-ethanone | 1.72 | 398.22 |
| 1-[5-(3,5-Difluoro-benzyl)-hexahydro-pyrrolo[3,4-c]pyrrol-2-yl]-2-(4-isopropyl-phenyl)-ethanone | 1.77 | 398.22 |
| 1-[5-(2,4-Difluoro-benzyl)-hexahydro-pyrrolo[3,4-c]pyrrol-2-yl]-2-m-tolyl-ethanone | 1.46 | 370.19 |
| 1-[5-(2,3-Difluoro-benzyl)-hexahydro-pyrrolo[3,4-c]pyrrol-2-yl]-2-m-tolyl-ethanone | 1.46 | 370.19 |
| 1-[5-(2,5-Difluoro-benzyl)-hexahydro-pyrrolo[3,4-c]pyrrol-2-yl]-2-m-tolyl-ethanone | 1.43 | 370.19 |
| 1-[5-(3,5-Difluoro-benzyl)-hexahydro-pyrrolo[3,4-c]pyrrol-2-yl]-2-m-tolyl-ethanone | 1.5 | 370.19 |
| 1-[5-(2,4-Difluoro-benzyl)-hexahydro-pyrrolo[3,4-c]pyrrol-2-yl]-2-p-tolyl-ethanone | 1.45 | 370.19 |
| 1-[5-(2,3-Difluoro-benzyl)-hexahydro-pyrrolo[3,4-c]pyrrol-2-yl]-2-p-tolyl-ethanone | 1.48 | 370.19 |
| 1-[5-(2,5-Difluoro-benzyl)-hexahydro-pyrrolo[3,4-c]pyrrol-2-yl]-2-p-tolyl-ethanone | 1.44 | 370.19 |
| 1-[5-(3,5-Difluoro-benzyl)-hexahydro-pyrrolo[3,4-c]pyrrol-2-yl]-2-p-tolyl-ethanone | 1.51 | 370.19 |
| 1-[5-(2,4-Difluoro-benzyl)-hexahydro-pyrrolo[3,4-c]pyrrol-2-yl]-2-(2,5-dimethyl-phenyl)-ethanone | 1.55 | 384.2 |
| 1-[5-(2,3-Difluoro-benzyl)-hexahydro-pyrrolo[3,4-c]pyrrol-2-yl]-2-(2,5-dimethyl-phenyl)-ethanone | 1.57 | 384.2 |
| 1-[5-(2,5-Difluoro-benzyl)-hexahydro-pyrrolo[3,4-c]pyrrol-2-yl]-2-(2,5-dimethyl-phenyl)-ethanone | 1.55 | 384.2 |
| 1-[5-(3,5-Difluoro-benzyl)-hexahydro-pyrrolo[3,4-c]pyrrol-2-yl]-2-(2,5-dimethyl-phenyl)-ethanone | 1.61 | 384.2 |
| 1-[5-(2,4-Difluoro-benzyl)-hexahydro-pyrrolo[3,4-c]pyrrol-2-yl]-2-naphthalen-1-yl-ethanone | 1.59 | 406.19 |
| 1-[5-(2,3-Difluoro-benzyl)-hexahydro-pyrrolo[3,4-c]pyrrol-2-yl]-2-naphthalen-1-yl-ethanone | 1.61 | 406.19 |
| 1-[5-(2,5-Difluoro-benzyl)-hexahydro-pyrrolo[3,4-c]pyrrol-2-yl]-2-naphthalen-1-yl-ethanone | 1.58 | 406.19 |
| 1-[5-(3,5-Difluoro-benzyl)-hexahydro-pyrrolo[3,4-c]pyrrol-2-yl]-2-naphthalen-1-yl-ethanone | 1.65 | 406.19 |
| 1-[5-(2,4-Difluoro-benzyl)-hexahydro-pyrrolo[3,4-c]pyrrol-2-yl]-2-(2,3,6-trifluoro-phenyl)-ethanone | 1.43 | 410.14 |
| 1-[5-(2,3-Difluoro-benzyl)-hexahydro-pyrrolo[3,4-c]pyrrol-2-yl]-2-(2,3,6-trifluoro-phenyl)-ethanone | 1.45 | 410.14 |
| 1-[5-(2,5-Difluoro-benzyl)-hexahydro-pyrrolo[3,4-c]pyrrol-2-yl]-2-(2,3,6-trifluoro-phenyl)-ethanone | 1.41 | 410.14 |
| 1-[5-(3,5-Difluoro-benzyl)-hexahydro-pyrrolo[3,4-c]pyrrol-2-yl]-2-(2,3,6-trifluoro-phenyl)-ethanone | 1.49 | 410.14 |
| 1-[5-(2,4-Difluoro-benzyl)-hexahydro-pyrrolo[3,4-c]pyrrol-2-yl]-2-phenyl-ethanone | 1.32 | 356.17 |
| 1-[5-(2,3-Difluoro-benzyl)-hexahydro-pyrrolo[3,4-c]pyrrol-2-yl]-2-phenyl-ethanone | 1.33 | 356.17 |
| 1-[5-(2,5-Difluoro-benzyl)-hexahydro-pyrrolo[3,4-c]pyrrol-2-yl]-2-phenyl-ethanone | 1.29 | 356.17 |
| 1-[5-(3,5-Difluoro-benzyl)-hexahydro-pyrrolo[3,4-c]pyrrol-2-yl]-2-phenyl-ethanone | 1.37 | 356.17 |
| 1-[5-(2,4-Difluoro-benzyl)-hexahydro-pyrrolo[3,4-c]pyrrol-2-yl]-2-(3,5-dimethyl-phenyl)-ethanone | 1.58 | 384.2 |
| 1-[5-(2,3-Difluoro-benzyl)-hexahydro-pyrrolo[3,4-c]pyrrol-2-yl]-2-(3,5-dimethyl-phenyl)-ethanone | 1.6 | 384.2 |
| 1-[5-(2,5-Difluoro-benzyl)-hexahydro-pyrrolo[3,4-c]pyrrol-2-yl]-2-(3,5-dimethyl-phenyl)-ethanone | 1.56 | 384.2 |

TABLE 1-continued

| Compound Name | Time (mins) | MW (found) |
|---|---|---|
| 1-[5-(3,5-Difluoro-benzyl)-hexahydro-pyrrolo[3,4-c]pyrrol-2-yl]-2-(3,5-dimethyl-phenyl)-ethanone | 1.63 | 384.2 |
| 1-[5-(2,4-Difluoro-benzyl)-hexahydro-pyrrolo[3,4-c]pyrrol-2-yl]-2-(2,4-dimethyl-phenyl)-ethanone | 1.56 | 384.2 |
| 1-[5-(2,3-Difluoro-benzyl)-hexahydro-pyrrolo[3,4-c]pyrrol-2-yl]-2-(2,4-dimethyl-phenyl)-ethanone | 1.58 | 384.2 |
| 1-[5-(2,5-Difluoro-benzyl)-hexahydro-pyrrolo[3,4-c]pyrrol-2-yl]-2-(2,4-dimethyl-phenyl)-ethanone | 1.55 | 384.2 |
| 1-[5-(3,5-Difluoro-benzyl)-hexahydro-pyrrolo[3,4-c]pyrrol-2-yl]-2-(2,4-dimethyl-phenyl)-ethanone | 1.61 | 384.2 |
| 1-[5-(2,3-Dimethoxy-benzyl)-hexahydro-pyrrolo[3,4-c]pyrrol-2-yl]-2-o-tolyl-ethanone | 1.45 | 394.23 |
| 1-[5-(2,4-Dimethyl-benzyl)-hexahydro-pyrrolo[3,4-c]pyrrol-2-yl]-2-o-tolyl-ethanone | 1.59 | 362.24 |
| 1-[5-(2-Chloro-3,4-dimethoxy-benzyl)-hexahydro-pyrrolo[3,4-c]pyrrol-2-yl]-2-o-tolyl-ethanone | 1.5 | 428.19 |

Example 2 illustrates the preparation of bicyclic diamine compounds of Formula I where x=1, y=1, w=1, z=1 and the linking group (L) is an amino acid.

Example 2
Preparation of [5-(2,4-difluoro-benzyl)-hexahydro-pyrrolo[3,4-c]pyrrol-2-yl]-(2-oxo-ethyl}carbamic acid tert-butyl ester (I-2a):

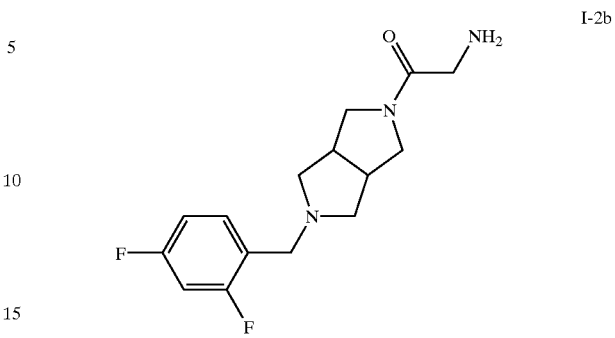

150 μL of Boc-protected glycine (0.2M in N,N-dimethylacetamide (DMA) and 3.75% TEA) was added to 100 μL of intermediate I-1g (0.2M in toluene (or DMA) and 3.75% n-methyl morpholine (NMM) followed by the addition of 150 μL (30 mmol) of O-benzotriazol-1-yl-N,N,N',N'-tetramethyl-uronium-hexa-fluoro-phosphate (HBTU) solution.(0.2M in DMA). The reaction was heated to 60° C. for six hours and then ran overnight at room temperature. Then, the reaction was quenched with 450 μl 10% NaOH, followed by the addition of 900 μL of ethyl acetate. The reaction was vigorously shaken for 15 minutes, and then let stand at room temperature for 30 minutes.

The reaction mixture was purified by liquid chromatography on a 1 g SCX SPE cartridge conditioned with MeOH. Elution with 1 M NH₃/MeOH afforded 5.0 mg of the desired product [5-(2,4-difluoro-benzyl)-hexahydro-pyrrolo[3,4-c]pyrrol-2-oxo-ethyl)carbamic acid tert-butylester (I-2a) as a yellow oil.

Preparation of 2-amino-1-[5-(2,4-difluoro-benzyl)-hexahydro-pyrrolo[3,4-c]pyrrol-2-yl]-ethanone (I-2b):

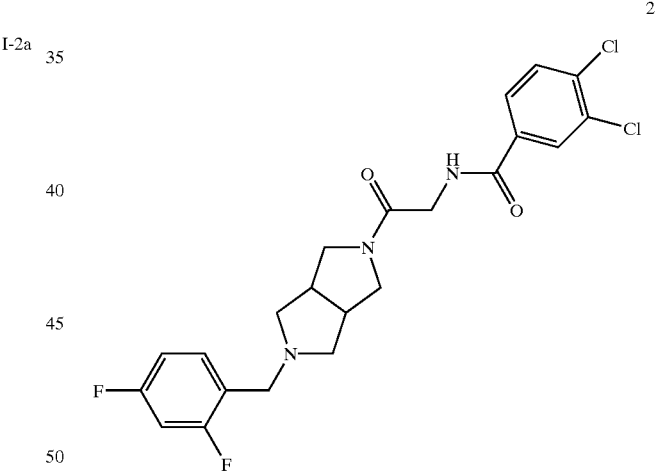

5.0 mg of desired [5-(2,4-difluoro-benzyl)-hexahydro-pyrrolo[3,4-c]pyrrol-2-oxo-ethyl]carbamic acid tert-butylester (I-2a) was dissolved in 250 μL of methylene chloride followed by addition of 250 μL of trifluoroacetic acid. The mixture was allowed to stir at room temperature for 30 minutes. Then, the solvent was removed in vacuo and the mixture was disolved in 250 μL of ethylacetate. The organic layer was basified with 1.0 N NaOH. The organic layer was collected, dried (MgSO₄) and concentrated in vacuo. The desired product 2-amino-1-[5-(2,4-difluoro-benzyl)-hexahydro-pyrrolo[3,4-c]pyrrol-2-yl]-ethanone (I-2b) was used immediately in the next reaction.

Preparation of 3,4-diclhoro-N-{2-[5-(2,4-difluoro-benzyl)-hexahydro-pyrrolo[3,4-c]pyrrol-2-yl]-(2-oxo-ethyl}benzamide (2):

50 μL of 3,4-dichlorobenzoic acid (0.2 M in N,N-dimethylacetamide (DMA) and 3.75% triethylamine (TEA)) was added to 33 μL of 2-amino-1-[5-(2,4-difluoro-benzyl)-hexahydro-pyrrolo[3,4-c]pyrrol-2-yl]-ethanone (I-2b)(0.2M in 1:1 toluene/DMA) and 3.75% n-methyl morpholine (NMM) followed by the addition of 50 μL (10 μmol) of O-benzotriazol-1-yl-N,N,N',N'-tetramethyl-uronium-hexa-fluoro-phosphate (HBTU) solution (0.2 M in DMA). The reaction was heated to 60° C. for six hours and then allowed to stir overnight at room temperature. Then, the reaction was quenched with 150 μL 10% NaOH, followed by the addition of 300 μL ethyl acetate. The reaction was vigorously shaken for 15 minutes, and then allowed to stand at room temperature for 30 minutes.

The reaction mixture was purified by liquid chromatography on a 1 g SCX SPE cartridge conditioned with with MeOH. Elution with 1 M NH₃/MeOH afforded 2.5 mg of the desired product (2) as a yellow oil.

The following compounds were prepared using the same general procedures described above for the preparation of compound (2) with the appropriate starting materials. Table 2 below lists the compounds made and their corresponding retention times (in minutes) using HPLC and their molecular weight (MS (CI) m/z (M+1)) as determined by chemical ionization mass spectroscopy.

TABLE 2

| Compound Name | Time (mins) | MW (found) |
|---|---|---|
| N-{1-[5-(2,4-Difluoro-benzyl)-hexahydro-pyrrolo[3,4-c]pyrrole-2-carbonyl]-3-methyl-butyl}-benzamide | 1.62 | 455.24 |
| N-{1-[5-(2,3-Difluoro-benzyl)-hexahydro-pyrrolo[3,4-c]pyrrole-2-carbonyl]-3-methyl-butyl}-benzamide | 1.63 | 455.24 |
| N-{1-[5-(2,5-Difluoro-benzyl)-hexahydro-pyrrolo[3,4-c]pyrrole-2-carbonyl]-3-methyl-butyl}-benzamide | 1.61 | 455.24 |
| N-{1-[5-(3,5-Difluoro-benzyl)-hexahydro-pyrrolo[3,4-c]pyrrole-2-carbonyl]-3-methyl-butyl}-benzamide | 1.69 | 455.24 |
| N-{1-Benzyl-2-[5-(2,4-difluoro-benzyl)-hexahydro-pyrrolo[3,4-c]pyrrol-2-yl]-2-oxo-ethyl}-2-phenyl-acetamide | 1.68 | 503.24 |
| N-{1-Benzyl-2-[5-(2,3-difluoro-benzyl)-hexahydro-pyrrolo[3,4-c]pyrrol-2-yl]-2-oxo-ethyl}-2-phenyl-acetamide | 1.68 | 503.24 |
| N-{1-Benzyl-2-[5-(2,5-difluoro-benzyl)-hexahydro-pyrrolo[3,4-c]pyrrol-2-yl]-2-oxo-ethyl}-2-phenyl-acetamide | 1.67 | 503.24 |
| N-{1-Benzyl-2-[5-(3,5-difluoro-benzyl)-hexahydro-pyrrolo[3,4-c]pyrrol-2-yl]-2-oxo-ethyl}-2-phenyl-acetamide | 1.73 | 503.24 |
| N-{2-[5-(2,4-Difluoro-benzyl)-hexahydro-pyrrolo[3,4-c]pyrrol-2-yl]-1-methyl-2-oxo-ethyl}-benzamide | 1.28 | 413.19 |
| N-{2-[5-(2,3-Difluoro-benzyl)-hexahydro-pyrrolo[3,4-c]pyrrol-2-yl]-1-methyl-2-oxo-ethyl}-benzamide | 1.28 | 413.19 |
| N-{2-[5-(2,5-Difluoro-benzyl)-hexahydro-pyrrolo[3,4-c]pyrrol-2-yl]-1-methyl-2-oxo-ethyl}-benzamide | 1.25 | 413.19 |
| N-{2-[5-(3,5-Difluoro-benzyl)-hexahydro-pyrrolo[3,4-c]pyrrol-2-yl]-1- methyl-2-oxo-ethyl}-benzamide | 1.34 | 413.19 |
| N-{1-Benzyl-2-[5-(2,4-difluoro-benzyl)-hexahydro-pyrrolo[3,4-c]pyrrol-2-yl]-2-oxo-ethyl}-benzamide | 1.63 | 489.22 |
| N-{1-Benzyl-2-[5-(2,3-difluoro-benzyl)-hexahydro-pyrrolo[3,4-c]pyrrol-2-yl]-2-oxo-ethyl}-benzamide | 1.65 | 489.22 |
| N-{1-Benzyl-2-[5-(2,5-difluoro-benzyl)-hexahydro-pyrrolo[3,4-c]pyrrol-2-yl]-2-oxo-ethyl}-benzamide | 1.62 | 489.22 |
| N-{1-Benzyl-2-[5-(3,5-difluoro-benzyl)-hexahydro-pyrrolo[3,4-c]pyrrol-2-yl]-2-oxo-ethyl}-benzamide | 1.7 | 489.22 |
| N-{1-[5-(2,4-Difluoro-benzyl)-hexahydro-pyrrolo[3,4-c]-pyrrole-2-carbonyl]-2-methyl-propyl}-benzamide | 1.48 | 441.22 |
| N-{1-[5-(2,3-Difluoro-benzyl)-hexahydro-pyrrolo[3,4-c]-pyrrole-2-carbonyl]-2-methyl-propyl}-benzamide | 1.48 | 441.22 |
| N-{1-[5-(2,5-Difluoro-benzyl)-hexahydro-pyrrolo[3,4-c]-pyrrole-2-carbonyl]-2-methyl-propyl}-benzamide | 1.46 | 441.22 |
| N-{1-[5-(3,5-Difluoro-benzyl)-hexahydro-pyrrolo[3,4-c]-pyrrole-2-carbonyl]-2-methyl-propyl}-benzamide | 1.54 | 441.22 |
| 1-[5-(2,4-Difluoro-benzyl)-hexahydro-pyrrolo[3,4-c]-pyrrol-2-yl]-3-methyl-2-(5-trifluoromethyl-pyridin-2-ylamino)-butan-1-one | 1.84 | 482.21 |
| 1-[5-(2,3-Difluoro-benzyl)-hexahydro-pyrrolo[3,4-c]-pyrrol-2-yl]-3-methyl-2-(5-trifluoromethyl-pyridin-2-ylamino)-butan-1-one | 1.85 | 482.21 |
| 1-[5-(2,5-Difluoro-benzyl)-hexahydro-pyrrolo[3,4-c]-pyrrol-2-yl]-3-methyl-2-(5-trifluoromethyl-pyridin-2-ylamino)-butan-1-one | 1.84 | 482.21 |
| 1-[5-(3,5-Difluoro-benzyl)-hexahydro-pyrrolo[3,4-c]pyrrol-2-yl]-3-methyl-2-(5-trifluoromethyl-pyridin-2-ylamino)-butan-1-one | 1.92 | 482.21 |
| N-{2-[5-(2,4-Difluoro-benzyl)-hexahydro-pyrrolo[3,4-c]-pyrrol-2-yl]-1-methyl-2-oxo-ethyl}-acetamide | 0.85 | 351.18 |
| N-{2-[5-(2,3-Difluoro-benzyl)-hexahydro-pyrrolo[3,4-c]-pyrrol-2-yl]-1-methyl-2-oxo-ethyl}-acetamide | 0.85 | 351.18 |
| N-{2-[5-(2,5-Difluoro-benzyl)-hexahydro-pyrrolo[3,4-c]-pyrrol-2-yl]-1-methyl-2-oxo-ethyl}-acetamide | 0.8 | 351.18 |
| 3-Chloro-N-{2-[5-(2,4-dimethyl-benzyl)-hexahydro-pyrrolo[3,4-c]pyrrol-2-yl]-2-oxo-ethyl}-benzamide | 1.55 | 425.19 |
| 4-Chloro-N-{2-[5-(2,4-dimethyl-benzyl)-hexahydro-pyrrolo[3,4-c]pyrrol-2-yl]-2-oxo-ethyl}-benzamide | 1.55 | 425.19 |
| N-{2-[5-(2,4-Dimethyl-benzyl)-hexahydro-pyrrolo[3,4-c]-pyrrol-2-yl]-2-oxo-ethyl}-3,5-bis-trifluoromethyl-benzamide | 1.91 | 527.2 |
| N-{2-[5-(2,4-Dimethyl-benzyl)-hexahydro-pyrrolo[3,4-c]pyrrol-2-yl]-2-oxo-ethyl}-4-trifluoromethyl-benzamide | 1.68 | 459.21 |
| 4-Bromo-N-{2-[5-(1H-indol-3-ylmethyl)-hexahydro-pyrrolo[3,4-c]pyrrol-2-yl]-2-oxo-ethyl}-benzamide | 1.48 | 480.12 |
| 2-Bromo-N-{2-[5-(1H-indol-3-ylmethyl)-hexahydro-pyrrolo[3,4-c]pyrrol-2-yl]-2-oxo-ethyl}-5-methoxy-benzamide | 1.38 | 510.13 |
| 3,4-Dichloro-N-{2-[5-(1H-indol-3-ylmethyl)-hexahydro-pyrrolo[3,4-c]pyrrol-2-yl]-2-oxo-ethyl}-benzamide | 1.59 | 470.13 |
| 4-tert-Butyl-N-{2-[5-(1H-indol-3-ylmethyl)-hexahydro-pyrrolo[3,4-c]pyrrol-2-yl]-2-oxo-ethyl}-benzamide | 1.71 | 458.27 |

TABLE 2-continued

| Compound Name | Time (mins) | MW (found) |
|---|---|---|
| 3-Bromo-N-{2-[5-(1H-indol-3-ylmethyl)-hexahydro-pyrrolo[3,4-c]pyrrol-2-yl]-2-oxo-ethyl}-4-methyl-benzamide | 1.57 | 494.13 |
| 3-Bromo-4-chloro-N-{2-[5-(1H-indol-3-ylmethyl)-hexahydro-pyrrolo[3,4-c]pyrrol-2-yl]-2-oxo-ethyl}-benzamide | 1.62 | 514.08 |
| 4-Bromo-N-{2-[5-(1H-indol-3-ylmethyl)-hexahydro-pyrrolo[3,4-c]pyrrol-2-yl]-2-oxo-ethyl}-3-methyl-benzamide | 1.59 | 494.13 |
| 3-Bromo-N-{2-[5-(1H-indol-3-ylmethyl)-hexahydro-pyrrolo[3,4-c]pyrrol-2-yl]-2-oxo-ethyl}-benzamide | 1.46 | 480.12 |
| N-{2-[5-(1H-Indol-3-ylmethyl)-hexahydro-pyrrolo[3,4-c]pyrrol-2-yl]-2-oxo-ethyl}-4-trifluoromethyl-benzamide | 1.56 | 470.19 |
| 3-Fluoro-N-{2-[5-(1H-indol-3-ylmethyl)-hexahydro-pyrrolo[3,4-c]pyrrol-2-yl]-2-oxo-ethyl}-benzamide | 1.31 | 420.2 |
| 3,4-Difluoro-N-{2-[5-(1H-indol-3-ylmethyl)-hexahydro-pyrrolo[3,4-c]pyrrol-2-yl]-2-oxo-ethyl}-benzamide | 1.38 | 438.19 |
| 4-Fluoro-N-{2-[5-(1H-indol-3-ylmethyl)-hexahydro-pyrrolo[3,4-c]pyrrol-2-yl]-2-oxo-ethyl}-benzamide | 1.31 | 420.2 |
| N-{2-[5-(1H-Indol-3-ylmethyl)-hexahydro-pyrrolo[3,4-c]pyrrol-2-yl]-2-oxo-ethyl}-3-methyl-benzamide | 1.37 | 416.22 |
| 3-Fluoro-N-{2-[5-(1H-indol-3-ylmethyl)-hexahydro-pyrrolo[3,4-c]pyrrol-2-yl]-2-oxo-ethyl}-4-methyl-benzamide | 1.45 | 434.21 |
| N-{2-[5-(1H-Indol-3-ylmethyl)-hexahydro-pyrrolo[3,4-c]pyrrol-2-yl]-2-oxo-ethyl}-benzamide | 1.24 | 402.21 |
| 3-Chloro-N-{2-[5-(1H-indol-3-ylmethyl)-hexahydro-pyrrolo[3,4-c]pyrrol-2-yl]-2-oxo-ethyl}-benzamide | 1.43 | 436.17 |
| 3,5-Difluoro-N-{2-[5-(1H-indol-3-ylmethyl)-hexahydro-pyrrolo[3,4-c]pyrrol-2-yl]-2-oxo-ethyl}-benzamide | 1.38 | 438.19 |
| N-{2-[5-(1H-Indol-3-ylmethyl)-hexahydro-pyrrolo[3,4-c]pyrrol-2-yl]-2-oxo-ethyl}-4-methyl-benzamide | 1.38 | 416.22 |
| N-{2-[5-(1H-Indol-3-ylmethyl)-hexahydro-pyrrolo[3,4-c]pyrrol-2-yl]-2-oxo-ethyl}-3,4-dimethyl-benzamide | 1.48 | 430.24 |
| 4-Chloro-N-{2-[5-(1H-indol-3-ylmethyl)-hexahydro-pyrrolo[3,4-c]pyrrol-2-yl]-2-oxo-ethyl}-benzamide | 1.44 | 436.17 |
| N-{2-[5-(1H-Indol-3-ylmethyl)-hexahydro-pyrrolo[3,4-c]pyrrol-2-yl]-2-oxo-ethyl}-3-trifluoromethyl-benzamide | 1.55 | 470.19 |
| 4-Ethylsulfanyl-N-{2-[5-(1H-indol-3-ylmethyl)-hexahydro-pyrrolo[3,4-c]pyrrol-2-yl]-2-oxo-ethyl}-benzamide | 1.57 | 462.21 |
| 4-Butyl-N-{2-[5-(1H-indol-3-ylmethyl)-hexahydro-pyrrolo[3,4-c]pyrrol-2-yl]-2-oxo-ethyl}-benzamide | 1.78 | 458.27 |
| N-{2-[5-(1H-Indol-3-ylmethyl)-hexahydro-pyrrolo[3,4-c]pyrrol-2-yl]-2-oxo-ethyl}-4-isopropyl-benzamide | 1.62 | 444.25 |
| N-{2-[5-(1H-Indol-3-ylmethyl)-hexahydro-pyrrolo[3,4-c]pyrrol-2-yl]-2-oxo-ethyl}-4-isopropoxy-benzamide | 1.52 | 460.25 |
| N-{2-[5-(1H-Indol-3-ylmethyl)-hexahydro-pyrrolo[3,4-c]pyrrol-2-yl]-2-oxo-ethyl}-4-propoxy-benzamide | 1.57 | 460.25 |
| 4-Bromo-N-{2-[5-(1H-indol-3-ylmethyl)-hexahydro-pyrrolo[3,4-c]pyrrol-2-yl]-2-oxo-ethyl}-2-methyl-benzamide | 1.54 | 494.13 |
| 2-Bromo-N-{2-[5-(1H-indol-3-ylmethyl)-hexahydro-pyrrolo[3,4-c]pyrrol-2-yl]-2-oxo-ethyl}-3-methyl-benzamide | 1.43 | 494.13 |
| 2-Bromo-N-{2-[5-(1H-indol-3-ylmethyl)-hexahydro-pyrrolo[3,4-c]pyrrol-2-yl]-2-oxo-ethyl}-5-methyl-benzamide | 1.44 | 494.13 |
| N-{2-[5-(1H-Indol-3-ylmethyl)-hexahydro-pyrrolo[3,4-c]pyrrol-2-yl]-2-oxo-ethyl}-2-methylsulfanyl-benzamide | 1.34 | 448.19 |
| N-{2-[5-(2,4-Dimethyl-benzyl)-hexahydro-pyrrolo[3,4-c]pyrrol-2-yl]-2-oxo-ethyl}-3-fluoro-4-trifluoromethyl-benzamide | 1.68 | 477.2 |
| 4-Bromo-N-{2-[5-(2,4-dimethyl-benzyl)-hexahydro-pyrrolo[3,4-c]pyrrol-2-yl]-2-oxo-ethyl}-benzamide | 1.58 | 469.14 |
| 2-Bromo-N-{2-[5-(2,4-dimethyl-benzyl)-hexahydro-pyrrolo[3,4-c]pyrrol-2-yl]-2-oxo-ethyl}-5-methoxy-benzamide | 1.52 | 499.15 |
| 3,4-Dichloro-N-{2-[5-(2,4-dimethyl-benzyl)-hexahydro-pyrrolo[3,4-c]pyrrol-2-yl]-2-oxo-ethyl}-benzamide | 1.71 | 459.15 |
| 4-tert-Butyl-N-{2-[5-(2,4-dimethyl-benzyl)-hexahydro-pyrrolo[3,4-c]pyrrol-2-yl]-2-oxo-ethyl}-benzamide | 1.81 | 447.29 |
| 3-Bromo-N-{2-[5-(2,4-dimethyl-benzyl)-hexahydro-pyrrolo[3,4-c]pyrrol-2-yl]-2-oxo-ethyl}-4-methyl-benzamide | 1.69 | 483.15 |
| 3-Bromo-N-{2-[5-(2,4-dimethyl-benzyl)-hexahydro-pyrrolo[3,4-c]pyrrol-2-yl]-2-oxo-ethyl}-4-methyl-benzamide | 1.73 | 503.1 |
| 4-Bromo-N-{2-[5-(2,4-dimethyl-benzyl)-hexahydro-pyrrolo[3,4-c]pyrrol-2-yl]-2-oxo-ethyl}-3-methyl-benzamide | 1.7 | 483.15 |
| 3-Bromo-N-{2-[5-(2,4-dimethyl-benzyl)-hexahydro-pyrrolo[3,4-c]pyrrol-2-yl]-2-oxo-ethyl}-benzamide | 1.53 | 469.14 |
| N-{2-[5-(2,4-Dimethyl-benzyl)-hexahydro-pyrrolo[3,4-c]pyrrol-2-yl]-2-oxo-ethyl}-3-fluoro-benzamide | 1.44 | 409.22 |
| N-{2-[5-(2,4-Dimethyl-benzyl)-hexahydro-pyrrolo[3,4-c]pyrrol-2-yl]-2-oxo-ethyl}-3,4-difluoro-benzamide | 1.52 | 427.21 |
| N-{2-[5-(2,4-Dimethyl-benzyl)-hexahydro-pyrrolo[3,4-c]pyrrol-2-yl]-2-oxo-ethyl}-4-fluoro-benzamide | 1.43 | 409.22 |
| N-{2-[5-(2,4-Dimethyl-benzyl)-hexahydro-pyrrolo[3,4-c]pyrrol-2-yl]-oxo-ethyl}-3-methyl-benzamide | 1.49 | 405.24 |
| N-{2-[5-(2,4-Dimethyl-benzyl)-hexahydro-pyrrolo[3,4-c]pyrrol-2-yl]-2-oxo-ethyl}-3-fluoro-4-methyl-benzamide | 1.49 | 423.23 |

TABLE 2-continued

| Compound Name | Time (mins) | MW (found) |
|---|---|---|
| N-{2-[5-(2,4-Dimethyl-benzyl)-hexahydro-pyrrolo[3,4-c]pyrrol-2-yl]-2-oxo-ethyl}-benzamide | 1.37 | 391.23 |
| N-{2-[5-(2,4-Dimethyl-benzyl)-hexahydro-pyrrolo[3,4-c]pyrrol-2-yl]-2-oxo-ethyl}-3,5-difluoro-benzamide | 1.3 | 391.23 |
| N-{2-[5-(2,4-Dimethyl-benzyl)-hexahydro-pyrrolo[3,4-c]pyrrol-2-yl]-2-oxo-ethyl}-4-methyl-benzamide | 1.5 | 427.21 |
| N-{2-[5-(2,4-Dimethyl-benzyl)-hexahydro-pyrrolo[3,4-c]pyrrol-2-yl]-2-oxo-ethyl}-3,4-dimethyl-benzamide | 1.43 | 405.24 |
| N-{2-[5-(2,4-Dimethyl-benzyl)-hexahydro-pyrrolo[3,4-c]pyrrol-2-yl]-2-oxo-ethyl}-4-ethylsulfanyl-benzamide | 1.49 | 405.24 |
| 4-Butyl-N-{2-[5-(2,4-dimethyl-benzyl)-hexahydro-pyrrolo[3,4-c]pyrrol-2-yl]-2-oxo-ethyl}-benzamide | 1.58 | 419.26 |
| N-{2-[5-(2,4-Dimethyl-benzyl)-hexahydro-pyrrolo[3,4-c]pyrrol-2-yl]-2-oxo-ethyl}-4-isopropyl-benzamide | 1.67 | 451.23 |
| N-{2-[5-(2,4-Dimethyl-benzyl)-hexahydro-pyrrolo[3,4-c]pyrrol-2-yl]-2-oxo-ethyl}-4-trifluoromethoxy-benzamide | 1.88 | 447.29 |
| N-{2-[5-(2,4-Dimethyl-benzyl)-hexahydro-pyrrolo[3,4-c]pyrrol-2-yl]-2-oxo-ethyl}-3,4,5-trifluoro-benzamide | 1.73 | 433.27 |
| N-{2-[5-(2,4-Dimethyl-benzyl)-hexahydro-pyrrolo[3,4-c]pyrrol-2-yl]-2-oxo-ethyl}-4-isopropoxy-benzamide | 1.73 | 475.21 |
| N-{2-[5-(2,4-Dimethyl-benzyl)-hexahydro-pyrrolo[3,4-c]pyrrol-2-yl]-2-oxo-ethyl}-4-propoxy-benzamide | 1.6 | 445.2 |
| 3-Chloro-N-{2-[5-(2,4-dimethyl-benzyl)-hexahydro-pyrrolo[3,4-c]pyrrol-2-yl]-2-oxo-ethyl}-4-fluoro-benzamide | 1.61 | 443.18 |
| N-{2-[5-(2,4-Dimethyl-benzyl)-hexahydro-pyrrolo[3,4-c]pyrrol-2-yl]-2-oxo-ethyl}-3-fluoro-5-trifluoromethyl-benzamide | 1.73 | 477.2 |
| 2-Bromo-N-{2-[5-(2,4-dimethyl-benzyl)-hexahydro-pyrrolo[3,4-c]pyrrol-2-yl]-2-oxo-ethyl}-benzamide | 1.44 | 469.14 |
| Bromo-2-chloro-N-{2-[5-(2,4-dimethyl-benzyl)-hexahydro-pyrrolo[3,4-c]pyrrol-2-yl]-2-oxo-ethyl}-benzamide | 1.61 | 503.1 |
| 2-Bromo-5-chloro-N-{2-[5-(2,4-dimethyl-benzyl)-hexahydro-pyrrolo[3,4-c]pyrrol-2-yl]-2-oxo-ethyl}-benzamide | 1.59 | 503.1 |
| 3-Bromo-N-{2-[5-(2,4-dimethyl-benzyl)-hexahydro-pyrrolo[3,4-c]pyrrol-2-yl]-2-oxo-ethyl}-2-fluoro-benzamide | 1.54 | 487.13 |
| 4-Bromo-N-{2-[5-(2,4-dimethyl-benzyl)-hexahydro-pyrrolo[3,4-c]pyrrol-2-yl]-2-oxo-ethyl}-2-methyl-benzamide | 1.64 | 483.15 |
| 4-Bromo-2-chloro-N-{2-[5-(2,4-dimethyl-benzyl)-hexahydro-pyrrolo[3,4-c]pyrrol-2-yl]-2-oxo-ethyl}-benzamide | 1.64 | 503.1 |
| 2-Bromo-4-chloro-N-{2-[5-(2,4-dimethyl-benzyl)-hexahydro-pyrrolo[3,4-c]pyrrol-2-yl]-2-oxo-ethyl}-benzamide | 1.63 | 503.1 |
| 2-Bromo-N-{2-[5-(2,4-dimethyl-benzyl)-hexahydro-pyrrolo[3,4-c]pyrrol-2-yl]-2-oxo-ethyl}-3-methyl-benzamide | 1.49 | 483.15 |
| 2-Bromo-N-{2-[5-(2,4-dimethyl-benzyl)-hexahydro-pyrrolo[3,4-c]pyrrol-2-yl]-2-oxo-ethyl}-5-methyl-benzamide | 1.56 | 483.15 |
| 3-Bromo-N-{2-[5-(2,4-dimethyl-benzyl)-hexahydro-pyrrolo[3,4-c]pyrrol-2-yl]-2-oxo-ethyl}-2-methyl-benzamide | 1.63 | 483.15 |
| N-{2-[5-(2,4-Dimethyl-benzyl)-hexahydro-pyrrolo[3,4-c]pyrrol-2-yl]-2-oxo-ethyl}-2-methylsulfanyl-benzamide | 1.46 | 437.21 |
| 3-Fluoro-N-{2-[5-(4-methyl-benzyl)-hexahydro-pyrrolo[3,4-c]pyrrol-2-yl]-2-oxo-ethyl}-4-trifluoromethyl-benzamide | 1.7 | 463.19 |
| 4-Bromo-N-{2-[5-(4-methyl-benzyl)-hexahydro-pyrrolo[3,4-c]pyrrol-2-yl]-2-oxo-ethyl}-benzamide | 1.53 | 455.12 |
| 2-Bromo-5-methoxy-N-{2-[5-(4-methyl-benzyl)-hexahydro-pyrrolo[3,4-c]pyrrol-2-yl]-2-oxo-ethyl}-benzamide | 1.45 | 485.13 |
| 3,4-Dichloro-N-{2-[5-(4-methyl-benzyl)-hexahydro-pyrrolo[3,4-c]pyrrol-2-yl]-2-oxo-ethyl}-benzamide | 1.65 | 445.13 |
| 4-tert-Butyl-N-{2-[5-(4-methyl-benzyl)-hexahydro-pyrrolo[3,4-c]pyrrol-2-yl]-2-oxo-ethyl}-benzamide | 1.77 | 433.27 |
| N-{2-[5-(4-Methyl-benzyl)-hexahydro-pyrrolo[3,4-c]pyrrol-2-yl]-2-oxo-ethyl}-3,5-bis-trifluoromethyl-benzamide | 1.87 | 513.19 |
| 3-Bromo-4-methyl-N-{2-[5-(4-methyl-benzyl)-hexahydro-pyrrolo[3,4-c]pyrrol-2-yl]-2-oxo-ethyl}-benzamide | 1.64 | 469.14 |
| 3-Bromo-4-chloro-N-{2-[5-(4-methyl-benzyl)-hexahydro-pyrrolo[3,4-c]pyrrol-2-yl]-2-oxo-ethyl}-benzamide | 1.68 | 489.08 |
| 4-Bromo-3-methyl-N-{2-[5-(4-methyl-benzyl)-hexahydro-pyrrolo[3,4-c]pyrrol-2-yl]-2-oxo-ethyl}-benzamide | 1.66 | 469.14 |
| 3-Bromo-N-{2-[5-(4-methyl-benzyl)-hexahydro-pyrrolo[3,4-c]pyrrol-2-yl]-2-oxo-ethyl}-benzamide | 1.52 | 455.12 |
| N-{2-[5-(4-Methyl-benzyl)-hexahydro-pyrrolo[3,4-c]pyrrol-2-yl]-2-oxo-ethyl}-4-trifluoromethyl-benzamide | 1.61 | 445.2 |
| 3-Fluoro-N-{2-[5-(4-methyl-benzyl)-hexahydro-pyrrolo[3,4-c]pyrrol-2-yl]-2-oxo-ethyl}-benzamide | 1.36 | 395.2 |
| 3,4-Difluoro-N-{2-[5-(4-methyl-benzyl)-hexahydro-pyrrolo[3,4-c]pyrrol-2-yl]-2-oxo-ethyl}-benzamide | 1.43 | 413.19 |
| 4-Fluoro-N-{2-[5-(4-methyl-benzyl)-hexahydro-pyrrolo[3,4-c]pyrrol-2-yl]-2-oxo-ethyl}-benzamide | 1.35 | 395.2 |
| 3-Methyl-N-{2-[5-(4-methyl-benzyl)-hexahydro-pyrrolo[3,4-c]pyrrol-2-yl]-2-oxo-ethyl}-benzamide | 1.42 | 391.23 |

TABLE 2-continued

| Compound Name | Time (mins) | MW (found) |
|---|---|---|
| 3-Fluoro-4-methyl-N-{2-[5-(4-methyl-benzyl)-hexahydro-pyrrolo[3,4-c]pyrrol-2-yl]-2-oxo-ethyl}-benzamide | 1.49 | 409.22 |
| N-{2-[5-(4-Methyl-benzyl)-hexahydro-pyrrolo[3,4-c]pyrrol-2-yl]-2-oxo-ethyl}-benzamide | 1.28 | 377.21 |
| 3-Chloro-N-{2-[5-(4-methyl-benzyl)-hexahydro-pyrrolo[3,4-c]-pyrrol-2-yl]-2-oxo-ethyl}-benzamide | 1.48 | 411.17 |
| 3,5-Difluoro-N-{2-[5-(4-methyl-benzyl)-hexahydro-pyrrolo[3,4-c]pyrrol-2-yl]-2-oxo-ethyl}-benzamide | 1.43 | 413.19 |
| 4-Methyl-N-{2-[5-(4-methyl-benzyl)-hexahydro-pyrrolo[3,4-c]pyrrol-2-yl]-2-oxo-ethyl}-benzamide | 1.43 | 391.23 |
| 3,4-Dimethyl-N-{2-[5-(4-methyl-benzyl)-hexahydro-pyrrolo[3,4-c]pyrrol-2-yl]-2-oxo-ethyl}-benzamide | 1.54 | 405.24 |
| 4-Chloro-N-{2-[5-(4-methyl-benzyl)-hexahydro-pyrrolo[3,4-c]pyrrol-2-yl]-2-oxo-ethyl}-benzamide | 1.49 | 411.17 |
| N-{2-[5-(4-Methyl-benzyl)-hexahydro-pyrrolo[3,4-c]-pyrrol-2-yl]-2-oxo-ethyl}-3-trifluoromethyl-benzamide | 1.63 | 445.2 |
| 4-Ethylsulfanyl-N-{2-[5-(4-methyl-benzyl)-hexahydro-pyrrolo-[3,4-c]pyrrol-2-yl]-2-oxo-ethyl}-benzamide | 1.64 | 437.21 |
| 4-Butyl-N-{2-[5-(4-methyl-benzyl)-hexahydro-pyrrolo[3,4-c]-pyrrol-2-yl]-2-oxo-ethyl}-benzamide | 1.85 | 433.27 |
| 4-Isopropyl-N-{2-[5-(4-methyl-benzyl)-hexahydro-pyrrolo[3,4-c]-pyrrol-2-yl]-2-oxo-ethyl}-benzamide | 1.69 | 419.26 |
| N-{2-[5-(4-Methyl-benzyl)-hexahydro-pyrrolo[3,4-c]-pyrrol-2-yl]-2-oxo-ethyl}-4-trifluoromethoxy-benzamide | 1.68 | 461.19 |
| 3,4,5-Trifluoro-N-{2-[5-(4-methyl-benzyl)-hexahydro-pyrrolo[3,4-c]pyrrol-2-yl]-2-oxo-ethyl}-benzamide | 1.54 | 431.18 |
| 4-Isopropoxy-N-{2-[5-(4-methyl-benzyl)-hexahydro-pyrrolo-[3,4-c]pyrrol-2-yl]-2-oxo-ethyl}-benzamide | 1.58 | 435.25 |
| N-{2-[5-(4-Methyl-benzyl)-hexahydro-pyrrolo[3,4-c]-pyrrol-2-yl]-2-oxo-ethyl}-4-propoxy-benzamide | 1.64 | 435.25 |
| 3-Chloro-4-fluoro-N-{2-[5-(4-methyl-benzyl)-hexahydro-pyrrolo[3,4-c]pyrrol-2-yl]-2-oxo-ethyl}-benzamide | 1.56 | 429.16 |
| 3-Fluoro-N-{2-[5-(4-methyl-benzyl)-hexahydro-pyrrolo[3,4-c]pyrrol-2-yl]-2-oxo-ethyl}-5-trifluoromethyl-benzamide | 1.68 | 463.19 |
| 2-Bromo-N-{2-[5-(4-methyl-benzyl)-hexahydro-pyrrolo[3,4-c]pyrrol-2-yl]-2-oxo-ethyl}-benzamide | 1.38 | 455.12 |
| 5-Bromo-2-chloro-N-{2-[5-(4-methyl-benzyl)-hexahydro-pyrrolo[3,4-c]pyrrol-2-yl]-2-oxo-ethyl}-benzamide | 1.56 | 489.08 |
| 2-Bromo-5-chloro-N-{2-[5-(4-methyl-benzyl)-hexahydro-pyrrolo[3,4-c]pyrrol-2-yl]-2-oxo-ethyl}-benzamide | 1.53 | 489.08 |
| 3-Bromo-2-fluoro-N-{2-[5-(4-methyl-benzyl)-hexahydro-pyrrolo[3,4-c]pyrrol-2-yl]-2-oxo-ethyl}-benzamide | 1.54 | 473.11 |
| 4-Bromo-2-methyl-N-{2-[5-(4-methyl-benzyl)-hexahydro-pyrrolo[3,4-c]pyrrol-2-yl]-2-oxo-ethyl}-benzamide | 1.6 | 469.14 |
| 4-Bromo-2-chloro-N-{2-[5-(4-methyl-benzyl)-hexahydro-pyrrolo[3,4-c]pyrrol-2-yl]-2-oxo-ethyl}-benzamide | 1.58 | 489.08 |
| 2-Bromo-4-chloro-N-{2-[5-(4-methyl-benzyl)-hexahydro-pyrrolo[3,4-c]pyrrol-2-yl]-2-oxo-ethyl}-benzamide | 1.58 | 489.08 |
| 2-Bromo-3-methyl-N-{2-[5-(4-methyl-benzyl)-hexahydro-pyrrolo[3,4-c]pyrrol-2-yl]-2-oxo-ethyl}-benzamide | 1.49 | 469.14 |
| 2-Bromo-5-methyl-N-{2-[5-(4-methyl-benzyl)-hexahydro-pyrrolo[3,4-c]pyrrol-2-yl]-2-oxo-ethyl}-benzamide | 1.5 | 469.14 |
| 3-Bromo-2-methyl-N-{2-[5-(4-methyl-benzyl)-hexahydro-pyrrolo[3,4-c]pyrrol-2-yl]-2-oxo-ethyl}-benzamide | 1.58 | 469.14 |
| N-{2-[5-(4-Methyl-benzyl)-hexahydro-pyrrolo[3,4-c]-pyrrol-2-yl]-2-oxo-ethyl}-2-methylsulfanyl-benzamide | 1.4 | 423.2 |
| N-{2-[5-(2,4-Dichloro-benzyl)-hexahydro-pyrrolo-[3,4-c]pyrrol-2-yl]-2-oxo-ethyl}-3-fluoro-4-trifluoromethyl-benzamide | 1.83 | 517.09 |
| 4-Bromo-N-{2-[5-(2,4-dichloro-benzyl)-hexahydro-pyrrolo[3,4-c]-pyrrol-2-yl]-2-oxo-ethyl}-benzamide | 1.66 | 509.03 |
| 2-Bromo-N-{2-[5-(2,4-dichloro-benzyl)-hexahydro-pyrrolo[3,4-c]-pyrrol-2-yl]-2-oxo-ethyl}-5-methoxy-benzamide | 1.58 | 539.04 |
| 3,4-Dichloro-N-{2-[5-(2,4-dichloro-benzyl)-hexahydro-pyrrolo[3,4-c]-pyrrol-2-yl]-2-oxo-ethyl}-benzamide | 1.8 | 499.04 |
| 4-tert-Butyl-N-{2-[5-(2,4-dichloro-benzyl)-hexahydro-pyrrolo[3,4-c]-pyrrol-2-yl]-2-oxo-ethyl}-benzamide | 1.89 | 487.18 |
| N-{2-[5-(2,4-Dichloro-benzyl)-hexahydro-pyrrolo[3,4-c]-pyrrol-2-yl]-2-oxo-ethyl}-3,5-bis-trifluoromethyl-benzamide | 2.01 | 567.09 |
| 3-Bromo-N-{2-[5-(2,4-dichloro-benzyl)-hexahydro-pyrrolo[3,4-c]pyrrol-2-yl]-2-oxo-ethyl}-4-methyl-benzamide | 1.78 | 523.04 |
| 3-Bromo-4-chloro-N-{2-[5-(2,4-dichloro-benzyl)-hexahydro-pyrrolo[3,4-c]pyrrol-2-yl]-2-oxo-ethyl}-benzamide | 1.82 | 542.99 |
| 4-Bromo-N-{2-[5-(2,4-dichloro-benzyl)-hexahydro-pyrrolo[3,4-c]pyrrol-2-yl]-2-oxo-ethyl}-3-methyl-benzamide | 1.8 | 523.04 |
| 3-Bromo-N-{2-[5-(2,4-dichloro-benzyl)-hexahydro-pyrrolo[3,4-c]pyrrol-2-yl]-2-oxo-ethyl}-benzamide | 1.66 | 509.03 |
| N-{2-[5-(2,4-Dichloro-benzyl)-hexahydro-pyrrolo[3,4-c]-pyrrol-2-yl]-2-oxo-ethyl}-4-trifluoromethyl-benzamide | 1.76 | 499.1 |

TABLE 2-continued

| Compound Name | Time (mins) | MW (found) |
|---|---|---|
| N-{2-[5-(2,4-Dichloro-benzyl)-hexahydro-pyrrolo[3,4-c]pyrrol-2-yl]-2-oxo-ethyl}-3-fluoro-benzamide | 1.5 | 449.11 |
| N-{2-[5-(2,4-Dichloro-benzyl)-hexahydro-pyrrolo[3,4-c]pyrrol-2-yl]-2-oxo-ethyl}-3,4-difluoro-benzamide | 1.58 | 467.1 |
| N-{2-[5-(2,4-Dichloro-benzyl)-hexahydro-pyrrolo[3,4-c]pyrrol-2-yl]-2-oxo-ethyl}-4-fluoro-benzamide | 1.5 | 449.11 |
| N-{2-[5-(2,4-Dichloro-benzyl)-hexahydro-pyrrolo[3,4-c]pyrrol-2-yl]-2-oxo-ethyl}-3-methyl-benzamide | 1.57 | 445.13 |
| N-{2-[5-(2,4-Dichloro-benzyl)-hexahydro-pyrrolo[3,4-c]pyrrol-2-yl]-2-oxo-ethyl}-3-fluoro-4-methyl-benzamide | 1.48 | 463.12 |
| N-{2-[5-(2,4-Dichloro-benzyl)-hexahydro-pyrrolo[3,4-c]pyrrol-2-yl]-2-oxo-ethyl}-benzamide | 1.44 | 431.12 |
| 3-Chloro-N-{2-[5-(2,4-dichloro-benzyl)-hexahydro-pyrrolo[3,4-c]pyrrol-2-yl]-2-oxo-ethyl}-benzamide | 1.63 | 465.08 |
| N-{2-[5-(2,4-Dichloro-benzyl)-hexahydro-pyrrolo[3,4-c]pyrrol-2-yl]-2-oxo-ethyl}-3,5-difluoro-benzamide | 1.58 | 467.1 |
| N-{2-[5-(2,4-Dichloro-benzyl)-hexahydro-pyrrolo[3,4-c]pyrrol-2-yl]-2-oxo-ethyl}-4-methyl-benzamide | 1.57 | 445.13 |
| N-{2-[5-(2,4-Dichloro-benzyl)-hexahydro-pyrrolo[3,4-c]pyrrol-2-yl]-2-oxo-ethyl}-3,4-dimethyl-benzamide | 1.68 | 459.15 |
| 4-Chloro-N-{2-[5-(2,4-dichloro-benzyl)-hexahydro-pyrrolo[3,4-c]pyrrol-2-yl]-2-oxo-ethyl}-benzamide | 1.65 | 465.08 |
| N-{2-[5-(2,4-Dichloro-benzyl)-hexahydro-pyrrolo[3,4-c]pyrrol-2-yl]-2-oxo-ethyl}-3-trifluoromethyl-benzamide | 1.76 | 499.1 |
| N-{2-[5-(2,4-Dichloro-benzyl)-hexahydro-pyrrolo[3,4-c]pyrrol-2-yl]-2-oxo-ethyl}-4-ethylsulfanyl-benzamide | 1.77 | 491.12 |
| 4-Butyl-N-{2-[5-(2,4-dichloro-benzyl)-hexahydro-pyrrolo[3,4-c]pyrrol-2-yl]-2-oxo-ethyl}-benzamide | 1.98 | 487.18 |
| N-{2-[5-(2,4-Dichloro-benzyl)-hexahydro-pyrrolo[3,4-c]pyrrol-2-yl]-2-oxo-ethyl}-4-isopropyl-benzamide | 1.82 | 473.16 |
| N-{2-[5-(2,4-Dichloro-benzyl)-hexahydro-pyrrolo[3,4-c]pyrrol-2-yl]-2-oxo-ethyl}-4-trifluoromethoxy-benzamide | 1.82 | 515.1 |
| N-{2-[5-(2,4-Dichloro-benzyl)-hexahydro-pyrrolo[3,4-c]pyrrol-2-yl]-2-oxo-ethyl}-3,4,5-trifluoro-benzamide | 1.68 | 485.09 |
| N-{2-[5-(2,4-Dichloro-benzyl)-hexahydro-pyrrolo[3,4-c]pyrrol-2-yl]-2-oxo-ethyl}-4-isopropoxy-benzamide | 1.71 | 489.16 |
| N-{2-[5-(2,4-Dichloro-benzyl)-hexahydro-pyrrolo[3,4-c]pyrrol-2-yl]-2-oxo-ethyl}-4-propoxy-benzamide | 1.78 | 489.16 |
| 3-Chloro-N-{2-[5-(2,4-dichloro-benzyl)-hexahydro-pyrrolo[3,4-c]pyrrol-2-yl]-2-oxo-ethyl}-4-fluoro-benzamide | 1.7 | 483.07 |
| N-{2-[5-(2,4-Dichloro-benzyl)-hexahydro-pyrrolo[3,4-c]pyrrol-2-yl]-2-oxo-ethyl}-3-fluoro-5-trifluoromethyl-benzamide | 1.82 | 517.09 |
| 2-Bromo-N-{2-[5-(2,4-dichloro-benzyl)-hexahydro-pyrrolo[3,4-c]pyrrol-2-yl]-2-oxo-ethyl}-benzamide | 1.51 | 509.03 |
| 5-Bromo-2-chloro-N-{2-[5-(2,4-dichloro-benzyl)-hexahydro-pyrrolo[3,4-c]pyrrol-2-yl]-2-oxo-ethyl}-benzamide | 1.69 | 542.99 |
| 2-Bromo-5-chloro-N-{2-[5-(2,4-dichloro-benzyl)-hexahydro-pyrrolo[3,4-c]pyrrol-2-yl]-2-oxo-ethyl}-benzamide | 1.68 | 542.99 |
| 3-Bromo-N-{2-[5-(2,4-dichloro-benzyl)-hexahydro-pyrrolo[3,4-c]pyrrol-2-yl]-2-oxo-ethyl}-2-fluoro-benzamide | 1.68 | 527.02 |
| 4-Bromo-N-{2-[5-(2,4-dichloro-benzyl)-hexahydro-pyrrolo[3,4-c]pyrrol-2-yl]-2-oxo-ethyl}-2-methyl-benzamide | 1.74 | 523.04 |
| 4-Bromo-2-chloro-N-{2-[5-(2,4-dichloro-benzyl)-hexahydro-pyrrolo[3,4-c]pyrrol-2-yl]-2-oxo-ethyl}-benzamide | 1.73 | 542.99 |
| 2-Bromo-4-chloro-N-{2-[5-(2,4-dichloro-benzyl)-hexahydro-pyrrolo[3,4-c]pyrrol-2-yl]-2-oxo-ethyl}-benzamide | 1.73 | 542.99 |
| 2-Bromo-N-{2-[5-(2,4-dichloro-benzyl)-hexahydro-pyrrolo[3,4-c]pyrrol-2-yl]-2-oxo-ethyl}-3-methyl-benzamide | 1.63 | 523.04 |
| 2-Bromo-N-{2-[5-(2,4-dichloro-benzyl)-hexahydro-pyrrolo[3,4-c]pyrrol-2-yl]-2-oxo-ethyl}-5-methyl-benzamide | 1.64 | 523.04 |
| 3-Bromo-N-{2-[5-(2,4-dichloro-benzyl)-hexahydro-pyrrolo[3,4-c]pyrrol-2-yl]-2-oxo-ethyl}-2-methyl-benzamide | 1.72 | 523.04 |
| N-{2-[5-(2,4-Dichloro-benzyl)-hexahydro-pyrrolo[3,4-c]pyrrol-2-yl]-2-oxo-ethyl}-2-methylsulfanyl-benzamide | 1.55 | 477.1 |
| N-{2-[5-(2,4-Dimethyl-benzyl)-hexahydro-pyrrolo[3,4-c]pyrrol-2-yl]-2-oxo-ethyl}-3-trifluoromethyl-benzamide | 1.74 | 459.21 |
| 3-Chloro-N-{2-[5-(2,4-dimethyl-benzyl)-hexahydro-pyrrolo[3,4-c]pyrrol-2-yl]-2-oxo-ethyl}-benzamide | 1.61 | 425.19 |
| N-{2-[5-(2,4-Dimethoxy-benzyl)-hexahydro-pyrrolo[3,4-c]pyrrol-2-yl]-2-oxo-ethyl}-3-trifluoromethyl-benzamide | 1.63 | 491.2 |
| 4-Chloro-N-{2-[5-(2,4-dimethyl-benzyl)-hexahydro-pyrrolo[3,4-c]pyrrol-2-yl]-2-oxo-ethyl}-benzamide | 1.61 | 425.19 |
| 3,4-Dichloro-N-{2-[5-(2,4-dimethyl-benzyl)-hexahydro-pyrrolo[3,4-c]pyrrol-2-yl]-2-oxo-ethyl}-benzamide | 1.78 | 459.15 |
| N-[2-(5-Naphthalen-2-ylmethyl-hexahydro-pyrrolo[3,4-c]pyrrol-2-yl)-2-oxo-ethyl]-3-trifluoromethyl-benzamide | 1.79 | 481.2 |
| 3-Bromo-4-chloro-N-[2-(5-naphthalen-2-ylmethyl-hexahydro-pyrrolo[3,4-c]pyrrol-2-yl)-2-oxo-ethyl]-benzamide | 1.82 | 525.08 |

TABLE 2-continued

| Compound Name | Time (mins) | MW (found) |
|---|---|---|
| 3,4-Dichloro-N-[2-(5-naphthalen-2-ylmethyl-hexahydro-pyrrolo-[3,4-c]pyrrol-2-yl)-2-oxo-ethyl]-benzamide | 1.79 | 481.13 |
| N-[2-(5-Naphthalen-1-ylmethyl-hexahydro-pyrrolo[3,4-c]pyrrol-2-yl)-2-oxo-ethyl]-3-trifluoromethyl-benzamide | 1.74 | 481.2 |
| 3-Bromo-4-chloro-N-[2-(5-naphthalen-1-ylmethyl-hexahydro-pyrrolo[3,4-c]pyrrol-2-yl)-2-oxo-ethyl]-benzamide | 1.78 | 525.08 |
| 3,4-Dichloro-N-[2-(5-naphthalen-1-ylmethyl-hexahydro-pyrrolo-[3,4-c]pyrrol-2-yl)-2-oxo-ethyl]-benzamide | 1.75 | 481.13 |
| N-[2-Oxo-2-(5-quinolin-2-ylmethyl-hexahydro-pyrrolo[3,4-c]pyrrol-2-yl)-ethyl]-3-trifluoromethyl-benzamide | 1.66 | 482.19 |
| 3-Bromo-4-chloro-N-[2-oxo-2-(5-quinolin-2-ylmethyl-hexahydro-pyrrolo[3,4-c]pyrrol-2-yl)-ethyl]-benzamide | 1.69 | 526.08 |
| 3,4-Dichloro-N-[2-oxo-2-(5-quinolin-2-ylmethyl-hexahydro-pyrrolo[3,4-c]pyrrol-2-yl)-ethyl]-benzamide | 1.66 | 482.13 |
| 3,4-Dichloro-N-{2-[5-(2,4-dimethoxy-benzyl)-hexahydro-pyrrolo[3,4-c]pyrrol-2-yl]-2-oxo-ethyl}-benzamide | 1.69 | 491.14 |
| 3,4-Dichloro-N-{2-oxo-2-[5-(2-trifluoromethyl-benzyl)-hexahydro-pyrrolo[3,4-c]pyrrol-2-yl]-ethyl}-benzamide | 1.73 | 499.1 |
| 3-Bromo-4-chloro-N-{2-oxo-2-[5-(2-trifluoromethyl-benzyl)-hexahydro-pyrrolo[3,4-c]pyrrol-2-yl]-ethyl}-benzamide | 1.76 | 543.05 |
| N-{2-Oxo-2-[5-(2-trifluoromethyl-benzyl)-hexahydro-pyrrolo[3,4-c]pyrrol-2-yl]-ethyl}-3-trifluoromethyl-benzamide | 1.7 | 499.17 |
| 3,4-Dichloro-N-{2-oxo-2-[5-(4-trifluoromethyl-benzyl)-hexahydro-pyrrolo[3,4-c]pyrrol-2-yl]-ethyl}-benzamide | 1.82 | 499.1 |
| 3-Bromo-4-chloro-N-{2-oxo-2-[5-(4-trifluoromethyl-benzyl)-hexahydro-pyrrolo[3,4-c]pyrrol-2-yl]-ethyl}-benzamide | 1.85 | 543.05 |
| N-{2-Oxo-2-[5-(4-trifluoromethyl-benzyl)-hexahydro-pyrrolo[3,4-c]pyrrol-2-yl]-ethyl}-3-trifluoromethyl-benzamide | 1.79 | 499.17 |
| 3,4-Dichloro-N-{2-[5-(4-fluoro-2-trifluoromethyl-benzyl)-hexahydro-pyrrolo[3,4-c]pyrrol-2-yl]-2-oxo-ethyl}-benzamide | 1.8 | 517.09 |
| 3-Bromo-4-chloro-N-{2-[5-(4-fluoro-2-trifluoromethyl-benzyl)-hexahydro-pyrrolo[3,4-c]pyrrol-2-yl]-2-oxo-ethyl}-benzamide | 1.84 | 561.04 |
| 3-Fluoro-N-[2-(5-naphthalen-2-ylmethyl-hexahydro-pyrrolo[3,4-c]pyrrol-2-yl)-2-oxo-ethyl]-4-trifluoromethyl-benzamide | 1.84 | 499.19 |
| 3-Fluoro-N-[2-(5-naphthalen-1-ylmethyl-hexahydro-pyrrolo[3,4-c]pyrrol-2-yl)-2-oxo-ethyl]-4-trifluoromethyl-benzamide | 1.79 | 499.19 |
| 3-Fluoro-N-[2-oxo-2-(5-quinolin-2-ylmethyl-hexahydro-pyrrolo[3,4-c]pyrrol-2-yl)-ethyl]-4-trifluoromethyl-benzamide | 1.72 | 500.18 |
| 4-Bromo-N-[2-(5-naphthalen-2-ylmethyl-hexahydro-pyrrolo[3,4-c]pyrrol-2-yl)-2-oxo-ethyl]-benzamide | 1.68 | 491.12 |
| 4-Bromo-N-[2-(5-naphthalen-1-ylmethyl-hexahydro-pyrrolo[3,4-c]pyrrol-2-yl)-2-oxo-ethyl]-benzamide | 1.64 | 491.12 |
| 4-Bromo-N-[2-oxo-2-(5-quinolin-2-ylmethyl-hexahydro-pyrrolo[3,4-c]pyrrol-2-yl)-ethyl]-benzamide | 1.54 | 492.12 |
| 2-Bromo-5-methoxy-N-[2-(5-naphthalen-2-ylmethyl-hexahydro-pyrrolo[3,4-c]pyrrol-2-yl)-2-oxo-ethyl]-benzamide | 1.61 | 521.13 |
| 2-Bromo-5-methoxy-N-[2-(5-naphthalen-1-ylmethyl-hexahydro-pyrrolo[3,4-c]pyrrol-2-yl)-2-oxo-ethyl]-benzamide | 1.56 | 521.13 |
| 2-Bromo-5-methoxy-N-[2-oxo-2-(5-quinolin-2-ylmethyl-hexahydro-pyrrolo[3,4-c]pyrrol-2-yl)-ethyl]-benzamide | 1.47 | 522.13 |
| 4-tert-Butyl-N-[2-(5-naphthalen-2-ylmethyl-hexahydro-pyrrolo[3,4-c]pyrrol-2-yl)-2-oxo-ethyl]-benzamide | 1.9 | 469.27 |
| 4-tert-Butyl-N-[2-(5-naphthalen-1-ylmethyl-hexahydro-pyrrolo[3,4-c]pyrrol-2-yl)-2-oxo-ethyl]-benzamide | 1.86 | 469.27 |
| 4-tert-Butyl-N-[2-oxo-2-(5-quinolin-2-ylmethyl-hexahydro-pyrrolo[3,4-c]pyrrol-2-yl)-ethyl]-benzamide | 1.78 | 470.27 |
| N-[2-(5-Naphthalen-2-ylmethyl-hexahydro-pyrrolo[3,4-c]pyrrol-2-yl)-2-oxo-ethyl]-3,5-bis-trifluoromethyl-benzamide | 1.98 | 549.19 |
| N-[2-(5-Naphthalen-1-ylmethyl-hexahydro-pyrrolo[3,4-c]pyrrol-2-yl)-2-oxo-ethyl]-3,5-bis-trifluoromethyl-benzamide | 1.96 | 549.19 |
| N-[2-Oxo-2-(5-quinolin-2-ylmethyl-hexahydro-pyrrolo[3,4-c]pyrrol-2-yl)-ethyl]-3,5-bis-trifluoromethyl-benzamide | 1.87 | 550.18 |
| 3-Bromo-4-methyl-N-[2-(5-naphthalen-2-ylmethyl-hexahydro-pyrrolo[3,4-c]pyrrol-2-yl)-2-oxo-ethyl]-benzamide | 1.79 | 505.14 |
| 3-Bromo-4-methyl-N-[2-(5-naphthalen-1-ylmethyl-hexahydro-pyrrolo[3,4-c]pyrrol-2-yl)-2-oxo-ethyl]-benzamide | 1.74 | 505.14 |
| 3-Bromo-4-methyl-N-[2-oxo-2-(5-quinolin-2-ylmethyl-hexahydro-pyrrolo[3,4-c]pyrrol-2-yl)-ethyl]-benzamide | 1.65 | 506.13 |
| 4-Bromo-3-methyl-N-[2-(5-naphthalen-2-ylmethyl-hexahydro-pyrrolo[3,4-c]pyrrol-2-yl)-2-oxo-ethyl]-benzamide | 1.78 | 505.14 |
| 4-Bromo-3-methyl-N-[2-(5-naphthalen-1-ylmethyl-hexahydro-pyrrolo[3,4-c]pyrrol-2-yl)-2-oxo-ethyl]-benzamide | 1.74 | 505.14 |
| 4-Bromo-3-methyl-N-[2-oxo-2-(5-quinolin-2-ylmethyl-hexahydro-pyrrolo[3,4-c]pyrrol-2-yl)-ethyl]-benzamide | 1.67 | 506.13 |
| 3-Bromo-N-[2-(5-naphthalen-2-ylmethyl-hexahydro-pyrrolo[3,4-c]pyrrol-2-yl)-2-oxo-ethyl]-benzamide | 1.67 | 491.12 |
| 3-Bromo-N-[2-(5-naphthalen-1-ylmethyl-hexahydro-pyrrolo[3,4-c]pyrrol-2-yl)-2-oxo-ethyl]-benzamide | 1.64 | 491.12 |
| 3-Bromo-N-[2-oxo-2-(5-quinolin-2-ylmethyl-hexahydro-pyrrolo-[3,4-c]pyrrol-2-yl)-ethyl]-benzamide | 1.53 | 492.12 |

TABLE 2-continued

| Compound Name | Time (mins) | MW (found) |
|---|---|---|
| 3-Bromo-N-[2-oxo-2-(5-quinolin-4-ylmethyl-hexahydro-pyrrolo[3,4-c]pyrrol-2-yl)-ethyl]-benzamide | 1.67 | 492.12 |
| N-[2-(5-Naphthalen-2-ylmethyl-hexahydro-pyrrolo[3,4-c]pyrrol-2-yl)-2-oxo-ethyl]-4-trifluoromethyl-benzamide | 1.76 | 481.2 |
| N-[2-(5-Naphthalen-1-ylmethyl-hexahydro-pyrrolo[3,4-c]pyrrol-2-yl)-2-oxo-ethyl]-4-trifluoromethyl-benzamide | 1.73 | 481.2 |
| N-[2-Oxo-2-(5-quinolin-2-ylmethyl-hexahydro-pyrrolo[3,4-c]pyrrol-2-yl)-ethyl]-4-trifluoromethyl-benzamide | 1.64 | 482.19 |
| N-[2-Oxo-2-(5-quinolin-4-ylmethyl-hexahydro-pyrrolo[3,4-c]pyrrol-2-yl)-ethyl]-4-trifluoromethyl-benzamide | 1.79 | 482.19 |
| 3-Fluoro-N-{2-oxo-2-[5-(4-trifluoromethyl-benzyl)-hexahydro-pyrrolo[3,4-c]pyrrol-2-yl]-ethyl}-4-trifluoromethyl-benzamide | 1.85 | 517.16 |
| 3-Fluoro-N-{2-oxo-2-[5-(2-trifluoromethyl-benzyl)-hexahydro-pyrrolo[3,4-c]pyrrol-2-yl]-ethyl}-4-trifluoromethyl-benzamide | 1.78 | 517.16 |
| 3-Fluoro-N-{2-[5-(4-fluoro-2-trifluoromethyl-benzyl)-hexahydro-pyrrolo[3,4-c]pyrrol-2-yl]-2-oxo-ethyl}-4-trifluoromethyl-benzamide | 1.84 | 535.15 |
| 4-Bromo-N-{2-oxo-2-[5-(4-trifluoromethyl-benzyl)-hexahydro-pyrrolo[3,4-c]pyrrol-2-yl]-ethyl}-benzamide | 1.7 | 509.09 |
| 4-Bromo-N-{2-oxo-2-[5-(2-trifluoromethyl-benzyl)-hexahydro-pyrrolo[3,4-c]pyrrol-2-yl]-ethyl}-benzamide | 1.6 | 509.09 |
| 4-Bromo-N-{2-[5-(2-fluoro-4-trifluoromethyl-benzyl)-hexahydro-pyrrolo[3,4-c]pyrrol-2-yl]-2-oxo-ethyl}-benzamide | 1.7 | 527.08 |
| 4-Bromo-N-{2-[5-(4-fluoro-2-trifluoromethyl-benzyl)-hexahydro-pyrrolo[3,4-c]pyrrol-2-yl]-2-oxo-ethyl}-benzamide | 1.66 | 527.08 |
| 2-Bromo-5-methoxy-N-{2-oxo-2-[5-(4-trifluoromethyl-benzyl)-hexahydro-pyrrolo[3,4-c]pyrrol-2-yl]-ethyl}-benzamide | 1.63 | 539.1 |
| 2-Bromo-5-methoxy-N-{2-oxo-2-[5-(2-trifluoromethyl-benzyl)-hexahydro-pyrrolo[3,4-c]pyrrol-2-yl]-ethyl}-benzamide | 1.52 | 539.1 |
| 2-Bromo-N-{2-[5-(4-fluoro-2-trifluoromethyl-benzyl)-hexahydro-pyrrolo[3,4-c]pyrrol-2-yl]-2-oxo-ethyl}-5-methoxy-benzamide | 1.59 | 557.09 |
| 4-tert-Butyl-N-{2-oxo-2-[5-(4-trifluoromethyl-benzyl)-hexahydro-pyrrolo[3,4-c]pyrrol-2-yl]-ethyl}-benzamide | 1.92 | 487.24 |
| 4-tert-Butyl-N-{2-oxo-2-[5-(2-trifluoromethyl-benzyl)-hexahydro-pyrrolo[3,4-c]pyrrol-2-yl]-ethyl}-benzamide | 1.84 | 487.24 |
| 4-tert-Butyl-N-{2-[5-(2-fluoro-4-trifluoromethyl-benzyl)-hexahydro-pyrrolo[3,4-c]pyrrol-2-yl]-2-oxo-ethyl}-benzamide | 1.92 | 505.24 |
| 4-tert-Butyl-N-{2-[5-(4-fluoro-2-trifluoromethyl-benzyl)-hexahydro-pyrrolo[3,4-c]pyrrol-2-yl]-2-oxo-ethyl}-benzamide | 1.93 | 505.24 |
| N-{2-Oxo-2-[5-(4-trifluoromethyl-benzyl)-hexahydro-pyrrolo[3,4-c]pyrrol-2-yl]-ethyl}-3,5-bis-trifluoromethyl-benzamide | 2.02 | 567.16 |
| N-{2-Oxo-2-[5-(2-trifluoromethyl-benzyl)-hexahydro-pyrrolo[3,4-c]pyrrol-2-yl]-ethyl}-3,5-bis-trifluoromethyl-benzamide | 1.97 | 567.16 |
| N-{2-[5-(4-Fluoro-2-trifluoromethyl-benzyl)-hexahydro-pyrrolo[3,4-c]pyrrol-2-yl]-2-oxo-ethyl}-3,5-bis-trifluoromethyl-benzamide | 2.04 | 585.15 |
| 3-Bromo-4-methyl-N-{2-oxo-2-[5-(4-trifluoromethyl-benzyl)-hexahydro-pyrrolo[3,4-c]pyrrol-2-yl]-ethyl}-benzamide | 1.81 | 523.11 |
| 3-Bromo-4-methyl-N-{2-oxo-2-[5-(2-trifluoromethyl-benzyl)-hexahydro-pyrrolo[3,4-c]pyrrol-2-yl]-ethyl}-benzamide | 1.72 | 523.11 |
| 3-Bromo-N-{2-[5-(2-fluoro-4-trifluoromethyl-benzyl)-hexahydro-pyrrolo[3,4-c]pyrrol-2-yl]-2-oxo-ethyl}-4-methyl-benzamide | 1.79 | 541.1 |
| 3-Bromo-N-{2-[5-(4-fluoro-2-trifluoromethyl-benzyl)-hexahydro-pyrrolo[3,4-c]pyrrol-2-yl]-2-oxo-ethyl}-4-methyl-benzamide | 1.78 | 541.1 |
| 4-Bromo-3-methyl-N-{2-oxo-2-[5-(4-trifluoromethyl-benzyl)-hexahydro-pyrrolo[3,4-c]pyrrol-2-yl]-ethyl}-benzamide | 1.83 | 523.11 |
| 4-Bromo-3-methyl-N-{2-oxo-2-[5-(2-trifluoromethyl-benzyl)-hexahydro-pyrrolo[3,4-c]pyrrol-2-yl]-ethyl}-benzamide | 1.74 | 523.11 |
| 4-Bromo-N-{2-[5-(2-fluoro-4-trifluoromethyl-benzyl)-hexahydro-pyrrolo[3,4-c]pyrrol-2-yl]-2-oxo-ethyl}-3-methyl-benzamide | 1.83 | 541.1 |
| 4-Bromo-N-{2-[5-(4-fluoro-2-trifluoromethyl-benzyl)-hexahydro-pyrrolo[3,4-c]pyrrol-2-yl]-2-oxo-ethyl}-3-methyl-benzamide | 1.81 | 541.1 |
| 3-Bromo-N-{2-oxo-2-[5-(4-trifluoromethyl-benzyl)-hexahydro-pyrrolo[3,4-c]pyrrol-2-yl]-ethyl}-benzamide | 1.71 | 509.09 |
| 3-Bromo-N-{2-oxo-2-[5-(2-trifluoromethyl-benzyl)-hexahydro-pyrrolo[3,4-c]pyrrol-2-yl]-ethyl}-benzamide | 1.61 | 509.09 |
| 3-Bromo-N-{2-[5-(4-fluoro-2-trifluoromethyl-benzyl)-hexahydro-pyrrolo[3,4-c]pyrrol-2-yl]-2-oxo-ethyl}-benzamide | 1.67 | 527.08 |
| N-{2-Oxo-2-[5-(4-trifluoromethyl-benzyl)-hexahydro-pyrrolo[3,4-c]pyrrol-2-yl]-ethyl}-4-trifluoromethyl-benzamide | 1.81 | 499.17 |
| N-{2-Oxo-2-[5-(2-trifluoromethyl-benzyl)-hexahydro-pyrrolo[3,4-c]pyrrol-2-yl]-ethyl}-4-trifluoromethyl-benzamide | 1.71 | 499.17 |
| N-{2-[5-(4-Fluoro-2-trifluoromethyl-benzyl)-hexahydro-pyrrolo[3,4-c]pyrrol-2-yl]-2-oxo-ethyl}-4-trifluoromethyl-benzamide | 1.78 | 517.16 |
| 3-Fluoro-N-[2-(5-naphthalen-2-ylmethyl-hexahydro-pyrrolo[3,4-c]pyrrol-2-yl)-2-oxo-ethyl]-benzamide | 1.56 | 431.2 |
| 3-Fluoro-N-[2-(5-naphthalen-1-ylmethyl-hexahydro-pyrrolo[3,4-c]pyrrol-2-yl)-2-oxo-ethyl]-benzamide | 1.51 | 431.2 |
| 3-Fluoro-N-[2-oxo-2-(5-quinolin-2-ylmethyl-hexahydro-pyrrolo[3,4-c]pyrrol-2-yl)-ethyl]-benzamide | 1.42 | 432.2 |
| 3,4-Difluoro-N-[2-(5-naphthalen-2-ylmethyl-hexahydro-pyrrolo[3,4-c]pyrrol-2-yl)-2-oxo-ethyl]-benzamide | 1.63 | 449.19 |

TABLE 2-continued

| Compound Name | Time (mins) | MW (found) |
|---|---|---|
| 3,4-Difluoro-N-[2-(5-naphthalen-1-ylmethyl-hexahydro-pyrrolo[3,4-c]-pyrrol-2-yl)-2-oxo-ethyl]-benzamide | 1.59 | 449.19 |
| 3,4-Difluoro-N-[2-oxo-2-(5-quinolin-2-ylmethyl-hexahydro-pyrrolo[3,4-c]pyrrol-2-yl)-ethyl]-benzamide | 1.5 | 450.19 |
| 4-Fluoro-N-[2-(5-naphthalen-2-ylmethyl-hexahydro-pyrrolo[3,4-c]-pyrrol-2-yl)-2-oxo-ethyl]-benzamide | 1.56 | 431.2 |
| 4-Fluoro-N-[2-(5-naphthalen-1-ylmethyl-hexahydro-pyrrolo[3,4-c]-pyrrol-2-yl)-2-oxo-ethyl]-benzamide | 1.5 | 431.2 |
| 4-Fluoro-N-[2-oxo-2-(5-quinolin-2-ylmethyl-hexahydro-pyrrolo[3,4-c]-pyrrol-2-yl)-ethyl]-benzamide | 1.4 | 432.2 |
| 3-Methyl-N-[2-(5-naphthalen-2-ylmethyl-hexahydro-pyrrolo[3,4-c]-pyrrol-2-yl)-2-oxo-ethyl]-benzamide | 1.61 | 427.23 |
| 3-Methyl-N-[2-(5-naphthalen-1-ylmethyl-hexahydro-pyrrolo[3,4-c]-pyrrol-2-yl)-2-oxo-ethyl]-benzamide | 1.56 | 427.23 |
| 3-Methyl-N-[2-oxo-2-(5-quinolin-2-ylmethyl-hexahydro-pyrrolo[3,4-c]-pyrrol-2-yl)-ethyl]-benzamide | 1.46 | 428.22 |
| 3-Fluoro-4-methyl-N-[2-(5-naphthalen-2-ylmethyl-hexahydro-pyrrolo[3,4-c]pyrrol-2-yl)-2-oxo-ethyl]-benzamide | 1.68 | 445.22 |
| 3-Fluoro-4-methyl-N-[2-(5-naphthalen-1-ylmethyl-hexahydro-pyrrolo[3,4-c]-pyrrol-2-yl)-2-oxo-ethyl]-benzamide | 1.63 | 445.22 |
| 3-Fluoro-4-methyl-N-[2-oxo-2-(5-quinolin-2-ylmethyl-hexahydro-pyrrolo[3,4-c]pyrrol-2-yl)-ethyl]-benzamide | 1.54 | 446.21 |
| 3-Fluoro-4-methyl-N-[2-oxo-2-(5-quinolin-4-ylmethyl-hexahydro-pyrrolo[3,4-c]pyrrol-2-yl)-ethyl]-benzamide | 2.14 | 446.21 |
| N-[2-(5-Naphthalen-2-ylmethyl-hexahydro-pyrrolo[3,4-c]pyrrol-2-yl)-2-oxo-ethyl]-benzamide | 1.48 | 413.21 |
| N-[2-(5-Naphthalen-1-ylmethyl-hexahydro-pyrrolo[3,4-c]pyrrol-2-yl)-2- oxo-ethyl]-benzamide | 1.44 | 413.21 |
| N-[2-Oxo-2-(5-quinolin-2-ylmethyl-hexahydro-pyrrolo[3,4-c]pyrrol-2-yl)-ethyl]-benzamide | 1.33 | 414.21 |
| 3-Chloro-N-[2-(5-naphthalen-2-ylmethyl-hexahydro-pyrrolo[3,4-c]-pyrrol-2-yl)-2-oxo-ethyl]-benzamide | 1.68 | 447.17 |
| 3-Chloro-N-[2-(5-naphthalen-1-ylmethyl-hexahydro-pyrrolo[3,4-c]-pyrrol-2-yl)-2-oxo-ethyl]-benzamide | 1.64 | 447.17 |
| 3-Chloro-N-[2-oxo-2-(5-quinolin-2-ylmethyl-hexahydro-pyrrolo[3,4-c]-pyrrol-2-yl)-ethyl]-benzamide | 1.52 | 448.17 |
| 3-Chloro-N-[2-oxo-2-(5-quinolin-4-ylmethyl-hexahydro-pyrrolo[3,4-c]-pyrrol-2-yl)-ethyl]-benzamide | 1.66 | 448.17 |
| 3,5-Difluoro-N-[2-(5-naphthalen-2-ylmethyl-hexahydro-pyrrolo[3,4-c]-pyrrol-2-yl)-2-oxo-ethyl]-benzamide | 1.62 | 449.19 |
| 3,5-Difluoro-N-[2-(5-naphthalen-1-ylmethyl-hexahydro-pyrrolo[3,4-c]-pyrrol-2-yl)-2-oxo-ethyl]-benzamide | 1.59 | 449.19 |
| 3,5-Difluoro-N-[2-oxo-2-(5-quinolin-2-ylmethyl-hexahydro-pyrrolo[3,4-c]-pyrrol-2-yl)-ethyl]-benzamide | 1.48 | 450.19 |
| 4-Methyl-N-[2-(5-naphthalen-2-ylmethyl-hexahydro-pyrrolo[3,4-c]-pyrrol-2-yl)-2-oxo-ethyl]-benzamide | 1.61 | 427.23 |
| 4-Methyl-N-[2-(5-naphthalen-1-ylmethyl-hexahydro-pyrrolo[3,4-c]-pyrrol-2-yl)-2-oxo-ethyl]-benzamide | 1.57 | 427.23 |
| 4-Methyl-N-[2-oxo-2-(5-quinolin-2-ylmethyl-hexahydro-pyrrolo[3,4-c]-pyrrol-2-yl)-ethyl]-benzamide | 1.46 | 428.22 |
| 3,4-Dimethyl-N-[2-(5-naphthalen-2-ylmethyl-hexahydro-pyrrolo[3,4-c]-pyrrol-2-yl)-2-oxo-ethyl]-benzamide | 1.7 | 441.24 |
| 3,4-Dimethyl-N-[2-(5-naphthalen-1-ylmethyl-hexahydro-pyrrolo[3,4-c]-pyrrol-2-yl)-2-oxo-ethyl]-benzamide | 1.66 | 441.24 |
| 3,4-Dimethyl-N-[2-oxo-2-(5-quinolin-2-ylmethyl-hexahydro-pyrrolo[3,4-c]-pyrrol-2-yl)-ethyl]-benzamide | 1.57 | 442.24 |
| 4-Chloro-N-[2-(5-naphthalen-2-ylmethyl-hexahydro-pyrrolo[3,4-c]-pyrrol-2-yl)-2-oxo-ethyl]-benzamide | 1.68 | 447.17 |
| 4-Chloro-N-[2-(5-naphthalen-1-ylmethyl-hexahydro-pyrrolo[3,4-c]-pyrrol-2-yl)-2-oxo-ethyl]-benzamide | 1.64 | 447.17 |
| 4-Chloro-N-[2-oxo-2-(5-quinolin-2-ylmethyl-hexahydro-pyrrolo[3,4-c]-pyrrol-2-yl)-ethyl]-benzamide | 1.5 | 448.17 |
| 3-Fluoro-N-{2-oxo-2-[5-(4-trifluoromethyl-benzyl)-hexahydro-pyrrolo[3,4-c]pyrrol-2-yl]-ethyl}-benzamide | 1.57 | 449.17 |
| 3-Fluoro-N-{2-oxo-2-[5-(2-trifluoromethyl-benzyl)-hexahydro-pyrrolo[3,4-c]pyrrol-2-yl]-ethyl}-benzamide | 1.44 | 449.17 |
| 3-Fluoro-N-{2-[5-(4-fluoro-2-trifluoromethyl-benzyl)-hexahydro-pyrrolo[3,4-c]pyrrol-2-yl]-2-oxo-ethyl}-benzamide | 1.51 | 467.16 |
| 3,4-Difluoro-N-{2-oxo-2-[5-(4-trifluoromethyl-benzyl)-hexahydro-pyrrolo[3,4-c]pyrrol-2-yl]-ethyl}-benzamide | 1.65 | 467.16 |
| 3,4-Difluoro-N-{2-oxo-2-[5-(2-trifluoromethyl-benzyl)-hexahydro-pyrrolo[3,4-c]pyrrol-2-yl]-ethyl}-benzamide | 1.52 | 467.16 |
| 3,4-Difluoro-N-{2-[5-(4-fluoro-2-trifluoromethyl-benzyl)-hexahydro-pyrrolo[3,4-c]pyrrol-2-yl]-2-oxo-ethyl}-benzamide | 1.59 | 485.15 |
| 4-Fluoro-N-{2-oxo-2-[5-(4-trifluoromethyl-benzyl)-hexahydro-pyrrolo[3,4-c]pyrrol-2-yl]-ethyl}-benzamide | 1.57 | 449.17 |
| 4-Fluoro-N-{2-oxo-2-[5-(2-trifluoromethyl-benzyl)-hexahydro-pyrrolo[3,4-c]pyrrol-2-yl]-ethyl}-benzamide | 1.43 | 449.17 |
| 4-Fluoro-N-{2-[5-(4-fluoro-2-trifluoromethyl-benzyl)-hexahydro-pyrrolo[3,4-c]pyrrol-2-yl]-2-oxo-ethyl}-benzamide | 1.51 | 467.16 |
| 3-Methyl-N-{2-oxo-2-[5-(4-trifluoromethyl-benzyl)-hexahydro-pyrrolo[3,4-c]pyrrol-2-yl]-ethyl}-benzamide | 1.63 | 445.2 |
| 3-Methyl-N-{2-oxo-2-[5-(2-trifluoromethyl-benzyl)-hexahydro-pyrrolo[3,4-c]pyrrol-2-yl]-ethyl}-benzamide | 1.5 | 445.2 |
| N-{2-[5-(2-Fluoro-4-trifluoromethyl-benzyl)-hexahydro-pyrrolo[3,4-c]pyrrol-2-yl]-2-oxo-ethyl}-3-methyl-benzamide | 1.62 | 463.19 |
| N-{2-[5-(4-Fluoro-2-trifluoromethyl-benzyl)-hexahydro-pyrrolo[3,4-c]pyrrol-2-yl]-2-oxo-ethyl}-3-methyl-benzamide | 1.58 | 463.19 |

TABLE 2-continued

| Compound Name | Time (mins) | MW (found) |
|---|---|---|
| 3-Fluoro-4-methyl-N-{2-oxo-2-[5-(4-trifluoromethyl-benzyl)-hexahydro-pyrrolo[3,4-c]-pyrrol-2-yl]-ethyl}-benzamide | 1.71 | 463.19 |
| 3-Fluoro-4-methyl-N-{2-oxo-2-[5-(2-trifluoromethyl-benzyl)-hexahydro-pyrrolo[3,4-c]-pyrrol-2-yl]-ethyl}-benzamide | 1.59 | 463.19 |
| 3-Fluoro-N-{2-[5-(4-fluoro-2-trifluoromethyl-benzyl)-hexahydro-pyrrolo[3,4-c]pyrrol-2-yl]-2-oxo-ethyl}-4-methyl-benzamide | 1.64 | 481.18 |
| N-{2-Oxo-2-[5-(4-trifluoromethyl-benzyl)-hexahydro-pyrrolo[3,4-c]-pyrrol-2-yl]ethyl}-benzamide | 1.51 | 431.18 |
| N-{2-Oxo-2-[5-(2-trifluoromethyl-benzyl)-hexahydro-pyrrolo[3,4-c]-pyrrol-2-yl]-ethyl}-benzamide | 1.37 | 431.18 |
| N-{2-[5-(4-Fluoro-2-trifluoromethyl-benzyl)-hexahydro-pyrrolo[3,4-c]pyrrol-2-yl]-2-oxo-ethyl}-benzamide | 1.43 | 449.17 |
| 3-Chloro-N-{2-oxo-2-[5-(4-trifluoromethyl-benzyl)-hexahydro-pyrrolo[3,4-c]pyrrol-2-yl]-ethyl}-benzamide | 1.7 | 465.14 |
| 3-Chloro-N-{2-oxo-2-[5-(2-trifluoromethyl-benzyl)-hexahydro-pyrrolo[3,4-c]pyrrol-2-yl]-ethyl}-benzamide | 1.57 | 465.14 |
| 3-Chloro-N-{2-[5-(4-fluoro-2-trifluoromethyl-benzyl)-hexahydro-pyrrolo[3,4-c]pyrrol-2-yl]-2-oxo-ethyl}-benzamide | 1.65 | 483.13 |
| 3,5-Difluoro-N-{2-oxo-2-[5-(2-trifluoromethyl-benzyl)-hexahydro-pyrrolo[3,4-c]pyrrol-2-yl]-ethyl}-benzamide | 1.52 | 467.16 |
| 3,5-Difluoro-N-{2-[5-(4-fluoro-2-trifluoromethyl-benzyl)-hexahydro-pyrrolo[3,4-c]pyrrol-2-yl]-2-oxo-ethyl}-benzamide | 1.59 | 485.15 |
| 4-Methyl-N-{2-oxo-2-[5-(4-trifluoromethyl-benzyl)-hexahydro-pyrrolo[3,4-c]pyrrol-2-yl]-ethyl}-benzamide | 1.64 | 445.2 |
| 4-Methyl-N-{2-oxo-2-[5-(2-trifluoromethyl-benzyl)-hexahydro-pyrrolo[3,4-c]pyrrol-2-yl]-ethyl}-benzamide | 1.51 | 445.2 |
| N-{2-[5-(2-Fluoro-4-trifluoromethyl-benzyl)-hexahydro-pyrrolo[3,4-c]pyrrol-2-yl]-2-oxo-ethyl}-4-methyl-benzamide | 1.62 | 463.19 |
| N-{2-[5-(4-Fluoro-2-trifluoromethyl-benzyl)-hexahydro-pyrrolo[3,4-c]pyrrol-2-yl]-2-oxo-ethyl}-4-methyl-benzamide | 1.57 | 463.19 |
| 3,4-Dimethyl-N-{2-oxo-2-[5-(4-trifluoromethyl-benzyl)-hexahydro-pyrrolo[3,4-c]pyrrol-2-yl]-ethyl}-benzamide | 1.73 | 459.21 |
| 3,4-Dimethyl-N-{2-oxo-2-[5-(2-trifluoromethyl-benzyl)-hexahydro-pyrrolo[3,4-c]pyrrol-2-yl]-ethyl}-benzamide | 1.62 | 459.21 |
| N-{2-[5-(2-Fluoro-4-trifluoromethyl-benzyl)-hexahydro-pyrrolo[3,4-c]pyrrol-2-yl]-2-oxo-ethyl}-3,4-dimethyl-benzamide | 1.72 | 477.2 |
| N-{2-[5-(4-Fluoro-2-trifluoromethyl-benzyl)-hexahydro-pyrrolo[3,4-c]pyrrol-2-yl]-2-oxo-ethyl}-3,4-dimethyl-benzamide | 1.68 | 477.2 |
| 4-Chloro-N-{2-oxo-2-[5-(4-trifluoromethyl-benzyl)-hexahydro-pyrrolo[3,4-c]pyrrol-2-yl]-ethyl}-benzamide | 1.7 | 465.14 |
| 4-Chloro-N-{2-oxo-2-[5-(2-trifluoromethyl-benzyl)-hexahydro-pyrrolo[3,4-c]pyrrol-2-yl]-ethyl}-benzamide | 1.59 | 465.14 |
| 4-Chloro-N-{2-[5-(2-fluoro-4-trifluoromethyl-benzyl)-hexahydro-pyrrolo[3,4-c]pyrrol-2-yl]-2-oxo-ethyl}-benzamide | 1.69 | 483.13 |
| 4-Chloro-N-{2-[5-(4-fluoro-2-trifluoromethyl-benzyl)-hexahydro-pyrrolo[3,4-c]pyrrol-2-yl]-2-oxo-ethyl}-benzamide | 1.66 | 483.13 |
| 4-Ethylsulfanyl-N-[2-(5-naphthalen-2-ylmethyl-hexahydro-pyrrolo[3,4-c]pyrrol-2-yl)-2-oxo-ethyl]-benzamide | 1.78 | 473.21 |
| 4-Ethylsulfanyl-N-[2-(5-naphthalen-1-ylmethyl-hexahydro-pyrrolo[3,4-c]pyrrol-2-yl)-2-oxo-ethyl]-benzamide | 1.74 | 473.21 |
| 4-Ethylsulfanyl-N-[2-oxo-2-(5-quinolin-2-ylmethyl-hexahydro-pyrrolo[3,4-c]pyrrol-2-yl)-ethyl]-benzamide | 1.65 | 474.21 |
| 4-Butyl-N-[2-(5-naphthalen-2-ylmethyl-hexahydro-pyrrolo[3,4-c]pyrrol-2-yl)-2-oxo-ethyl]-benzamide | 1.99 | 469.27 |
| 4-Butyl-N-[2-(5-naphthalen-1-ylmethyl-hexahydro-pyrrolo[3,4-c]pyrrol-2-yl)-2-oxo-ethyl]-benzamide | 1.95 | 469.27 |
| 4-Butyl-N-[2-oxo-2-(5-quinolin-2-ylmethyl-hexahydro-pyrrolo[3,4-c]pyrrol-2-yl)-ethyl]-benzamide | 1.88 | 470.27 |
| 4-Isopropyl-N-[2-(5-naphthalen-2-ylmethyl-hexahydro-pyrrolo[3,4-c]-pyrrol-2-yl)-2-oxo-ethyl]-benzamide | 1.84 | 455.26 |
| 4-Isopropyl-N-[2-(5-naphthalen-1-ylmethyl-hexahydro-pyrrolo[3,4-c]-pyrrol-2-yl)-2-oxo-ethyl]-benzamide | 1.8 | 455.26 |
| 4-Isopropyl-N-[2-oxo-2-(5-quinolin-2-ylmethyl-hexahydro-pyrrolo[3,4-c]pyrrol-2-yl)-ethyl]-benzamide | 1.71 | 456.25 |
| N-[2-(5-Naphthalen-2-ylmethyl-hexahydro-pyrrolo[3,4-c]pyrrol-2-yl)-2-oxo-ethyl]-4-trifluoromethoxy-benzamide | 1.83 | 497.19 |
| N-[2-(5-Naphthalen-1-ylmethyl-hexahydro-pyrrolo[3,4-c]pyrrol-2-yl)-2-oxo-ethyl]-4-trifluoromethoxy-benzamide | 1.79 | 497.19 |
| N-[2-Oxo-2-(5-quinolin-2-ylmethyl-hexahydro-pyrrolo[3,4-c]pyrrol-2-yl)-ethyl]-4-trifluoromethoxy-benzamide | 1.71 | 498.19 |
| 3,4,5-Trifluoro-N-[2-(5-naphthalen-2-ylmethyl-hexahydro-pyrrolo[3,4-c]pyrrol-2-yl)-2-oxo-ethyl]-benzamide | 1.72 | 467.18 |
| 3,4,5-Trifluoro-N-[2-(5-naphthalen-1-ylmethyl-hexahydro-pyrrolo[3,4-c]pyrrol-2-yl)-2-oxo-ethyl]-benzamide | 1.67 | 467.18 |
| 3,4,5-Trifluoro-N-[2-oxo-2-(5-quinolin-2-ylmethyl-hexahydro-pyrrolo[3,4-c]pyrrol-2-yl)-ethyl]-benzamide | 1.57 | 468.18 |

TABLE 2-continued

| Compound Name | Time (mins) | MW (found) |
|---|---|---|
| N-[2-(5-Naphthalen-2-ylmethyl-hexahydro-pyrrolo[3,4-c]pyrrol-2-yl)-2-oxo-ethyl]-4-propyl-benzamide | 1.85 | 455.26 |
| N-[2-(5-Naphthalen-1-ylmethyl-hexahydro-pyrrolo[3,4-c]pyrrol-2-yl)-2-oxo-ethyl]-4-propyl-benzamide | 1.82 | 455.26 |
| N-[2-Oxo-2-(5-quinolin-2-ylmethyl-hexahydro-pyrrolo[3,4-c]pyrrol-2-yl)-ethyl]-4-propyl-benzamide | 1.74 | 456.25 |
| N-[2-Oxo-2-(5-quinolin-4-ylmethyl-hexahydro-pyrrolo[3,4-c]pyrrol-2-yl)-ethyl]-4-propyl-benzamide | 1.85 | 456.25 |
| 4-Isopropoxy-N-[2-(5-naphthalen-2-ylmethyl-hexahydro-pyrrolo[3,4-c]pyrrol-2-yl)-2-oxo-ethyl]-benzamide | 1.73 | 471.25 |
| 4-Isopropoxy-N-[2-(5-naphthalen-1-ylmethyl-hexahydro-pyrrolo[3,4-c]pyrrol-2-yl)-2-oxo-ethyl]-benzamide | 1.7 | 471.25 |
| 4-Isopropoxy-N-[2-oxo-2-(5-quinolin-2-ylmethyl-hexahydro-pyrrolo[3,4-c]pyrrol-2-yl)-ethyl]-benzamide | 1.61 | 472.25 |
| N-[2-(5-Naphthalen-2-ylmethyl-hexahydro-pyrrolo[3,4-c]pyrrol-2-yl)-2-oxo-ethyl]-4-propoxy-benzamide | 1.79 | 471.25 |
| N-[2-(5-Naphthalen-1-ylmethyl-hexahydro-pyrrolo[3,4-c]pyrrol-2-yl)-2-oxo-ethyl]-4-propoxy-benzamide | 1.76 | 471.25 |
| N-[2-Oxo-2-(5-quinolin-2-ylmethyl-hexahydro-pyrrolo[3,4-c]pyrrol-2-yl)-ethyl]-4-propoxy-benzamide | 1.66 | 472.25 |
| 3-Chloro-4-fluoro-N-[2-(5-naphthalen-2-ylmethyl-hexahydro-pyrrolo[3,4-c]pyrrol-2-yl)-2-oxo-ethyl]-benzamide | 1.73 | 465.16 |
| 3-Chloro-4-fluoro-N-[2-(5-naphthalen-1-ylmethyl-hexahydro-pyrrolo[3,4-c]pyrrol-2-yl)-2-oxo-ethyl]-benzamide | 1.68 | 465.16 |
| 3-Chloro-4-fluoro-N-[2-oxo-2-(5-quinolin-2-ylmethyl-hexahydro-pyrrolo[3,4-c]pyrrol-2-yl)-ethyl]-benzamide | 1.57 | 466.16 |
| 3-Fluoro-N-[2-(5-naphthalen-2-ylmethyl-hexahydro-pyrrolo[3,4-c]pyrrol-2-yl)-2-oxo-ethyl]-5-trifluoromethyl-benzamide | 1.83 | 499.19 |
| 3-Fluoro-N-[2-(5-naphthalen-1-ylmethyl-hexahydro-pyrrolo[3,4-c]pyrrol-2-yl)-2-oxo-ethyl]-5-trifluoromethyl-benzamide | 1.8 | 499.19 |
| 3-Fluoro-N-[2-oxo-2-(5-quinolin-2-ylmethyl-hexahydro-pyrrolo[3,4-c]pyrrol-2-yl)-ethyl]-5-trifluoromethyl-benzamide | 1.71 | 500.18 |
| N-{2-[5-(4-Fluoro-2-trifluoromethyl-benzyl)-hexahydro-pyrrolo[3,4-c]pyrrol-2-yl]-2-oxo-ethyl}-3-trifluoromethyl-benzamide | 1.77 | 517.16 |
| 4-Ethylsulfanyl-N-{2-oxo-2-[5-(4-trifluoromethyl-benzyl)-hexahydro-pyrrolo[3,4-c]pyrrol-2-yl]-ethyl}-benzamide | 1.8 | 491.19 |
| 4-Ethylsulfanyl-N-{2-oxo-2-[5-(2-trifluoromethyl-benzyl)-hexahydro-pyrrolo[3,4-c]pyrrol-2-yl]-ethyl}-benzamide | 1.7 | 491.19 |
| 4-Ethylsulfanyl-N-{2-[5-(2-fluoro-4-trifluoromethyl-benzyl)-hexahydro-pyrrolo[3,4-c]pyrrol-2-yl]-2-oxo-ethyl}-benzamide | 1.8 | 509.18 |
| 4-Ethylsulfanyl-N-{2-[5-(4-fluoro-2-trifluoromethyl-benzyl)-hexahydro-pyrrolo[3,4-c]pyrrol-2-yl]-2-oxo-ethyl}-benzamide | 1.77 | 509.18 |
| 4-Butyl-N-{2-oxo-2-[5-(4-trifluoromethyl-benzyl)-hexahydro-pyrrolo[3,4-c]pyrrol-2-yl]-ethyl}-benzamide | 2.02 | 487.24 |
| 4-Butyl-N-{2-oxo-2-[5-(2-trifluoromethyl-benzyl)-hexahydro-pyrrolo[3,4-c]pyrrol-2-yl]-ethyl}-benzamide | 1.94 | 487.24 |
| 4-Butyl-N-{2-[5-(2-fluoro-4-trifluoromethyl-benzyl)-hexahydro-pyrrolo[3,4-c]pyrrol-2-yl]-2-oxo-ethyl}-benzamide | 2.02 | 505.24 |
| 4-Butyl-N-{2-[5-(4-fluoro-2-trifluoromethyl-benzyl)-hexahydro-pyrrolo[3,4-c]pyrrol-2-yl]-2-oxo-ethyl}-benzamide | 2.01 | 505.24 |
| 4-Isopropyl-N-{2-oxo-2-[5-(4-trifluoromethyl-benzyl)-hexahydro-pyrrolo[3,4-c]pyrrol-2-yl]-ethyl}-benzamide | 1.86 | 473.23 |
| 4-Isopropyl-N-{2-oxo-2-[5-(2-trifluoromethyl-benzyl)-hexahydro-pyrrolo[3,4-c]pyrrol-2-yl]-ethyl}-benzamide | 1.77 | 473.23 |
| N-{2-[5-(2-Fluoro-4-trifluoromethyl-benzyl)-hexahydro-pyrrolo[3,4-c]pyrrol-2-yl]-2-oxo-ethyl}-4-isopropyl-benzamide | 1.86 | 491.22 |
| N-{2-[5-(4-Fluoro-2-trifluoromethyl-benzyl)-hexahydro-pyrrolo[3,4-c]pyrrol-2-yl]-2-oxo-ethyl}-4-isopropyl-benzamide | 1.84 | 491.22 |
| N-{2-Oxo-2-[5-(4-trifluoromethyl-benzyl)-hexahydro-pyrrolo[3,4-c]pyrrol-2-yl]-ethyl}-4-trifluoromethoxy-benzamide | 1.86 | 515.16 |
| N-{2-Oxo-2-[5-(2-trifluoromethyl-benzyl)-hexahydro-pyrrolo[3,4-c]pyrrol-2-yl]-ethyl}-4-trifluoromethoxy-benzamid | 1.77 | 515.16 |
| 3,4,5-Trifluoro-N-{2-oxo-2-[5-(4-trifluoromethyl-benzyl)-hexahydro-pyrrolo[3,4-c]pyrrol-2-yl]-ethyl}-benzamide | 1.75 | 485.15 |
| 3,4,5-Trifluoro-N-{2-oxo-2-[5-(2-trifluoromethyl-benzyl)-hexahydro-pyrrolo[3,4-c]pyrrol-2-yl]-ethyl}-benzamide | 1.63 | 485.15 |
| N-{2-Oxo-2-[5-(4-trifluoromethyl-benzyl)-hexahydro-pyrrolo[3,4-c]pyrrol-2-yl]-ethyl}-4-propyl-benzamide | 1.89 | 473.23 |
| N-{2-Oxo-2-[5-(2-trifluoromethyl-benzyl)-hexahydro-pyrrolo[3,4-c]pyrrol-2-yl]-ethyl}-4-propyl-benzamide | 1.8 | 473.23 |
| N-{2-[5-(2-Fluoro-4-trifluoromethyl-benzyl)-hexahydro-pyrrolo[3,4-c]pyrrol-2-yl]-2-oxo-ethyl}-4-propyl-benzamide | 1.89 | 491.22 |
| N-{2-[5-(4-Fluoro-2-trifluoromethyl-benzyl)-hexahydro-pyrrolo[3,4-c]pyrrol-2-yl]-2-oxo-ethyl}-4-propyl-benzamide | 1.86 | 491.22 |
| 4-Isopropoxy-N-{2-oxo-2-[5-(4-trifluoromethyl-benzyl)-hexahydro-pyrrolo[3,4-c]pyrrol-2-yl]-ethyl}-benzamide | 1.78 | 489.22 |

TABLE 2-continued

| Compound Name | Time (mins) | MW (found) |
|---|---|---|
| 4-Isopropoxy-N-{2-oxo-2-[5-(2-trifluoromethyl-benzyl)-hexahydro-pyrrolo[3,4-c]pyrrol-2-yl]-ethyl}-benzamide | 1.67 | 489.22 |
| N-{2-[5-(2-Fluoro-4-trifluoromethyl-benzyl)-hexahydro-pyrrolo[3,4-c]pyrrol-2-yl]-2-oxo-ethyl}-4-isopropoxy-benzamide | 1.76 | 507.21 |
| N-{2-[5-(4-Fluoro-2-trifluoromethyl-benzyl)-hexahydro-pyrrolo[3,4-c]pyrrol-2-yl]-2-oxo-ethyl}-4-isopropoxy-benzamide | 1.73 | 507.21 |
| N-{2-Oxo-2-[5-(4-trifluoromethyl-benzyl)-hexahydro-pyrrolo[3,4-c]pyrrol-2-yl]-ethyl}-4-propoxy-benzamide | 1.84 | 489.22 |
| N-{2-Oxo-2-[5-(2-trifluoromethyl-benzyl)-hexahydro-pyrrolo[3,4-c]pyrrol-2-yl]-ethyl}-4-propoxy-benzamide | 1.73 | 489.22 |
| N-{2-[5-(2-Fluoro-4-trifluoromethyl-benzyl)-hexahydro-pyrrolo[3,4-c]pyrrol-2-yl]-2-oxo-ethyl}-4-propoxy-benzamide | 1.82 | 507.21 |
| N-{2-[5-(4-Fluoro-2-trifluoromethyl-benzyl)-hexahydro-pyrrolo[3,4-c]pyrrol-2-yl]-2-oxo-ethyl}-4-propoxy-benzamide | 1.79 | 507.21 |
| 3-Chloro-4-fluoro-N-{2-oxo-2-[5-(4-trifluoromethyl-benzyl)-hexahydro-pyrrolo[3,4-c]-pyrrol-2-yl]-ethyl}-benzamide | 1.76 | 483.13 |
| 3-Chloro-4-fluoro-N-{2-oxo-2-[5-(2-trifluoromethyl-benzyl)-hexahydro-pyrrolo[3,4-c]-pyrrol-2-yl]-ethyl}-benzamide | 1.64 | 483.13 |
| 3-Chloro-4-fluoro-N-{2-[5-(4-fluoro-2-trifluoromethyl-benzyl)-hexahydro-pyrrolo[3,4-c]pyrrol-2-yl]-2-oxo-ethyl}-benzamide | 1.71 | 501.12 |
| 3-Fluoro-N-{2-oxo-2-[5-(4-trifluoromethyl-benzyl)-hexahydro-pyrrolo[3,4-c]pyrrol-2-yl]-ethyl}-5-trifluoromethyl-benzamide | 1.87 | 517.16 |
| 3-Fluoro-N-{2-oxo-2-[5-(2-trifluoromethyl-benzyl)-hexahydro-pyrrolo[3,4-c]-pyrrol-2-yl]-ethyl}-5-trifluoromethyl-benzamide | 1.78 | 517.16 |
| 3-Fluoro-N-{2-[5-(4-fluoro-2-trifluoromethyl-benzyl)-hexahydro-pyrrolo[3,4-c]pyrrol-2-yl]-2-oxo-ethyl}-5-trifluoromethyl-benzamide | 1.86 | 535.15 |
| N-{2-[5-(1-Methyl-1H-indol-3-ylmethyl)-hexahydro-pyrrolo[3,4-c]pyrrol-2-yl]-2-oxo-ethyl}-3-trifluoromethyl-benzamide | 1.69 | 484.21 |
| 4-Chloro-N-{2-[5-(1-methyl-1H-indol-3-ylmethyl)-hexahydro-pyrrolo[3,4-c]pyrrol-2-yl]-2-oxo-ethyl}-benzamide | 1.58 | 450.18 |
| 3,4-Dichloro-N-{2-[5-(1-methyl-1H-indol-3-ylmethyl)-hexahydro-pyrrolo[3,4-c]pyrrol-2-yl]-2-oxo-ethyl}-benzamide | 1.73 | 484.14 |
| 3-Chloro-N-{2-[5-(1-methyl-1H-indol-3-ylmethyl)-hexahydro-pyrrolo[3,4-c]pyrrol-2-yl]-2-oxo-ethyl}-benzamide | 1.57 | 450.18 |
| N-[2-Oxo-2-(5-quinolin-3-ylmethyl-hexahydro-pyrrolo[3,4-c]pyrrol-2-yl)-ethyl]-3-trifluoromethyl-benzamide | 1.58 | 482.19 |
| 3,4-Dichloro-N-[2-oxo-2-(5-quinolin-3-ylmethyl-hexahydro-pyrrolo[3,4-c]pyrrol-2-yl)-ethyl]-benzamide | 1.58 | 482.13 |
| 3-Chloro-N-[2-oxo-2-(5-quinolin-3-ylmethyl-hexahydro-pyrrolo[3,4-c]pyrrol-2-yl)-ethyl]-benzamide | 1.39 | 448.17 |
| 4-Chloro-N-[2-oxo-2-(5-quinolin-4-ylmethyl-hexahydro-pyrrolo[3,4-c]pyrrol-2-yl)-ethyl]-benzamide | 1.34 | 448.17 |
| N-{2-[5-(4-Chloro-benzyl)-hexahydro-pyrrolo[3,4-c]pyrrol-2-yl]-2-oxo-ethyl}-3-trifluoromethyl-benzamide | 1.66 | 465.14 |
| 4-Chloro-N-{2-[5-(4-chloro-benzyl)-hexahydro-pyrrolo[3,4-c]pyrrol-2-yl]-2-oxo-ethyl}-benzamide | 1.55 | 431.12 |
| 3,4-Dichloro-N-{2-[5-(4-chloro-benzyl)-hexahydro-pyrrolo[3,4-c]pyrrol-2-yl]-2-oxo-ethyl}-benzamide | 1.7 | 465.08 |
| 3-Chloro-N-{2-[5-(4-chloro-benzyl)-hexahydro-pyrrolo[3,4-c]pyrrol-2-yl]-2-oxo-ethyl}-benzamide | 1.55 | 431.12 |
| N-{2-[5-(5-Bromo-2-methoxy-benzyl)-hexahydro-pyrrolo[3,4-c]pyrrol-2-yl]-2-oxo-ethyl}-3-trifluoromethyl-benzamide | 1.74 | 539.1 |
| N-{2-[5-(5-Bromo-2-methoxy-benzyl)-hexahydro-pyrrolo[3,4-c]pyrrol-2-yl]-2-oxo-ethyl}-4-chloro-benzamide | 1.63 | 505.08 |
| N-{2-[5-(5-Bromo-2-methoxy-benzyl)-hexahydro-pyrrolo[3,4-c]pyrrol-2-yl]-2-oxo-ethyl}-3,4-dichloro-benzamide | 1.78 | 539.04 |
| N-{2-[5-(5-Bromo-2-methoxy-benzyl)-hexahydro-pyrrolo[3,4-c]pyrrol-2-yl]-2-oxo-ethyl}-3-chloro-benzamide | 1.62 | 505.08 |
| N-{2-[5-(3-Bromo-4-methoxy-benzyl)-hexahydro-pyrrolo[3,4-c]pyrrol-2-yl]-2-oxo-ethyl}-3-trifluoromethyl-benzamide | 1.7 | 539.1 |
| N-{2-[5-(3-Bromo-4-methoxy-benzyl)-hexahydro-pyrrolo[3,4-c]pyrrol-2-yl]-2-oxo-ethyl}-4-chloro-benzamide | 1.59 | 505.08 |
| N-{2-[5-(3-Bromo-4-methoxy-benzyl)-hexahydro-pyrrolo[3,4-c]pyrrol-2-yl]-2-oxo-ethyl}-3-chloro-benzamide | 1.56 | 505.08 |
| N-{2-[5-(3,5-Dichloro-benzyl)-hexahydro-pyrrolo-[3,4-c]pyrrol-2-yl]-2-oxo-ethyl}-3-trifluoromethyl-benzamide | 1.79 | 499.1 |
| 4-Chloro-N-{2-[5-(3,5-dichloro-benzyl)-hexahydro-pyrrolo[3,4-c]pyrrol-2-yl]-2-oxo-ethyl}-benzamide | 1.68 | 465.08 |
| 3,4-Dichloro-N-{2-[5-(3,5-dichloro-benzyl)-hexahydro-pyrrolo[3,4-c]pyrrol-2-yl]-2-oxo-ethyl}-benzamide | 1.83 | 499.04 |
| 3-Chloro-N-{2-[5-(3,5-dichloro-benzyl)-hexahydro-pyrrolo[3,4-c]pyrrol-2-yl]-2-oxo-ethyl}-benzamide | 1.67 | 465.08 |

TABLE 2-continued

| Compound Name | Time (mins) | MW (found) |
|---|---|---|
| N-{2-[5-(3-Bromo-4-fluoro-benzyl)-hexahydro-pyrrolo[3,4-c]pyrrol-2-yl]-2-oxo-ethyl}-3-trifluoromethyl-benzamide | 1.72 | 527.08 |
| N-{2-[5-(3-Bromo-4-fluoro-benzyl)-hexahydro-pyrrolo[3,4-c]pyrrol-2-yl]-2-oxo-ethyl}-4-chloro-benzamide | 1.6 | 493.06 |
| N-{2-[5-(3-Bromo-4-fluoro-benzyl)-hexahydro-pyrrolo[3,4-c]pyrrol-2-yl]-2-oxo-ethyl}-3,4-dichloro-benzamide | 1.76 | 527.02 |
| N-{2-[5-(3-Bromo-4-fluoro-benzyl)-hexahydro-pyrrolo[3,4-c]pyrrol-2-yl]-2-oxo-ethyl}-3-chloro-benzamide | 1.61 | 493.06 |
| N-{2-[5-(3-Chloro-4-fluoro-benzyl)-hexahydro-pyrrolo[3,4-c]pyrrol-2-yl]-2-oxo-ethyl}-3-trifluoromethyl-benzamide | 1.7 | 483.13 |
| 4-Chloro-N-{2-[5-(3-chloro-4-fluoro-benzyl)-hexahydro-pyrrolo[3,4-c]pyrrol-2-yl]-2-oxo-ethyl}-benzamide | 1.59 | 449.11 |
| 3,4-Dichloro-N-{2-[5-(3-chloro-4-fluoro-benzyl)-hexahydro-pyrrolo[3,4-c]pyrrol-2-yl]-2-oxo-ethyl}-benzamide | 1.74 | 483.07 |
| 3-Chloro-N-{2-[5-(3-chloro-4-fluoro-benzyl)-hexahydro-pyrrolo[3,4-c]pyrrol-2-yl]-2-oxo-ethyl}-benzamide | 1.59 | 449.11 |
| N-{2-[5-(4-Bromo-benzyl)-hexahydro-pyrrolo[3,4-c]pyrrol-2-yl]-2-oxo-ethyl}-3-trifluoromethyl-benzamide | 1.7 | 509.09 |
| N-{2-[5-(4-Bromo-benzyl)-hexahydro-pyrrolo[3,4-c]pyrrol-2-yl]-2-oxo-ethyl}-4-chloro-benzamide | 1.58 | 475.07 |
| N-{2-[5-(4-Bromo-benzyl)-hexahydro-pyrrolo[3,4-c]pyrrol-2-yl]-2-oxo-ethyl}-3,4-dichloro-benzamide | 1.73 | 509.03 |
| N-{2-[5-(4-Bromo-benzyl)-hexahydro-pyrrolo[3,4-c]pyrrol-2-yl]-2-oxo-ethyl}-3-chloro-benzamide | 1.57 | 475.07 |
| N-{2-[5-(3,4-Dichloro-benzyl)-hexahydro-pyrrolo[3,4-c]pyrrol-2-yl]-2-oxo-ethyl}-3-trifluoromethyl-benzamide | 1.79 | 499.1 |
| 4-Chloro-N-{2-[5-(3,4-dichloro-benzyl)-hexahydro-pyrrolo[3,4-c]pyrrol-2-yl]-2-oxo-ethyl}-benzamide | 1.69 | 465.08 |
| 3,4-Dichloro-N-{2-[5-(3,4-dichloro-benzyl)-hexahydro-pyrrolo[3,4-c]pyrrol-2-yl]-2-oxo-ethyl}-benzamide | 1.83 | 499.04 |
| 3-Chloro-N-{2-[5-(3,4-dichloro-benzyl)-hexahydro-pyrrolo[3,4-c]pyrrol-2-yl]-2-oxo-ethyl}-benzamide | 1.69 | 465.08 |
| 3-Chloro-N-{2-[5-(2-methyl-benzyl)-hexahydro-pyrrolo[3,4-c]pyrrol-2-yl]-2-oxo-ethyl}-benzamide | 1.5 | 411.17 |
| 4-Chloro-N-{2-[5-(2-methyl-benzyl)-hexahydro-pyrrolo[3,4-c]pyrrol-2-yl]-2-oxo-ethyl}-benzamide | 1.5 | 411.17 |
| N-[2-(5-Biphenyl-4-ylmethyl-hexahydro-pyrrolo[3,4-c]-pyrrol-2-yl)-2-oxo-ethyl]-4-chloro-benzamide | 1.82 | 473.19 |
| N-[2-(5-Biphenyl-4-ylmethyl-hexahydro-pyrrolo[3,4-c]-pyrrol-2-yl)-2-oxo-ethyl]-3,4-dichloro-benzamide | 1.96 | 507.15 |
| N-[2-(5-Biphenyl-4-ylmethyl-hexahydro-pyrrolo[3,4-c]-pyrrol-2-yl)-2-oxo-ethyl]-3-chloro-benzamide | 1.82 | 473.19 |
| N-{2-Oxo-2-[5-(3-phenoxy-benzyl)-hexahydro-pyrrolo[3,4-c]pyrrol-2-yl]-ethyl}-3-trifluoromethyl-benzamide | 1.93 | 523.21 |
| 4-Chloro-N-{2-oxo-2-[5-(3-phenoxy-benzyl)-hexahydro-pyrrolo[3,4-c]pyrrol-2-yl]-ethyl}-benzamide | 1.84 | 489.18 |
| 3,4-Dichloro-N-{2-oxo-2-[5-(3-phenoxy-benzyl)-hexahydro-pyrrolo[3,4-c]pyrrol-2-yl]-ethyl}-benzamide | 1.98 | 523.14 |
| 3-Chloro-N-{2-oxo-2-[5-(3-phenoxy-benzyl)-hexahydro-pyrrolo[3,4-c]pyrrol-2-yl]-ethyl}-benzamide | 1.83 | 489.18 |
| N-{2-[5-(2-Methoxy-naphthalen-1-ylmethyl)-hexahydro-pyrrolo[3,4-c]pyrrol-2-yl]-2-oxo-ethyl}-3-trifluoromethyl-benzamide | 1.8 | 511.21 |
| 4-Chloro-N-{2-[5-(2-methoxy-naphthalen-1-ylmethyl)-hexahydro-pyrrolo[3,4-c]-pyrrol-2-yl]-2-oxo-ethyl}-benzamide | 1.69 | 477.18 |
| 3,4-Dichloro-N-{2-[5-(2-methoxy-naphthalen-1-ylmethyl)-hexahydro-pyrrolo-[3,4-c]pyrrol-2-yl]-2-oxo-ethyl}-benzamide | 1.84 | 511.14 |
| 3-Chloro-N-{2-[5-(2-methoxy-naphthalen-1-ylmethyl)-hexahydro-pyrrolo[3,4-c]-pyrrol-2-yl]-2-oxo-ethyl}-benzamide | 1.69 | 477.18 |
| N-{2-[5-(2-Ethoxy-naphthalen-1-ylmethyl)-hexahydro-pyrrolo[3,4-c]pyrrol-2-yl]-2-oxo-ethyl}-3-trifluoromethyl-benzamide | 1.87 | 525.22 |
| 4-Chloro-N-{2-[5-(2-ethoxy-naphthalen-1-ylmethyl)-hexahydro-pyrrolo[3,4-c]-pyrrol-2-yl]-2-oxo-ethyl}-benzamide | 1.78 | 491.2 |
| 3,4-Dichloro-N-{2-[5-(2-ethoxy-naphthalen-1-ylmethyl)-hexahydro-pyrrolo[3,4-c]-pyrrol-2-yl]-2-oxo-ethyl}-benzamide | 1.92 | 525.16 |
| 3-Chloro-N-{2-[5-(2-ethoxy-naphthalen-1-ylmethyl)-hexahydro-pyrrolo[3,4-c]pyrrol-2-yl]-2-oxo-ethyl}-benzamide | 1.78 | 491.2 |

TABLE 2-continued

| Compound Name | Time (mins) | MW (found) |
|---|---|---|
| N-{2-Oxo-2-[5-(3-p-tolyloxy-benzyl)-hexahydro-pyrrolo[3,4-c]pyrrol-2-yl]-ethyl}-3-trifluoromethyl-benzamide | 2.03 | 537.22 |
| 4-Chloro-N-{2-oxo-2-[5-(3-p-tolyloxy-benzyl)-hexahydro-pyrrolo[3,4-c]pyrrol-2-yl]-ethyl}-benzamide | 1.94 | 503.2 |
| 3,4-Dichloro-N-{2-oxo-2-[5-(3-p-tolyloxy-benzyl)-hexahydro-pyrrolo[3,4-c]pyrrol-2-yl]-ethyl}-benzamide | 2.07 | 537.16 |
| 3-Chloro-N-{2-oxo-2-[5-(3-p-tolyloxy-benzyl)-hexahydro-pyrrolo[3,4-c]pyrrol-2-yl]-ethyl}-benzamide | 1.94 | 503.2 |
| N-{2-[5-(4-Methyl-naphthalen-1-ylmethyl)-hexahydro-pyrrolo[3,4-c]pyrrol-2-yl]-2-oxo-ethyl}-3-trifluoromethyl-benzamide | 1.84 | 495.21 |
| 4-Chloro-N-{2-[5-(4-methyl-naphthalen-1-ylmethyl)-hexahydro-pyrrolo[3,4-c]pyrrol-2-yl]-2-oxo-ethyl}-benzamide | 1.74 | 461.19 |
| 3,4-Dichloro-N-{2-[5-(4-methyl-naphthalen-1-ylmethyl)-hexahydro-pyrrolo[3,4-c]pyrrol-2-yl]-2-oxo-ethyl}-benzamide | 1.89 | 495.15 |
| 3-Chloro-N-{2-[5-(4-methyl-naphthalen-1-ylmethyl)-hexahydro-pyrrolo[3,4-c]pyrrol-2-yl]-2-oxo-ethyl}-benzamide | 1.73 | 461.19 |
| N-{2-[5-(2'-Methyl-biphenyl-2-ylmethyl)-hexahydro-pyrrolo[3,4-c]pyrrol-2-yl]-2-oxo-ethyl}-3-trifluoromethyl-benzamide | 1.95 | 521.23 |
| 4-Chloro-N-{2-[5-(2'-methyl-biphenyl-2-ylmethyl)-hexahydro-pyrrolo[3,4-c]pyrrol-2-yl]-2-oxo-ethyl}-benzamide | 1.84 | 487.2 |
| 3,4-Dichloro-N-{2-[5-(2'-methyl-biphenyl-2-ylmethyl)-hexahydro-pyrrolo[3,4-c]pyrrol-2-yl]-2-oxo-ethyl}-benzamide | 1.98 | 521.16 |
| 3-Chloro-N-{2-[5-(2'-methyl-biphenyl-2-ylmethyl)-hexahydro-pyrrolo[3,4-c]pyrrol-2-yl]-2-oxo-ethyl}-benzamide | 1.85 | 487.2 |
| N-{2-[5-(2'-Methoxy-biphenyl-2-ylmethyl)-hexahydro-pyrrolo[3,4-c]pyyrrol-2-yl]-2-oxo-ethyl}-3-trifluoromethyl-benzamide | 1.87 | 537.22 |
| 4-Chloro-N-{2-[5-(2'-methoxy-biphenyl-2-ylmethyl)-hexahydro-pyrrolo-[3,4-c]pyrrol-2-yl]-2-oxo-ethyl}-benzamide | 1.77 | 503.2 |
| 3,4-Dichloro-N-{2-[5-(2'-methoxy-biphenyl-2-ylmethyl)-hexahydro-pyrrolo-[3,4-c]pyrrol-2-yl]-2-oxo-ethyl}-benzamide | 1.92 | 537.16 |
| 3-Chloro-N-{2-[5-(2'-methoxy-biphenyl-2-ylmethyl)-hexahydro-pyrrolo-[3,4-c]pyrrol-2-yl]-2-oxo-ethyl}-benzamide | 1.78 | 503.2 |
| N-{2-[5-(6-Methoxy-naphthalen-2-ylmethyl)-hexahydro-pyrrolo[3,4-c]-pyrrol-2-yl]-2-oxo-ethyl}-3-trifluoromethyl-benzamide | 1.89 | 511.21 |
| 3,4-Dichloro-N-{2-[5-(6-methoxy-naphthalen-2-ylmethyl)-hexahydro-pyrrolo[3,4-c]-pyrrol-2-yl]-2-oxo-ethyl}-benzamide | 1.71 | 477.18 |
| 3-Chloro-N-{2-[5-(6-methoxy-naphthalen-2-ylmethyl)-hexahydro-pyrrolo-[3,4-c]pyrrol-2-yl]-2-oxo-ethyl}-benzamide | 1.85 | 511.14 |
| 4-Chloro-N-{2-[5-(2,4-dimethoxy-benzyl)-hexahydro-pyrrolo[3,4-c]pyrrol-2-yl]-2-oxo-ethyl}-benzamide | 1.7 | 477.18 |
| 4-Chloro-N-{2-[5-(2,4-dimethoxy-benzyl)-hexahydro-pyrrolo[3,4-c]pyrrol-2-yl]-2-oxo-ethyl}-benzamide | 1.53 | 457.18 |
| 3-Chloro-N-{2-[5-(2,4-dimethoxy-benzyl)-hexahydro-pyrrolo[3,4-c]pyrrol-2-yl]-2-oxo-ethyl}-benzamide | 1.53 | 457.18 |
| N-{2-[5-(2-Methyl-benzyl)-hexahydro-pyrrolo[3,4-c]-pyrrol-2-yl]-2-oxo-ethyl}-3-trifluoromethyl-benzamide | 1.61 | 445.2 |
| 3,4-Dichloro-N-{2-[5-(2-methyl-benzyl)-hexahydro-pyrrolo[3,4-c]pyrrol-2-yl]-2-oxo-ethyl}-benzamide | 1.67 | 445.13 |
| N-{2-[5-(2-Ethoxy-benzyl)-hexahydro-pyrrolo-[3,4-c]pyrrol-2-yl]-2-oxo-ethyl}-3-trifluoromethyl-benzamide | 1.7 | 475.21 |
| 4-Chloro-N-{2-[5-(2-ethoxy-benzyl)-hexahydro-pyrrolo[3,4-c]pyrrol-2-yl]-2-oxo-ethyl}-benzamide | 1.57 | 441.18 |
| 3,4-Dichloro-N-{2-[5-(2-ethoxy-benzyl)-hexahydro-pyrrolo[3,4-c]pyrrol-2-yl]-2-oxo-ethyl}-benzamide | 1.73 | 475.14 |
| 3-Chloro-N-{2-[5-(2-ethoxy-benzyl)-hexahydro-pyrrolo[3,4-c]pyrrol-2-yl]-2-oxo-ethyl}-benzamide | 1.57 | 441.18 |
| N-{2-[5-(2-Methoxy-benzyl)-hexahydro-pyrrolo-[3,4-c]pyrrol-2-yl]-2-oxo-ethyl}-3-trifluoromethyl-benzamide | 1.59 | 461.19 |
| 4-Chloro-N-{2-[5-(2-methoxy-benzyl)-hexahydro-pyrrolo[3,4-c]pyrrol-2-yl]-2-oxo-ethyl}-benzamide | 1.46 | 427.17 |
| 3,4-Dichloro-N-{2-[5-(2-methoxy-benzyl)-hexahydro-pyrrolo[3,4-c]pyrrol-2-yl]-2-oxo-ethyl}-benzamide | 1.64 | 461.13 |
| 3-Chloro-N-{2-[5-(2-methoxy-benzyl)-hexahydro-pyrrolo[3,4-c]pyrrol-2-yl]-2-oxo-ethyl}-benzamide | 1.45 | 427.17 |

TABLE 2-continued

| Compound Name | Time (mins) | MW (found) |
|---|---|---|
| N-{2-[5-(2,5-Dimethoxy-benzyl)-hexahydro-pyrrolo-[3,4-c]pyrrol-2-yl]-2-oxo-ethyl}-3-trifluoromethyl-benzamide | 1.63 | 491.2 |
| 4-Chloro-N-{2-[5-(2,5-dimethoxy-benzyl)-hexahydro-pyrrolo[3,4-c]pyrrol-2-yl]-2-oxo-ethyl}-benzamide | 1.52 | 457.18 |
| 3,4-Dichloro-N-{2-[5-(2,5-dimethoxy-benzyl)-hexahydro-pyrrolo[3,4-c]pyrrol-2-yl]-2-oxo-ethyl}-benzamide | 1.67 | 491.14 |
| 3-Chloro-N-{2-[5-(2,5-dimethoxy-benzyl)-hexahydro-pyrrolo[3,4-c]pyrrol-2-yl]-2-oxo-ethyl}-benzamide | 1.5 | 457.18 |
| N-{2-[5-(2,5-Dimethyl-benzyl)-hexahydro-pyrrolo-[3,4-c]pyrrol-2-yl]-2-oxo-ethyl}-3-trifluoromethyl-benzamide | 1.72 | 459.21 |
| 4-Chloro-N-{2-[5-(2,5-dimethyl-benzyl)-hexahydro-pyrrolo[3,4-c]pyrrol-2-yl]-2-oxo-ethyl}-benzamide | 1.61 | 425.19 |
| 3,4-Dichloro-N-{2-[5-(2,5-dimethyl-benzyl)-hexahydro-pyrrolo[3,4-c]pyrrol-2-yl]-2-oxo-ethyl}-benzamide | 1.77 | 459.15 |
| 3-Chloro-N-{2-[5-(2,5-dimethyl-benzyl)-hexahydro-pyrrolo[3,4-c]pyrrol-2-yl]-2-oxo-ethyl}-benzamide | 1.61 | 425.19 |
| N-{2-[5-(4-Methoxy-2,5-dimethyl-benzyl)-hexahydro-pyrrolo[3,4-c]pyrrol-2-yl]-2-oxo-ethyl}-3-trifluoromethyl-benzamide | 1.76 | 489.22 |
| 4-Chloro-N-{2-[5-(4-methoxy-2,5-dimethyl-benzyl)-hexahydro-pyrrolo[3,4-c]pyrrol-2-yl]-2-oxo-ethyl}-benzamide | 1.65 | 455.2 |
| 3,4-Dichloro-N-{2-[5-(4-methoxy-2,5-dimethyl-benzyl)-hexahydro-pyrrolo-[3,4-c]pyrrol-2-yl]-2-oxo-ethyl}-benzamide | 1.82 | 489.16 |
| 3-Chloro-N-{2-[5-(4-methoxy-2,5-dimethyl-benzyl)-hexahydro-pyrrolo-[3,4-c]pyrrol-2-yl]-2-oxo-ethyl}-benzamide | 1.65 | 455.2 |
| N-{2-[5-(4-Methoxy-2,3-dimethyl-benzyl)-hexahydro-pyrrolo[3,4-c]pyrrol-2-yl]-2-oxo-ethyl}-3-trifluoromethyl-benzamide | 1.78 | 489.22 |
| 4-Chloro-N-{2-[5-(4-methoxy-2,3-dimethyl-benzyl)-hexahydro-pyrrolo-[3,4-c]pyrrol-2-yl]-2-oxo-ethyl}-benzamide | 1.66 | 455.2 |
| 3,4-Dichloro-N-{2-[5-(4-methoxy-2,3-dimethyl-benzyl)-hexahydro-pyrrolo[3,4-c]-pyrrol-2-yl]-2-oxo-ethyl}-benzamide | 1.81 | 489.16 |
| 3-Chloro-N-{2-[5-(4-methoxy-2,3-dimethyl-benzyl)-hexahydro-pyrrolo[3,4-c]-pyrrol-2-yl]-2-oxo-ethyl}-benzamide | 1.66 | 455.2 |
| N-{2-[5-(2-Benzyloxy-benzyl)-hexahydro-pyrrolo[3,4-c]-pyrrol-2-yl]-2-oxo-ethyl}-3-trifluoromethyl-benzamide | 1.93 | 537.22 |
| N-{2-[5-(2-Benzyloxy-benzyl)-hexahydro-pyrrolo[3,4-c]pyrrol-2-yl]-2-oxo-ethyl}-4-chloro-benzamide | 1.83 | 503.2 |
| N-{2-[5-(2-Benzyloxy-benzyl)-hexahydro-pyrrolo[3,4-c]pyrrol-2-yl]-2-oxo-ethyl}-3,4-dichloro-benzamide | 1.98 | 537.16 |
| N-{2-[5-(2-Benzyloxy-benzyl)-hexahydro-pyrrolo[3,4-c]pyrrol-2-yl]-2-oxo-ethyl}-3-chloro-benzamide | 1.84 | 503.2 |
| N-{2-[5-(3-Cyclopentyloxy-4-methoxy-benzyl)-hexahydro-pyrrolo-[3,4-c]pyrrol-2-yl]-2-oxo-ethyl}-3-trifluoromethyl-benzamide | 1.86 | 545.25 |
| 4-Chloro-N-{2-[5-(3-cyclopentyloxy-4-methoxy-benzyl)-hexahydro-pyrrolo[3,4-c]-pyrrol-2-yl]-2-oxo-ethyl}-benzamide | 1.75 | 511.22 |
| 3,4-Dichloro-N-{2-[5-(3-cyclopentyloxy-4-methoxy-benzyl)-hexahydro-pyrrolo[3,4-c]-pyrrol-2-yl]-2-oxo-ethyl}-benzamide | 1.9 | 545.18 |
| 3-Chloro-N-{2-[5-(3-cyclopentyloxy-4-methoxy-benzyl)-hexahydro-pyrrolo[3,4-c]-pyrrol-2-yl]-2-oxo-ethyl}-benzamide | 1.75 | 511.22 |
| 3,4-Dichloro-N-[2-(hexahydro-pyrrolo[3,4-c]pyrrol-2-yl)-2-oxo-ethyl]-benzamide | 2.14 | 342 |
| 3,4-Dichloro-N-[2-oxo-2-(5-quinolin-2-ylmethyl-hexahydro-pyrrolo[3,4-c]pyrrol-2-yl)-ethyl]-benzamide | 2 | 483, 485 dichloro |
| 1H-Indole-2-carboxylic acid [2-oxo-2-(5-quinolin-2-ylmethyl-hexahydro-pyrrolo[3,4-c]pyrrol-2-yl)-ethyl]-amide | 2.1 | 454 |
| 3-Bromo-4-chloro-N-[2-oxo-2-(5-quinolin-2-ylmethyl-hexahydro-pyrrolo[3,4-c]pyrrol-2-yl)-ethyl]-benzamide | 2.1 | 528 |
| 2-Amino-5-chloro-N-[2-oxo-2-(5-quinolin-2-ylmethyl-hexahydro-pyrrolo[3,4-c]pyrrol-2-yl)-ethyl]-benzamide | 1.8 | 464 |
| 2-Amino-5-bromo-N-[2-oxo-2-(5-quinolin-2-ylmethyl-hexahydro-pyrrolo[3,4-c]pyrrol-2-yl)-ethyl]-benzamide | 1.9 | 510 |
| N-[2-Oxo-2-(5-quinolin-2-ylmethyl-hexahydro-pyrrolo-[3,4-c]pyrrol-2-yl)-ethyl]-3-trifluoromethyl-benzamide | 1.9 | 483 |
| 3,4-Dichloro-N-[2-oxo-2-(5-quinolin-4-ylmethyl-hexahydro-pyrrolo[3,4-c]pyrrol-2-yl)-ethyl]-benzamide | 1.8 | 483, 485 dichloro |
| 1H-Indole-2-carboxylic acid [2-oxo-2-(5-quinolin-4-ylmethyl-hexahydro-pyrrolo[3,4-c]-pyrrol-2-yl)-ethyl]-amide | 1.5 | 454 |
| 3-Bromo-4-chloro-N-[2-oxo-2-(5-quinolin-4-ylmethyl-hexahydro-pyrrolo[3,4-c]pyrrol-2-yl)-ethyl]-benzamide | 1.9 | 529 |
| 2-Amino-5-chloro-N-[2-oxo-2-(5-quinolin-4-ylmethyl-hexahydro-pyrrolo[3,4-c]pyrrol-2-yl)-ethyl]-benzamide | 1.4 | 464 |

TABLE 2-continued

| Compound Name | Time (mins) | MW (found) |
|---|---|---|
| 2-Amino-5-bromo-N-[2-oxo-2-(5-quinolin-4-ylmethyl-hexahydro-pyrrolo[3,4-c]pyrrol-2-yl)-ethyl]-benzamide | 1.5 | 510 |
| N-[2-Oxo-2-(5-quinolin-4-ylmethyl-hexahydro-pyrrolo[3,4-c]pyrrol-2-yl)-ethyl]-3-trifluoromethyl-benzamide | 1.7 | 483 |
| 3,4-Dichloro-N-[2-(5-naphthalen-1-ylmethyl-hexahydro-pyrrolo[3,4-c]-pyrrol-2-yl)-2-oxo-ethyl]-benzamide | 2.1 | 483 |
| 1H-Indole-2-carboxylic acid [2-(5-naphthalen-1-ylmethyl-hexahydro-pyrrolo[3,4-c]-pyrrol-2-yl)-2-oxo-ethyl]-amide | 2 | 454 |
| 3-Bromo-4-chloro-N-[2-(5-naphthalen-1-ylmethyl-hexahydro-pyrrolo[3,4-c]-pyrrol-2-yl)-2-oxo-ethyl]-benzamide | 2.2 | 528 |
| 2-Amino-5-chloro-N-[2-(5-naphthalen-1-ylmethyl-hexahydro-pyrrolo[3,4-c]-pyrrol-2-yl)-2-oxo-ethyl]-benzamide | 1.9 | 463 |
| 2-Amino-5-bromo-N-[2-(5-naphthalen-1-ylmethyl-hexahydro-pyrrolo[3,4-c]-pyrrol-2-yl)-2-oxo-ethyl]-benzamide | 2 | 509 |
| N-[2-(5-Naphthalen-1-ylmethyl-hexahydro-pyrrolo[3,4-c]pyrrol-2-yl)-2-oxo-ethyl]-3-trifluoromethyl-benzamide | 2.1 | 483 |
| 3,4-Dichloro-N-[2-(5-naphthalen-2-ylmethyl-hexahydro-pyrrolo[3,4-c]-pyrrol-2-yl)-2-oxo-ethyl]-benzamide | 2.2 | 483 |
| 3-Bromo-4-chloro-N-[2-(5-naphthalen-2-ylmethyl-hexahydro-pyrrolo[3,4-c]-pyrrol-2-yl)-2-oxo-ethyl]-benzamide | 2.2 | 528 |
| 2-Amino-5-chloro-N-[2-(5-naphthalen-2-ylmethyl-hexahydro-pyrrolo[3,4-c]-pyrrol-2-yl)-2-oxo-ethyl]-benzamide | 2 | 463 |
| 2-Amino-5-bromo-N-[2-(5-naphthalen-2-ylmethyl-hexahydro-pyrrolo[3,4-c]-pyrrol-2-yl)-2-oxo-ethyl]-benzamide | 2.1 | 509 |
| N-[2-(5-Naphthalen-2-ylmethyl-hexahydro-pyrrolo[3,4-c]pyrrol-2-yl)-2-oxo-ethyl]-3-trifluoromethyl-benzamide | 2.1 | 482 |
| 2-Amino-1-(5-quinolin-2-ylmethyl-hexahydro-pyrrolo[3,4-c]pyrrol-2-yl)-ethanone | 1.85 | 310 |
| 2-Amino-1-(5-quinolin-4-ylmethyl-hexahydro-pyrrolo[3,4-c]pyrrol-2-yl)-ethanone | 1.84 | 310 |
| 2-Amino-1-(5-naphthalen-1-ylmethyl-hexahydro-pyrrolo[3,4-c]pyrrol-2-yl)-ethanone | 2.3 | 309 |
| 2-Amino-1-(5-naphthalen-2-ylmethyl-hexahydro-pyrrolo[3,4-c]pyrrol-2-yl)-ethanone | 2.25 | 309 |
| N-{2-[5-(2,4-Difluoro-benzyl)-hexahydro-pyrrolo[3,4-c]-pyrrol-2-yl]-2-oxo-ethyl}-3,5-bis-trifluoromethyl-benzamide | 2 | 536.2 |
| N-{2-[5-(2,4-Difluoro-benzyl)-hexahydro-pyrrolo[3,4-c]pyrrol-2-yl]-2-oxo-ethyl}-3-trifluoromethyl-benzamide | 1.7 | 468.3 |
| N-{2-[5-(2,5-Difluoro-benzyl)-hexahydro-pyrrolo[3,4-c]pyrrol-2-yl]-2-oxo-ethyl}-3,5-bis-trifluoromethyl-benzamide | 2 | 536.2 |
| N-{2-[5-(2,5-Difluoro-benzyl)-hexahydro-pyrrolo[3,4-c]pyrrol-2-yl]-2-oxo-ethyl}-3-trifluoromethyl-benzmide | 1.7 | 468 |
| N-{2-[5-(2,4-Dimethyl-benzyl)-hexahydro-pyrrolo[3,4-c]pyrrol-2-yl]-2-oxo-ethyl}-2-fluoro-3-trifluoromethyl-benzamide | 2.1 | 478.1 |
| 3-Chloro-N-{2-[5-(2,4-dimethyl-benzyl)-hexahydro-pyrrolo[3,4-c]pyrrol-2-yl]-2-oxo-ethyl}-benzamide | 1.9 | 426.1 |
| N-{2-[5-(2,4-Dimethyl-benzyl)-hexahydro-pyrrolo[3,4-c]pyrrol-2-yl]-2-oxo-ethyl}-2-phenoxy-benzamide | 2.2 | 484.2 |
| N-{2-[5-(2,4-Dimethyl-benzyl)-hexahydro-pyrrolo[3,4-c]pyrrol-2-yl]-2-oxo-ethyl}-5-fluoro-2-methyl-benzamide | 1.7 | 424.1 |
| 3-Chloro-N-{2-[5-(2,4-dimethyl-benzyl)-hexahydro-pyrrolo[3,4-c]pyrrol-2-yl]-2-oxo-ethyl}-2-fluoro-benzamide | 1.9 | 444.1 |
| N-{2-[5-(2,4-Dimethoxy-benzyl)-hexahydro-pyrrolo-[3,4-c]pyrrol-2-yl]-2-oxo-ethyl}-3-trifluoromethyl-benzamide | 1.9 | 492.1 |
| 4-Chloro-N-{2-[5-(2,4-dimethyl-benzyl)-hexahydro-pyrrolo[3,4-c]pyrrol-2-yl]-2-oxo-ethyl}-benzamide | 1.9 | 426.1 |
| N-{2-[5-(2,4-Dimethyl-benzyl)-hexahydro-pyrrolo[3,4-c]pyrrol-2-yl]-2-oxo-ethyl}-3,5-bis-trifluoromethyl-benzamide | 2.3 | 528.1 |
| N-{2-[5-(2,4-Dimethyl-benzyl)-hexahydro-pyrrolo[3,4-c]pyrrol-2-yl]-2-oxo-ethyl}-4-trifluoromethyl-benzamide | 2.1 | 460.1 |
| 2-Amino-5-bromo-N-{2-[5-(2,4-dimethyl-benzyl)-hexahydro-pyrrolo[3,4-c]pyrrol-2-yl]-2-oxo-ethyl}-benzamide | 1.9 | 487.1 |
| N-{2-[5-(2,4-Dimethyl-benzyl)-hexahydro-pyrrolo[3,4-c]pyrrol-2-yl]-2-oxo-ethyl}-2-methyl-5-nitro-benzamide | 1.8 | 451.1 |
| 2-Amino-5-chloro-N-{2-[5-(2,4-dimethyl-benzyl)-hexahydro-pyrrolo[3,4-c]pyrrol-2-yl]-2-oxo-ethyl}-benzamide | 1.9 | 441.1 |
| 5-Chloro-N-{2-[5-(2,4-dimethyl-benzyl)-hexahydro-pyrrolo[3,4-c]pyrrol-2-yl]-2-oxo-ethyl}-2-nitro-benzamide | 1.9 | 471.1 |
| N-{2-[5-(2,4-Dimethyl-benzyl)-hexahydro-pyrrolo[3,4-c]pyrrol-2-yl]-2-oxo-ethyl}-3-nitro-5-trifluoromethyl-benzamide | 2.1 | 505.1 |
| 2-Amino-N-{2-[5-(2,4-difluoro-benzyl)-hexahydro-pyrrolo[3,4-c]pyrrol-2-yl]-2-oxo-ethyl}-5-iodo-benzamide | 1.6 | 541.3 |
| 2-Amino-N-{2-[5-(2,4-difluoro-benzyl)-hexahydro-pyrrolo[3,4-c]pyrrol-2-yl]-2-oxo-ethyl}-5-nitro-benzamide | 1.3 | 460.5 |
| N-{2-[5-(2,4-Dimethyl-benzyl)-hexahydro-pyrrolo[3,4-c]pyrrol-2-yl]-2-oxo-ethyl}-2-ethoxy-benzamide | 2 | 436.2 |
| 2,4-Dichloro-N-{2-[5-(2,4-dimethyl-benzyl)-hexahydro-pyrrolo[3,4-c]pyrrol-2-yl]-2-oxo-ethyl}-benzamide | 2 | 460.1 |
| N-{2-[5-(2,4-Dimethyl-benzyl)-hexahydro-pyrrolo[3,4-c]pyrrol-2-yl]-2-oxo-ethyl}-2,6-difluoro-benzamide | 1.5 | 428.2 |

TABLE 2-continued

| Compound Name | Time (mins) | MW (found) |
|---|---|---|
| 2-Chloro-N-{2-[5-(2,4-dimethyl-benzyl)-hexahydro-pyrrolo[3,4-c]pyrrol-2-yl]-2-oxo-ethyl}-6-fluoro-benzamide | 1.7 | 444.2 |
| N-{2-[5-(2,4-Dimethyl-benzyl)-hexahydro-pyrrolo[3,4-c]pyrrol-2-yl]-2-oxo-ethyl}-2,4-difluoro-benzamide | 1.7 | 428.2 |
| N-{2-[5-(2,4-Dimethyl-benzyl)-hexahydro-pyrrolo[3,4-c]pyrrol-2-yl]-2-oxo-ethyl}-2,3-difluoro-benzamide | 1.7 | 428.2 |
| N-{2-[5-(2,4-Dimethyl-benzyl)-hexahydro-pyrrolo[3,4-c]pyrrol-2-yl]-2-oxo-ethyl}-2-trifluoromethyl-benzamide | 1.9 | 460.2 |
| N-{2-[5-(2,4-Dimethyl-benzyl)-hexahydro-pyrrolo[3,4-c]pyrrol-2-yl]-2-oxo-ethyl}-2,3,4-trifluoro-benzamide | 1.9 | 446.2 |
| 2,3-Dichloro-N-{2-[5-(2,4-dimethyl-benzyl)-hexahydro-pyrrolo[3,4-c]pyrrol-2-yl]-2-oxo-ethyl}-benzamide | 2 | 460.1 |
| N-{2-[5-(2,4-Dimethyl-benzyl)-hexahydro-pyrrolo[3,4-c]pyrrol-2-yl]-2-oxo-ethyl}-2,4-bis-trifluoromethyl-benzamide | 2.2 | 528.2 |
| N-{2-[5-(2,4-Dimethyl-benzyl)-hexahydro-pyrrolo[3,4-c]pyrrol-2-yl]-2-oxo-ethyl}-2-fluoro-4-trifluoromethyl-benzamide | 2.1 | 478.2 |
| N-{2-[5-(2,4-Dimethyl-benzyl)-hexahydro-pyrrolo[3,4-c]pyrrol-2-yl]-2-oxo-ethyl}-4-fluoro-2-trifluoromethyl-benzamide | 1.9 | 478.2 |
| 2-Chloro-N-{2-[5-(2,4-dimethyl-benzyl)-hexahydro-pyrrolo[3,4-c]pyrrol-2-yl]-2-oxo-ethyl}-4-fluoro-benzamide | 1.8 | 444.2 |
| 2-Chloro-N-{2-[5-(2,4-dimethyl-benzyl)-hexahydro-pyrrolo[3,4-c]pyrrol-2-yl]-2-oxo-ethyl}-4,5-difluoro-benzamide | 1.9 | 462.2 |
| N-{2-[5-(2,4-Dimethyl-benzyl)-hexahydro-pyrrolo[3,4-c]pyrrol-2-yl]-2-oxo-ethyl}-2,4,5-trifluoro-benzamide | 1.9 | 446.2 |
| 3-Chloro-N-{2-[5-(2,4-dimethyl-benzyl)-hexahydro-pyrrolo[3,4-c]pyrrol-2-yl]-2-oxo-ethyl}-2,6-dimethoxy-benzamide | 1.9 | 486.2 |
| N-{2-[5-(2,4-Dimethyl-benzyl)-hexahydro-pyrrolo[3,4-c]pyrrol-2-yl]-2-oxo-ethyl}-2-fluoro-6-trifluoromethyl-benzamide | 1.9 | 478.2 |
| N-{2-[5-(2,4-Dimethyl-benzyl)-hexahydro-pyrrolo[3,4-c]pyrrol-2-yl]-2-oxo-ethyl}-2-trifluoromethoxy-benzamide | 2 | 476.2 |
| N-{2-[5-(2,4-Dimethyl-benzyl)-hexahydro-pyrrolo[3,4-c]pyrrol-2-yl]-2-oxo-ethyl}-2,3,6-trimethoxy-benzamide | 1.7 | 482.3 |
| N-{2-[5-(2,4-Dimethyl-benzyl)-hexahydro-pyrrolo[3,4-c]pyrrol-2-yl]-2-oxo-ethyl}-2,6-dimethoxy-benzamide | 1.6 | 452.2 |
| N-{2-[5-(2,4-Dimethyl-benzyl)-hexahydro-pyrrolo[3,4-c]pyrrol-2-yl]-2-oxo-ethyl}-2,6-dimethyl-benzamide | 1.7 | 420.2 |
| 4-Chloro-N-{2-[5-(2,4-dimethyl-benzyl)-hexahydro-pyrrolo[3,4-c]pyrrol-2-yl]-2-oxo-ethyl}-2-fluoro-benzamide | 1.9 | 444.2 |
| 2-Amino-3,5-dibromo-N-{2-[5-(2,4-dimethyl-benzyl)-hexahydro-pyrrolo[3,4-c]pyrrol-2-yl]-2-oxo-ethyl}-benzamide | 2.3 | 565 |
| N-{2-[5-(2,4-Dimethyl-benzyl)-hexahydro-pyrrolo[3,4-c]pyrrol-2-yl]-2-oxo-ethyl}-2-fluoro-5-trifluoromethyl-benzamide | 2.2 | 478.2 |
| 2-Chloro-N-{2-[5-(2,4-dimethyl-benzyl)-hexahydro-pyrrolo[3,4-c]pyrrol-2-yl]-2-oxo-ethyl}-3-trifluoromethyl-benzamide | 2.2 | 494.1 |
| 2-Acetylamino-5-bromo-N-{2-[5-(2,4-dimethyl-benzyl)-hexahydro-pyrrolo[3,4-c]pyrrol-2-yl]-2-oxo-ethyl}-benzamide | 2.1 | 529.1 |
| 2-Amino-N-{2-[5-(2,4-dimethyl-benzyl)-hexahydro-pyrrolo[3,4-c]pyrrol-2-yl]-2-oxo-ethyl}-3-trifluoromethyl-benzamide | 2.2 | 475.2 |
| N-{2-[5-(2,4-Dimethyl-benzyl)-hexahydro-pyrrolo[3,4-c]pyrrol-2-yl]-2-oxo-ethyl}-2-methoxy-benzamide | 1.9 | 422.2 |
| 2-Amino-N-{2-[5-(2,4-dimethyl-benzyl)-hexahydro-pyrrolo[3,4-c]pyrrol-2-yl]-2-oxo-ethyl}-5-fluoro-benzamide | 1.7 | 425.1 |
| 2-{2-[5-(2,4-Dimethyl-benzyl)-hexahydro-pyrrolo[3,4-c]pyrrol-2-yl]-2-oxo-ethyl}-isoindole-1,3-dione | 1.8 | 418.1 |
| Naphthalene-2-carboxylic acid {2-[5-(2,4-dimethyl-benzyl)-hexahydro-pyrrolo[3,4-c]pyrrol-2-yl]-2-oxo-ethyl}-amide | 1.8 | 442.2 |
| N-{2-[5-(2,4-Difluoro-benzyl)-hexahydro-pyrrolo[3,4-c]pyrrol-2-yl]-2-oxo-ethyl}-2-(2-trifluoromethyl-phenyl)-acetamide | 1.6 | 482.3 |
| N-{2-[5-(2,5-Difluoro-benzyl)-hexahydro-pyrrolo[3,4-c]pyrrol-2-yl]-2-oxo-ethyl}-2-(2-trifluoromethyl-phenyl)-acetamide | 1.6 | 482.3 |
| N-{2-[5-(2,4-Difluoro-benzyl)-hexahydro-pyrrolo[3,4-c]pyrrol-2-yl]-2-oxo-ethyl}-3-trifluoromethyl-benzamide | 1.7 | 468.3 |
| 5-Chloro-N-{2-[5-(2,4-dimethyl-benzyl)-hexahydro-pyrrolo[3,4-c]pyrrol-2-yl]-2-oxo-ethyl}-2-methyl-benzamide | 1.9 | 440.1 |
| N-{2-[5-(2,4-Dimethyl-benzyl)-hexahydro-pyrrolo[3,4-c]pyrrol-2-yl]-2-oxo-ethyl}-2,5-bis-trifluoromethyl-benzamide | 2.1 | 528.1 |
| N-{2-[5-(2,4-Dimethyl-benzyl)-hexahydro-pyrrolo[3,4-c]pyrrol-2-yl]-2-oxo-ethyl}-2-nitro-benzamide | 1.6 | 437.1 |
| N-{2-[5-(2,4-Dimethyl-benzyl)-hexahydro-pyrrolo[3,4-c]pyrrol-2-yl]-2-oxo-ethyl}-2-nitro-benzamide | 1.9 | 460 |
| N-{2-[5-(2,4-Dimethyl-benzyl)-hexahydro-pyrrolo[3,4-c]pyrrol-2-yl]-2-oxo-ethyl}-2-methyl-benzamide | 1.7 | 406.1 |
| N-{2-[5-(2,4-Dimethyl-benzyl)-hexahydro-pyrrolo[3,4-c]pyrrol-2-yl]-2-oxo-ethyl}-2,5-dimethyl-benzamide | 1.9 | 420.1 |
| N-{2-[5-(2,4-Dimethyl-benzyl)-hexahydro-pyrrolo[3,4-c]pyrrol-2-yl]-2-oxo-ethyl}-3-(4-hydroxy-phenyl)-propionamide | 1.5 | 436.1 |

TABLE 2-continued

| Compound Name | Time (mins) | MW (found) |
|---|---|---|
| 1-(4-Methoxy-phenyl)-cyclopropanecarboxylic acid {2-[5-(2,4-dimethylbenzyl)-hexahydro-pyrrolo[3,4-c]-pyrrol-2-yl]-2-oxo-ethyl}amide | 2 | 462.2 |
| 1-(4-Chloro-phenyl)-cyclopropanecarboxylic acid {2-[5-(2,4-dimethyl-benzyl)-hexahydro-pyrrolo-[3,4-c]pyrrol-2-yl]-2-oxo-ethyl}-amide | 2.1 | 466.1 |
| 1-p-Tolyl-cyclopropanecarboxylic acid {2-[5-(2,4-dimethyl-benzyl)-hexahydro-pyrrolo[3,4-c]-pyrrol-2-yl]-2-oxo-ethyl}-amide | 2.1 | 446.2 |
| 2-(4-Chloro-phenyl)-N-{2-[5-(2,4-dimethyl-benzyl)-hexahydro-pyrrolo[3,4-c]pyrrol-2-yl]-2-oxo-ethyl}-isobutyramide | 2.2 | 468.1 |
| N-{2-[5-(2,4-Dimethyl-benzyl)-hexahydro-pyrrolo[3,4-c]pyrrol-2-yl]-2-oxo-ethyl}-2-(2-fluoro-biphenyl-4-yl)-propionamide | 2.4 | 514.2 |
| 1H-Indole-3-carboxylic acid {2-[5-(2,4-dimethyl-benzyl)-hexahydro-pyrrolo[3,4-c]pyrrol-2-yl]-2-oxo-ethyl}-amide | 1.8 | 431.1 |
| 1-(4-Chloro-phenyl)-5-trifluoromethyl-1H-pyrazole-4-carboxylic acid {2-[5-(2,4-dimethyl-benzyl)-hexahydro-pyrrolo[3,4-c]pyrrol-2-yl]-2-oxo-ethyl}-amide | 2.3 | 560.2 |
| 1-Phenyl-5-trifluoromethyl-1H-pyrazole-4-carboxylic acid {2-[5-(2,4-dimethyl-benzyl)-hexahydro-pyrrolo[3,4-c]pyrrol-2-yl]-2-oxo-ethyl}-amide | 2.1 | 526.2 |
| 5-Methyl-1-phenyl-1H-pyrazole-4-carboxylic acid {2-[5-(2,4-dimethyl-benzyl)-hexahydro-pyrrolo-[3,4-c]pyrrol-2-yl]-2-oxo-ethyl}-amide | 1.9 | 472.2 |
| N-{2-[5-(2,4-Dimethyl-benzyl)-hexahydro-pyrrolo[3,4-c]pyrrol-2-yl]-2-oxo-ethyl}-2-(2-trifluoromethyl-phenyl)-acetamide | 2 | 474.1 |
| N-{2-[5-(2,4-Dimethyl-benzyl)-hexahydro-pyrrolo[3,4-c]pyrrol-2-yl]-2-oxo-ethyl}-2-naphthalen-1-yl-acetamide | 2.1 | 456.3 |
| N-{2-[5-(2,4-Dimethyl-benzyl)-hexahydro-pyrrolo[3,4-c]pyrrol-2-yl]-2-oxo-ethyl}-2-phenyl-acetamide | 1.7 | 406.2 |
| 2-Biphenyl-4-yl-N-{2-[5-(2,4-dimethyl-benzyl)-hexahydro-pyrrolo[3,4-c]pyrrol-2-yl]-2-oxo-ethyl}-acetamide | 2.3 | 482.3 |
| N-{2-[5-(2,4-Dimethyl-benzyl)-hexahydro-pyrrolo[3,4-c]pyrrol-2-yl]-2-oxo-ethyl}-2-o-tolyl-acetamide | 1.9 | 420.2 |
| N-{2-[5-(2,4-Dimethyl-benzyl)-hexahydro-pyrrolo[3,4-c]pyrrol-2-yl]-2-oxo-ethyl}-2-m-tolyl-acetamide | 1.9 | 420.2 |
| N-{2-[5-(2,4-Dimethyl-benzyl)-hexahydro-pyrrolo[3,4-c]pyrrol-2-yl]-2-oxo-ethyl}-2-p-tolyl-acetamide | 1.9 | 420.2 |
| N-{2-[5-(2,4-Dimethyl-benzyl)-hexahydro-pyrrolo[3,4-c]pyrrol-2-yl]-2-oxo-ethyl}-2-(3-trifluoromethyl-phenyl)-acetamide | 2.1 | 474.2 |
| 2-(3,5-Bis-trifluoromethyl-phenyl)-N-{2-[5-(2,4-dimethyl-benzyl)-hexahydro-pyrrolo[3,4-c]pyrrol-2-yl]-2-oxo-ethyl}-acetamide | 2.4 | 542.2 |
| N-{2-[5-(2,4-Dimethyl-benzyl)-hexahydro-pyrrolo[3,4-c]pyrrol-2-yl]-2-oxo-ethyl}-2-(2-fluoro-3-trifluoromethyl-phenyl)-acetamide | 2.1 | 492.2 |
| N-{2-[5-(2,4-Dimethyl-benzyl)-hexahydro-pyrrolo[3,4-c]pyrrol-2-yl]-2-oxo-ethyl}-2-(2,3,6-trifluoro-phenyl)-acetamide | 1.9 | 460.2 |
| N-{2-[5-(2,4-Dimethyl-benzyl)-hexahydro-pyrrolo[3,4-c]pyrrol-2-yl]-2-oxo-ethyl}-2-(2,4,6-trifluoro-phenyl)-acetamide | 1.9 | 460.2 |
| N-{2-[5-(2,4-Dimethyl-benzyl)-hexahydro-pyrrolo[3,4-c]pyrrol-2-yl]-2-oxo-ethyl}-2-(3-fluoro-4-trifluoromethyl-phenyl)-acetamide | 2.2 | 492.2 |
| N-{2-[5-(2,4-Dimethyl-benzyl)-hexahydro-pyrrolo[3,4-c]pyrrol-2-yl]-2-oxo-ethyl}-2-(5-fluoro-2-trifluoromethyl-phenyl)-acetamide | 2.1 | 492.2 |
| N-{2-[5-(2,4-Dimethyl-benzyl)-hexahydro-pyrrolo[3,4-c]pyrrol-2-yl]-2-oxo-ethyl}-2-(4-isopropyl-phenyl)-acetamide | 2.2 | 448.3 |
| N-{2-[5-(2,4-Dimethyl-benzyl)-hexahydro-pyrrolo[3,4-c]pyrrol-2-yl]-2-oxo-ethyl}-2-(2,5-dimethyl-phenyl)-acetamide | 2 | 434.3 |
| N-{2-[5-(2,4-Dimethyl-benzyl)-hexahydro-pyrrolo[3,4-c]pyrrol-2-yl]-2-oxo-ethyl}-2-(4-trifluoromethyl-phenyl)-acetamide | 2.1 | 474.2 |
| 2-(3,4-Difluoro-phenyl)-N-{2-[5-(2,4-dimethyl-benzyl)-hexahydro-pyrrolo[3,4-c]pyrrol-2-yl]-2-oxo-ethyl}-acetamide | 1.9 | 442.2 |
| 2-(2,4-Bis-trifluoromethyl-phenyl)-N-{2-[5-(2,4-dimethyl-benzyl)-hexahydro-pyrrolo[3,4-c]pyrrol-2-yl]-2-oxo-ethyl}-acetamide | 2.3 | 542.2 |
| 9H-Xanthene-9-carboxylic acid {2-[5-(2,4-dimethyl-benzyl)-hexahydro-pyrrolo[3,4-c]pyrrol-2-yl]-2-oxo-ethyl}-amide | 2.3 | 496.2 |
| 1-Methyl-1H-indole-3-carboxylic acid {2-[5-(2,4-dimethyl-benzyl)=hexahydro-pyrrolo[3,4-c]-pyrrol-2-yl]-2-oxo-ethyl}-amide | 1.9 | 445.5 |
| 2-Amino-N-{2-[5-(2,4-dimethyl-benzyl)-hexahydro-pyrrolo[3,4-c]pyrrol-2-yl]-2-oxo-ethyl}-5-nitro-benzamide | 1.9 | 452.1 |
| 2-Amino-N-{2-[5-(2,4-dimethyl-benzyl)-hexahydro-pyrrolo[3,4-c]pyrrol-2-yl]-2-oxo-ethyl}-5-iodo-benzamide | 2.2 | 533.1 |
| N-{2-[5-(2,4-Dimethyl-benzyl)-hexahydro-pyrrolo[3,4-c]pyrrol-2-yl]-2-oxo-ethyl}-3-nitro-benzamide | 1.9 | 437.1 |
| N-{2-[5-(2,4-Dimethyl-benzyl)-hexahydro-pyrrolo[3,4-c]pyrrol-2-yl]-2-oxo-ethyl}-2-(1,3-dioxo-1,3-dihydro-isoindol-2-yl)-acetamide | 1.7 | 475.1 |
| 3-(3,4-Dichloro-phenyl)-N-{2-[5-(2,4-dimethyl-benzyl)-hexahydro-pyrrolo[3,4-c]pyrrol-2-yl]-2-oxo-ethyl}-acrylamide | 2.3 | 486.1 |
| 5-Fluoro-1H-indole-2-carboxylic acid {2-[5-(2,4-dimethyl-benzyl)-hexahydro-pyrrolo[3,4-c]pyrrol-2-yl]-2-oxo-ethyl}-amide | 2.1 | 449.1 |

TABLE 2-continued

| Compound Name | Time (mins) | MW (found) |
|---|---|---|
| 7-Nitro-1H-indole-2-carboxylic acid {2-[5-(2,4-dimethyl-benzyl)-hexahydro-pyrrolo[3,4-c]pyrrol-2-yl]-2-oxo-ethyl}-amide | 2.1 | 476.1 |
| 1-Benzyl-1H-indole-3-carboxylic acid {2-[5-(2,4-dimethyl-benzyl)-hexahydro-pyrrolo[3,4-c]pyrrol-2-yl]-2-oxo-ethyl}-amide | 2.3 | 521.2 |
| 5-Bromo-1H-indole-2-carboxylic acid {2-[5-(2,4-dimethyl-benzyl)-hexahydro-pyrrolo[3,4-c]pyrrol-2-yl]-2-oxo-ethyl}-amide | 2.2 | 511 |
| 1H-Indole-2-carboxylic acid {2-[5-(2,4-dimethyl-benzyl)-hexahydro- pyrrolo[3,4-c]pyrrol-2-yl]-2-oxo-ethyl}-amide | 1.7 | 431.2 |
| 3,4-Dichloro-N-{2-oxo-2-[5-(2-trifluoromethyl-benzyl)-hexahydro-pyrrolo[3,4-c]pyrrol-2-yl]-ethyl}-benzamide | 2.1 | 500.3 |
| 3-Bromo-4-chloro-N-{2-oxo-2-[5-(2-trifluoromethyl-benzyl)-hexahydro-pyrrolo[3,4-c]pyrrol-2-yl]-ethyl}-benzamide | 2.1 | 545.9 |
| 2-Amino-5-chloro-N-{2-oxo-2-[5-(2-trifluoromethyl-benzyl)-hexahydro-pyrrolo[3,4-c]pyrrol-2-yl]-ethyl}-benzamide | 1.9 | 481.3 |
| 2-Amino-5-bromo-N-{2-oxo-2-[5-(2-trifluoromethyl-benzyl)-hexahydro-pyrrolo[3,4-c]pyrrol-2-yl]-ethyl}-benzamide | 1.9 | 525.3 |
| N-{2-Oxo-2-[5-(2-trifluoromethyl-benzyl)-hexahydro-pyrrolo[3,4-c]pyrrol-2-yl]-ethyl}-3-trifluoromethyl-benzamide | 2 | 500.2 |
| 3,4-Dichloro-N-{2-oxo-2-[5-(4-trifluoromethyl-benzyl)-hexahydro-pyrrolo[3,4-c]-pyrrol-2-yl]-ethyl}-benzamide | 2.2 | 500.3 |
| 3-Bromo-4-chloro-N-{2-oxo-2-[5-(4-trifluoromethyl-benzyl)-hexahydro-pyrrolo[3,4-c]-pyrrol-2-yl]-ethyl}-benzamide | 2.2 | 545.9 |
| 2-Amino-5-bromo-N-{2-oxo-2-[5-(4-trifluoromethyl-benzyl)-hexahydro-pyrrolo[3,4-c]-pyrrol-2-yl]-ethyl}-benzamide | 2 | 527.3 |
| N-{2-Oxo-2-[5-(4-trifluoromethyl-benzyl)-hexahydro-pyrrolo[3,4-c]pyrrol-2-yl]-ethyl}-3-trifluoromethyl-benzamide | 2.1 | 500.1 |
| 3,4-Dichloro-N-{2-[5-(2-fluoro-4-trifluoromethyl-benzyl)-hexahydro-pyrrolo[3,4-c]pyrrol-2-yl]-2-oxo-ethyl}-benzamide | 2.2 | 518.1 |
| 3-Bromo-4-chloro-N-{2-[5-(2-fluoro-4-trifluoromethyl-benzyl)-hexahydro-pyrrolo[3,4-c]-pyrrol-2-yl]-2-oxo-ethyl}-benzamide | 2.3 | 563.9 |
| N-{2-[5-(2-Fluoro-4-trifluoromethyl-benzyl)-hexahydro-pyrrolo[3,4-c]pyrrol-2-yl]-2-oxo-ethyl}-3-trifluoromethyl-benzamide | 2.1 | 518.4 |
| 3,4-Dichloro-N-{2-[5-(4-fluoro-2-trifluoromethyl-benzyl)-hexahydro-pyrrolo[3,4-c]-pyrrol-2-yl]-2-oxo-ethyl}-benzamide | 2.1 | 518.3 |
| 1H-Indole-2-carboxylic acid {2-[5-(2-fluoro-4-trifluoromethyl-benzyl)-hexahydro-pyrrolo[3,4-c]-pyrrol-2-yl]-2-oxo-ethyl}-amide | 2 | 489.2 |
| 3-Bromo-4-chloro-N-{2-[5-(4-fluoro-2-trifluoromethyl-benzyl)-hexahydro-pyrrolo[3,4-c]pyrrol-2-yl]-2-oxo-ethyl}-benzamide | 2.2 | 564.2 |
| 2-Amino-5-chloro-N-{2-[5-(2-fluoro-4-trifluoromethyl-benzyl)-hexahydro-pyrrolo[3,4-c]pyrrol-2-yl]-2-oxo-ethyl}-benzamide | 2 | 499.3 |
| 2-Amino-1-[5-(2,4-difluoro-benzyl)-hexahydro-pyrrolo[3,4-c]pyrrol-2-yl]-ethanone | NA | 296.1 |
| 2-Amino-1-[5-(2,3-difluoro-benzyl)-hexahydro-pyrrolo[3,4-c]pyrrol-2-yl]-ethanone | NA | 296.1 |
| 2-Amino-1-[5-(3,5-difluoro-benzyl)-hexahydro-pyrrolo[3,4-c]pyrrol-2-yl]-ethanone | 0.2 | 296.4 |
| 2-Amino-1-[5-(2,5-difluoro-benzyl)-hexahydro-pyrrolo[3,4-c]pyrrol-2-yl]-ethanone | NA | 296.2 |
| 2-Amino-1-[5-(2,4-dimethyl-benzyl)-hexahydro-pyrrolo[3,4-c]pyrrol-2-yl]-ethanone | 0.3 | 288.3 |
| N-{2-[5-(2,4-Dimethyl-benzyl)-hexahydro-pyrrolo[3,4-c]pyrrol-2-yl]-2-oxo-ethyl}-3-trifluoromethyl-benzenesulfonamide | 2 | 496.1 |
| 2-Amino-1-[5-(2,4-dimethoxy-benzyl)-hexahydro-pyrrolo[3,4-c]pyrrol-2-yl]-ethanone | 0.2 | 320.1 |
| 2-Amino-1-[5-(2-trifluoromethyl-benzyl)-hexahydro-pyrrolo[3,4-c]pyrrol-2-yl]-ethanone | 0.3 | 328.5 |
| 2-Amino-1-[5-(4-trifluoromethyl-benzyl)-hexahydro-pyrrolo[3,4-c]pyrrol-2-yl]-ethanone | 0.4 | 328.5 |
| 2-Amino-1-[5-(2-fluoro-4-trifluoromethyl-benzyl)-hexahydro-pyrrolo[3,4-c]pyrrol-2-yl]-ethanone | NA | 346.1 |
| 2-Amino-1-[5-(4-fluoro-2-trifluoromethyl-benzyl)-hexahydro-pyrrolo[3,4-c]pyrrol-2-yl]-ethanone | NA | 346.2 |
| 1-{2-[5-(2,4-Dimethyl-benzyl)-hexahydro-pyrrolo[3,4-c]pyrrol-2-yl]-2-oxo-ethyl}-3-(3-trifluoromethyl-phenyl)-urea | 2 | 475.5 |
| 3,4-Dichloro-N-{2-[5-(2,4-dimethoxy-benzyl)-hexahydro-pyrrolo[3,4-c]pyrrol-2-yl]-2-oxo-ethyl}-benzamide | 2 | 492.4 |
| 3-Bromo-4-chloro-N-{2-[5-(2,4-dimethoxy-benzyl)-hexahydro-pyrrolo[3,4-c]pyrrol-2-yl]-2-oxo-ethyl}-benzamide | 2.1 | 538.3 |
| 2-Amino-5-bromo-N-{2-[5-(2,4-dimethoxy-benzyl)-hexahydro-pyrrolo[3,4-c]pyrrol-2-yl]-2-oxo-ethyl}-benzamide | 1.9 | 517.4 |
| 2-Amino-N-{2-[5-(2,4-dimethoxy-benzyl)-hexahydro-pyrrolo[3,4-c]pyrrol-2-yl]-2-oxo-ethyl}-5-iodo-benzamide | 2 | 565.3 |
| 5-Bromo-1H-indole-2-carboxylic acid {2-[5-(2,4-dimethoxy-benzyl)-hexahydro-pyrrolo[3,4-c]-pyrrol-2-yl]-2-oxo-ethyl}-amide | 2.1 | 541.4 |
| 7-Nitro-1H-indole-2-carboxylic acid {2-[5-(2,4-dimethoxy-benzyl)-hexahydro-pyrrolo[3,4-c]pyrrol-2-yl]-2-oxo-ethyl}-amide | 2 | 508.4 |
| 3,5-Dichloro-N-{2-[5-(2,4-dimethyl-benzyl)-hexahydro-pyrrolo[3,4-c]pyrrol-2-yl]-2-oxo-ethyl}-benzamide | 2.2 | 460 |

TABLE 2-continued

| Compound Name | Time (mins) | MW (found) |
|---|---|---|
| 2,3-Dihydro-benzo[1,4]dioxine-2-carboxylic acid {2-[5-(2,4-dimethyl-benzyl)-hexahydro-pyrrolo[3,4-c]pyrrol-2-yl]-2-oxo-ethyl}-amide | 2 | 450.1 |
| Biphenyl-4-carboxylic acid {2-[5-(2,4-dimethyl-benzyl)-hexahydro-pyrrolo[3,4-c]pyrrol-2-yl]-2-oxo-ethyl}-amide | 2.3 | 468.2 |
| N-{2-[5-(2,4-Dimethyl-benzyl)-hexahydro-pyrrolo[3,4-c]pyrrol-2-yl]-2-oxo-ethyl}-3,4-dimethoxy-benzamide | 1.7 | 452.2 |
| N-{2-[5-(2,4-Dimethyl-benzyl)-hexahydro-pyrrolo[3,4-c]pyrrol-2-yl]-2-oxo-ethyl}-2-phenoxy-acetamide | 1.9 | 422.1 |
| 2-(3,4-Dimethoxy-phenyl)-N-{2-[5-(2,4-dimethyl-benzyl)-hexahydro-pyrrolo[3,4-c]pyrrol-2-yl]-2-oxo-ethyl}-acetamide | 1.7 | 466.2 |
| N-{2-[5-(2,4-Dimethyl-benzyl)-hexahydro-pyrrolo[3,4-c]pyrrol-2-yl]-2-oxo-ethyl}-3-phenoxy-propionamide | 1.9 | 436.2 |
| Thiophene-2-carboxylic acid {2-[5-(2,4-dimethyl-benzyl)-hexahydro-pyrrolo[3,4-c]pyrrol-2-yl]-2-oxo-ethyl}-amide | 1.6 | 398.1 |
| N-{2-[5-(2,4-Dimethyl-benzyl)-hexahydro-pyrrolo[3,4-c]pyrrol-2-yl]-2-oxo-ethyl}-4-thiophen-2-yl-butyramide | 2 | 440.1 |
| Benzofuran-2-carboxylic acid {2-[5-(2,4-dimethyl-benzyl)-hexahydro-pyrrolo[3,4-c]pyrrol-2-yl]-2-oxo-ethyl}-amide | 2 | 432.1 |
| N-{2-[5-(2,4-Dimethyl-benzyl)-hexahydro-pyrrolo[3,4-c]pyrrol-2-yl]-2-oxo-ethyl}-nicotinamide | 1.1 | 393.1 |
| 2-(4-Chloro-phenoxy)-N-{2-[5-(2,4-dimethyl-benzyl)-hexahydro-pyrrolo[3,4-c]pyrrol-2-yl]-2-oxo-ethyl}-acetamide | 2.1 | 456.1 |
| 5-Methyl-3-phenyl-isoxazole-4-carboxylic acid {2-[5-(2,4-dimethyl-benzyl)-hexahydro-pyrrolo[3,4-c]pyrrol-2-yl]-2-oxo-ethyl}-amide | 2 | 473.1 |
| Cinnoline-4-carboxylic acid {2-[5-(2,4-dimethyl-benzyl)-hexahydro-pyrrolo[3,4-c]pyrrol-2-yl]-2-oxo-ethyl}-amide | 1.6 | 445.2 |
| N-{2-[5-(2,4-Dimethyl-benzyl)-hexahydro-pyrrolo[3,4-c]pyrrol-2-yl]-2-oxo-ethyl}-4-pentyloxy-benzamide | 2.5 | 478.2 |
| Biphenyl-2-carboxylic acid {2-[5-(2,4-dimethyl-benzyl)-hexahydro-pyrrolo[3,4-c]pyrrol-2-yl]-2-oxo-ethyl}-amide | 2.1 | 468.2 |
| 1-Methyl-1H-indole-2-carboxylic acid {2-[5-(2,4-dimethyl-benzyl)-hexahydro-pyrrolo[3,4-c]pyrrol-2-yl]-2-oxo-ethyl}-amide | 2.1 | 445.2 |
| N-{2-[5-(2,4-Dimethyl-benzyl)-hexahydro-pyrrolo[3,4-c]pyrrol-2-yl]-2-oxo-ethyl}-2-(3-fluoro-phenyl)-acetamide | 1.9 | 424.1 |
| Pyridine-2-carboxylic acid {2-[5-(2,4-dimethyl-benzyl)-hexahydro-pyrrolo[3,4-c]pyrrol-2-yl]-2-oxo-ethyl}-amide | 1.5 | 393.1 |
| Furan-3-carboxylic acid {2-[5-(2,4-dimethyl-benzyl)-hexahydro-pyrrolo[3,4-c]pyrrol-2-yl]-2-oxo-ethyl}-amide | 1.3 | 382.1 |
| N-{2-[5-(2,4-Dimethyl-benzyl)-hexahydro-pyrrolo[3,4-c]pyrrol-2-yl]-2-oxo-ethyl}-3-(4-methoxy-phenyl)-propionamide | 1.9 | 450.2 |
| 1-Methyl-1H-pyrrole-2-carboxylic acid {2-[5-(2,4-dimethyl-benzyl)-hexahydro-pyrrolo[3,4-c]pyrrol-2-yl]-2-oxo-ethyl}-amide | 2 | 395.1 |
| 3-Methoxy-cyclohexanecarboxylic acid {2-[5-(2,4-dimethyl-benzyl)-hexahydro-pyrrolo[3,4-c]pyrrol-2-yl]-2-oxo-ethyl}-amide | 1.7 | 428.2 |
| N-{2-[5-(2,4-Dimethyl-benzyl)-hexahydro-pyrrolo[3,4-c]pyrrol-2-yl]-2-oxo-ethyl}-2-thiophen-2-yl-acetamide | 2.5 | 412 |
| N-{2-[5-(2,4-Dimethyl-benzyl)-hexahydro-pyrrolo[3,4-c]pyrrol-2-yl]-2-oxo-ethyl}-2-(4-phenoxy-phenyl)-acetamide | 2.3 | 498.2 |
| 3-Chloro-N-{2-[5-(2,4-dimethyl-benzyl)-hexahydro-pyrrolo[3,4-c]pyrrol-2-yl]-2-oxo-ethyl}-4-methoxy-benzamide | 2 | 456.1 |
| 1,2,3,4-Tetrahydro-naphthalene-2-carboxylic acid {2-[5-(2,4-dimethyl-benzyl)-hexahydro-pyrrolo[3,4-c]pyrrol-2-yl]-2-oxo-ethyl}-amide | 2.1 | 446.2 |
| 3-(4-Chloro-phenyl)-N-{2-[5-(2,4-dimethyl-benzyl)-hexahydro-pyrrolo[3,4-c]pyrrol-2-yl]-2-oxo-ethyl}-propionamide | 2.1 | 454.1 |
| 2-(2,4-Difluoro-phenyl)-N-{2-[5-(2,4-dimethyl-benzyl)-hexahydro-pyrrolo[3,4-c]pyrrol-2-yl]-2-oxo-ethyl}-acetamide | 1.9 | 442.1 |
| 2-Cyclopentyl-N-{2-[5-(2,4-dimethyl-benzyl)-hexahydro-pyrrolo[3,4-c]pyrrol-2-yl]-2-oxo-ethyl}-acetamide | 1.9 | 398.1 |
| N-{2-[5-(2,4-Dimethyl-benzyl)-hexahydro-pyrrolo[3,4-c]pyrrol-2-yl]-2-oxo-ethyl}-2-phenethyl-benzamide | 2.4 | 496.2 |
| 2-Ethoxy-naphthalene-1-carboxylic acid {2-[5-(2,4-dimethyl-benzyl)-hexahydro-pyrrolo[3,4-c]pyrrol-2-yl]-2-oxo-ethyl}-amide | 2.1 | 486.2 |
| 4-Cyclohexyl-N-{2-[5-(2,4-dimethyl-benzyl)-hexahydro-pyrrolo[3,4-c]pyrrol-2-yl]-2-oxo-ethyl}-benzamide | 2.5 | 474.2 |
| 3-Chloro-N-{2-[5-(2,4-dimethyl-benzyl)-hexahydro-pyrrolo[3,4-c]pyrrol-2-yl]-2-oxo-ethyl}-4-methyl-benzamide | 2.1 | 440.1 |
| N-{2-[5-(2,4-Dimethyl-benzyl)-hexahydro-pyrrolo[3,4-c]pyrrol-2-yl]-2oxo-ethyl}-3-ethoxy-benzamide | 2 | 436.1 |
| 4-Diethylamino-N-{2-[5-(2,4-dimethyl-benzyl)-hexahydro-pyrrolo[3,4-c]pyrrol-2-yl]-2-oxo-ethyl}-benzamide | 2 | 463.2 |
| N-{2-[5-(2,4-Dimethyl-benzyl)-hexahydro-pyrrolo[3,4-c]pyrrol-2-yl]-2-oxo-ethyl}-4-ethyl-benzamide | 2.1 | 420.1 |
| N-{2-[5-(2,4-Dimethyl-benzyl)-hexahydro-pyrrolo[3,4-c]pyrrol-2-yl]-2-oxo-ethyl}-2-(4-isopropyl-phenoxy)-acetamide | 2.3 | 464.2 |

TABLE 2-continued

| Compound Name | Time (mins) | MW (found) |
|---|---|---|
| N-{2-[5-(2,4-Dimethyl-benzyl)-hexahydro-pyrrolo[3,4-c]pyrrol-2-yl]-2-oxo-ethyl}-2-(4-ethoxy-phenyl)-acetamide | 2 | 450.2 |
| N-{2-[5-(2,4-Dimethyl-benzyl)-hexahydro-pyrrolo[3,4-c]pyrrol-2-yl]-2-oxo-ethyl}-3-(3,4,5-trimethoxy-phenyl)-propionamide | 1.9 | 510.2 |
| N-{2-[5-(2,4-Dimethyl-benzyl)-hexahydro-pyrrolo[3,4-c]pyrrol-2-yl]-2-oxo-ethyl}-3-m-tolyl-propionamide | 2.1 | 434.2 |
| N-{2-[5-(2,4-Dimethyl-benzyl)-hexahydro-pyrrolo[3,4-c]pyrrol-2-yl]-2-oxo-ethyl}-3-(4-fluoro-phenyl)-propionamide | 2 | 438.1 |
| 3-Methyl-benzofuran-2-carboxylic acid {2-[5-(2,4-dimethyl-benzyl)-hexahydro-pyrrolo[3,4-c]pyrrol-2-yl]-2-oxo-ethyl}-amide | 2.2 | 445.2 |
| 7-Methoxy-benzofuran-2-carboxylic acid {2-[5-(2,4-dimethyl-benzyl)-hexahydro-pyrrolo[3,4-c]pyrrol-2-yl]-2-oxo-ethyl}-amide | 2.1 | 462.1 |
| 5-Methyl-2-phenyl-2H-[1,2,3]triazole-4-carboxylic acid {2-[5-(2,4-dimethyl-benzyl)-hexahydro-pyrrolo-[3,4-c]pyrrol-2-yl]-2-oxo-ethyl}-amide | 2.3 | 473.1 |
| N-{2-[5-(2,4-Dimethyl-benzyl)-hexahydro-pyrrolo[3,4-c]pyrrol-2-yl]-2-oxo-ethyl}-3-fluoro-4-methoxy-benzamide | 1.9 | 440.1 |
| Chroman-2-carboxylic acid {2-[5-(2,4-dimethyl-benzyl)-hexahydro-pyrrolo[3,4-c]pyrrol-2-yl]-2-oxo-ethyl}-amide | 2.1 | 448.1 |
| 5-Pyridin-2-yl-thiophene-2-carboxylic acid {2-[5-(2,4-dimethyl-benzyl)-hexahydro-pyrrolo[3,4-c]pyrrol-2-yl]-2-oxo-ethyl}-amide | 2 | 475.1 |
| 2-Cyclopropyl-N-{2-[5-(2,4-dimethyl-benzyl)-hexahydro-pyrrolo[3,4-c]pyrrol-2-yl]-2-oxo-ethyl}-acetamide | 1.4 | 370.1 |
| N-{2-[5-(2,4-Dimethyl-benzyl)-hexahydro-pyrrolo[3,4-c]pyrrol-2-yl]-2-oxo-ethyl}-3-naphthalen-1-yl-propionamide | 2.3 | 470.2 |
| 2-Chloro-N-{2-[5-(2,4-dimethyl-benzyl)-hexahydro-pyrrolo[3,4-c]pyrrol-2-yl]-2-oxo-ethyl}-3-methyl-benzamide | 1.9 | 440.1 |
| 3-Chloro-thiophene-2-carboxylic acid {2-[5-(2,4-dimethyl-benzyl)-hexahydro-pyrrolo[3,4-c]pyrrol-2-yl]-2-oxo-ethyl}-amide | 1.9 | 432 |
| 2,7-Dimethyl-pyrazolo[1,5-a]pyrimidine-6-carboxylic acid {2-[5-(2,4-dimethyl-benzyl)-hexahydro-pyrrolo[3,4-c]pyrrol-2-yl]-2-oxoethyl}-amide | 1.6 | 461.1 |
| 4-Methoxy-thiophene-3-carboxylic acid {2-[5-(2,4-dimethyl-benzyl)-hexahydro-pyrrolo[3,4-c]pyrrol-2-yl]-2-oxo-ethyl}-amide | 1.8 | 428.1 |
| 2-(5-Chloro-3-methyl-benzo[b]thiophen-2-yl)-N-{2-[5-(2,4-dimethyl-benzyl)-hexahydro-pyrrolo-[3,4-c]pyrrol-2-yl]-2-oxo-ethyl}-acetamide | 2.4 | 510.1 |
| 2,5-Dimethyl-furan-3-carboxylic acid {2-[5-(2,4-dimethyl-benzyl)-hexahydro-pyrrolo[3,4-c]pyrrol-2-yl]-2-oxo-ethyl}-amide | 1.9 | 410.1 |
| N-{2-[5-(2,4-Dimethyl-benzyl)-hexahydro-pyrrolo[3,4-c]pyrrol-2-yl]-2-oxo-ethyl}-4-pyrrol-1-yl-benzamide | 2.1 | 457.2 |
| 2-Pyrazin-2-yl-thiazole-4-carboxylic acid {2-[5-(2,4-dimethyl-benzyl)-hexahydro-pyrrolo[3,4-c]pyrrol-2-yl]-2-oxo-ethyl}-amide | 1.7 | 477.1 |
| Isoxazole-5-carboxylic acid {2-[5-(2,4-dimethyl-benzyl)-hexahydropyrrolo-[3,4-c]pyrrol-2-yl]-2-oxo-ethyl}-amide | 1.2 | 383.1 |
| Benzo[1,2,5]oxadiazole-5-carboxylic acid {2-[5-(2,4-dimethyl-benzyl)-hexahydro-pyrrolo[3,4-c]pyrrol-2-yl]-2-oxo-ethyl}-amide | 1.9 | 434.1 |
| 5-Methyl-isoxazole-4-carboxylic acid {2-[5-(2,4-dimethyl-benzyl)-hexahydro-pyrrolo[3,4-c]pyrrol-2-yl]-2-oxo-ethyl}-amide | 1.5 | 397.1 |
| 5-Methyl-isoxazole-3-carboxylic acid {2-[5-(2,4-dimethyl-benzyl)-hexahydro-pyrrolo[3,4-c]pyrrol-2-yl]-2-oxo-ethyl}-amide | 1.5 | 397.1 |
| 4,6-Dichloro-1H-indole-2-carboxylic acid {2-[5-(2,4-dimethyl-benzyl)-hexahydro-pyrrolo[3,4-c]pyrrol-2-yl]-2-oxo-ethyl}-amide | 2.5 | 499.1 |
| 4-Chloro-N-{2-[5-(2-methyl-benzyl)-hexahydro-pyrrolo[3,4-c]pyrrol-2-yl]-2-oxo-ethyl}-benzamide | 1.6 | 412.4 |
| 4-Chloro-N-{2-oxo-2-[5-(3-trifluoromethyl-benzyl)-hexahydro-pyrrolo[3,4-c]pyrrol-2-yl]-ethyl}-benzamide | 1.9 | 466.3 |
| 4-Chloro-N-{2-[5-(5-methoxy-1H-indol-3-ylmethyl)-hexahydro-pyrrolo[3,4-c]pyrrol-2-yl]-2-oxo-ethyl}-benzamide | 1.7 | 467.4 |
| 3-Chloro-N-{2-[5-(2-methyl-benzyl)-hexahydro-pyrrolo[3,4-c]pyrrol-2-yl]-2-oxo-ethyl}-benzamide | 1.6 | 412.4 |
| 3-Chloro-N-{2-oxo-2-[5-(3-trifluoromethyl-benzyl)-hexahydro-pyrrolo[3,4-c]pyrrol-2-yl]-ethyl}-benzamide | 1.9 | 466.4 |
| 1-(3,4-Dichloro-benzyl)-3-methyl-4-oxo-4,5,6,7-tetrahydro-1H-indole-2-carboxylic acid {2-[5-(2,4-dimethyl-benzyl)-hexahydro-pyrrolo[3,4-c]pyrrol-2-yl]-2-oxo-ethyl}-amide | 2.3 | 621.4 |
| 1-(3,4-Dichloro-benzyl)-2-[5-(2,4-dimethyl-benzyl)-hexahydro-pyrrolo[3,4-c]pyrrole-2-carbonyl]-3-methyl-1,5,6,7-tetrahydro-indol-4-one | 2.3 | 564.3 |
| 2-Amino-1-[5-(3,4-dichloro-benzyl)-hexahydro-pyrrolo[3,4-c]pyrrol-2-yl]-ethanone | NA | 327.9 |
| N-{2-[5-(3,4-Dichloro-benzyl)-hexahydro-pyrrolo[3,4-c]pyrrol-2-yl]-2-oxo-ethyl}-3-fluoro-benzamide | 1.63 | 449.11 |
| N-{2-[5-(4-Chloro-benzyl)-hexahydro-pyrrolo[3,4-c]pyrrol-2-yl]-2-oxo-ethyl}-3-fluoro-benzamide | 1.47 | 415.15 |
| N-{2-[5-(3,4-Dichloro-benzyl)-hexahydro-pyrrolo[3,4-c]pyrrol-2-yl]-2-oxo-ethyl}-3,4-difluoro-benzamide | 1.71 | 467.1 |

TABLE 2-continued

| Compound Name | Time (mins) | MW (found) |
|---|---|---|
| N-{2-[5-(3,4-Dichloro-benzyl)-hexahydro-pyrrolo[3,4-c]pyrrol-2-yl]-2-oxo-ethyl}-4-fluoro-benzamide | 1.64 | 449.11 |
| N-{2-[5-(4-Chloro-benzyl)-hexahydro-pyrrolo[3,4-c]pyrrol-2-yl]-2-oxo-ethyl}-4-fluoro-benzamide | 1.48 | 415.15 |
| N-{2-[5-(4-Chloro-benzyl)-hexahydro-pyrrolo[3,4-c]pyrrol-2-yl]-2-oxo-ethyl}-3-methyl-benzamide | 1.54 | 411.17 |
| N-{2-[5-(3,4-Dichloro-benzyl)-hexahydro-pyrrolo[3,4-c]pyrrol-2-yl]-2-oxo-ethyl}-3-fluoro-4-methyl-benzamide | 1.77 | 463.12 |
| N-{2-[5-(4-Chloro-benzyl)-hexahydro-pyrrolo[3,4-c]pyrrol-2-yl]-2-oxo-ethyl}-3-fluoro-4-methyl-benzamide | 1.6 | 429.16 |
| N-{2-[5-(4-Chloro-benzyl)-hexahydro-pyrrolo[3,4-c]-pyrrol-2-yl]-2-oxo-ethyl}-benzamide | 1.4 | 397.16 |
| N-{2-[5-(3,4-Dichloro-benzyl)-hexahydro-pyrrolo[3,4-c]pyrrol-2-yl]-2-oxo-ethyl}-3,5-difluoro-benzamide | 1.7 | 467.1 |
| N-{2-[5-(4-Chloro-benzyl)-hexahydro-pyrrolo[3,4-c]pyrrol-2-yl]-2-oxo-ethyl}-3,5-difluoro-benzamide | 1.54 | 433.14 |
| N-{2-[5-(3,4-Dichloro-benzyl)-hexahydro-pyrrolo[3,4-c]pyrrol-2-yl]-2-oxo-ethyl}-4-methyl-benzamide | 1.69 | 445.13 |
| N-{2-[5-(4-Chloro-benzyl)-hexahydro-pyrrolo[3,4-c]pyrrol-2-yl]-2-oxo-ethyl}-4-methyl-benzamide | 1.53 | 411.17 |
| N-{2-[5-(4-Chloro-benzyl)-hexahydro-pyrrolo[3,4-c]pyrrol-2-yl]-2-oxo-ethyl}-3,4-dimethyl-benzamide | 1.65 | 425.19 |
| N-{2-[5-(3,4-Dichloro-benzyl)-hexahydro-pyrrolo[3,4-c]pyrrol-2-yl]-2-oxo-ethyl}-4-ethylsulfanyl-benzamide | 1.87 | 491.12 |
| N-{2-[5-(4-Chloro-benzyl)-hexahydro-pyrrolo[3,4-c]pyrrol-2-yl]-2-oxo-ethyl}-4-ethylsulfanyl-benzamide | 1.74 | 457.16 |
| 4-Butyl-N-{2-[5-(3,4-dichloro-benzyl)-hexahydro-pyrrolo[3,4-c]pyrrol-2-yl]-2-oxo-ethyl}-benzamide | 2.07 | 487.18 |
| 4-Butyl-N-{2-[5-(4-chloro-benzyl)-hexahydro-pyrrolo[3,4-c]-pyrrol-2-yl]-2-oxo-ethyl}-benzamide | 1.96 | 453.22 |
| N-{2-[5-(4-Chloro-benzyl)-hexahydro-pyrrolo[3,4-c]pyrrol-2-yl]-2-oxo-ethyl}-4-isopropyl-benzamide | 1.8 | 439.2 |
| N-{2-[5-(4-Chloro-benzyl)-hexahydro-pyrrolo[3,4-c]-pyrrol-2-yl]-2-oxo-ethyl}-4-trifluoromethoxy-benzamide | 1.8 | 481.14 |
| N-{2-[5-(3,4-Dichloro-benzyl)-hexahydro-pyrrolo[3,4-c]-pyrrol-2-yl]-2-oxo-ethyl}-3,4,5-trifluoro-benzamide | 1.8 | 485.09 |
| N-{2-[5-(4-Chloro-benzyl)-hexahydro-pyrrolo[3,4-c]-pyrrol-2-yl]-2-oxo-ethyl}-3,4,5-trifluoro-benzamide | 1.66 | 451.13 |
| N-{2-[5-(4-Chloro-benzyl)-hexahydro-pyrrolo[3,4-c]-pyrrol-2-yl]-2-oxo-ethyl}-4-propyl-benzamide | 1.83 | 439.2 |
| N-{2-[5-(4-Chloro-benzyl)-hexahydro-pyrrolo[3,4-c]-pyrrol-2-yl]-2-oxo-ethyl}-4-isopropoxy-benzamide | 1.7 | 455.2 |
| N-{2-[5-(4-Chloro-benzyl)-hexahydro-pyrrolo[3,4-c]-pyrrol-2-yl]-2-oxo-ethyl}-4-propoxy-benzamide | 1.76 | 455.2 |
| 3-Chloro-N-{2-[5-(3,4-dichloro-benzyl)-hexahydro-pyrrolo[3,4-c]pyrrol-2-yl]-2-oxo-ethyl}-4-fluoro-benzamide | 1.83 | 483.07 |
| 3-Chloro-N-{2-[5-(4-chloro-benzyl)-hexahydro-pyrrolo[3,4-c]pyrrol-2-yl]-2-oxo-ethyl}-4-fluoro-benzamide | 1.67 | 449.11 |
| N-{2-[5-(4-Chloro-benzyl)-hexahydro-pyrrolo[3,4-c]-pyrrol-2-yl]-2-oxo-ethyl}-3-fluoro-5-trifluoromethyl-benzamide | 1.8 | 483.13 |
| N-{2-[5-(4-Chloro-benzyl)-hexahydro-pyrrolo[3,4-c]pyrrol-2-yl]-2-oxo-ethyl}-3-fluoro-4-trifluoromethyl-benzamide | 1.84 | 483.13 |
| 4-Bromo-N-{2-[5-(3,4-dichloro-benzyl)-hexahydro-pyrrolo[3,4-c]pyrrol-2-yl]-2-oxo-ethyl}-benzamide | 1.82 | 509.03 |
| 4-Bromo-N-{2-[5-(4-chloro-benzyl)-hexahydro-pyrrolo[3,4-c]pyrrol-2-yl]-2-oxo-ethyl}-benzamide | 1.66 | 475.07 |
| 2-Bromo-N-{2-[5-(3,4-dichloro-benzyl)-hexahydro-pyrrolo[3,4-c]pyrrol-2-yl]-2-oxo-ethyl}-5-methoxy-benzamide | 1.72 | 539.04 |
| 2-Bromo-N-{2-[5-(4-chloro-benzyl)-hexahydro-pyrrolo[3,4-c]pyrrol-2-yl]-2-oxo-ethyl}-5-methoxy-benzamide | 1.57 | 505.08 |
| 4-tert-Butyl-N-{2-[5-(3,4-dichloro-benzyl)-hexahydro-pyrrolo[3,4-c]pyrrol-2-yl]-2-oxo-ethyl}-benzamide | 2.03 | 487.18 |
| 4-tert-Butyl-N-{2-[5-(4-chloro-benzyl)-hexahydro-pyrrolo[3,4-c]pyrrol-2-yl]-2-oxo-ethyl}-benzamide | 1.9 | 453.22 |
| N-{2-[5-(3,4-Dichloro-benzyl)-hexahydro-pyrrolo-[3,4-c]pyrrol-2-yl]-2-oxo-ethyl}-3,5-bis-trifluoromethyl-benzamide | 2.12 | 567.09 |
| N-{2-[5-(4-Chloro-benzyl)-hexahydro-pyrrolo[3,4-c]-pyrrol-2-yl]-2-oxo-ethyl}-3,5-bis-trifluoromethyl-benzamide | 2 | 533.13 |
| 3-Bromo-N-{2-[5-(4-chloro-benzyl)-hexahydro-pyrrolo[3,4-c]pyrrol-2-yl]-2-oxo-ethyl}-4-methyl-benzamide | 1.79 | 489.08 |
| 3-Bromo-4-chloro-N-{2-[5-(3,4-dichloro-benzyl)-hexahydro-pyrrolo[3,4-c]pyrrol-2-yl]-2-oxo-ethyl}-benzamide | 1.97 | 542.99 |
| 3-Bromo-4-chloro-N-{2-[5-(4-chloro-benzyl)-hexahydro-pyrrolo[3,4-c]pyrrol-2-yl]-2-oxo-ethyl}-benzamide | 1.83 | 509.03 |

TABLE 2-continued

| Compound Name | Time (mins) | MW (found) |
|---|---|---|
| 3-Bromo-N-{2-[5-(3,4-dichloro-benzyl)-hexahydro-pyrrolo[3,4-c]pyrrol-2-yl]-2-oxo-ethyl}-benzamide | 1.81 | 509.03 |
| 3-Bromo-N-{2-[5-(4-chloro-benzyl)-hexahydro-pyrrolo[3,4-c]pyrrol-2-yl]-2-oxo-ethyl}-benzamide | 1.65 | 475.07 |
| N-{2-[5-(3,4-Dichloro-benzyl)-hexahydro-pyrrolo[3,4-c]pyrrol-2-yl]-2-oxo-ethyl}-4-trifluoromethyl-benzamide | 1.89 | 499.1 |
| N-{2-[5-(4-Chloro-benzyl)-hexahydro-pyrrolo[3,4-c]pyrrol-2-yl]-2-oxo-ethyl}-4-trifluoromethyl-benzamide | 1.77 | 465.14 |
| 2-Chloro-N-{2-[5-(3,4-dichloro-benzyl)-hexahydro-pyrrolo[3,4-c]pyrrol-2-yl]-2-oxo-ethyl}-3-methyl-benzamide | 1.75 | 479.09 |
| 2-Chloro-N-{2-[5-(4-chloro-benzyl)-hexahydro-pyrrolo[3,4-c]pyrrol-2-yl]-2-oxo-ethyl}-3-methyl-benzamide | 1.57 | 445.13 |
| N-{2-[5-(3,4-Dichloro-benzyl)-hexahydro-pyrrolo-[3,4-c]pyrrol-2-yl]-2-oxo-ethyl}-2-fluoro-5-methyl-benzamide | 1.73 | 463.12 |
| N-{2-[5-(4-Chloro-benzyl)-hexahydro-pyrrolo[3,4-c]pyrrol-2-yl]-2-oxo-ethyl}-2-fluoro-5-methyl-benzamide | 1.58 | 429.16 |
| N-{2-[5-(3,4-Dichloro-benzyl)-hexahydro-pyrrolo[3,4-c]pyrrol-2-yl]-2-oxo-ethyl}-2-fluoro-benzamide | 1.6 | 449.11 |
| N-{2-[5-(4-Chloro-benzyl)-hexahydro-pyrrolo[3,4-c]pyrrol-2-yl]-2-oxo-ethyl}-2-fluoro-benzamide | 1.43 | 415.15 |
| N-{2-[5-(4-Chloro-benzyl)-hexahydro-pyrrolo[3,4-c]pyrrol-2-yl]-2-oxo-ethyl}-2,5-dimethyl-benzamide | 1.58 | 425.19 |
| N-{2-[5-(4-Chloro-benzyl)-hexahydro-pyrrolo[3,4-c]pyrrol-2-yl]-2-oxo-ethyl}-5-fluoro-2-methyl-benzamide | 1.51 | 429.16 |
| N-{2-[5-(4-Chloro-benzyl)-hexahydro-pyrrolo[3,4-c]pyrrol-2-yl]-2-oxo-ethyl}-2,4-dimethyl-benzamide | 1.6 | 425.19 |
| 2-Chloro-N-{2-[5-(3,4-dichloro-benzyl)-hexahydro-pyrrolo[3,4-c]pyrrol-2-yl]-2-oxo-ethyl}-benzamide | 1.63 | 465.08 |
| 2-Chloro-N-{2-[5-(4-chloro-benzyl)-hexahydro-pyrrolo[3,4-c]pyrrol-2-yl]-2-oxo-ethyl}-benzamide | 1.46 | 431.12 |
| N-{2-[5-(4-Chloro-benzyl)-hexahydro-pyrrolo[3,4-c]pyrrol-2-yl]-2-oxo-ethyl}-2,3-dimethyl-benzamide | 1.57 | 425.19 |
| N-{2-[5-(3,4-Dichloro-benzyl)-hexahydro-pyrrolo[3,4-c]pyrrol-2-yl]-2-oxo-ethyl}-3-fluoro-2-methyl-benzamide | 1.7 | 463.12 |
| N-{2-[5-(4-Chloro-benzyl)-hexahydro-pyrrolo[3,4-c]pyrrol-2-yl]-2-oxo-ethyl}-3-fluoro-2-methyl-benzamide | 1.53 | 429.16 |
| N-{2-[5-(4-Chloro-benzyl)-hexahydro-pyrrolo[3,4-c]pyrrol-2-yl]-2-oxo-ethyl}-2-methyl-benzamide | 1.46 | 411.17 |
| N-{2-[5-(2,4-Dimethyl-benzyl)-hexahydro-pyrrolo[3,4-b]pyrrol-1-yl]-2-oxo-ethyl}-3-trifluoromethyl-benzamide | 1.86 | 459.21 |
| N-{2-[5-(4-Chloro-benzyl)-hexahydro-pyrrolo[3,4-b]pyrrol-1-yl]-2-oxo-ethyl}-3-trifluoromethyl-benzamide | 1.82 | 465.14 |
| 4-Chloro-N-{2-[5-(4-chloro-benzyl)-hexahydro-pyrrolo[3,4-b]pyrrol-1-yl]-2-oxo-ethyl}-benzamide | 1.73 | 431.12 |
| N-{2-[5-(5-Bromo-2-methoxy-benzyl)-hexahydro-pyrrolo[3,4-b]pyrrol-1-yl]-2-oxo-ethyl}-3-trifluoromethyl-benzamide | 1.86 | 539.1 |
| N-{2-[5-(5-Bromo-2-methoxy-benzyl)-hexahydro-pyrrolo[3,4-b]pyrrol-1-yl]-2-oxo-ethyl}-4-chloro-benzamide | 1.76 | 505.08 |
| N-{2-[5-(3-Bromo-4-methoxy-benzyl)-hexahydro-pyrrolo[3,4-b]pyrrol-1-yl]-2-oxo-ethyl}-3-trifluoromethyl-benzamide | 1.85 | 539.1 |
| N-{2-[5-(3-Bromo-4-methoxy-benzyl)-hexahydro-pyrrolo[3,4-b]pyrrol-1-yl]-2-oxo-ethyl}-4-chloro-benzamide | 1.75 | 505.08 |
| N-{2-[5-(3-Chloro-benzyl)-hexahydro-pyrrolo[3,4-b]pyrrol-1-yl]-2-oxo-ethyl}-3-trifluoromethyl-benzamide | 1.81 | 465.14 |
| 4-Chloro-N-{2-[5-(3-chloro-benzyl)-hexahydro-pyrrolo[3,4-b]pyrrol-1-yl]-2-oxo-ethyl}-benzamide | 1.7 | 431.12 |
| N-{2-[5-(3,5-Dichloro-benzyl)-hexahydro-pyrrolo-[3,4-b]pyrrol-1-yl]-2-oxo-ethyl}-3-trifluoromethyl-benzamide | 1.97 | 499.1 |
| 4-Chloro-N-{2-[5-(3,5-dichloro-benzyl)-hexahydro-pyrrolo[3,4-b]pyrrol-1-yl]-2-oxo-ethyl}-benzamide | 1.86 | 465.08 |
| N-{2-[5-(3-Bromo-4-fluoro-benzyl)-hexahydro-pyrrolo[3,4-b]pyrrol-1-yl]-2-oxo-ethyl}-3-trifluoromethyl-benzamide | 1.89 | 527.08 |
| N-{2-[5-(3-Bromo-4-fluoro-benzyl)-hexahydro-pyrrolo[3,4-b]pyrrol-1-yl]-2-oxo-ethyl}-4-chloro-benzamide | 1.81 | 493.06 |
| N-{2-[5-(4-Bromo-benzyl)-hexahydro-pyrrolo[3,4-b]pyrrol-1-yl]-2-oxo-ethyl}-3-trifluoromethyl-benzamide | 1.89 | 509.09 |
| N-{2-[5-(4-Bromo-benzyl)-hexahydro-pyrrolo[3,4-b]pyrrol-1-yl]-2-oxo-ethyl}-4-chloro-benzamide | 1.79 | 475.07 |
| N-{2-[5-(3,4-Dibromo-benzyl)-hexahydro-pyrrolo[3,4-b]pyrrol-1-yl]-2-oxo-ethyl}-3-trifluoromethyl-benzamide | 2.05 | 587 |
| N-{2-[5-(3,4-Dichloro-benzyl)-hexahydro-pyrrolo[3,4-b]pyrrol-1-yl]-2-oxo-ethyl}-3-trifluoromethyl-benzamide | 2 | 499.1 |
| 4-Chloro-N-{2-[5-(3,4-dichloro-benzyl)-hexahydro-pyrrolo[3,4-b]pyrrol-1-yl]-2-oxo-ethyl}-benzamide | 1.91 | 465.08 |

TABLE 2-continued

| Compound Name | Time (mins) | MW (found) |
|---|---|---|
| N-{2-[5-(5-Methyl-thiophen-2-ylmethyl)-hexahydro-pyrrolo[3,4-b]pyrrol-1-yl]-2-oxo-ethyl}-3-trifluoromethyl-benzamide | 1.72 | 451.15 |
| 4-Chloro-N-{2-[5-(5-methyl-thiophen-2-ylmethyl)-hexahydro-pyrrolo[3,4-b]pyrrol-1-yl]-2-oxo-ethyl}-benzamide | 1.59 | 417.13 |
| N-{2-[5-(5-Bromo-thiophen-2-ylmethyl)-hexahydro-pyrrolo[3,4-b]pyrrol-1-yl]-2-oxo-ethyl}-3-trifluoromethyl-benzamide | 1.84 | 515.05 |
| N-{2-[5-(5-Bromo-thiophen-2-ylmethyl)-hexahydro-pyrrolo[3,4-b]pyrrol-1-yl]-2-oxo-ethyl}-4-chloro-benzamide | 1.74 | 481.02 |
| N-{2-[5-(5-Methyl-furan-2-ylmethyl)-hexahydro-pyrrolo[3,4-b]pyrrol-1-yl]-2-oxo-ethyl}-3-trifluoromethyl-benzamide | 1.63 | 435.18 |
| 4-Chloro-N-{2-[5-(5-methyl-furan-2-ylmethyl)-hexahydro-pyrrolo[3,4-b]pyrrol-1-yl]-2-oxo-ethyl}-benzamide | 1.49 | 401.15 |
| N-{2-[5-(3-Methyl-thiophen-2-ylmethyl)-hexahydro-pyrrolo[3,4-b]pyrrol-1-yl]-2-oxo-ethyl}-3-trifluoromethyl-benzamide | 1.67 | 451.15 |
| 4-Chloro-N-{2-[5-(3-methyl-thiophen-2-ylmethyl)-hexahydro-pyrrolo[3,4-b]pyrrol-1-yl]-2-oxo-ethyl}-benzamide | 1.61 | 417.13 |
| N-{2-[5-(4-Bromo-thiophen-2-ylmethyl)-hexahydro-pyrrolo[3,4-b]pyrrol-1-yl]-2-oxo-ethyl}-3-trifluoromethyl-benzamide | 1.81 | 515.05 |
| N-{2-[5-(4-Bromo-thiophen-2-ylmethyl)-hexahydro-pyrrolo[3,4-b]pyrrol-1-yl]-2-oxo-ethyl}-4-chloro-benzamide | 1.72 | 481.02 |
| N-[2-Oxo-2-(5-thiazol-2-ylmethyl-hexahydro-pyrrolo[3,4-b]pyrrol-1-yl)-ethyl]-3-trifluoromethyl-benzamide | 1.45 | 438.13 |
| 4-Chloro-N-[2-oxo-2-(5-thiazol-2-ylmethyl-hexahydro-pyrrolo[3,4-b]pyrrol-1-yl)-ethyl]-benzamide | 1.32 | 404.11 |
| N-[2-(5-Benzofuran-2-ylmethyl-hexahydro-pyrrolo[3,4-b]pyrrol-1-yl)-2-oxo-ethyl]-3-trifluoromethyl-benzamide | 1.82 | 471.18 |
| N-[2-(5-Benzofuran-2-ylmethyl-hexahydro-pyrrolo[3,4-b]pyrrol-1-yl)-2-oxo-ethyl]-4-chloro-benzamide | 1.72 | 437.15 |
| N-{2-[5-(4-Bromo-furan-2-ylmethyl)-hexahydro-pyrrolo[3,4-b]pyrrol-1yl]-2-oxo-ethyl}-3-trifluoromethyl-benzamide | 1.72 | 499.07 |
| N-{2-[5-(4-Bromo-furan-2-ylmethyl)-hexahydro-pyrrolo[3,4-b]pyrrol-1-yl]-2-oxo-ethyl}-4-chloro-benzamide | 1.61 | 465.05 |
| N-{2-[5-(5-Methylsulfanyl-thiophen-2-ylmethyl)-hexahydro-pyrrolo[3,4-b]pyrrol-1-yl]-2-oxo-ethyl}-3-trifluoromethyl-benzamide | 1.84 | 483.13 |
| 4-Chloro-N-{2-[5-(5-methylsulfanyl-thiophen-2-ylmethyl)-hexahydro-pyrrolo[3,4-b]pyrrol-1-yl]-2-oxo-ethyl}-benzamide | 1.74 | 449.1 |
| N-{2-[5-(3-Methyl-benzyl)-hexahydro-pyrrolo[3,4-b]pyrrol-1-yl]-2-oxo-ethyl}-3-trifluoromethyl-benzamide | 1.77 | 445.2 |
| 4-Chloro-N-{2-[5-(3-methyl-benzyl)-hexahydro-pyrrolo[3,4-b]pyrrol-1-yl]-2-oxo-ethyl}-benzamide | 1.66 | 411.17 |
| N-{2-[5-(3-Bromo-benzyl)-hexahydro-pyrrolo[3,4-b]pyrrol-1-yl]-2-oxo-ethyl}-3-trifluoromethyl-benzamide | 1.85 | 509.09 |
| N-{2-[5-(3-Bromo-benzyl)-hexahydro-pyrrolo[3,4-b]pyrrol-1-yl]-2-oxo-ethyl}-4-chloro-benzamide | 1.76 | 475.07 |
| N-{2-[5-(4-Methyl-benzyl)-hexahydro-pyrrolo[3,4-b]pyrrol-1-yl]-2-oxo-ethyl}-3-trifluoromethyl-benzamide | 1.77 | 445.2 |
| 4-Chloro-N-{2-[5-(4-methyl-benzyl)-hexahydro-pyrrolo[3,4-b]pyrrol-1-yl]-2-oxo-ethyl}-benzamide | 1.67 | 411.17 |
| N-{2-[5-(4-Isopropyl-benzyl)-hexahydro-pyrrolo[3,4-b]pyrrol-1-yl]-2-oxo-ethyl}-3-trifluoromethyl-benzamide | 2 | 473.23 |
| 4-Chloro-N-{2-[5-(4-isopropyl-benzyl)-hexahydro-pyrrolo[3,4-b]pyrrol-1-yl]-2-oxo-ethyl}-benzamide | 1.89 | 439.2 |
| N-{2-[5-(4-tert-Butyl-benzyl)-hexahydro-pyrrolo[3,4-b]pyrrol-1-yl]-2-oxo-ethyl}-3-trifluoromethyl-benzamide | 2.07 | 487.24 |
| N-{2-[5-(4-tert-Butyl-benzyl)-hexahydro-pyrrolo[3,4-b]pyrrol-1-yl]-2-oxo-ethyl}-4-chloro-benzamide | 1.99 | 453.22 |
| N-{2-[5-(4-Ethyl-benzyl)-hexahydro-pyrrolo[3,4-b]pyrrol-1-yl]-2-oxo-ethyl}-3-trifluoromethyl-benzamide | 1.9 | 459.21 |
| 4-Chloro-N-{2-[5-(4-ethyl-benzyl)-hexahydro-pyrrolo[3,4-b]pyrrol-1-yl]-2-oxo-ethyl}-benzamide | 1.79 | 425.19 |
| N-{2-[5-(3,5-Dimethyl-benzyl)-hexahydro-pyrrolo[3,4-b]pyrrol-1-yl]-2-oxo-ethyl}-3-trifluoromethyl-benzamide | 1.88 | 459.21 |
| 4-Chloro-N-{2-[5-(3,5-dimethyl-benzyl)-hexahydro-pyrrolo[3,4-b]pyrrol-1-yl]-2-oxo-ethyl}-benzamide | 1.79 | 425.19 |
| N-[2-(5-Benzyl-hexahydro-pyrrolo[3,4-b]pyrrol-1-yl)-2-oxo-ethyl]-3-trifluoromethyl-benzamide | 1.65 | 431.18 |
| N-[2-(5-Benzyl-hexahydro-pyrrolo-[3,4-b]pyrrol-1-yl)-2-oxo-ethyl]-4-chloro-benzamide | 1.53 | 397.16 |
| N-{2-[5-(4-Butyl-benzyl)-hexahydro-pyrrolo[3,4-b]pyrrol-1-yl]-2-oxo-ethyl}-3-trifluoromethyl-benzamide | 2.15 | 487.24 |
| N-{2-[5-(4-Butyl-benzyl)-hexahydro-pyrrolo[3,4-b]pyrrol-1-yl]-2-oxo-ethyl}-4-chloro-benzamide | 2.06 | 453.22 |
| N-{2-[5-(2,4-Dimethoxy-benzyl)-hexahydro-pyrrolo-[3,4-b]pyrrol-1-yl]-2-oxo-ethyl}-3-trifluoromethyl-benzamide | 1.75 | 491.2 |
| 4-Chloro-N-{2-[5-(2,4-dimethoxy-benzyl)-hexahydro-pyrrolo[3,4-b]pyrrol-1-yl]-2-oxo-ethyl}-benzamide | 1.74 | 457.18 |

TABLE 2-continued

| Compound Name | Time (mins) | MW (found) |
|---|---|---|
| N-{2-[5-(2-Methyl-benzyl)-hexahydro-pyrrolo[3,4-b]pyrrol-1-yl]-2-oxo-ethyl}-3-trifluoromethyl-benzamide | 1.74 | 445.2 |
| 4-Chloro-N-{2-[5-(2-methyl-benzyl)-hexahydro-pyrrolo[3,4-b]pyrrol-1-yl]-2-oxo-ethyl}-benzamide | 1.74 | 411.17 |
| N-{2-[5-(2-Ethoxy-benzyl)-hexahydro-pyrrolo[3,4-b]pyrrol-1-yl]-2-oxo-ethyl}-3-trifluoromethyl-benzamide | 1.8 | 475.21 |
| 4-Chloro-N-{2-[5-(2-ethoxy-benzyl)-hexahydro-pyrrolo[3,4-b]pyrrol-1-yl]-2-oxo-ethyl}-benzamide | 1.7 | 441.18 |
| N-{2-[5-(2-Methoxy-benzyl)-hexahydro-pyrrolo[3,4-b]pyrrol-1-yl]-2-oxo-ethyl}-3-trifluoromethyl-benzamide | 1.71 | 461.19 |
| 4-Chloro-N-{2-[5-(2-methoxy-benzyl)-hexahydro-pyrrolo[3,4-b]pyrrol-1-yl]-2-oxo-ethyl}-benzamide | 1.59 | 427.17 |
| N-{2-[5-(2,5-Dimethoxy-benzyl)-hexahydro-pyrrolo-[3,4-b]pyrrol-1-yl]-2-oxo-ethyl}-3-trifluoromethyl-benzamide | 1.74 | 491.2 |
| 4-Chloro-N-{2-[5-(2,5-dimethoxy-benzyl)-hexahydro-pyrrolo[3,4b]pyrrol-1-yl]-2-oxo-ethyl}-benzamide | 1.62 | 457.18 |
| N-{2-[5-(2,5-Dimethyl-benzyl)-hexahydro-pyrrolo[3,4-b]pyrrol-1-yl]-2-oxo-ethyl}-3-trifluoromethyl-benzamide | 1.85 | 459.21 |
| 4-Chloro-N-{2-[5-(2,5-dimethyl-benzyl)-hexahydro-pyrrolo[3,4-b]pyrrol-1-yl]-2-oxo-ethyl}-benzamide | 1.74 | 425.19 |
| N-{2-[5-(4-Methoxy-2,5-dimethyl-benzyl)-hexahydro-pyrrolo[3,4-b]pyrrol-1-yl]-2-oxo-ethyl}-3-trifluoromethyl-benzamide | 1.89 | 489.22 |
| 4-Chloro-N-{2-[5-(4-methoxy-2,5-dimethyl-benzyl)-hexahydro-pyrrolo[3,4-b]pyrrol-1-yl]-2-oxo-ethyl}-benzamide | 1.8 | 455.2 |
| N-{2-[5-(4-Methoxy-2,3-dimethyl-benzyl)-hexahydro-pyrrolo[3,4-b]pyrrol-1-yl]-2-oxo-ethyl}-3-trifluoromethyl-benzami | 1.9 | 489.22 |
| 4-Chloro-N-{2-[5-(4-methoxy-2,3-dimethyl-benzyl)-hexahydro-pyrrolo[3,4-b]pyrrol-1-yl]-2-oxo-ethyl}-benzamide | 1.8 | 455.2 |
| 4-Chloro-N-{2-[5-(2,4-dimethyl-benzyl)-hexahydro-pyrrolo[3,4-b]pyrrol-1-yl]-2-oxo-ethyl}-benzamide | 1.75 | 425.19 |
| N-{2-[5-(2-Benzyloxy-benzyl)-hexahydro-pyrrolo[3,4-b]pyrrol-1-yl]-2-oxo-ethyl}-3-trifluoromethyl-benzamide | 2.05 | 537.22 |
| N-{2-[5-(2-Benzyloxy-benzyl)-hexahydro-pyrrolo[3,4-b]pyrrol-1-yl]-2-oxo-ethyl}-4-chloro-benzamide | 1.96 | 503.2 |
| N-{2-[5-(3-Cyclopentyloxy-4-methoxy-benzyl)-hexahydro-pyrrolo-[3,4-b]pyrrol-1-yl]-2-oxo-ethyl}-3-trifluoromethyl-benzamide | 1.98 | 545.25 |
| 4-Chloro-N-{2-[5-(3-cyclopentyloxy-4-methoxy-benzyl)-hexahydro-pyrrolo-[3,4-b]pyrrol-1-yl]-2-oxo-ethyl}-benzamide | 1.9 | 511.22 |
| N-{2-[5-(2,4-Dimethyl-benzyl)-hexahydro-pyrrolo[3,4-c]-pyrrol-2-yl]-2-oxo-ethyl}-3-triflouromethyl-benzamide | 1.67 | 459.21 |
| N-{1-[5-(2,4-Difluoro-benzyl)-hexahydro-pyrrolo[3,4-c]-pyrrol-2-yl]-2-oxo-ethylcarbamoyl}-3-methylbutyl)-benzamide | 1.66 | 512.26 |
| N-{1-[5-(2,3-Difluoro-benzyl)-hexahydro-pyrrolo[3,4-c]-pyrrol-2-yl]-2-oxo-ethylcarbamoyl}-3-methylbutyl)-benzamide | 1.69 | 512.26 |
| N-{1-[5-(2,5-Difluoro-benzyl)-hexahydro-pyrrolo[3,4-c]-pyrrol-2-yl]-2-oxo-ethylcarbamoyl}-3-methylbutyl)-benzamide | 1.67 | 512.26 |
| N-{1-[5-(3,5-Difluoro-benzyl)-hexahydro-pyrrolo[3,4-c]-pyrrol-2-yl]-2-oxo-ethylcarbamoyl}-3-methylbutyl)-benzamide | 1.75 | 512.26 |
| N-{2-[5-(2,4-Difluoro-benzyl)-hexahydro-pyrrolo[3,4-c]-pyrrol-2-yl]-2-oxo-ethyl}-3-phenylacetyl amino-propioamide | 1.8 | 560.26 |
| N-{2-[5-(2,4-Difluoro-benzyl)-hexahydro-pyrrolo[3,4-c]-pyrrol-2-yl]-2-oxo-ethyl}-3-phenyl-2-phenylacetylamino-propioamide | 1.8 | 560.26 |
| N-{2-[5-(2,5-Difluoro-benzyl)-hexahydro-pyrrolo[3,4-c]pyrrol-2-yl]-2-oxo-ethyl}-3-phenyl-2-phenylacetylamino-propionamide | 1.78 | 560.26 |
| N-{2-[5-(3,5-Difluoro-benzyl)-hexahydro-pyrrolo[3,4-c]pyrrol-2-yl]-2-oxo-ethyl}-3-phenyl-2-phenylacetylamino-propionamide | 1.84 | 560.26 |
| N-(1-{2-[5-(2,4-Difluoro-benzyl)-hexahydro-pyrrolo[3,4-c]pyrrol-2-yl]-2-oxo-ethylcarbamoyl}-ethyl)-benzamide | 1.34 | 470.21 |
| N-(1-{2-[5-(2,3-Difluoro-benzyl)-hexahydro-pyrrolo[3,4-c]pyrrol-2-yl]-2-oxo-ethylcarbamoyl}-ethyl)-benzamide | 1.35 | 470.21 |
| N-(1-{2-[5-(2,5-Difluoro-benzyl)-hexahydro-pyrrolo[3,4-c]pyrrol-2-yl]-2-oxo-ethylcarbamoyl}-ethyl)-benzamide | 1.32 | 470.21 |
| N-(1-{2-[5-(3,5-Difluoro-benzyl)-hexahydro-pyrrolo[3,4-c]pyrrol-2-yl]-2-oxo-ethylcarbamoyl}-ehtyl)-benzamide | 1.41 | 470.21 |
| N-(1-{2-[5-(2,4-Difluoro-benzyl)-hexahydro-pyrrolo[3,4-c]pyrrol-2-yl]-2-oxo-ethylcarbamoyl}-2-phenyl-ethyl)-benzamide | 1.75 | 546.24 |
| N-(1-{2-[5-(2,3-Difluoro-benzyl)-hexahydro-pyrrolo[3,4-c]pyrrol-2-yl]-2-oxo-ethylcarbamoyl}-2-phenyl-ethyl)-benzamide | 1.75 | 546.24 |
| N-(1-{2-[5-(2,5-Difluoro-benzyl)-hexahydro-pyrrolo[3,4-c]pyrrol-2-yl]-2-oxo-ethylcarbamoyl}-2-phenyl-ethyl)-benzamide | 1.72 | 546.24 |
| N-(1-{2-[5-(3,5-Difluoro-benzyl)-hexahydro-pyrrolo[3,4-c]pyrrol-2-yl]-2-oxo-ethylcarbamoyl}-2-phenyl-ethyl)-benzamide | 1.79 | 546.24 |
| N-(1-{2-[5-(2,4-Difluoro-benzyl)-hexahydro-pyrrolo[3,4-c]pyrrol-2-yl]-2-oxo-ethylcarbamoyl}-2-methyl-propyl)-benzamide | 1.53 | 498.24 |

TABLE 2-continued

| Compound Name | Time (mins) | MW (found) |
|---|---|---|
| N-(1-{2-[5-(2,3-Difluoro-benzyl)-hexahydro-pyrrolo[3,4-c]pyrrol-2-yl]-2-oxo-ethylcarbamoyl}-2-methyl-propyl)-benzamide | 1.54 | 498.24 |
| N-(1-{2-[5-(2,5-Difluoro-benzyl)-hexahydro-pyrrolo[3,4-c]pyrrol-2-yl]-2-oxo-ethylcarbamoyl}-2-methyl-propyl)-benzamide | 1.52 | 498.24 |
| N-(1-{2-[5-(3,5-Difluoro-benzyl)-hexahydro-pyrrolo[3,4-c]pyrrol-2-yl]-2-oxo-ethylcarbamoyl}-2-methyl-propyl)-benzamide | 1.59 | 498.24 |
| 5-Oxo-pyrrolidine-2-carboxylic acid {2-[5-(3,5-difluoro-benzyl)-hexahydro-pyrrolo[3,4-c]pyrrol-2-yl]-2-oxo-ethyl}-amide | 1.05 | 406.18 |
| 2-Acetylamino-N-{2-[5-(3,5-difluoro-benzyl)-hexahydro-pyrrolo[3,4-c]pyrrol-2-yl]-2-oxo-ethyl}-propionamide | 1.07 | 408.2 |
| N-(2-{2-[5-(2,4-Difluoro-benzyl)-hexahydro-pyrrolo[3,4-c]pyrrol-2-yl]-2-oxo-ethylcarbamoyl}-cyclohexyl)-benzamide | 1.6 | 524.26 |
| N-(2-{2-[5-(2,3-Difluoro-benzyl)-hexahydro-pyrrolo[3,4-c]pyrrol-2-yl]-2-oxo-ethylcarbamoyl}-cyclohexyl)-benzamide | 1.59 | 524.26 |
| N-(2-{2-[5-(2,5-Difluoro-benzyl)-hexahydro-pyrrolo[3,4-c]pyrrol-2-yl]-2-oxo-ethylcarbamoyl}-cyclohexyl)-benzamide | 1.57 | 524.26 |
| N-(2-{2-[5-(3,5-Difluoro-benzyl)-hexahydro-pyrrolo[3,4-c]pyrrol-2-yl]-2-oxo-ethylcarbamoyl}-cyclohexyl)-benzamide | 1.65 | 524.26 |
| 3-Cyclohexyl-N-{2-[5-(2,4-difluoro-benzyl)-hexahydro-pyrrolo[3,4-c]pyrrol-2-yl]-2-oxo-ethyl}-propionamide | 1.78 | 433.25 |
| 3-Cyclohexyl-N-{2-[5-(2,3-difluoro-benzyl)-hexahydro-pyrrolo[3,4-c]pyrrol-2-yl]-2-oxo-ethyl}-propionamide | 1.79 | 433.25 |
| 3-Cyclohexyl-N-{2-[5-(2,5-difluoro-benzyl)-hexahydro-pyrrolo[3,4-c]pyrrol-2-yl]-2-oxo-ethyl}-propionamide | 1.77 | 433.25 |
| 3-Cyclohexyl-N-{2-[5-(3,5-difluoro-benzyl)-hexahydro-pyrrolo[3,4-c]pyrrol-2-yl]-2-oxo-ethyl}-propionamide | 1.85 | 433.25 |
| N-{2-[5-(2,4-Difluoro-benzyl)-hexahydro-pyrrolo[3,4-c]-pyrrol-2-yl]-2-oxo-ethyl}-2-(9H-fluoren-9-yl)-acetamide | 1.9 | 501.22 |
| N-{2-[5-(2,3-Difluoro-benzyl)-hexahydro-pyrrolo[3,4-c]-pyrrol-2-yl]-2-oxo-ethyl}-2-(9H-fluoren-9-yl)-acetamide | 1.9 | 501.22 |
| N-{2-[5-(2,5-Difluoro-benzyl)-hexahydro-pyrrolo[3,4-c]-pyrrol-2-yl]-2-oxo-ethyl}-2-(9H-fluoren-9-yl)-acetamide | 1.88 | 501.22 |
| N-{2-[5-(3,5-Difluoro-benzyl)-hexahydro-pyrrolo[3,4-c]-pyrrol-2-yl]-2-oxo-ethyl}-2-(9H-fluoren-9-yl)-acetamide | 1.95 | 501.22 |
| N-{2-[5-(2,4-Difluoro-benzyl)-hexahydro-pyrrolo[3,4-c]pyrrol-2-yl]-2-oxo-ethyl}-2-(2-isopropyl-5-methyl-cyclohexyloxy)-acetamide | 2.11 | 491.3 |
| N-{2-[5-(2,3-Difluoro-benzyl)-hexahydro-pyrrolo[3,4-c]pyrrol-2-yl]-2-oxo-ethyl}-2-(2-isopropyl-5-methyl-cyclohexyloxy)-acetamide | 2.11 | 491.3 |
| N-{2-[5-(2,5-Difluoro-benzyl)-hexahydro-pyrrolo[3,4-c]pyrrol-2-yl]-2-oxo-ethyl}-2-(2-isopropyl-5-methyl-cyclohexyloxy)-acetamide | 2.1 | 491.3 |
| N-{2-[5-(3,5-Difluoro-benzyl)-hexahydro-pyrrolo[3,4-c]pyrrol-2-yl]-2-oxo-ethyl}-2-(2-isopropyl-5-methyl-cyclohexyloxy)-acetamide | 2.17 | 491.3 |
| 5-Oxo-5-phenyl-pentanoic acid {2-[5-(2,4-difluoro-benzyl)-hexahydro-pyrrolo[3,4-c]-pyrrol-2-yl]-2-oxo-ethyl}-amide | 1.53 | 469.22 |
| 5-Oxo-5-phenyl-pentanoic acid {2-[5-(2,3-difluoro-benzyl)-hexahydro-pyrrolo[3,4-c]-pyrrol-2-yl]-2-oxo-ethyl}-amide | 1.53 | 469.22 |
| 5-Oxo-5-phenyl-pentanoic acid {2-[5-(2,5-difluoro-benzyl)-hexahydro-pyrrolo[3,4-c]-pyrrol-2-yl]-2-oxo-ethyl}-amide | 1.51 | 469.22 |
| 5-Oxo-5-phenyl-pentanoic acid {2-[5-(3,5-difluoro-benzyl)-hexahydro-pyrrolo[3,4-c]-pyrrol-2-yl]-2-oxo-ethyl}-amide | 1.59 | 469.22 |
| 3-Cyclopentyl-N-{2-[5-(2,4-difluoro-benzyl)-hexahydro-pyrrolo[3,4-c]pyrrol-2-yl]-2-oxo-ethyl}-propionamide | 1.65 | 419.24 |
| 3-Cyclopentyl-N-{2-[5-(2,3-difluoro-benzyl)-hexahydro-pyrrolo[3,4-c]pyrrol-2-yl]-2-oxo-ethyl}-propionamide | 1.66 | 419.24 |
| 3-Cyclopentyl-N-{2-[5-(2,5-difluoro-benzyl)-hexahydro-pyrrolo[3,4-c]pyrrol-2-yl]-2-oxo-ethyl}-propionamide | 1.64 | 419.24 |
| 3-Cyclopentyl-N-{2-[5-(3,5-difluoro-benzyl)-hexahydro-pyrrolo[3,4-c]pyrrol-2-yl]-2-oxo-ethyl}-propionamide | 1.72 | 419.24 |
| N-{2-[5-(2,4-Difluoro-benzyl)-hexahydro-pyrrolo[3,4-c]-pyrrol-2-yl]-2-oxo-ethyl}-4-phenyl-butyramide | 1.65 | 441.22 |
| N-{2-[5-(2,3-Difluoro-benzyl)-hexahydro-pyrrolo[3,4-c]-pyrrol-2-yl]-2-oxo-ethyl}-4-phenyl-butyramide | 1.64 | 441.22 |
| N-{2-[5-(2,5-Difluoro-benzyl)-hexahydro-pyrrolo[3,4-c]-pyrrol-2-yl]-2-oxo-ethyl}-4-phenyl-butyramide | 1.63 | 441.22 |
| N-{2-[5-(3,5-Difluoro-benzyl)-hexahydro-pyrrolo[3,4-c]-pyrrol-2-yl]-oxo-ethyl}-4-phenyl-butyramide | 1.7 | 441.22 |
| N-{2-[5-(2,4-Difluoro-benzyl)-hexahydro-pyrrolo[3,4-c]-pyrrol-2-yl]-2-oxo-ethyl}-3-o-tolyl-propionamide | 1.63 | 441.22 |
| N-{2-[5-(2,3-Difluoro-benzyl)-hexahydro-pyrrolo[3,4-c]-pyrrol-2-yl]-2-oxo-ethyl}-3-o-tolyl-propionamide | 1.64 | 441.22 |
| N-{2-[5-(2,5-Difluoro-benzyl)-hexahydro-pyrrolo[3,4-c]-pyrrol-2-yl]-2-oxo-ethyl}-3-o-tolyl-propionamide | 1.62 | 441.22 |

TABLE 2-continued

| Compound Name | Time (mins) | MW (found) |
|---|---|---|
| N-{2-[5-(3,5-Difluoro-benzyl)-hexahydro-pyrrolo[3,4-c]pyrrol-2-yl]-2-oxo-ethyl}-3-o-tolyl-propionamide | 1.69 | 441.22 |
| 3-(3,5-Bis-trifluoromethyl-phenyl)-N-{2-[5-(2,4-difluoro-benzyl)-hexahydro-pyrrolo[3,4-c]pyrrol-2-yl]-2-oxo-ethyl}-propionamide | 2.06 | 563.18 |
| 3-(3,5-Bis-trifluoromethyl-phenyl)-N-{2-[5-(2,3-difluoro-benzyl)-hexahydro-pyrrolo[3,4-c]pyrrol-2-yl]-2-oxo-ethyl}-propionamide | 2.07 | 563.18 |
| 3-(3,5-Bis-trifluoromethyl-phenyl)-N-{2-[5-(2,5-difluoro-benzyl)-hexahydro-pyrrolo[3,4-c]pyrrol-2-yl]-2-oxo-ethyl}-propionamide | 2.06 | 563.18 |
| 3-(3,5-Bis-trifluoromethyl-phenyl)-N-{2-[5-(3,5-difluoro-benzyl)-hexahydro-pyrrolo[3,4-c]pyrrol-2-yl]-2-oxo-ethyl}-propionamide | 2.12 | 563.18 |
| N-{2-[5-(2,4-Difluoro-benzyl)-hexahydro-pyrrolo[3,4-c]pyrrol-2-yl]-2-oxo-ethyl}-3-phenyl-butyramide | 1.61 | 441.22 |
| N-{2-[5-(2,3-Difluoro-benzyl)-hexahydro-pyrrolo[3,4-c]pyrrol-2-yl]-2-oxo-ethyl}-3-phenyl-butyramide | 1.61 | 441.22 |
| N-{2-[5-(2,5-Difluoro-benzyl)-hexahydro-pyrrolo[3,4-c]pyrrol-2-yl]-2-oxo-ethyl}-3-phenyl-butyramide | 1.58 | 441.22 |
| N-{2-[5-(3,5-Difluoro-benzyl)-hexahydro-pyrrolo[3,4-c]pyrrol-2-yl]-2-oxo-ethyl}-3-phenyl-butyramide | 1.67 | 441.22 |
| 4-Bromo-phenyl)-N-{2-[5-(2,4-difluoro-benzyl)-hexahydro-pyrrolo[3,4-c]pyrrol-2-yl]-2-oxo-ethyl}-4-oxo-butyramide | 1.73 | 533.11 |
| 4-(4-Bromo-phenyl)-N-{2-[5-(2,3-difluoro-benzyl)-hexahydro-pyrrolo[3,4-c]pyrrol-2-yl]-2-oxo-ethyl}-4-oxo-butyramide | 1.75 | 533.11 |
| 4-(4-Bromo-phenyl)-N-{2-[5-(2,5-difluoro-benzyl)-hexahydro-pyrrolo[3,4-c]pyrrol-2-yl]-2-oxo-ethyl}-4-oxo-butyramide | 1.72 | 533.11 |
| 4-(4-Bromo-phenyl)-N-{2-[5-(3,5-difluoro-benzyl)-hexahydro-pyrrolo[3,4-c]pyrrol-2-yl]-2-oxo-ethyl}-4-oxo-butyramide | 1.79 | 533.11 |
| 3-(2-Chloro-phenyl)-N-{2-[5-(2,4-difluoro-benzyl)-hexahydro-pyrrolo[3,4-c]pyrrol-2-yl]-2-oxo-ethyl}-propionamide | 1.68 | 461.17 |
| 3-(2-Chloro-phenyl)-N-{2-[5-(2,3-difluoro-benzyl)-hexahydro-pyrrolo[3,4-c]pyrrol-2-yl]-2-oxo-ethyl}-propionamide | 1.68 | 461.17 |
| 3-(2-Chloro-phenyl)-N-{2-[5-(2,5-difluoro-benzyl)-hexahydro-pyrrolo[3,4-c]pyrrol-2-yl]-2-oxo-ethyl}-propionamide | 1.65 | 461.17 |
| 3-(2-Chloro-phenyl)-N-{2-[5-(3,5-difluoro-benzyl)-hexahydro-pyrrolo[3,4-c]pyrrol-2-yl]-2-oxo-ethyl}-propionamide | 1.74 | 461.17 |
| 2,4-Dichloro-N-{2-[5-(2,4-difluoro-benzyl)-hexahydro-pyrrolo[3,4-c]pyrrol-2-yl]-2-oxo-ethyl}-benzamide | 1.65 | 467.1 |
| 2,4-Dichloro-N-{2-[5-(2,3-difluoro-benzyl)-hexahydro-pyrrolo[3,4-c]pyrrol-2-yl]-2-oxo-ethyl}-benzamide | 1.64 | 467.1 |
| 2,4-Dichloro-N-{2-[5-(2,5-difluoro-benzyl)-hexahydro-pyrrolo[3,4-c]pyrrol-2-yl]-2-oxo-ethyl}-benzamide | 1.6 | 467.1 |
| 2,4-Dichloro-N-{2-[5-(3,5-difluoro-benzyl)-hexahydro-pyrrolo[3,4-c]pyrrol-2-yl]-2-oxo-ethyl}-benzamide | 1.69 | 467.1 |
| 2,5-Dichloro-N-{2-[5-(2,4-difluoro-benzyl)-hexahydro-pyrrolo[3,4-c]pyrrol-2-yl]-2-oxo-ethyl}-benzamide | 1.58 | 467.1 |
| 2,5-Dichloro-N-{2-[5-(2,3-difluoro-benzyl)-hexahydro-pyrrolo[3,4-c]pyrrol-2-yl]-2-oxo-ethyl}-benzamide | 1.58 | 467.1 |
| 2,5-Dichloro-N-{2-[5-(2,5-difluoro-benzyl)-hexahydro-pyrrolo[3,4-c]pyrrol-2-yl]-2-oxo-ethyl}-benzamide | 1.56 | 467.1 |
| 2,5-Dichloro-N-{2-[5-(3,5-difluoro-benzyl)-hexahydro-pyrrolo[3,4-c]pyrrol-2-yl]-2-oxo-ethyl}-benzamide | 1.65 | 467.1 |
| 2,3-Dichloro-N-{2-[5-(2,4-difluoro-benzyl)-hexahydro-pyrrolo[3,4-c]pyrrol-2-yl]-2-oxo-ethyl}-benzamide | 1.61 | 467.1 |
| 2,3-Dichloro-N-{2-[5-(2,3-difluoro-benzyl)-hexahydro-pyrrolo[3,4,c]pyrrol-2-yl]-2-oxo-ethyl}-benzamide | 1.62 | 467.1 |
| 2,3-Dichloro-N-{2-[5-(2,5-difluoro-benzyl)-hexahydro-pyrrolo[3,4-c]pyrrol-2-yl]-2-oxo-ethyl}-benzamide | 1.59 | 467.1 |
| 2,3-Dichloro-N-{2-[5-(3,5-difluoro-benzyl)-hexahydro-pyrrolo[3,4-c]pyrrol-2-yl]-2-oxo-ethyl}-benzamide | 1.67 | 467.1 |
| N-{2-[5-(2,4-Difluoro-benzyl)-hexahydro-pyrrolo[3,4-c]pyrrol-2-yl]-2-oxo-ethyl}-2,5-difluoro-benzamide | 1.44 | 435.16 |
| N-{2-[5-(2,3-Difluoro-benzyl)-hexahydro-pyrrolo[3,4-c]pyrrol-2-yl]-2-oxo-ethyl}-2,5-difluoro-benzamide | 1.46 | 435.16 |
| N-{2-[5-(2,5-Difluoro-benzyl)-hexahydro-pyrrolo[3,4-c]pyrrol-2-yl]-2-oxo-ethyl}-2,5-difluoro-benzamide | 1.42 | 435.16 |
| N-{2-[5-(3,5-Difluoro-benzyl)-hexahydro-pyrrolo[3,4-c]pyrrol-2-yl]-2-oxo-ethyl}-2,5-difluoro-benzamide | 1.52 | 435.16 |

TABLE 2-continued

| Compound Name | Time (mins) | MW (found) |
|---|---|---|
| N-{2-[5-(2,4-Difluoro-benzyl)-hexahydro-pyrrolo[3,4-c]pyrrol-2-yl]-2-oxo-ethyl}-2,3-difluoro-benzamide | 1.46 | 435.16 |
| N-{2-[5-(2,3-Difluoro-benzyl)-hexahydro-pyrrolo[3,4-c]pyrrol-2-yl]-2-oxo-ethyl}-2,3-difluoro-benzamide | 1.46 | 435.16 |
| N-{2-[5-(2,5-Difluoro-benzyl)-hexahydro-pyrrolo[3,4-c]pyrrol-2-yl]-2-oxo-ethyl}-2,3-difluoro-benzamide | 1.42 | 435.16 |
| N-{2-[5-(3,5-Difluoro-benzyl)-hexahydro-pyrrolo[3,4-c]pyrrol-2-yl]-2-oxo-ethyl}-2,3-difluoro-benzamide | 1.52 | 435.16 |
| N-{2-[5-(2,4-Difluoro-benzyl)-hexahydro-pyrrolo[3,4-c]pyrrol-2-yl]-2-oxo-ethyl}-2,4-difluoro-benzamide | 1.46 | 435.16 |
| N-{2-[5-(2,3-Difluoro-benzyl)-hexahydro-pyrrolo[3,4-c]pyrrol-2-yl]-2-oxo-ethyl}-2,4-difluoro-benzamide | 1.45 | 435.16 |
| N-{2-[5-(2,5-Difluoro-benzyl)-hexahydro-pyrrolo[3,4-c]pyrrol-2-yl]-2-oxo-ethyl}-2,4-difluoro-benzamide | 1.44 | 435.16 |
| N-{2-[5-(3,5-Difluoro-benzyl)-hexahydro-pyrrolo[3,4-c]pyrrol-2-yl]-2-oxo-ethyl}-2,4-difluoro-benzamide | 1.52 | 435.16 |
| 2-Chloro-N-{2-[5-(2,4-difluoro-benzyl)-hexahydro-pyrrolo[3,4-c]pyrrol-2-yl]-2-oxo-ethyl}-4-fluoro-benzamide | 1.48 | 451.13 |
| 2-Chloro-N-{2-[5-(2,3-difluoro-benzyl)-hexahydro-pyrrolo[3,4-c]pyrrol-2-yl]-2-oxo-ethyl}-4-fluoro-benzamide | 1.49 | 451.13 |
| 2-Chloro-N-{2-[5-(2,5-difluoro-benzyl)-hexahydro-pyrrolo[3,4-c]pyrrol-2-yl]-2-oxo-ethyl}-4-fluoro-benzamide | 1.47 | 451.13 |
| 2-Chloro-N-{2-[5-(3,5-difluoro-benzyl)-hexahydro-pyrrolo[3,4,c]pyrrol-2-yl]-2-oxo-ethyl}-4-fluoro-benzamide | 1.54 | 451.13 |
| N-{2-[5-(2,4-Difluoro-benzyl)-hexahydro-pyrrolo[3,4-c]pyrrol-2-yl]-2-oxo-ethyl}-2,4,5-trifluoro-benzamide | 1.54 | 453.15 |
| N-{2-[5-(2,3-Difluoro-benzyl)-hexahydro-pyrrolo[3,4-c]pyrrol-2-yl]-2-oxo-ethyl}-2,4,5-trifluoro-benzamide | 1.55 | 453.15 |
| N-{2-[5-(2,5-Difluoro-benzyl)-hexahydro-pyrrolo[3,4-c]pyrrol-2-yl]-2-oxo-ethyl}-2,4,5-trifluoro-benzamide | 1.52 | 453.15 |
| N-{2-[5-(3,5-Difluoro-benzyl)-hexahydro-pyrrolo[3,4-c]pyrrol-2-yl]-2-oxo-ethyl}-2,4,5-trifluoro-benzamide | 1.61 | 453.15 |
| 2-Chloro-N-{2-[5-(2,4-difluoro-benzyl)-hexahydro-pyrrolo[3,4-c]pyrrol-2-yl]-2-oxo-ethyl}-4,5-difluoro-benzamide | 1.56 | 469.12 |
| 2-Chloro-N-{2-[5-(2,3-difluoro-benzyl)-hexahydro-pyrrolo[3,4-c]pyrrol-2-yl]-2-oxo-ethyl}-4,5-difluoro-benzamide | 1.56 | 469.12 |
| 2-Chloro-N-{2-[5-(2,5-difluoro-benzyl)-hexahydro-pyrrolo[3,4-c]pyrrol-2-yl]-2-oxo-ethyl}-4,5-difluoro-benzamide | 1.52 | 469.12 |
| 2-Chloro-N-{2-[5-(3,5-difluoro-benzyl)-hexahydro-pyrrolo[3,4-c]pyrrol-2-yl]-2-oxo-ethyl}-4,5-difluoro-benzamide | 1.62 | 469.12 |
| 4-Chloro-N-{2-[5-(2,4-difluoro-benzyl)-hexahydro-pyrrolo[3,4-c]pyrrol-2-yl]-2-oxo-ethyl}-2-fluoro-benzamide | 1.6 | 451.13 |
| 4-Chloro-N-{2-[5-(2,3-difluoro-benzyl)-hexahydro-pyrrolo[3,4-c]pyrrol-2-yl]-2-oxo-ethyl}-2-fluoro-benzamide | 1.61 | 451.13 |
| 4-Chloro-N-{2-[5-(2,5-difluoro-benzyl)-hexahydro-pyrrolo[3,4-c]pyrrol-2-yl]-2-oxo-ethyl}-2-fluoro-benzamide | 1.58 | 451.13 |
| 4-Chloro-N-{2-[5-(3,5-difluoro-benzyl)-hexahydro-pyrrolo[3,4-c]pyrrol-2-yl]-2-oxo-ethyl}-2-fluoro-benzamide | 1.66 | 451.13 |
| 3-Chloro-N-{2-[5-(2,4-difluoro-benzyl)-hexahydro-pyrrolo[3,4-c]pyrrol-2-yl]-2-oxo-ethyl}-2-fluoro-benzamide | 1.58 | 451.13 |
| 3-Chloro-N-{2-[5-(2,3-difluoro-benzyl)-hexahydro-pyrrolo[3,4-c]pyrrol-2-yl]-2-oxo-ethyl}-2-fluoro-benzamide | 1.59 | 451.13 |
| 3-Chloro-N-{2-[5-(2,5-difluoro-benzyl)-hexahydro-pyrrolo[3,4-c]pyrrol-2-yl]-2-oxo-ethyl}-2-fluoro-benzamide | 1.55 | 451.13 |
| 3-Chloro-N-{2-[5-(3,5-difluoro-benzyl)-hexahydro-pyrrolo[3,4-c]pyrrol-2-yl]-2-oxo-ethyl}-2-fluoro-benzamide | 1.63 | 451.13 |
| N-{2-[5-(2,4-Difluoro-benzyl)-hexahydro-pyrrolo-[3,4-c]pyrrol-2-yl]-2-oxo-ethyl}-2-ethoxy-benzamide | 1.42 | 443.2 |
| N-{2-[5-(2,3-Difluoro-benzyl)-hexahydro-pyrrolo-[3,4-c]pyrrol-2-yl]-2-oxo-ethyl}-2-ethoxy-benzamide | 1.41 | 443.2 |

TABLE 2-continued

| Compound Name | Time (mins) | MW (found) |
|---|---|---|
| N-{2-[5-(2,5-Difluoro-benzyl)-hexahydro-pyrrolo-[3,4-c]pyrrol-2-yl]-2-oxo-ethyl}-2-ethoxy-benzamide | 1.41 | 443.2 |
| N-{2-[5-(3,5-Difluoro-benzyl)-hexahydro-pyrrolo-[3,4-c]pyrrol-2-yl]-2-oxo-ethyl}-2-ethoxy-benzamide | 1.46 | 443.2 |
| N-{2-[5-(2,4-Difluoro-benzyl)-hexahydro-pyrrolo-[3,4-c]pyrrol-2-yl]-2-oxo-ethyl}-2-trifluoromethyl-benzamide | 1.36 | 467.16 |
| N-{2-[5-(2,3-Difluoro-benzyl)-hexahydro-pyrrolo-[3,4-c]pyrrol-2-yl]-2-oxo-ethyl}-2-trifluoromethyl-benzamide | 1.36 | 467.16 |
| N-{2-[5-(2,5-Difluoro-benzyl)-hexahydro-pyrrolo-[3,4-c]pyrrol-2-yl]-2-oxo-ethyl}-2-trifluoromethyl-benzamide | 1.33 | 467.16 |
| N-{2-[5-(3,5-Difluoro-benzyl)-hexahydro-pyrrolo-[3,4-c]pyrrol-2-yl]-2-oxo-ethyl}-2-trifluoromethyl-benzamide | 1.41 | 467.16 |
| N-{2-[5-(2,4-Difluoro-benzyl)-hexahydro-pyrrolo-[3,4-c]pyrrol-2-yl]-2-oxo-ethyl}-2-fluoro-4-trifluoromethyl-benzamide | 1.55 | 485.15 |
| N-{2-[5-(2,3-Difluoro-benzyl)-hexahydro-pyrrolo-[3,4-c]pyrrol-2-yl]-2-oxo-ethyl}-2-fluoro-4-trifluoromethyl-benzamide | 1.55 | 485.15 |
| N-{2-[5-(2,5-Difluoro-benzyl)-hexahydro-pyrrolo-[3,4-c]pyrrol-2-yl]-2-oxo-ethyl}-2-fluoro-4-trifluoromethyl-benzamide | 1.54 | 485.15 |
| N-{2-[5-(3,5-Difluoro-benzyl)-hexahydro-pyrrolo-[3,4-c]pyrrol-2-yl]-2-oxo-ethyl}-2-fluoro-4-trifluoromethyl-benzamide | 1.6 | 485.15 |
| N-{2-[5-(2,4-Difluoro-benzyl)-hexahydro-pyrrolo-[3,4-c]pyrrol-2-yl]-2-oxo-ethyl}-2,5-bis-trifluoromethyl-benzamide | 1.61 | 535.15 |
| N-{2-[5-(2,3-Difluoro-benzyl)-hexahydro-pyrrolo-[3,4-c]pyrrol-2-yl]-2-oxo-ethyl}-2,5-bis-trifluoromethyl-benzamide | 1.62 | 535.15 |
| N-{2-[5-(2,5-Difluoro-benzyl)-hexahydro-pyrrolo-[3,4-c]pyrrol-2-yl]-2-oxo-ethyl}-2,5-bis-trifluoromethyl-benzamide | 1.59 | 535.15 |
| N-{2-[5-(3,5-Difluoro-benzyl)-hexahydro-pyrrolo-[3,4-c]pyrrol-2-yl]-2-oxo-ethyl}-2,5-bis-trifluoromethyl-benzamide | 1.66 | 535.15 |
| N-{2-[5-(2,4-Difluoro-benzyl)-hexahydro-pyrrolo-[3,4-c]pyrrol-2-yl]-2-oxo-ethyl}-2,3,4-trifluoro-benzamide | 1.35 | 453.15 |
| N-{2-[5-(2,3-Difluoro-benzyl)-hexahydro-pyrrolo-[3,4-c]pyrrol-2-yl]-2-oxo-ethyl}-2,3,4-trifluoro-benzamide | 1.37 | 453.15 |
| N-{2-[5-(2,5-Difluoro-benzyl)-hexahydro-pyrrolo-[3,4-c]pyrrol-2-yl]-2-oxo-ethyl}-2,3,4-trifluoro-benzamide | 1.34 | 453.15 |
| N-{2-[5-(3,5-Difluoro-benzyl)-hexahydro-pyrrolo-[3,4-c]pyrrol-2-yl]-2-oxo-ethyl}-2,3,4-trifluoro-benzamide | 1.41 | 453.15 |
| N-{2-[5-(3,5-Difluoro-benzyl)-hexahydro-pyrrolo-[3,4-c]pyrrol-2-yl]-2-oxo-ethyl}-2,3,4-trifluoro-benzamide | 1.52 | 485.15 |
| N-{2-[5-(2,3-Difluoro-benzyl)-hexahydro-pyrrolo-[3,4-c]pyrrol-2-yl]-2-oxo-ethyl}-2-fluoro-3-trifluoromethyl-benzamide | 1.54 | 485.15 |
| N-{2-[5-(2,5-Difluoro-benzyl)-hexahydro-pyrrolo-[3,4-c]pyrrol-2-yl]-2-oxo-ethyl}-2-fluoro-3-trifluoromethyl-benzamide | 1.51 | 485.15 |
| N-{2-[5-(3,5-Difluoro-benzyl)-hexahydro-pyrrolo-[3,4-c]pyrrol-2-yl]-2-oxo-ethyl}-2-fluoro-3-trifluoromethyl-benzamide | 1.58 | 485.15 |
| N-{2-[5-(2,4-Difluoro-benzyl)-hexahydro-pyrrolo-[3,4-c]pyrrol-2-yl]-2-oxo-ethyl}-2,4-bis-trifluoromethyl-benzamide | 1.67 | 535.15 |
| N-{2-[5-(2,3-Difluoro-benzyl)-hexahydro-pyrrolo-[3,4-c]pyrrol-2-yl]-2-oxo-ethyl}-2,4-bis-trifluoromethyl-benzamide | 1.69 | 535.15 |
| N-{2-[5-(2,5-Difluoro-benzyl)-hexahydro-pyrrolo-[3,4-c]pyrrol-2-yl]-2-oxo-ethyl}-2,4-bis-trifluoromethyl-benzamide | 1.67 | 535.15 |
| N-{2-[5-(3,5-Difluoro-benzyl)-hexahydro-pyrrolo-[3,4-c]pyrrol-2-yl]-2-oxo-ethyl}-2,4-bis-trifluoromethyl-benzamide | 1.73 | 535.15 |
| N-{2-[5-(2,4-Difluoro-benzyl)-hexahydro-pyrrolo-[3,4-c]pyrrol-2-yl]-2-oxo-ethyl}-4-fluoro-2-trifluoromethyl-benzamide | 1.42 | 485.15 |
| N-{2-[5-(2,3-Difluoro-benzyl)-hexahydro-pyrrolo-[3,4-c]pyrrol-2-yl]-2-oxo-ethyl}-4-fluoro-2-trifluoromethyl-benzamide | 1.42 | 485.15 |
| N-{2-[5-(2,5-Difluoro-benzyl)-hexahydro-pyrrolo-[3,4-c]pyrrol-2-yl]-2-oxo-ethyl}-4-fluoro-2-trifluoromethyl-benzamide | 1.41 | 485.15 |
| N-{2-[5-(3,5-Difluoro-benzyl)-hexahydro-pyrrolo-[3,4-c]pyrrol-2-yl]-2-oxo-ethyl}-4-fluoro-2-trifluoromethyl-benzamide | 1.48 | 485.15 |

TABLE 2-continued

| Compound Name | Time (mins) | MW (found) |
|---|---|---|
| N-{2-[5-(2,4-Difluoro-benzyl)-hexahydro-pyrrolo-[3,4-c]pyrrol-2-yl]-2-oxo-ethyl}-2-trifluoromethoxy-benzamide | 1.42 | 483.16 |
| N-{2-[5-(2,3-Difluoro-benzyl)-hexahydro-pyrrolo-[3,4-c]pyrrol-2-yl]-2-oxo-ethyl}-2-trifluoromethoxy-benzamide | 1.44 | 483.16 |
| N-{2-[5-(2,5-Difluoro-benzyl)-hexahydro-pyrrolo-[3,4-c]pyrrol-2-yl]-2-oxo-ethyl}-2-trifluoromethoxy-benzamide | 1.42 | 483.16 |
| N-{2-[5-(3,5-Difluoro-benzyl)-hexahydro-pyrrolo-[3,4-c]pyrrol-2-yl]-2-oxo-ethyl}-2-trifluoromethoxy-benzamide | 1.48 | 483.16 |
| 2-Chloro-N-{2-[5-(2,4-difluoro-benzyl)-hexahydro-pyrrolo[3,4-c]pyrrol-2-yl]-2-oxo-ethyl}-3-trifluoromethyl-benzamide | 1.54 | 501.12 |
| 2-Chloro-N-{2-[5-(2,3-difluoro-benzyl)-hexahydro-pyrrolo[3,4-c]pyrrol-2-yl]-2-oxo-ethyl}-3-trifluoromethyl-benzamide | 1.55 | 501.12 |
| 2-Chloro-N-{2-[5-(2,5-difluoro-benzyl)-hexahydro-pyrrolo[3,4-c]pyrrol-2-yl]-2-oxo-ethyl}-3-trifluoromethyl-benzamide | 1.53 | 501.12 |
| 2-Chloro-N-{2-[5-(3,5-difluoro-benzyl)-hexahydro-pyrrolo[3,4-c]pyrrol-2-yl]-2-oxo-ethyl}-3-trifluoromethyl-benzamide | 1.59 | 501.12 |
| N-{2-[5-(2,4-Difluoro-benzyl)-hexahydro-pyrrolo[3,4-c]-pyrrol-2-yl]-2-oxo-ethyl}-2-difluoromethoxy-benzamide | 1.34 | 465.17 |
| N-{2-[5-(2,3-Difluoro-benzyl)-hexahydro-pyrrolo[3,4-c]-pyrrol-2-yl]-2-oxo-ethyl}-2-difluoromethoxy-benzamide | 1.35 | 465.17 |
| N-{2-[5-(2,5-Difluoro-benzyl)-hexahydro-pyrrolo[3,4-c]-pyrrol-2-yl]-2-oxo-ethyl}-2-difluoromethoxy-benzamide | 1.31 | 465.17 |
| N-{2-[5-(3,5-Difluoro-benzyl)-hexahydro-pyrrolo[3,4-c]-pyrrol-2-yl]-2-oxo-ethyl}-2-difluoromethoxy-benzamide | 1.39 | 465.17 |
| 2,6-Dichloro-N-{2-[5-(2,4-difluoro-benzyl)-hexahydro-pyrrolo[3,4-c]pyrrol-2-yl]-2-oxo-ethyl}-benzamide | 1.27 | 467.1 |
| 2,6-Dichloro-N-{2-[5-(2,3-difluoro-benzyl)-hexahydro-pyrrolo[3,4-c]pyrrol-2-yl]-2-oxo-ethyl}-benzamide | 1.27 | 467.1 |
| 2,6-Dichloro-N-{2-[5-(2,5-difluoro-benzyl)-hexahydro-pyrrolo[3,4-c]pyrrol-2-yl]-2-oxo-ethyl}-benzamide | 1.24 | 467.1 |
| 2,6-Dichloro-N-{2-[5-(3,5-difluoro-benzyl)-hexahydro-pyrrolo[3,4-c]pyrrol-2-yl]-2-oxo-ethyl}-benzamide | 1.33 | 467.1 |
| N-{2-[5-(2,4-Difluoro-benzyl)-hexahydro-pyrrolo-[3,4-c]pyrrol-2-yl]-2-oxo-ethyl}-2,6-dimethyl-benzamide | 1.28 | 427.21 |
| N-{2-[5-(2,3-Difluoro-benzyl)-hexahydro-pyrrolo-[3,4-c]pyrrol-2-yl]-2-oxo-ethyl}-2,6-dimethyl-benzamide | 1.29 | 427.21 |
| N-{2-[5-(2,5-Difluoro-benzyl)-hexahydro-pyrrolo-[3,4-c]pyrrol-2-yl]-2-oxo-ethyl}-2,6-dimethyl-benzamide | 1.25 | 427.21 |
| N-{2-[5-(3,5-Difluoro-benzyl)-hexahydro-pyrrolo-[3,4-c]pyrrol-2-yl]-2-oxo-ethyl}-2,6-dimethyl-benzamide | 1.32 | 427.21 |
| 2-Chloro-N-{2-[5-(2,4-difluoro-benzyl)-hexahydro-pyrrolo[3,4-c]pyrrol-2-yl]-2-oxo-ethyl}-6-fluoro-benzamide | 1.23 | 451.13 |
| 2-Chloro-N-{2-[5-(2,3-difluoro-benzyl)-hexahydro-pyrrolo[3,4-c]pyrrol-2-yl]-2-oxo-ethyl}-6-fluoro-benzamide | 1.23 | 451.13 |
| 2-Chloro-N-{2-[5-(2,5-difluoro-benzyl)-hexahydro-pyrrolo[3,4-c]pyrrol-2-yl]-2-oxo-ethyl}-6-fluoro-benzamide | 1.19 | 451.13 |
| 2-Chloro-N-{2-[5-(3,5-difluoro-benzyl)-hexahydro-pyrrolo[3,4-c]pyrrol-2-yl]-2-oxo-ethyl}-6-fluoro-benzamide | 1.28 | 451.13 |
| N-{2-[5-(2,4-Difluoro-benzyl)-hexahydro-pyrrolo-[3,4-c]pyrrol-2-yl]-2-oxo-ethyl}-2,6-difluoro-benzamide | 1.16 | 435.16 |
| N-{2-[5-(2,3-Difluoro-benzyl)-hexahydro-pyrrolo-[3,4-c]pyrrol-2-yl]-2-oxo-ethyl}-2,6-difluoro-benzamide | 1.16 | 435.16 |
| N-{2-[5-(2,5-Difluoro-benzyl)-hexahydro-pyrrolo-[3,4-c]pyrrol-2-yl]-2-oxo-ethyl}-2,6-difluoro-benzamide | 1.08 | 435.16 |
| N-{2-[5-(3,5-Difluoro-benzyl)-hexahydro-pyrrolo-[3,4-c]pyrrol-2-yl]-2-oxo-ethyl}-2,6-difluoro-benzamide | 1.21 | 435.16 |
| N-{2-[5-(2,4-Difluoro-benzyl)-hexahydro-pyrrolo-[3,4-c]pyrrol-2-yl]-2-oxo-ethyl}-2,3,6-trifluoro-benzamide | 1.23 | 453.15 |
| N-{2-[5-(2,3-Difluoro-benzyl)-hexahydro-pyrrolo-[3,4-c]pyrrol-2-yl]-2-oxo-ethyl}-2,3,6-trifluoro-benzamide | 1.25 | 453.15 |
| N-{2-[5-(2,5-Difluoro-benzyl)-hexahydro-pyrrolo-[3,4-c]pyrrol-2-yl]-2-oxo-ethyl}-2,3,6-trifluoro-benzamide | 1.21 | 453.15 |
| N-{2-[5-(3,5-Difluoro-benzyl)-hexahydro-pyrrolo-[3,4-c]pyrrol-2-yl]-2-oxo-ethyl}-2,3,6-trifluoro-benzamide | 1.29 | 453.15 |

TABLE 2-continued

| Compound Name | Time (mins) | MW (found) |
|---|---|---|
| N-{2-[5-(2,4-Difluoro-benzyl)-hexahydro-pyrrolo-[3,4-c]pyrrol-2-yl]-2-oxo-ethyl}-2-fluoro-6-trifluoromethyl-benzamide | 1.33 | 485.15 |
| N-{2-[5-(2,3-Difluoro-benzyl)-hexahydro-pyrrolo-[3,4-c]pyrrol-2-yl]-2-oxo-ethyl}-2-fluoro-6-trifluoromethyl-benzamide | 1.35 | 485.15 |
| N-{2-[5-(2,5-Difluoro-benzyl)-hexahydro-pyrrolo-[3,4-c]pyrrol-2-yl]-2-oxo-ethyl}-2-fluoro-6-trifluoromethyl-benzamide | 1.31 | 485.15 |
| N-{2-[5-(3,5-Difluoro-benzyl)-hexahydro-pyrrolo-[3,4-c]pyrrol-2-yl]-2-oxo-ethyl}-2-fluoro-6-trifluoromethyl-benzamide | 1.39 | 485.15 |
| N-{2-[5-(2,4-Difluoro-benzyl)-hexahydro-pyrrolo-[3,4-c]pyrrol-2-yl]-2-oxo-ethyl}-2,4,6-trifluoro-benzamide | 1.23 | 453.15 |
| N-{2-[5-(2,3-Difluoro-benzyl)-hexahydro-pyrrolo-[3,4-c]pyrrol-2-yl]-2-oxo-ethyl}-2,4,6-trifluoro-benzamide | 1.22 | 453.15 |
| N-{2-[5-(2,5-Difluoro-benzyl)-hexahydro-pyrrolo-[3,4-c]pyrrol-2-yl]-2-oxo-ethyl}-2,4,6-trifluoro-benzamide | 1.2 | 453.15 |
| N-{2-[5-(3,5-Difluoro-benzyl)-hexahydro-pyrrolo-[3,4-c]pyrrol-2-yl]-2-oxo-ethyl}-2,4,6-trifluoro-benzamide | 1.28 | 453.15 |
| N-{2-[5-(2,4-Difluoro-benzyl)-hexahydro-pyrrolo-[3,4-c]pyrrol-2-yl]-2-oxo-ethyl}-2,6-dimethoxy-benzamide | 1.15 | 459.2 |
| N-{2-[5-(2,3-Difluoro-benzyl)-hexahydro-pyrrolo-[3,4-c]pyrrol-2-yl]-2-oxo-ethyl}-2,6-dimethoxy-benzamide | 1.16 | 459.2 |
| N-{2-[5-(2,5-Difluoro-benzyl)-hexahydro-pyrrolo-[3,4-c]pyrrol-2-yl]-2-oxo-ethyl}-2,6-dimethoxy-benzamide | 1.09 | 459.2 |
| N-{2-[5-(3,5-Difluoro-benzyl)-hexahydro-pyrrolo-[3,4-c]pyrrol-2-yl]-2-oxo-ethyl}-2,6-dimethoxy-benzamide | 1.21 | 459.2 |
| N-{2-[5-(2,4-Difluoro-benzyl)-hexahydro-pyrrolo-[3,4-c]pyrrol-2-yl]-2-oxo-ethyl}-2,3,6-trimethoxy-benzamide | 1.2 | 489.21 |
| N-{2-[5-(2,3-Difluoro-benzyl)-hexahydro-pyrrolo-[3,4-c]pyrrol-2-yl]-2-oxo-ethyl}-2,3,6-trimethoxy-benzamide | 1.21 | 489.21 |
| N-{2-[5-(2,5-Difluoro-benzyl)-hexahydro-pyrrolo-[3,4-c]pyrrol-2-yl]-2-oxo-ethyl}-2,3,6-trimethoxy-benzamide | 1.18 | 489.21 |
| N-{2-[5-(3,5-Difluoro-benzyl)-hexahydro-pyrrolo-[3,4-c]pyrrol-2-yl]-2-oxo-ethyl}-2,3,6-trimethoxy-benzamide | 1.25 | 489.21 |
| 3-Chloro-N-{2-[5-(2,4-difluoro-benzyl)-hexahydro-pyrrolo-[3,4-c]pyrrol-2-yl]-2-oxo-ethyl}-2,6-dimethoxy-benzamide | 1.36 | 493.16 |
| 3-Chloro-N-{2-[5-(2,3-difluoro-benzyl)-hexahydro-pyrrolo-[3,4-c]pyrrol-2-yl]-2-oxo-ethyl}-2,6-dimethoxy-benzamide | 1.37 | 493.16 |
| 3-Chloro-N-{2-[5-(2,5-difluoro-benzyl)-hexahydro-pyrrolo-[3,4-c]pyrrol-2-yl]-2-oxo-ethyl}-2,6-dimethoxy-benzamide | 1.34 | 493.16 |
| 3-Chloro-N-{2-[5-(3,5-difluoro-benzyl)-hexahydro-pyrrolo-[3,4-c]pyrrol-2-yl]-2-oxo-ethyl}-2,6-dimethoxy-benzamide | 1.41 | 493.16 |
| N-{2-[5-(2,4-Difluoro-benzyl)-hexahydro-pyrrolo-[3,4-c]pyrrol-2-yl]-2-oxo-ethyl}-2-o-tolyl-acetamide | 1.34 | 427.21 |
| N-{2-[5-(2,3-Difluoro-benzyl)-hexahydro-pyrrolo-[3,4-c]pyrrol-2-yl]-2-oxo-ethyl}-2-o-tolyl-acetamide | 1.34 | 427.21 |
| N-{2-[5-(2,5-Difluoro-benzyl)-hexahydro-pyrrolo-[3,4-c]pyrrol-2-yl]-2-oxo-ethyl}-2-o-tolyl-acetamide | 1.32 | 427.21 |
| N-{2-[5-(3,5-Difluoro-benzyl)-hexahydro-pyrrolo-[3,4-c]pyrrol-2-yl]-2-oxo-ethyl}-2-o-tolyl-acetamide | 1.39 | 427.21 |
| 2-Biphenyl-4-yl-N-{2-[5-(2,4-difluoro-benzyl)-hexahydro-pyrrolo-[3,4-c]pyrrol-2-yl]-2-oxo-ethyl}-acetamide | 1.69 | 489.22 |
| 2-Biphenyl-4-yl-N-{2-[5-(2,3-difluoro-benzyl)-hexahydro-pyrrolo-[3,4-c]pyrrol-2-yl]-2-oxo-ethyl}-acetamide | 1.7 | 489.22 |
| 2-Biphenyl-4-yl-N-{2-[5-(2,5-difluoro-benzyl)-hexahydro-pyrrolo-[3,4-c]pyrrol-2-yl]-2-oxo-ethyl}-acetamide | 1.69 | 489.22 |
| 2-Biphenyl-4-yl-N-{2-[5-(3,5-difluoro-benzyl)-hexahydro-pyrrolo[3,4-c]pyrrol-2-yl]-2-oxo-ethyl}-acetamide | 1.73 | 489.22 |
| N-{2-[5-(2,4-Difluoro-benzyl)-hexahydro-pyrrolo-[3,4-c]pyrrol-2-yl]-2-oxo-ethyl}-2-(4-isopropyl-phenyl)-acetamide | 1.65 | 455.24 |
| N-{2-[5-(2,3-Difluoro-benzyl)-hexahydro-pyrrolo-[3,4-c]pyrrol-2-yl]-2-oxo-ethyl}-2-(4-isopropyl-phenyl)-acetamide | 1.65 | 455.24 |
| N-{2-[5-(2,5-Difluoro-benzyl)-hexahydro-pyrrolo-[3,4-c]pyrrol-2-yl]-2-oxo-ethyl}-2-(4-isopropyl-phenyl)-acetamide | 1.64 | 455.24 |

TABLE 2-continued

| Compound Name | Time (mins) | MW (found) |
|---|---|---|
| N-{2-[5-(3,5-Difluoro-benzyl)-hexahydro-pyrrolo-[3,4-c]pyrrol-2-yl]-2-oxo-ethyl}-2-(4-isopropyl-phenyl)-acetamide | 1.69 | 455.24 |
| N-{2-[5-(2,4-Difluoro-benzyl)-hexahydro-pyrrolo-[3,4-c]pyrrol-2-yl]-2-oxo-ethyl}-2-m-tolyl-acetamide | 1.38 | 427.21 |
| N-{2-[5-(2,3-Difluoro-benzyl)-hexahydro-pyrrolo-[3,4-c]pyrrol-2-yl]-2-oxo-ethyl}-2-m-tolyl-acetamide | 1.38 | 427.21 |
| N-{2-[5-(2,5-Difluoro-benzyl)-hexahydro-pyrrolo-[3,4-c]pyrrol-2-yl]-2-oxo-ethyl}-2-m-tolyl-acetamide | 1.35 | 427.21 |
| N-{2-[5-(3,5-Difluoro-benzyl)-hexahydro-pyrrolo-[3,4-c]pyrrol-2-yl]-2- oxo-ethyl}-2-m-tolyl-acetamide | 1.42 | 427.21 |
| N-{2-[5-(2,4-Difluoro-benzyl)-hexahydro-pyrrolo-[3,4-c]pyrrol-2-yl]-2-oxo-ethyl}-2-p-tolyl-acetamide | 1.38 | 427.21 |
| N-{2-[5-(2,3-Difluoro-benzyl)-hexahydro-pyrrolo-[3,4-c]pyrrol-2-yl]-2-oxo-ethyl}-2-p-tolyl-acetamide | 1.39 | 427.21 |
| N-{2-[5-(2,5-Difluoro-benzyl)-hexahydro-pyrrolo-[3,4-c]pyrrol-2-yl]-2-oxo-ethyl}-2-p-tolyl-acetamide | 1.36 | 427.21 |
| N-{2-[5-(3,5-Difluoro-benzyl)-hexahydro-pyrrolo-[3,4-c]pyrrol-2-yl]-2-oxo-ethyl}-2-p-tolyl-acetamide | 1.43 | 427.21 |
| N-{2-[5-(2,4-Difluoro-benzyl)-hexahydro-pyrrolo-[3,4-c]pyrrol-2-yl]-2-oxo-ethyl}-2-(2,5-dimethyl-phenyl)-acetamide | 1.47 | 441.22 |
| N-{2-[5-(2,3-Difluoro-benzyl)-hexahydro-pyrrolo-[3,4-c]pyrrol-2-yl]-2-oxo-ethyl}-2-(2,5-dimethyl-phenyl)-acetamide | 1.48 | 441.22 |
| N-{2-[5-(2,5-Difluoro-benzyl)-hexahydro-pyrrolo-[3,4-c]pyrrol-2-yl]-2-oxo-ethyl}-2-(2,5-dimethyl-phenyl)-acetamide | 1.46 | 441.22 |
| N-{2-[5-(3,5-Difluoro-benzyl)-hexahydro-pyrrolo-[3,4-c]pyrrol-2-yl]-2-oxo-ethyl}-2-(2,5-dimethyl-phenyl)-acetamide | 1.52 | 441.22 |
| N-{2-[5-(2,4-Difluoro-benzyl)-hexahydro-pyrrolo-[3,4-c]pyrrol-2-yl]-2-oxo-ethyl}-2-naphthalen-1-yl-acetamide | 1.5 | 463.21 |
| N-{2-[5-(2,3-Difluoro-benzyl)-hexahydro-pyrrolo-[3,4-c]pyrrol-2-yl]-2-oxo-ethyl}-2-naphthalen-1-yl-acetamide | 1.52 | 463.21 |
| N-{2-[5-(2,5-Difluoro-benzyl)-hexahydro-pyrrolo-[3,4-c]pyrrol-2-yl]-2-oxo-ethyl}-2-naphthalen-1-yl-acetamide | 1.49 | 463.21 |
| N-{2-[5-(3,5-Difluoro-benzyl)-hexahydro-pyrrolo-[3,4-c]pyrrol-2-yl]-2-oxo-ethyl}-2-naphthalen-1-yl-acetamide | 1.56 | 463.21 |
| N-{2-[5-(2,4-Difluoro-benzyl)-hexahydro-pyrrolo-[3,4-c]pyrrol-2-yl]-2-oxo-ethyl}-2-(2,3,6-trifluoro-phenyl)-acetamide | 1.34 | 467.16 |
| N-{2-[5-(2,3-Difluoro-benzyl)-hexahydro-pyrrolo-[3,4-c]pyrrol-2-yl]-2-oxo-ethyl}-2-(2,3,6-trifluoro-phenyl)-acetamide | 1.34 | 467.16 |
| N-{2-[5-(2,5-Difluoro-benzyl)-hexahydro-pyrrolo-[3,4-c]pyrrol-2-yl]-2-oxo-ethyl}-2-(2,3,6-trifluoro-phenyl)-acetamide | 1.32 | 467.16 |
| N-{2-[5-(3,5-Difluoro-benzyl)-hexahydro-pyrrolo-[3,4-c]pyrrol-2-yl]-2-oxo-ethyl}-2-(2,3,6-trifluoro-phenyl)-acetamide | 1.4 | 467.16 |
| N-{2-[5-(2,4-Difluoro-benzyl)-hexahydro-pyrrolo-[3,4-c]pyrrol-2-yl]-2- oxo-ethyl}-2-phenyl-acetamide | 1.24 | 413.19 |
| N-{2-[5-(2,3-Difluoro-benzyl)-hexahydro-pyrrolo-[3,4-c]pyrrol-2-yl]-2-oxo-ethyl}-2-phenyl-acetamide | 1.25 | 413.19 |
| N-{2-[5-(2,5-Difluoro-benzyl)-hexahydro-pyrrolo-[3,4-c]pyrrol-2-yl]-2-oxo-ethyl}-2-phenyl-acetamide | 1.22 | 413.19 |
| N-{2-[5-(3,5-Difluoro-benzyl)-hexahydro-pyrrolo-[3,4-c]pyrrol-2-yl]-2-oxo-ethyl}-2-phenyl-acetamide | 1.3 | 413.19 |
| N-{2-[5-(2,5-Difluoro-benzyl)-hexahydro-pyrrolo-[3,4-c]pyrrol-2-yl]-2-oxo-ethyl}-2-(3,5-dimethyl-phenyl)-acetamide | 1.5 | 441.22 |
| N-{2-[5-(3,5-Difluoro-benzyl)-hexahydro-pyrrolo-[3,4-c]pyrrol-2-yl]-2-oxo-ethyl}-2-(3,5-dimethyl-phenyl)-acetamide | 1.56 | 441.22 |
| N-{2-[5-(2,4-Difluoro-benzyl)-hexahydro-pyrrolo-[3,4-c]pyrrol-2-yl]-2-oxo-ethyl}-2-(2,4-dimethyl-phenyl)-acetamide | 1.48 | 441.22 |
| N-{2-[5-(3,5-Difluoro-benzyl)-hexahydro-pyrrolo-[3,4-c]pyrrol-2-yl]-2-oxo-ethyl}-2-(2,4-dimethyl-phenyl)-acetamide | 1.53 | 441.22 |
| 2-Amino-1-[5-(2,4-dimethyl-benzyl)-hexahydro-pyrrolo-[3,4-c]pyrrol-2-yl]-3-methyl-butan-1-one | 0.6 | 330.6 |
| [5-(2,4-Dimethyl-benzyl)-hexahydro-pyrrolo-[3,4-c]pyrrol-2-yl]-pyrrolidin-2-yl-methanone | 0.4 | 328.6 |
| 2-Amino-1-[5-(2,4-dimethyl-benzyl)-hexahydro-pyrrolo-[3,4-c]pyrrol-2-yl]-propan-1-one | 0.4 | 302.6 |

TABLE 2-continued

| Compound Name | Time (mins) | MW (found) |
|---|---|---|
| N-{1-[5-(2,4-Dimethyl-benzyl)-hexahydro-pyrrolo-[3,4-c]pyrrole-2-carbonyl]-2-methyl-propyl}-3-trifluoromethyl-benzamide | 2.3 | 502.2 |
| 2-Amino-N-{1-[5-(2,4-dimethyl-benzyl)-hexahydro-pyrrolo-[3,4-c]pyrrole-2-carbonyl]-2-methyl-propyl}-5-fluoro-benzamide | 2.1 | 467.2 |
| 2-Amino-N-{1-[5-(2,4-dimethyl-benzyl)-hexahydro-pyrrolo-[3,4-c]pyrrole-2-carbonyl]-2-methyl-propyl}-5-iodo-benzamide | 2.3 | 575.2 |
| N-{1-[5-(2,4-Dimethyl-benzyl)-hexahydro-pyrrolo-[3,4-c]pyrrole-2-carbonyl]-2-methyl-propyl}-3-nitro-5-trifluoromethyl-benzamide | 2.5 | 547.2 |
| 5-Chloro-N-{1-[5-(2,4-dimethyl-benzyl)-hexahydro-pyrrolo-[3,4-c]pyrrole-2-carbonyl]-2-methyl-propyl}-2-nitro-benzamide | 2.2 | 513.2 |
| 2-Amino-5-bromo-N-{1-[5-(2,4-dimethyl-benzyl)-hexahydro-pyrrolo[3,4-c]-pyrrole-2-carbonyl]-2-methyl-propyl}-benzamide | 2.3 | 529.1 |
| 2-Amino-5-chloro-N-{1-[5-(2,4-dimethyl-benzyl)-hexahydro-pyrrolo[3,4-c]-pyrrole-2-carbonyl]-2-methyl-propyl}-benzamide | 2.2 | 483.2 |
| 3-Bromo-4-chloro-N-{1-[5-(2,4-dimethyl-benzyl)-hexahydro-pyrrolo[3,4-c]-pyrrole-2-carbonyl]-2-methyl-propyl}-benzamide | 2.4 | 548.1 |
| 3-Bromo-N-{1-[5-(2,4-dimethyl-benzyl)-hexahydro-pyrrolo-[3,4-c]pyrrole-2-carbonyl]-2-methyl-propyl}-4-methyl-benzamide | 2.4 | 528.2 |
| 3,4-Dichloro-N-{1-[5-(2,4-dimethyl-benzyl)-hexahydro-pyrrolo[3,4-c]-pyrrole-2-carbonyl]-2-methyl-propyl}-benzamide | 2.3 | 502.4 |
| [5-(2,4-Dimethyl-benzyl)-hexahydro-pyrrolo[3,4-c]pyrrol-2-yl]-[1-(3-trifluoromethyl-benzoyl)-pyrrolidin-2-yl]-methanone | 2.2 | 500.2 |
| [1-(2-Amino-5-fluoro-benzoyl)-pyrrolidin-2-yl]-[5-(2,4-dimethyl-benzyl)-hexahydro-pyrrolo[3,4-c]-pyrrol-2-yl]-methanone | 1.9 | 465.2 |
| [1-(2-Amino-5-iodo-benzoyl)-pyrrolidin-2-yl]-[5-(2,4-dimethyl-benzyl)-hexahydro-pyrrolo[3,4-c]-pyrrol-2-yl]-methanone | 2.1 | 573.1 |
| [5-(2,4-Dimethyl-benzyl)-hexahydro-pyrrolo-[3,4-c]pyrrol-2-yl]-[1-(3-nitro-5-trifluoromethyl-benzoyl)-pyrrolidin-2-yl]-methanone | 2.2 | 545.2 |
| [1-(5-Chloro-2-nitro-benzoyl)-pyrrolidin-2-yl]-[5-(2,4-dimethyl-benzyl)-hexahydro-pyrrolo[3,4-c]pyrrol-2-yl]-methanone | 2.1 | 511.1 |
| [1-(2-Amino-5-bromo-benzoyl)-pyrrolidin-2-yl]-[5-(2,4-dimethyl-benzyl)-hexahydro-pyrrolo[3,4-c]pyrrol-2-yl]-methanone | 2.1 | 527.1 |
| [1-(2-Amino-5-chloro-benzoyl)-pyrrolidin-2-yl]-[5-(2,4-dimethyl-benzyl)-hexahydro-pyrrolo[3,4-c]pyrrol-2-yl]-methanone | 2.1 | 481.2 |
| [1-(3-Bromo-4-chloro-benzoyl)-pyrrolidin-2-yl]-[5-(2,4-dimethyl-benzyl)-hexahydro-pyrrolo[3,4-c]pyrrol-2-yl]-methanone | 2.3 | 546.1 |
| [1-(3-Bromo-4-methyl-benzoyl)-pyrrolidin-2-yl]-[5-(2,4-dimethyl-benzyl)-hexahydro-pyrrolo[3,4-c]pyrrol-2-yl]-methanone | 2.2 | 526.1 |
| [1-(3,4-Dichloro-benzoyl)-pyrrolidin-2-yl]-[5-(2,4-dimethyl-benzyl)-hexahydro-pyrrolo[3,4-c]pyrrol-2-yl]-methanone | 2 | 500.4 |
| N-{2-[5-(2,4-Dimethyl-benzyl)-hexahydro-pyrrolo-[3,4-c]pyrrol-2-yl]-1-methyl-2-oxo-ethyl}-3-trifluoromethyl-benzamide | 2.2 | 474.2 |
| 2-Amino-N-{2-[5-(2,4-dimethyl-benzyl)-hexahydro-pyrrolo-[3,4-c]pyrrol-2-yl]-1-methyl-2-oxo-ethyl}-5-fluoro-benzamide | 1.8 | 439.2 |
| 2-Amino-N-{2-[5-(2,4-dimethyl-benzyl)-hexahydro-pyrrolo-[3,4-c]pyrrol-2-yl]-1-methyl-2-oxo-ethyl}-5-iodo-benzamide | 2.1 | 547.1 |
| N-{2-[5-(2,4-Dimethyl-benzyl)-hexahydro-pyrrolo-[3,4-c]pyrrol-2-yl]-1-methyl-2-oxo-ethyl}-3-nitro-5-trifluoromethyl-benzamide | 2.3 | 519.2 |
| 5-Chloro-N-{2-[5-(2,4-dimethyl-benzyl)-hexahydro-pyrrolo-[3,4-c]pyrrol-2-yl]-1-methyl-2-oxo-ethyl}-2-nitro-benzamide | 1.9 | 485.1 |
| 2-Amino-5-bromo-N-{2-[5-(2,4-dimethyl-benzyl)-hexahydro-pyrrolo[3,4-c]pyrrol-2-yl]-1-methyl-2-oxo-ethyl}-benzamide | 2.1 | 501.1 |
| 2-Amino-5-chloro-N-{2-[5-(2,4-dimethyl-benzyl)-hexahydro-pyrrolo-[3,4-c]pyrrol-2-yl]-1-methyl-2-oxo-ethyl}-benzamide | 2 | 455.1 |
| 3-Bromo-4-chloro-N-{2-[5-(2,4-dimethyl-benzyl)-hexahydro-pyrrolo-[3,4-c]pyrrol-2-yl]-1-methyl-2-oxo-ethyl}-benzamide | 2.3 | 520 |
| 3-Bromo-N-{2-[5-(2,4-dimethyl-benzyl)-hexahydro-pyrrolo-[3,4-c]pyrrol-2-yl]-1-methyl-2-oxo-ethyl}-4-methyl-benzamide | 2.2 | 500.1 |
| 3,4-Dichloro-N-{2-[5-(2,4-dimethyl-benzyl)-hexahydro-pyrrolo-[3,4-c]pyrrol-2-yl]-1-methyl-2-oxo-ethyl}-benzamide | 2 | 474.4 |

TABLE 2-continued

| Compound Name | Time (mins) | MW (found) |
|---|---|---|
| (1-{5-[1-(3,5-Bis-trifluoromethyl-phenyl)-5-methyl-1H-pyrazole-4-carbonyl]-hexahydro-pyrrolo[3,4-c]pyrrole-2-carbonyl}-2-methyl-propyl)-carbamic acid tert-butyl ester | 2.8 | 632.2 |
| N-{1-[5-(2,4-Dimethoxy-benzyl)-hexahydro-pyrrolo-[3,4-c]pyrrole-2-carbonyl]-3-methyl-butyl}-benzamide | 1.66 | 479.28 |
| N-{1-[5-(2,3-Dimethoxy-benzyl)-hexahydro-pyrrolo-[3,4-c]pyrrole-2-carbonyl]-3-methyl-butyl}-benzamide | 1.63 | 479.28 |
| N-{1-[5-(2,4-Dimethyl-benzyl)-hexahydro-pyrrolo-[3,4-c]pyrrole-2-carbonyl]-3-methyl-butyl}-benzamide | 1.71 | 447.29 |
| N-{1-[5-(2-Chloro-3,4-dimethoxy-benzyl)-hexahydro-pyrrolo[3,4-c]pyrrole-2-carbonyl]-3-methyl-butyl}-benzamide | 1.67 | 513.24 |
| N-{1-Benzyl-2-[5-(2,4-dimethoxy-benzyl)-hexahydro-pyrrolo-[3,4-c]pyrrol-2-yl]-2-oxo-ethyl}-2-phenyl-acetamide | 1.71 | 527.28 |
| N-{1-Benzyl-2-[5-(2,3-dimethoxy-benzyl)-hexahydro-pyrrolo-[3,4-c]pyrrol-2-yl]-2-oxo-ethyl}-2-phenyl-acetamide | 1.68 | 527.28 |
| N-{1-Benzyl-2-[5-(2,4-dimethyl-benzyl)-hexahydro-pyrrolo-[3,4-c]pyrrol-2-yl]-2-oxo-ethyl}-2-phenyl-acetamide | 1.8 | 495.29 |
| N-{1-Benzyl-2-[5-(2-chloro-3,4-dimethoxy-benzyl)-hexahydro-pyrrolo[3,4-c]pyrrol-2-yl]-2-oxo-ethyl}-2-phenyl-acetamide | 1.72 | 561.24 |
| N-{2-[5-(2,4-Dimethoxy-benzyl)-hexahydro-pyrrolo-[3,4-c]pyrrol-2-yl]-1-methyl-2-oxo-ethyl}-benzamide | 1.35 | 437.23 |
| N-{2-[5-(2,3-Dimethoxy-benzyl)-hexahydro-pyrrolo-[3,4-c]pyrrol-2-yl]-1-methyl-2-oxo-ethyl}-benzamide | 1.31 | 437.23 |
| N-{2-[5-(2,4-Dimethyl-benzyl)-hexahydro-pyrrolo-[3,4-c]pyrrol-2-yl]-1-methyl-2-oxo-ethyl}-benzamide | 1.45 | 405.24 |
| N-{2-[5-(2-Chloro-3,4-dimethoxy-benzyl)-hexahydro-pyrrolo-[3,4-c]pyrrol-2-yl]-1-methyl-2-oxo-ethyl}-benzamide | 1.35 | 471.19 |
| N-{1-Benzyl-2-[5-(2,4-dimethoxy-benzyl)-hexahydro-pyrrolo-[3,4-c]pyrrol-2-yl]-2-oxo-ethyl}-benzamide | 1.67 | 513.26 |
| N-{1-Benzyl-2-[5-(2,3-dimethoxy-benzyl)-hexahydro-pyrrolo[3,4-c]pyrrol-2-yl]-2-oxo-ethyl}-benzamide | 1.65 | 513.26 |
| N-{1-Benzyl-2-[5-(2,4-dimethyl-benzyl)-hexahydro-pyrrolo[3,4-c]pyrrol-2-yl]-2-oxo-ethyl}-benzamide | 1.72 | 481.27 |
| N-{1-Benzyl-2-[5-(2-chloro-3,4-dimethoxy-benzyl)-hexahydro-pyrrolo[3,4-c]pyrrol-2-yl]-2-oxo-ethyl}-benzamide | 1.68 | 547.22 |
| N-{1-[5-(2,4-Dimethoxy-benzyl)-hexahydro-pyrrolo-[3,4-c]pyrrole-2-carbonyl]-2-methyl-propyl}-benzamide | 1.53 | 465.26 |
| N-{1-[5-(2,3-Dimethoxy-benzyl)-hexahydro-pyrrolo-[3,4-c]pyrrole-2-carbonyl]-2-methyl-propyl}-benzamide | 1.5 | 465.26 |
| N-{1-[5-(2,4-Dimethyl-benzyl)-hexahydro-pyrrolo-[3,4-c]pyrrole-2-carbonyl]-2-methyl-propyl}-benzamide | 1.63 | 433.27 |
| N-{1-[5-(2-Chloro-3,4-dimethoxy-benzyl)-hexahydro-pyrrolo-[3,4-c]pyrrole-2-carbonyl]-2-methyl-propyl}-benzamide | 1.54 | 499.22 |
| 1-[5-(2,4-Dimethoxy-benzyl)-hexahydro-pyrrolo-[3,4-c]pyrrol-2-yl]-3-methyl-2-(5-trifluoromethyl-pyridin-2-ylamino)-butan-1-one | 1.83 | 506.25 |
| 1-[5-(2,3-Dimethoxy-benzyl)-hexahydro-pyrrolo-[3,4-c]pyrrol-2-yl]-3-methyl-2-(5-trifluoromethyl-pyridin-2-ylamino)-butan-1-one | 1.81 | 506.25 |
| 1-[5-(2,4-Dimethyl-benzyl)-hexahydro-pyrrolo-[3,4-c]pyrrol-2-yl]-3-methyl-2-(5-trifluoromethyl-pyridin-2-ylamino)-butan-1-one | 1.92 | 474.26 |
| 1-[5-(2-Chloro-3,4-dimethoxy-benzyl)-hexahydro-pyrrolo-[3,4-c]pyrrol-2-yl]-3-methyl-2-(5-trifluoromethyl-pyridin-2-ylamino)-butan-1-one | 1.84 | 540.21 |
| N-{2-[5-(2,4-Dimethoxy-benzyl)-hexahydro-pyrrolo-[3,4-c]pyrrol-2-yl]-1-methyl-2-oxo-ethyl}-acetamide | 0.98 | 375.22 |
| N-{2-[5-(2,3-Dimethoxy-benzyl)-hexahydro-pyrrolo-[3,4-c]pyrrol-2-yl]-1-methyl-2-oxo-ethyl}-acetamide | 0.93 | 375.22 |
| N-{2-[5-(2,4-Dimethyl-benzyl)-hexahydro-pyrrolo-[3,4-c]pyrrol-2-yl]-1-methyl-2-oxo-ethyl}-acetamide | 1.07 | 343.23 |
| N-{2-[5-(2-Chloro-3,4-dimethoxy-benzyl)-hexahydro-pyrrolo-[3,4-c]pyrrol-2-yl]-1-methyl-2-oxo-ethyl}-acetamide | 0.81 | 409.18 |

* NA = not available

Example 3 illustrates the preparation of bicyclic diamine compounds of Formula I where x=0, w=2, y=1, z=1 (enantiomer: x=2, w=0, y=1, z=1).

Example 3

Preparation of Ethyl N-(2,2-dimethoxyethyl)-carbamate (I-3a):

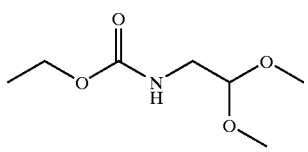

I-3a

A two-liter, three-necked round bottom flask was fitted with a 125-mL addition funnel and a digital thermometer probe. To this flask was added 65 g (618 mmol) of aminoacetaldehyde dimethyl acetal, 310 mL of toluene, and a solution of 27.8 g (695 mmol) of NaOH in 155 mL of water. This reaction mixture was cooled to 10° C. via ice bath. Ethyl chloroformate (59.1 mL, 618 mmol) was then added dropwise to the reaction mixture via addition funnel over a 15–20 minute period making sure the reaction temperature stayed near 10° C. Once addition was complete the reaction was stirred at room temperature for two hours. The aqueous layer was then separated, saturated with solid sodium chloride, and extracted with 3×50 mL of toluene. The toluene layers were combined, dried over magnesium sulfate, filtered, and concentrated in vacuo.

The $^1$H NMR was consistent with pure product (I-3a). Yield: 108.5 g (99%), pale yellow oil.

Preparation of Ethyl N-(2,2-dimethoxyethyl)-carbamate (I-3b):

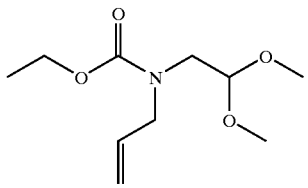

I-3b

To a two-liter, three-necked round bottom flask fitted with a 125-mL addition funnel was added 108.5 g (612 mmol) of ethyl N-(2,2-dimethoxyethyl)-carbamate (I-3a), 585 mL of toluene, 135.6 grams of powdered KOH (crushed KOH pellets in a mortar & pestle, added portionwise), and 2.17 g (9.5 mmol) of triethylbenzylammonium chloride. Finally, 53.5 mL (618 mmol) of allyl bromide was added dropwise via addition funnel over a 15 minute period to the reaction mixture at room temperature. Once addition was complete, the reaction mixture was stirred at room temperature overnight. The reaction mixture was then filtered to remove salts and unreacted KOH. The filtrate was washed once with 500 mL of brine, was then dried over potassium carbonate, and finally concentrated in vacuo.

$^1$H NMR was consistent with product I-3b (77% pure). Yield: 123.25 g (71% of theory, accounting for purity).

Preparation of Ethyl N-allyl-N-(2-oxoethyl)-carbamate (I-3c):

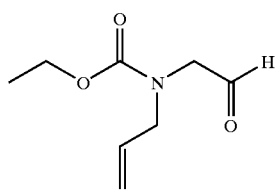

I-3c

To a two-liter round bottom flask was added 123 g (566 mmol, 77% pure) of ethyl N-(2,2-dimethoxyethyl)-carbamate (I-3b) and 270 mL of formic acid. The reaction mixture was refluxed for one hour. The reaction mixture was then poured over 1.5 liters of crushed ice, and extracted with (5×300 mL) dichloromethane. The organic extracts were combined, washed with (2×500 mL) saturated sodium bicarbonate solution, dried over magnesium sulfate, filtered, and concentrated in vacuo. $^1$H NMR was consistent with product (I-3c) and was carried on as the crude material. Mass spectrometry was consistent with product (I-3c). (MH$^+$) 172, FW=171.20.

Yield: 87.1 grams (89%).

Preparation of N-Benzylglycine (I-3d):

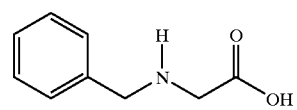

I-3d

N-benzylglycine ethyl ester (97.0 g, 503 mmol) was refluxed in 260 mL of water (with 480 mg of KOH, 0.5 wt %) overnight. The reaction mixture was filtered. The filtercake was washed with chloroform and dried under vacuum. The filtrate was extracted with tert-butyl methyl ether. The aqueous phase from this extraction was separated, adjusted to pH 2 with 6M HCl, and then concentrated in vacuo. The residue was filtered and this filtercake was washed with chloroform and dried under vacuum. The two filtercakes were combined.

$^1$H NMR spectrum was consistent with product. Mass spectrometry was consistent with product (I-3d). (MH$^+$) 275, FW=274.32. Yield: 78.8 grams (95%).

Preparation of Ethyl 2-benzyl-2,7-diazabicyclo[3.3.0] octane-7-carboxylate (I-3e):

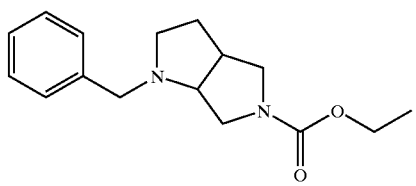

I-3e

To a two-liter round bottom flask was added 81.5 g (476 mmol) of ethyl N-allyl-N-(2-oxoethyl)-carbamate (I-3c), 78.6 g (476 mmol) of N-benzylglycine (I-3d), and 1.2 liters of toluene. The reaction mixture was refluxed for 24 hours. The reaction mixture was then decanted to remove sludge residue which formed on the bottom of the flask. The decanted solution was concentrated in vacuo to a brown syrup.

$^1$H NMR was consistent with crude product. Mass spectrometry was consistent with product (I-3e). (MH$^+$) 166, FW=165.19. Yield: 75.04 grams (58%).

Preparation of 2-Benzyl-2,7-diazabicyclo[3.3.0]octane (I-3f):

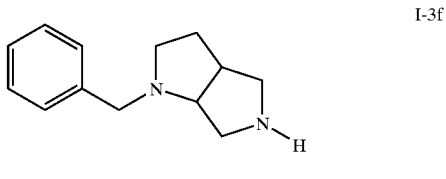

I-3f

To a one-liter flask fitted with a condenser was added 37.5 g (137 mmol) ethyl 2-benzyl-2,7-diazabicyclo[3.3.0]octane-7-carboxylate (I-3e) and 225 mL of concentrated hydrochloric acid. The reaction mixture was refluxed overnight under a positive pressure of nitrogen. The exhaust gases were bubbled through a solution of saturated sodium bicarbonate in order to neutralize any HCl fumes present in the exhaust. The reaction mixture was then adjusted to pH 9 with solid potassium carbonate and extracted with 3×180 mL chloroform. The organic extracts were combined, dried over potassium carbonate, filtered, and concentrated in vacuo to a black oil.

$^1$H NMR was consistent with product I-3f (75% pure). Mass spectrometry was consistent with product (I-3f). (MH$^+$) 203, FW=202.30. Yield: 22.7 grams (61% of theory, accounting for purity)

Preparation of 1-Benzyl-hexahydro-pyrrolo[3.4.b]pyrrole-5-carboxylic acid t-butyl ester (I-3g):

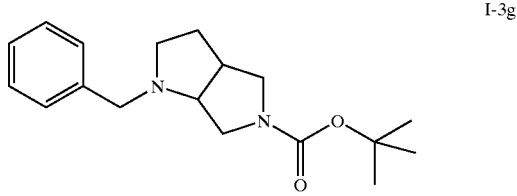

I-3g

A 250 mL, three-necked flask was fitted with a 125 mL addition funnel and a digital thermometer. To this flask was added 15.18 g (75 mmol) of 2-benzyl-2,7-diazabicyclo[3.3.0]octane (I-3f), 50 mL of water, and 31.2 mL (225 mmol) of triethylamine. This mixture was cooled to 0° C. via an ice bath, and 90 mL (90 mmol) of di-tert-butyl dicarbonate (1.0 M in tetrahydrofuran) was added dropwise over a 15 minute period while keeping the reaction temperature below 5° C. The reaction mixture was stirred at 0° C. for 2 hours. The reaction mixture was then concentrated in vacuo to remove the tetrahydrofuran. The residue was poured into 250 mL of saturated sodium bicarbonate and was extracted with 3×200 mL chloroform. The organic layers were combined, dried over sodium sulfate, filtered, and concentrated in vacuo to give a black oil (crude weight=24 grams). Product was purified by flash column chromatography (silica gel packed Biotage flash 75m) using a 0.5 to 2% methanol/chloroform solvent gradient. Purification yielded a light brown oil.

$^1$H NMR was consistent with product (I-3g). Mass spectrometry was consistent with product (I-3g). MH$^+$ is 303, FW=302.42. Yield: 16.2 grams (71% of theory).

Preparation of Hexahydro-pyrrolo[3.4-b]pyrrole-5-carboxylic Acid t-butyl ester (I-3 h):

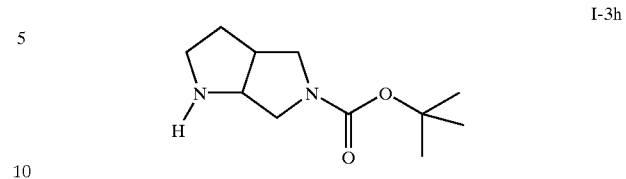

I-3h

To a 2.5 liter Parr shaker bottle, flushed with nitrogen, was added 4.05 grams (25 wt %) of palladium on activated carbon catalyst (10% Pd). Next was added 100 mL of ethanol, followed by a solution of 1-benzyl-hexahydro-pyrrolo[3,4,b]pyrrole-5-carboxylic acid tert-butyl ester I-3g (16.2 grams, 53.6 mmol) in 600 mL of ethanol. The reaction mixture was shaken under an atmosphere of hydrogen (45 psi or 0.3 MPa) for one day at room temp. Mass spectroscopy showed the reaction was incomplete so another 0.25 equivalent (4.05 grams) of palladium on carbon catalyst was added. The reaction mixture was then shaken under an atmosphere of hydrogen at room temperature for 3 days. Mass spectroscopy showed that the reaction was complete. The reaction mixture was then filtered through diatomaceous earth and the filtrate was concentrated in vacuo.

$^1$H NMR was consistent with product (I-3h). Mass spectrometry was consistent with product (I-3h). MH$^+$ is 213, FW=212.29. Yield: 11.25 grams

Preparation of 1-[(3-Trifluoromethyl-benzoylamino)-acetyl]-hexahydro-pyrrole-5-carboxylic acid tert-butyl ester (I-3i):

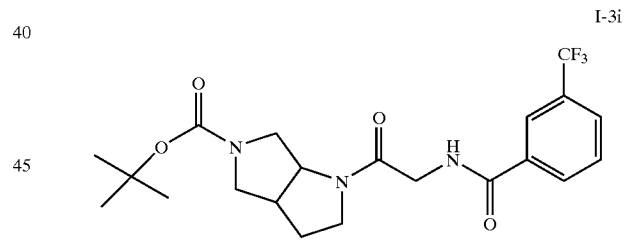

I-3i

Intermediate I-3h (72.7 mg, 0.342 mmoles) was dissolved in 5 mL anhydrous dichloromethane and 84.6 mg (0.342 mmoles) of {3-trifluoromethylbenzoylamino}-acetic acid was added. To this mixture at room temperature was then added 78.7 mg 1-(3-dimethylaminopropyl)-3-ethylcarbodiimide hydrochloride (0.41 mmoles). This mixture was stirred at room temperature for 16 hours. The dichloromethane was evaporated and the residue was dissolved in 5 mL EtOAc in a separatory funnel. This was then washed with 1×2 mL of 0.1 N NaOH, 1×2 mL 0.1N HCl and 1×2 mL brine. The ethyl acetate layer was dried over sodium sulfate, filtered and concentrated in vacuo to a hard pale yellow foam (120 mg, 0.272 mmoles, 79% yield.

H$^1$ NMR(CD$_3$OD) and MS (441) were consistent with product (I-3i).

Preparation of N-[2-(Hexahydro-pyrrolo[3,4-b]pyrrol-1-yl)-2-oxo-ethyl]-3-trifluoromethy-benzamide (I-3i):

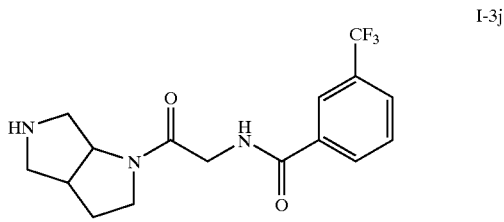

I-3j

Intermediate I-3i (120 mg, 0.272 mmoles) was dissolved in 1 mL dichloromethane and this was cooled in a wet-ice acetone bath and 0.5 mL of trifluoroacetic acid was added. This mixture was then stirred at room temperature for 20 minutes. The reaction mixture was then concentrated by evaporation and the residue was dissolved in 2 mL 2N HCl and this was washed with 2×1 mL ETOAc. The aqueous layer was made basic (pH=10) by adding 6N NaOH with ice bath cooling and the product was extracted into 2×2 mL ETOAc. The ETOAc layer was dried over anhydrous sodium sulfate and concentrated in vacuo to a clear pale yellow gum (90 mg, 0.263 mmoles, 97% yield).

$H^1$ NMR (CD$_3$OD) and MS (341) were consistent with compound I-3i.

Preparation of N-{2-[5-(2,4-Dimethylbenzyl)-hexahydro-pyrrolo[3,4-b]pyrrol-1-yl-2-oxo-ethyl}-3-trifluoromethyl-benzamide (3):

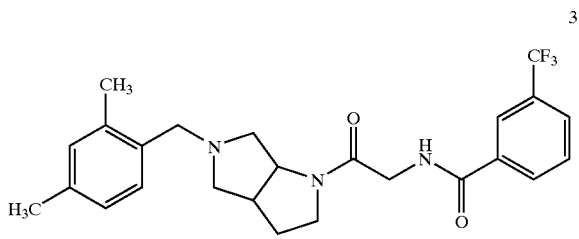

3

Intermediate I-3i (90 mg, 0.264 mmoles) was dissolved in 1.35 mL MeOH and then 106 mg (0.396 mmoles, 1.5 equivalents) of 2,4-dimethylbenzaldehyde was added and this mixture was stirred at room temperature for 16 hours. Then, 30 mg (0.792 mmoles, 3 equivalents) of sodium borohydride was added. This mixture was stirred at room temperature for 2 hours. The MeOH was evaporated and the residue was partitioned between 3 mL EtOAc and 1 mL 1N NaOH in a separatory funnel. The organic layer was separated and the aqueous layer was washed with 2×2 mL EtOAc. The EtOAc layers were combined, dried over sodium sulfate and concentrated in vacuo to a pale yellow gum. This gum was dissolved in 0.5 mL dichloromethane and charged onto a Biotage 12S cartridge and the column was eluted with the following gradient. 60 mL 5:1 EtOAc:hexanes, 60 mL 9:1 EtOAc:hexanes and finally 120 mL EtOAc. The fractions containing the desired product were combined and concentrated in vacuo to a hard white foam (70 mg, 0.152 mmoles, 58% yield).

$H^1$ NMR (CD$_3$OD) and MS (460) were consistent with the desired product (3). The enantiomers were separated using a Chiralpak™ AD column (5 cm×50 cm), 75 mL/min flow rate and an 85/15 ratio of heptanes/isopropyl alcohol. Enantiomer 3A had a retention time of 7.061 min. and enantiomer 3B at 8.567 min.

Example 4 illustrates the preparation of bicyclic diamine compounds of Formula I where w=1, x=1, y=1, z=0 (enantiomer: w=1, x=1, y=0, z=1) and the linking group (L) is an amino acid.

Example 4

Preparation of 3-(Benzyl-ethoxycarbonylmethylamino) propionic acid ethyl ester (I-4a):

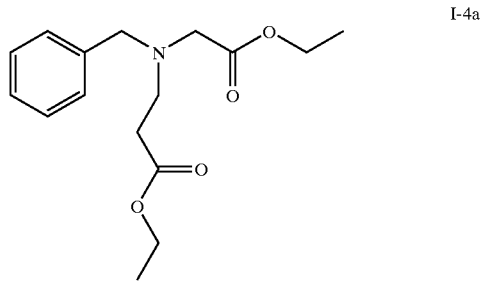

I-4a

Ethyl N-benzylglycinate (0.1295 mol, 1 eq), ethyl acrylate (0.142 mol, 1.1 eq) and 155 μL of Triton™ B (available from Sigma-Aldrich, St. Louis, Mo.) were combined at room temperature under N$_2$. The mixture was then heated to reflux overnight. An aliquot was removed and NMR spectrum was taken of the crude material. The product was present plus both starting materials. The excess of the ethyl acrylate was removed under vacuum at 10 mmHg (60° C. water bath). The crude amber oil that resulted was dissolved in 50 mL of CH$_2$Cl$_2$ and was charge onto a Biotage™ 75L cartridge and eluted with the following gradient 0.5% by volume acetone in hexanes, 1% (1200 mL), 1.5% (1200 mL) and 2.5% (3600 mL). The fractions containing the desired product were combined and concentrated to a colorless oil which was dried under high vacuum for 2 hours to afford 29 g (76%) of product (I-4a). $^1$H NMR spectrum (CDCl$_3$) and LC/MS (294) were consistent with the compound I-4a.

Preparation of 1-Benzyl-4-oxo-pyrrolidine-3-carboxylic acid ethyl ester (I-4b):

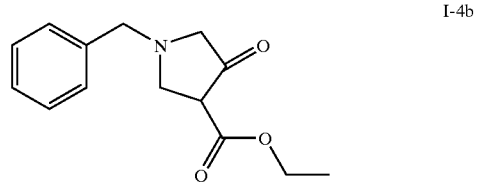

I-4b

Potassium t-butoxide (0.099 mol, 11.1 g, 1 eq) was slurried in 100 mL of anhydrous toluene under N$_2$. The slurry was cooled to 5° C. and intermediate I-4a (0.099 mol, 29 g, 1 eq) in 50 mL of anhydrous toluene was added dropwise over a 2 hour period maintaining the temperature below 10° C. The reaction mixture was allowed to warm to room temperature over a period of 3 hours. The mixture was cooled to 0° C. and 100 mL of water was added in 5 mL portions over a period of 2 hours. The solution was placed in a separation funnel and 100 mL of 1 N NaOH was added. The organic layer was separated and washed with 4×100 mL of water. The aqueous layers were combined and extracted with 100 mL of EtOAc. During this first extraction a white solid began to precipitate out of the organic layer. This solid was filtered and dried under high vacuum overnight affording 7.96 g (32%).

$^1$H NMR spectrum on 5 mg of the residue and LC/MS (248) were consistent with the structure for compound I-4b.

Preparation of 1-Benzyl-4-hydroxymethyl-pyrrolidin-3-ol (I-4c):

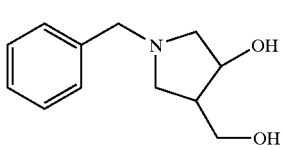

I-4c

Intermediate I-4b (0.0162 mol, 4.0 g, 1eq) was dissolved in 60 mL of MeOH and the cooled to 0° C. NaBH₄ (0.0971, 3.67 g, 6 eq) was added in 250 mg portions over an hour period. The mixture was warmed to room temperature and allowed to stir overnight. The MeOH was removed in vacuo and the residue was taken up in EtOAc (60 mL) and 2N NaOH (20 mL). The mixture was shaken for approximately 2 to 3 minutes in a separation funnel. The organic phase was separated and the aqueous phase was washed with 2×50 mL more EtOAc. The organic layers were combined, dried over sodium sulfate and concentrated in vacuo to a pale yellow oil which was placed under high vacuum for 2 hours to afford a clear pale yellow gum 2.06 g (65%).

¹H NMR spectrum (CD₃OD) and LC/MS (208) was consistent with the desired product (I-4c).

Preparation of Methanesulfonic Acid 1-benzyl-4-methanesulfonylmethyl-pyrrolidine-3-yl ester-trans isomer (I-4d):

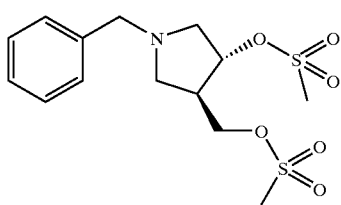

I-4d

Intermediate I-4c (0.00995 mol, 2.06 g, 1 eq) was dissolved in 30 mL of CH₂Cl₂ and TEA (0.0248 mol, 3.45 mL, 2.5 eq) was added. This solution was cooled to 0° C. and methane sulfonyl chloride was added dropwise over a 30 minute period. The mixture was allowed to warm to room temperature and was stirred vigorously for 2 hours. The reaction mixture was then concentrated to dryness, taken up in 100 mL of EtOAc and washed with 2×25 mL of 1 N NaOH and 25 mL of brine. The organic layer was dried over sodium sulfate and concentrated in vacuo to a dark brown gum. The crude product was dissolved in 7 mL of CH₂Cl₂ and this was charge onto a Biotage 40 M cartridge and eluted with the following gradient: 2.5% by volume EtOAc in CH₂Cl₂ (200 mL), 5% (200 mL), 7.5% (200 mL), 10% (200 mL) 15% (200 mL), 20% (200 mL), 25% (200 mL), 33% (400 mL). Fractions were collected in succession and fractions containing the trans isomer (confirmed by TLC and NMR spectroscopy) were combined and concentrated in vacuo to a clear very pale brown gum. The gum was dried overnight under high vacuum.

¹H NMR spectrum (CD₃OD) confirmed the presence of the desired product (I-4d): Yield; 1.98 g (55%).

Preparation of methane sulfonic acid 4-azidomethyl-1-benzyl-pyrrolidine-3-yl ester (I-4e):

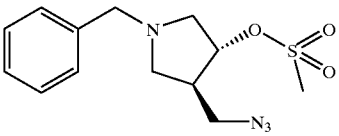

I-4e

Intermediate I-4d (0.00545 moles, 1.98 g) and 30 mL of DMF were combined. Then sodium azide (0.00545 moles, 354 mg) was added in 25 mg portions over a 1 hour period. The mixture was stirred at room temperature for 82 hours. TLC (hexanes-acetones, 2:1, two passes) indicated complete conversion to the less polar product. The reaction mixture was placed in a separation funnel, diluted with 900 mL EtOAc and this solution was washed with 9×50 mL H₂O. The organic layer was dried over anhydrous sodium sulfate and concentrated in vacuo to a clear pale yellow gum. This was dried under high vacuum overnight affording 1.67 g (98%). The ¹H NMR spectrum and LC/MS (311) were consistent with the structure for compound I-4e.

Preparation of methane sulfonic acid-4-aminomethyl-1-benzyl-pyrrolidine-3-yl ester (I-4f):

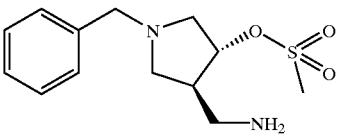

I-4f

In a Parr bottle were mixed intermediate I-4e (0.00506 mol, 1.5 g), PtO₂ (157 mg) and MeOH (23.5 mL) and agitated at 2 psi (0.01 MPa) H₂ for 30 minutes. Thin layer chromatography (CH₂Cl₂-EtOAc 2:1 with 3% diethylamine) indicated less polar impurity, no starting material and a single more polar spot at Rf 0.1. The reaction mixture was filtered through Celite™ and the pad was washed with 6×30 mL of MeOH. The filtrate was concentrated in vacuo to a clear pale yellow gum that contains more polar impurity by thin layer chromatography (TLC) and LC/MS. The crude product was dissolved in 7 mL of THF and charged onto a Biotage™ 40M cartridge and eluted with the following solvent gradient: CH₂Cl₂-EtOAc 2:1 (600 mL), with 5% diethylamine (200 mL), CH₂Cl₂-EtOAc 1:1 with 5% diethylamine (200 mL), 2:1 EtOAc-CH₂Cl₂ with 5% diethylamine (200 mL), EtOAc-MeOH 3:1 with 5% diethylamine (200 mL), EtOAc-MeOH 2:1 with 5% diethylamine (600 mL). The fractions containing the desired product were combined and concentrated in vacuo to a clear colorless gum, which was dried under high vacuum overnight affording 860 mg (60%) of compound I-4f.

¹H NMR and LC/MS (284) were consistent with the structure for compound I-4f.

Preparation of 3-benzyl-3,6-diazabicyclo[3.2.0]heptane (I-4g):

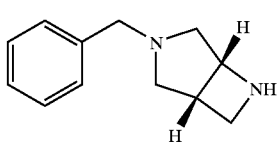

Intermediate I-4f (350 mg) was refluxed in 1,4-dioxane for 2 hrs. MS (188) and ¹H NMR (CD₃OD) indicated product present plus side product impurities. Due to the extreme polarity of the product, the crude material was taken on as is. Approximately 35 mg (10% yield).

Preparation of N-[2-(3-benzyl-3,6-diazabicyclo[3.2.0]hept-6-yl)-2-oxo-ethyl]-3-trifluoromethyl-benzamide (4A):

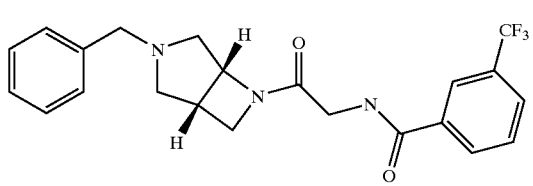

35 mg (0.186 mmoles) of intermediate I-4g was dissolved in 0.53 mL of CH₂Cl₂ in a 1 dram micro reaction vial fitted with a magnetic stir bar. To this solution was then added 46 mg (0.186 mmoles) of (3-trifluoromethylbenzoyl-amino)-acetic acid and then 43 mg (0.223 mmoles, 1.2 equivalents) of 1-(3-dimethylaminopropyl)-3-ethylcarbodiimide hydrochloride. The mixture was stirred at room temperature for 16 hours. The dichloromethane was removed in vacuo and the residue was taken up into 4 mL ethyl acetate and washed with 0.5 mL 0.1N NaOH and 0.5 mL brine. The organic layer was dried over anhydrous sodium sulfate and then concentrated in vacuo to a clear pale yellow gum. The gum was dissolved in 0.5 mL dichloromethane and charged onto a Biotage™ 12S cartridge. The column was eluted with ethyl acetate:hexanes 9:1 (50 mL), ethyl acetate:hexanes 5:1 (50 mL) and ethyl acetate 200 mL. The fractions containing the desired product were combined and concentrated in vacuo to a clear colorless gum (25 mg, 33% yield).

¹H NMR spectrum (CD₃OD) and LC/MS (417) were consistent with the structure for compound 4A.

Compound 4A can be further modified to produce other compounds of Formula (I) using the following general procedures.

Preparation of N-[2-(3,6-diazabicyclo[3.2.0]hept-6-yl)-2-oxo-ethyl]-3-trifluoromethyl-benzamide (I-4h):

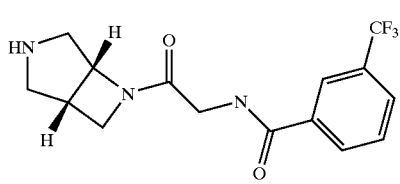

Compound 4A (25 mg) was dissolved in 0.5 mL methanol in a 125 mL Parr bottle. Then 2 mL of 0.1 N aqueous hydrochloric acid, 1 drop of 6N aqueous hydrochloric acid and 5 mg of 10% Pd/C (50% water wet) were added. This mixture was agitated under 3 psi (0.02 MPa) H₂ for 14 hours. The reaction mixture was filtered through Celite™ and the pad was washed with 3×10 mL portions of methanol. The filtrate was concentrated in vacuo to dryness and the residue was taken up into 5 mL 1 N hydrochloric acid and was washed with 2×3 mL ethyl acetate. The aqueous layer was made basic (pH=10) and washed with 3×5 mL ethyl acetate. The organic layers were dried over anhydrous sodium sulfate and concentrated in vacuo to a colorless gum (9 mg, 50% yield).

¹H NMR spectrum (CD₃OD) and MS (327) were consistent with compound I-4h.

Preparation of N{2[3−2,4-dimethyl-benzyl)-3,6-diazabicyclo[3.2.0]hept-6-yl])-2-oxo-ethyl}-3-trifluoromethyl-benzamide (4B):

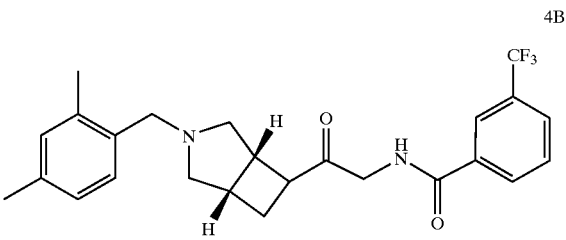

Intermediate I-4h (9 mg, 0.0275 mmoles) was dissolved in 0.25 mL of methanol and then 5.5 mg (0.041 mmoles, 1.5 equivalents) of 2,4-dimethylbenzaldehyde was added at room temperature under a nitrogen atmosphere. This mixture was stirred for 16 hours. Then 3 mg of sodium borohydride was added and the mixture was stirred at room temperature for 1.5 hours. The methanol was evaporated and the residue was partitioned between 3 mL ethyl acetate and 0.75 mL 1N NaOH. The layers were separated and the aqueous was washed with 3×2 mL ethyl acetate. The organic layers were combined, dried over anhydrous sodium sulfate and concentrated in vacuo to a clear pale yellow gum (10 mg). The crude product was separated using a Biotage™ 12S cartridge with the following solvent gradient EtOAc:hexanes (5:1, 40 mL), EtOAc:hexanes 9:1(40 mL) and EtOAc 100 mL. The product was isolated in the latter fractions (2.1 mg, 0.00472 mmoles, 17% yield).

¹H NMR spectrum (CD₃OD) and MS (445) were consistent with the structure for compound 4B.

Biological Assays

The utility of the compounds of Formula (I), the stereoisomers and prodrugs thereof, and the pharmaceutically acceptable salts of the compounds, stereoisomers, and prodrugs in the practice of the instant invention, can be evidenced by activity in at least one of the protocols described hereinbelow.

Chemotaxis Activity

Chemotaxis activity of the compounds of the present invention can be determined by the amount of monocytes that migrate in response to the chemoattractant MCP-1 relative to control, in THP-1 cells. THP-1 monocytes are rinsed 2 times with PBS and then suspended at a concentration of 1.0×10⁶ cells/mL in chemotaxis buffer consisting of RPMI 1640 medium supplemented with 0.1% BSA. Three microliters of MCP-1 (available from Peprotech, Inc. Rocky Hill, N.J.) is added to the lower chamber of a 48-well microchemotaxis Boyden chamber at a concentration of 10 nM in chemotaxis buffer (RPMI Medium available from Gibco, Rockville, Md., 0.10% BSA (Bovine Serum Albumin available from Sigma, St. Louis, Mo.), endotoxin free).

Three microliters of the compound diluted in chemotaxis buffer are then added to appropriate wells at concentrations of 10, 1, 0.1 and 0.01 μM. Chemotaxis buffer (23 μL) is added to the wells for a final volume of 29 μL/well. The cell suspension (45 μL) is added to the upper chamber, which is separated from the lower chamber by a 5-μm-pore-size polycarbonate membrane (Poretics™ available from Osmonics, Inc. Livermore, Calif.). After incubation for 1 hour at 37° C. in a 5% $CO_2$ atmosphere, the side of the polycarbonate membrane in contact with the cell suspension is scraped and washed to remove any cells. After fixation, the migrated cells adhering to the underside of the membrane facing the chemoattractant are stained with thiazine dye mixture (Diff-Quik Stain Set available from Dade Behring, Inc. Newark, Del.). The number of cells that migrate through the filter is determined by counting the cells in 20× fields under a microscope. Chemotaxis induced by MCP-1 without compound is considered the positive control.

The effect of these compounds to inhibit integrin expression is determined using whole human blood. Human peripheral blood is collected by venipuncture into EDTA Vacutainer tubes. NUNC Minisorp tubes (12×75 mm) (available from Nalge Nunc Interantional Naperville, Ill.) containing 400 μL blood and 40 μL of PBS (Dulbecco's phopshate buffered saline available from Gibco, Rockville, Md.) supplemented with 0.2% BSA, pH 7.4 or compound diluted in PBS/BSA at concentrations of 10, 1, 0.1 and 0.01 μM are placed in a 37° C. water bath for 5 minutes. MCP-1 (20 μL) is added to a second set of NUNC Minisorp tubes (12×75 mm) at a final concentration of $10^{-9}$M and placed in a 37° C. water bath. The blood is gently mixed and 200 μL added to the second set of tubes containing MCP-1. After incubation for 15 minutes at 37° C. the tubes are removed from the water bath and placed in an ice water bath. The cells are washed with PBS supplemented with 2% FBS and 0.2% sodium azide, then centrifuged at 1000×g for 10 minutes at 4° C. The supernatant is aspirated, and cells resuspended by gently shaking tubes, followed by the addition of 10 μL heat aggregated (HA) IgG (1 mg HA IgG/mL PBS-wash) (available from Jackson ImmunoResearch Lab, West Grove, Pa.) to each tube. After incubating the tubes for 10 minutes at 4° C., 20 μL mouse IgG1 FITC is added to appropriate tubes (Isotype Controls); 20 μL CD11b FITC antibody (available from CALTAG Lab, Burlingame, Calif.) is added to appropriate tubes (Compound effect) and 20 μL Anti-CD14-PE (available from PharMingen, San Diego, Calif.) is added to all tubes. After mixing gently by shaking, the samples are shielded from direct light and samples incubated for 30 minutes at 4° C. Samples are then washed 1× with PBS, supernatant aspirated and 1.5 mL of FACS Brand Lysing solution (available from Becton Dickinson Immunocytometry Systems, San Jose, Calif.) added to all tubes. After an incubation at room temperature for 10 minutes (vortex every 5 minutes for complete RBC lysis), cells are centrifuged, supernatant aspirated and washed 2× with PBS wash buffer. Cells are then resuspended in 0.5 mL of 0.5% Paraformaldehyde and vortexed immediately. Samples can then be stored at 4° C. up to one week before quantitation of fluorescent staining of CD11b by flow cytometry.

In Vivo Atherosclerosis Assay

Anti-atherosclerotic effects of the compounds can be determined by the amount of compound required to reduce the lipid deposition in rabbit aorta. Male New Zealand White rabbits are fed a diet containing 0.2% cholesterol and 10% coconut oil for 4 days (meal-fed once per day). Rabbits are bled from the marginal ear vein and total plasma cholesterol values are determined from these samples. The rabbits are then assigned to treatment groups so that each group has a similar mean±SD for total plasma cholesterol concentration, HDL cholesterol concentration and triglyceride concentration. After group assignment, rabbits are dosed daily with compound given as a dietary admix or on a small piece of gelatin based confection. Control rabbits receive only the dosing vehicle, be it the food or the gelatin confection. The cholesterol/coconut oil diet is continued along with the compound administration throughout the study. Plasma cholesterol, HDL-cholesterol, LDL cholesterol and triglyceride values can be determined at any point during the study by obtaining blood from the marginal ear vein. After 3–5 months, the rabbits are sacrificed and the aortae are removed from the thoracic arch to the branch of the iliac arteries. The aortae are cleaned of adventitia, opened longitudinally and then stained with Sudan IV as described by Holman et. al. (*Lab. Invest.*, 7, 42–47 (1958)). The percent of the surface area stained is quantitated by densitometry using an Optimas Image Analyzing System (Image Processing Solutions; North Reading Mass.). Reduced lipid deposition is indicated by a reduction in the percent surface area stained in the compound-receiving group in comparison with the control rabbits.

Inhibtion of Eotaxin Binding to its Receptor

The inhibition of eotaxin binding to its receptor is done in whole cells containing buffer medium: RPMI 1640 with L-glutamine, 10 mM HEPES, 1% penicillin/streptomycin, 0.5% FBS (available from GIBCO, Rockville, Md.) in 96 well polypropylene U-bottom plates (available from Falcon, Franklin Lakes, N.J.) in a volume of 95 μL buffer/well. Log dilutions of compounds were made in DMSO, and 5 μL added per well in triplicate. Controls were 5 μL DMSO or 5 μL 10 μM recombinant human eotaxin (R&D Systems, Minneapolis, Minn.). $^{125}$I-Bolton-Hunter labeled eotaxin (100 μCi/mL, available from PerkinElmer, Boston, Mass.) diluted to 1 μCi/mL then 50 μL/well was added at a final concentration of 10–100 pM [$^{125}$I]eotaxin. Finally 100 μL of CCR3-expressed 300–19 cells were added. These murine pre-B cells, stably expressing human CCR3, were passed daily in culture medium: Hybridoma-SFM (serum free medium), 10% FBS, 2 mM L-glutamine, 1% penicillin/streptomycin, 0.4 mg/mL geneticin, 10 mM HEPES buffer solution, and 55 μM 2-mercaptoethanol (GIBCO). Cells were pelleted just before the assay then resuspended to 5e+6 cells/mL in binding buffer and 100 μL were added to each well. Final assay volume was 250 μL. Assay plates were incubated at room temperature for 2 hours. Cells were then harvested onto 96-well GF/B Unifilter plates (Unifilter-96Harvester, Packard Instrument Co., Meriden, Conn.) pre-soaked for 2 hours at RT in 0.3% polyethyleneimine and washed 4 times with 500 mM NaCl with 10 mM HEPES. The Unifilter plates were air-dried overnight at room temperature, followed by addition of scintillation cocktail microscinto (available from Packard Instrument Co.), then counted on a Top Count (available from Packard Instrument Co.).

In general, the compounds listed in the Examples provided CCR2 activity based on chemotaxis from about 5 to about 100% inhibition at 1 μM concentration. The compounds having the general Formula (1B) below provided higher activity for inhibition of binding to its CCR2 receptor and showed less activity for inhibition of binding to the CCR3 receptor. Whereas, compounds having the general Formula (1C) provided higher activity for inhibition of binding to the CCR3 receptor and less activity for binding to the CCR2 receptor.

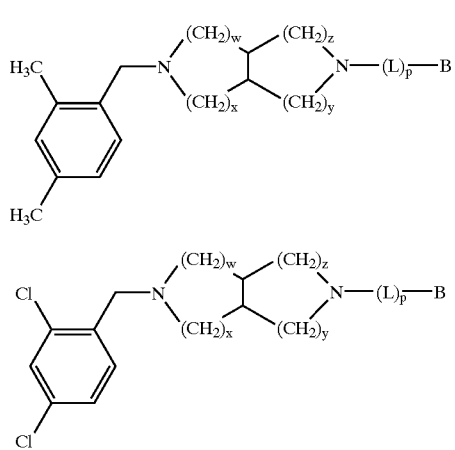

What is claimed is:
1. A compound of the formula (I)

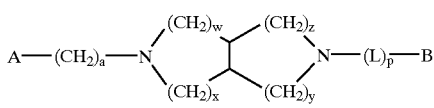

wherein

A is a substituted or unsubstituted ($C_1$–$C_6$)alkyl, substituted or unsubstituted ($C_2$–$C_6$)alkenyl, substituted or unsubstituted partially saturated or fully saturated ($C_3$–$C_6$)cycloalkyl, substituted or unsubstituted partially saturated or fully saturated 5 to 6 membered heterocyclic ring, substituted or unsubstituted aryl, or substituted or unsubstituted heteroaryl group;

a is 0, 1, 2 or 3;

w, x, y and z are each independently 0, 1 or 2 with the proviso that (i) w is not 0 when x is 0; (ii) y is not 0 when z is 0; (iii) x is not 0 when w is 1, y is 0 and z is 1; (iv) x is not 0 when w is 1, z is 0 and y is 1; (v) x is not 0 when y is 0; and (vi) w is not 0 when z is 0;

p is 0 or 1;

L is a linking group selected from the group consisting of —($CH_2$)$_q$—X—, where X is NH, O, or oxo and q is an integer from 1 to 4, —S(O)$_r$—($CH_2$)$_t$—NH—, where r is 0, 1 or 2 and t is an integer from 1 to 4, —(aryl)-NH—, -(heteroaryl)-NH—, and an amino acid residue whree the amino nitrogen of said amino acid residue is attached to B and the carbonyl of said amino acid residue is attached to the ring nitrogen; and B is a substituted or unsubstituted ($C_1$–$C_6$)alkylcarbonyl, substituted or unsubstituted arylcarbonyl, substituted or unsubstituted ($C_1$–$C_6$)alkoxycarbonyl, substituted or unsubstituted aryloxycarbonyl, substituted or unsubstituted ($C_1$–$C_6$)alkylsulfonyl, substituted or unsubstituted arylsulfonyl, substituted or unsubstituted ($C_1$–$C_6$) alkylsulfonyl, substituted or unsubstituted arylsulfonyl, substituted or unsubstituted ($C_1$–$C_6$)alkylthiocarbonyl, substituted or unsubstituted arylthiocarbonyl, substituted or unsubstituted ($C_1$–$C_6$)alkylcarbamoyl, substituted or unsubstituted arylcarbamoyl, substituted or unsubstituted ($C_1$–$C_6$)alkyl-C(=NH)—, substituted or unsubstituted aryl-C(=NH)—, or a protecting group;

a prodrug thereof, or a pharmaceutically acceptable salt, hydrate, or solvate of the compoundor the prodrug.

2. The compound of claim 1 wherein L is an amino acid residue of the formula

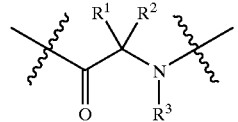

where the α-amino nitrogen of said amino acid residue is attached to B, $R^1$ and $R^2$ are each independently ydrogen, substituted or unsubstituted ($C_1$–$C_6$)alkyl, substituted or unsubstituted ($C_2$–$C_6$)alkenyl, substituted or unsubstituted partially saturated or fully saturated ($C_3$–$C_6$)cycloalkyl, substituted or unsutstituted partially saturated or fully saturated 5 to 6 membered heterocyclic ring, substituted or unsubstituted aryl, or substituted or unsubstituted heteroaryl group; or $R_1$ or $R^2$ is taken together with $R^3$ to form a 5 to 6 membered ring; or $R^1$ and $R^2$ are taken together to form a 3 to 6 membered ring; and $R^3$ is hydrogen, taken together with a substituent of B forms a substituted or unsubstituted five or six membered partially saturated or fully saturated heterocyclic ring, or taken together with $R^1$ or $R^2$ forms a 5 to 6 membered ring;

a prodrug thereof, or a pharmaceutically acceptable salt, hydrate or solvate of said compound or said prodrug.

3. A compound of the formula (IA):

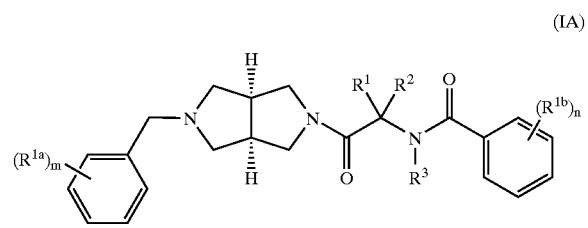

wherein $R^{1a}$ for each occurrence is independently hydrogen, halo, ($C_1$–$C_6$)alkyl, ($C_1$–$C_6$)alkoxy, aryl($C_1$–$C_6$)alkoxy, or two adjacent $R^{1a}$ groups taken together form a substituted unsubstituted carboxylic, heterocyclic, aromatic or heteroaromatic 5 to 6 membered fused ring;

m is 0, 1, 2, 3, 4, or 5;

$R^1$ and $R^2$ are independently hydrogen, ($C_1$–$C_6$)alkyl, or aryl($C_1$–$C_6$)alkyl, or $R^1$ and $R^2$ are taken together to form a three- or six-membered ring, $R^1$ or $R^2$ are taken together with $R^3$ to form a five to six membered ring;

$R^3$ is hydrogen, taken together with $R^{1b}$ forms a substituted or unsubstituted five or six membered partially saturated or fully saturated heterocyclic ring, or taken together with $R^1$ or $R^2$ form a five to six membered ring;

$R^{1b}$ for each occurrence is independently hydrogen, halo, ($C_1$–$C_6$)alkyl, halo($C_1$–$C_6$)alkyl, ($C_1$–$C_6$)alkoxy, halo ($C_1$–$C_6$)alkoxy, amino, amido, nitro, aryloxy, ($C_1$–$C_6$) alkylthio, taken together with $R^3$ forms a substituted or unsubstituted five or six membered partially saturated or fully saturated heterocyclic ring, or two adjacent $R_{1b}$ substituents taken together form a heteroaromatic 5 to 6 membered fused ring; and n is 0, 1, 2, 3, 4, or 5;

a prodrug thereof, or a pharmaceutically acceptable salt, hydrate, or solvate of the compound or the prodrug.

4. The compound of claim 3 wherein $R^{1a}$ is methyl or chloro; m is 2; $R^1$ is hydrogen; $R^2$ is hydrogen; $R^3$ is hydrogen; $R^{1b}$ is methyl, trifluoromethyl, amino, iodo, bromo, chloro or nitro; and n is 1 or 2;

a prodrug thereof, or a pharmaceutically acceptable salt, hydrate, or solvate of the compound or the prodrug.

5. A compound selected from the group consisting of

N-{2-[5-(2,4-dimethyl-benzyl)-hexahydro-pyrrolo[3,4-c]pyrrol-2-yl]-2-oxo-ethyl}-3-triflouromethyl-benzamide;

2-amino-N-{2-[5-(2,4-dimethyl-benzyl)-hexahydro-pyrrolo[3,4-c]pyrrol-2-yl]-2-oxo-ethyl}-5-nitro-benzamide;

2-amino-N-{2-[5-(2,4-dimethyl-benzyl)-hexahydro-pyrrolo[3,4-c]pyrrol-2-yl]-2-oxo-ethyl}-5-iodo-benzamide;

2-amino-5-bromo-N-{2-[5-(2,4-dimethyl-benzyl)-hexahydro-pyrrolo[3,4-c]pyrrol-2-yl]-2-oxo-ethyl}benzylamide;

3-bromo-4-chloro-N-{2-[5-(2,4-dimethyl-benzyl)-hexahydro-pyrrolo[3,4-c]pyrrol-2-yl]-2-oxo-ethyl}-benzamide;

3,4-dichloro-N-{2-[5-(2,4-dimethyl-benzyl)-hexahydro-pyrrolo[3,4-c]pyrrol-2-yl]-2-oxo-ethyl}-benzamide;

3-chloro-N-{2-[5-(2,4-dichloro-benzyl)-hexahydro-pyrrolo[3,4-c]pyrrol-2-yl-2-oxo-ethyl}-4-fluoro-benzamide;

3,4-dichloro-N-{2-[5-(2,4-dichloro-benzyl)-hexahydro-pyrrolo[3,4-c]pyrrol-2-yl]-2-oxo-ethyl}-benzamide;

3-bromo-4-chloro-N-{2-[5-(2,4-dichloro-benzyl)-hexahydro-pyrrolo[3,4-c]pyrrol-2-yl]-2-oxo-ethyl}-benzamide;

3-bromo-N-{2-[5-(2,4-dichloro-benzyl)-hexahydro-pyrrolo[3,4-c]pyrrol-2-yl]-2-oxo-ethyl}-benzamide; and 3-chloro-N-{2-[5-(2,4-dichloro-benzyl)-hexahydro-pyrrolo[3,4-c]pyrrol-2-yl]-2-oxo-ethyl}-benzamide;

a prodrug thereof, or a pharmaceutically acceptable salt, hydrate, or solvate of said compound or said prodrug.

6. A pharmaceutical composition comprising a compound of claim 1, a prodrug thereof, or a pharmaceutically acceptable salt, hydrate or solvate of said compound or said prodrug and a pharmaceutically acceptable excipient, diluent or carrier.

7. The pharmaceutical composition of claim 6 wherein said compound, a prodrug thereof, or pharmaceutically acceptable salt, hydrate or solvate of said compound or said prodrug is present in a therapeutically effective amount for the treatment of a disease associated with monocyte accumulation, lymphocyte accumulation or both.

8. The pharmaceutical composition of claim 6 wherein said compound, a prodrug thereof, or pharmaceutically acceptable salt, hydrate or solvate of said compound or said prodrug is present in a therapeutically effective amount for the treatment of a disease associated with leucocyte accumulation.

9. A method for treating a disease associated with monocyte accumulation, lymphocyte accumulation or leucocyte accumulation wherein said disease is atherosclerosis, restenosis, gingivitis, psoriasis, rheumatoid arthritis, glomerulonephritis, wound healing, Crohn's disease, chronic inflammatory disease, encephalomyelitis or transplant rejection, said method comprising the step of administering a therapeutically effective amount of a compound of claim 1, a prodrug thereof, or pharmaceutically acceptable salt, hydrate or solvate of said compound or said prodrug to an animal in need thereof.

10. The method of claim 9 wherein said disease is atherosclerosis.

11. The method of claim 9 or 10 wherein said compound is a compound of Formula 1B

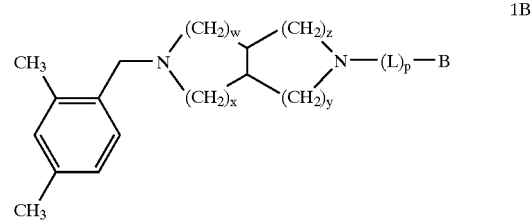

where w, x, y and z are each independently 0, 1 or 2 with the proviso that (i) w is not 0 when x is 0; (ii) y is not 0 when z is 0; (iii) x is not 0 when w is 1, y is 0 and z is 1; (iv) x is not 0 when w is 1, z is 0 and y is 1; (v) x is not 0 when y is 0; and (vi) w is not 0 when z is 0;

p is 0 or 1;

L is a linking group selected from the group consisting of —$(CH_2)_g$—X—, where X is NH, O, or oxo and g is an integer from 1 to 4, —$S(O)_r$—$(CH_2)_t$—NH—, where r is 0, 1 or 2 and t is an integer from 1 to 4, -(aryl)-NH—, -(heteroaryl)-NH—, and an amino acid residue whree the amino nitrogen of said amino acid residue is attached to B and the carbonyl of said amino acid residue is attached to the ring nitrogen; and B is a substituted or unsubstituted $(C_1-C_6)$alkylcarbonyl, substituted or unsubstituted arylcarbonyl, substituted or unsubstituted $(C_1-C_6)$alkoxycarbonyl, substituted or unsubstituted aryloxycarbonyl, substituted or unsubstituted $(C_1-C_6)$alkylsulfonyl, substituted or unsubstituted arylsulfonyl, substituted or unsubstituted $(C_1-C_6)$ alkylsulfonyl, substituted or unsubstituted arylsulfonyl, substituted or unsubstituted $(C_1-C_6)$alkylthiocarbonyl, substituted or unsubstituted arylthiocarbonyl, substituted or unsubstituted $(C_1-C_6)$alkylcarbamoyl, substituted or unsubstituted arylcarbonyl, substituted or unsubstituted $(C_1-C_6)$alkyl-C(=NH)—, substituted or unsubstituted aryl-C(=NH)—, or a protecting group;

a prodrug thereof, or a pharmaceutically acceptable salt, hydrate or solvate of said compound or said prodrug.

12. The method of claim 11 wherein said compound is selected from the group consisting of N-{2-[5-(2,4-dimethyl-benzyl)-hexahydro-pyrrolo[3,4-c]pyrrol-2-yl]-2-oxo-ethyl}-3-trifluoromethyl-benzamide;

2-amino-N-{2-[5-(2,4-dimethyl-benzyl)-hexahydro-pyrrolo[3,4-c]pyrrol-2-yl]-2-oxo-ethyl}-5-nitro-benzamide;

2-amino-N-{2-[5-(2,4-dimethyl-benzyl)-hexahydro-pyrrolo[3,4-c]pyrrol-2-yl]-2-oxo-ethyl}-5-iodo-benzamide;

2-amino-5-bromo-N-{2-[5-(2,4-dimethyl-benzyl)-hexahydro-pyrrolo[3,4-c]pyrrol-2-yl]-2-oxo-ethyl}-benzamide;

3,4-dichloro-N-{2-[5-(2,4-dimethyl-benzyl)-hexahydro-pyrrolo[3,4-c]pyrrol-2-yl]-2-oxo-ethyl}-benzamide;

3-bromo-4-chloro-N-{2-[5-(2,4-dimethyl-benzyl)-hexahydro-pyrrolo[3,4-c]pyrrol-2-yl]-2-oxo-ethyl}-benzamide;

a prodrug thereof, or a pharmaceutically acceptable salt, hydrate or solvate of said compound or said prodrug.

13. The method of claim 9 wherein said disease is a chronic inflammatory disease.

14. The method of claim 13 wherein said chronic inflammatory disease is selected from the group consisting If allergic rhinitis, eczema and atopic dermatitis.

15. The method of claim 13 or 14 wherein said compound is a compound of Formula 1C

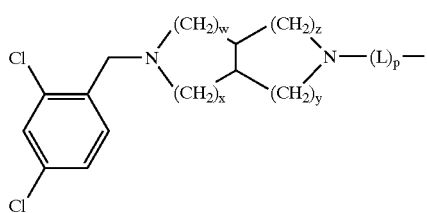

where x, y, w, z, L, p, and B are as defined in claim 1; a prodrug thereof, or a pharmaceutically acceptable salt, hydrate or solvate of said compound or said prodrug.

16. The method of claim 1 wherein said compound is selected from the group consisting of 3,4-dichloro-N-{2-[5-(2,4-dichloro-benzyl)-hexahydro-pyrrolo[3,4-c]pyrrol-2-yl]-2-oxo-ethyl}-benzamide;

3-bromo-4-chloro-N-{2-[5-(2,4-dichloro-benzyl)-hexahydro-pyrrolo[3,4-c]pyrrol-2-yl]-2-oxo-ethyl}-benzamide;

3-bromo-N-{2-[5-(2,4-dichloro-benzyl)-hexahydro-pyrrolo[3,4-c]pyrrol-2-yl]-2-oxo-ethyl}-benzamide;

3-chloro-N-{2-[5-(2,4-dichloro-benzyl)-hexahydro-pyrrolo[3,4-c]pyrrol-2-yl]-2-oxo-ethyl}-benzamide;

3-chloro-N-{2-[5-(2,4-dichloro-benzyl)-hexahydro-pyrrolo[3,4-c]pyrrol-2-yl]-2-oxo-ethyl}-4-fluoro-benzamide;

a prodrug thereof, or a pharmaceutically acceptable salt, hydrate or solvate of said compound or said prodrug.

17. A pharmaceutical kit comprising a) a suitable dosage form comprising a compound of claim 1, a prodrug thereof, or a pharmaceutically acceptable salt, hydrate or solvate of said compound or said prodrug; and b) instructions describing a method of using the dosage form to treat a disease associated with monocyte accumulation, lymphocyte accumulation or leucocyte accumulation.

18. A pharmaceutical combination comprising a compound of claim 1, a prodrug thereof, or a pharmaceutically acceptable salt, hydrate or solvate of said compound or said prodrug and at least one other pharmaceutical agent selected from the group consisting of a nutraceutical, a cholesterol absorption inhibitor, a HMG-CoA reductase inhibitor, a MTP/Apo B secretion inhibitor, a HMG-CoA synthase inhibitor, a HMG-CoA reductase transcription inhibitor, a HMG-CoA reductase translation inhibitor, a CETP inhibitor, a squalene synthetase inhibitor, a squalene epoxidase inhibitor, a squalene cyclase inhibitor, an ACAT inhibitor, a lipase inhibitor, a peroxisome proliferator-activated receptor agonist, a nonsteroidal anti-inflammatory drug and a COX-2 inhibitor.

19. A pharmaceutical kit comprising:
a) a compound of claim 1, a prodrug thereof, or a pharmaceutically acceptable salt, solvate, or hydrate of said compound or said prodrug, and a pharmaceutically acceptable carrier, excipient or diluent in a first unit dosage form;
b) a pharmaceutical agent selected from the group consisting of a nutraceutical, a cholesterol absorption inhibitor, a HMG-CoA reductase inhibitor, a MTP/Apo B secretion inhibitor, a HMG-CoA synthase inhibitor, a HMG-CoA reductase transcription inhibitor, a HMG-CoA reductase translation inhibitor, a CETP inhibitor, a squalene synthetase inhibitor, a squalene epoxidase inhibitor, a squalene cyclase inhibitor, an ACAT inhibitor, a lipase inhibitor, a peroxisome proliferator-activated receptor agonist, a nonsteroidal anti-inflammatory drug and a COX-2 inhibitor, and a pharmaceutically acceptable carrier, excipient or diluent in a second unit dosage form; and
c) a container.

20. A method for treating a disease associated with monocyte accumulation, lymphocyte accumulation or leucocyte accumulation wherein said disease is atherosclerosis, restenosis, gingivitis, psoriasis, rheumatoid arthritis, glomerulonephritis, wound healing, Crohn's disease, encephalomyelitis or transplant rejection, said method comprising administering to a mammal in need of such treatment
a) a therapeutically effective amount of a compound of claim 1, a prodrug thereof, or a pharmaceutically acceptable salt, solvate, or hydrate of said compound or said prodrug; and
b) a therapeutically effective amount of at least one pharmaceutical agent selected from the group consisting of a a nutraceutical, a cholesterol absorption inhibitor, a HMG-CoA reductase inhibitor, a MTP/Apo B secretion inhibitor, a HMG-CoA synthase inhibitor, a HMG-CoA reductase transcription inhibitor, a HMG-CoA reductase translation inhibitor, a CETP inhibitor, a squalene synthetase inhibitor, a squalene epoxidase inhibitor, a squalene cyclase inhibitor, an ACAT inhibitor, a lipase inhibitor, a peroxisome proliferator-activated receptor agonist, a nonsteroidal anti-inflammatory drug and a COX-2 inhibitor.

21. The method of claim 20 wherein said compound, prodrug thereof, or pharmaceutically acceptable salt, hydrate or solvate of said compound or said prodrug, and said pharmaceutical agent is administered simultaneously.

22. The method of claim 20 wherein said compound, prodrug thereof, or pharmaceutically acceptable salt, hydrate or solvate of said compound or said prodrug, and said pharmaceutical agent is administered sequentially.

23. The method of claim 20 wherein said compound, prodrug thereof, or pharmaceutically acceptable salt, hydrate or solvate of said compound or said prodrug, and said pharmaceutical agent is administered as a single pharmaceutical composition comprising said compound of claim 1, prodrug thereof, or pharmaceutically acceptable salt, hydrate or solvate of said compound or said prodrug, said pharmaceutical agent, and a pharmaceutically acceptable excipient, diluent, carrier or mixtures thereof.

24. The method of claim 20 wherein said compound, prodrug thereof, or pharmaceutically acceptable salt, hydrate or solvate of said compound or said prodrug, and said pharmaceutical agent is administered as two separate pharmaceutical compositions comprising (i) a first composition comprising said compound of claim 1, a thereof, or pharmaceutically acceptable salt, hydrate or solvate of said compound or said prodrug and a pharmaceutically acceptable excipient, diluent, carrier or mixtures thereof; and (ii) a second composition comprising said pharmaceutical agent and a pharmaceutically acceptable excipient, diluent, carrier or mixtures thereof.

25. The method of claim 24 wherein said first composition and said second composition are administered simultaneously.

26. The method of claim 24 wherein said first composition and said second composition are administered sequentially.

* * * * *